US012782344B2

(12) United States Patent
Perera et al.

(10) Patent No.: US 12,782,344 B2
(45) Date of Patent: Nov. 3, 2026

(54) FLUIDIC MEDIA FOR SINGLE-ANALYTE ARRAYS

(71) Applicant: Nautilus Subsidiary, Inc., Seattle, WA (US)

(72) Inventors: Rukshan Perera, Newark, CA (US); Maryam Jouzi, Hayward, CA (US); Cassandra Stawicki, Foster City, CA (US); Torri Elise Rinker, San Francisco, CA (US); Chol Yun, San Diego, CA (US); Kenneth Kuhn, San Diego, CA (US); Raymond Mak, San Francisco, CA (US)

(73) Assignee: Nautilus Subsidiary, Inc., Seattle, WA (US)

(*) Notice: Subject to any disclaimer, the term of this patent is extended or adjusted under 35 U.S.C. 154(b) by 501 days.

(21) Appl. No.: 18/533,104

(22) Filed: Dec. 7, 2023

(65) Prior Publication Data

US 2024/0192202 A1 Jun. 13, 2024

Related U.S. Application Data

(60) Provisional application No. 63/584,288, filed on Sep. 21, 2023, provisional application No. 63/508,618, filed on Jun. 16, 2023, provisional application No. 63/386,833, filed on Dec. 9, 2022.

(51) Int. Cl.

| | |
|---|---|
| ***G16B 30/00*** | (2019.01) |
| ***G01N 33/543*** | (2006.01) |
| ***G01N 33/58*** | (2006.01) |

(52) U.S. Cl.

CPC ..... *G01N 33/54306* (2013.01); *G01N 33/582* (2013.01)

(58) Field of Classification Search

None

See application file for complete search history.

(56) References Cited

U.S. PATENT DOCUMENTS

| | | | |
|---|---|---|---|
| 5,445,934 | A | 8/1995 | Fodor et al. |
| 5,695,934 | A | 12/1997 | Brenner |
| 5,849,878 | A | 12/1998 | Cantor et al. |
| 5,863,722 | A | 1/1999 | Brenner |
| 5,888,737 | A | 3/1999 | Dubridge et al. |
| 6,140,489 | A | 10/2000 | Brenner |
| 6,175,002 | B1 | 1/2001 | Dubridge et al. |
| 6,720,595 | B2 | 4/2004 | Clevenger et al. |
| 6,998,241 | B2 | 2/2006 | Boga |
| 7,122,482 | B2 | 10/2006 | Xu et al. |
| 7,181,122 | B1 | 2/2007 | Levene et al. |
| 7,252,954 | B2 | 8/2007 | Wang et al. |
| 7,302,146 | B2 | 11/2007 | Turner et al. |
| 7,306,904 | B2 | 12/2007 | Landegren et al. |
| 7,313,308 | B2 | 12/2007 | Turner et al. |
| 7,329,860 | B2 | 2/2008 | Feng et al. |
| 7,351,528 | B2 | 4/2008 | Landegren |
| 7,842,793 | B2 | 11/2010 | Rothemund |
| 7,855,054 | B2 | 12/2010 | Schneider et al. |
| 7,932,060 | B2 | 4/2011 | Nadeau et al. |
| 7,964,356 | B2 | 6/2011 | Zichi et al. |
| 8,013,134 | B2 | 9/2011 | Fredriksson |
| 8,148,264 | B2 | 4/2012 | Henry et al. |
| 8,222,047 | B2 | 7/2012 | Duffy et al. |
| 8,236,574 | B2 | 8/2012 | Duffy et al. |
| 8,268,554 | B2 | 9/2012 | Schallmeiner |
| 8,404,830 | B2 | 3/2013 | Zichi et al. |
| 8,415,171 | B2 | 4/2013 | Rissin et al. |
| 8,765,359 | B2 | 7/2014 | Fernandez et al. |
| 8,798,414 | B2 | 8/2014 | Quan et al. |
| 8,945,830 | B2 | 2/2015 | Heil et al. |
| 8,951,781 | B2 | 2/2015 | Williamson et al. |
| 8,975,026 | B2 | 3/2015 | Zichi et al. |
| 8,975,388 | B2 | 3/2015 | Zichi et al. |
| 9,163,056 | B2 | 10/2015 | Rohloff et al. |
| 9,164,053 | B2 | 10/2015 | Collins et al. |
| 9,193,996 | B2 | 11/2015 | Buermann et al. |
| 9,340,416 | B2 | 5/2016 | Maune et al. |
| 9,347,829 | B2 | 5/2016 | Loncar et al. |
| 9,395,359 | B2 | 7/2016 | Walt et al. |
| 9,404,919 | B2 | 8/2016 | Schneider et al. |
| 9,410,887 | B2 | 8/2016 | Walavalkar et al. |
| 9,528,984 | B2 | 12/2016 | Mitra |
| 9,606,058 | B2 | 3/2017 | Rothberg et al. |
| 9,625,469 | B2 | 4/2017 | Marcotte et al. |

(Continued)

FOREIGN PATENT DOCUMENTS

| | | | |
|---|---|---|---|
| CN | 1938430 | A | 3/2007 |
| CN | 100500865 | C | 6/2009 |

(Continued)

OTHER PUBLICATIONS

International Search Report and Written Opinion in PCT/US2023/083006, mailed Mar. 4, 2024, 13 pages.

Aebersold et al., "How many human proteoforms are there?," Nature Chemical Biology, Mar. 2018, vol. 14, No. 3, pp. 206-214.

Arnold et al., "The majority of immunogenic epitopes generate CD4+ T cells that are dependent on MHC class II-bound peptide-flanking residues," The Journal of Immunology, Jul. 2002, vol. 169, No. 2, pp. 739-749.

Ayoglu et al., "Autoantibody profiling in multiple sclerosis using arrays of human protein fragments," Molecular & Cellular Proteomics, Sep. 2013, vol. 12, No. 9, pp. 2657-2672.

(Continued)

*Primary Examiner* — Ann Montgomery

(74) *Attorney, Agent, or Firm* — Orrick, Herrington & Sutcliffe, LLP

(57) ABSTRACT

Methods of minimizing detection of unintended signals during array-based processes are provided. Methods include the use of sets of fluidic media that inhibit sources of unintended signals during array-based processes. Also provided are systems containing the sets of fluidic media that are configured to perform the array-based processes provided herein.

20 Claims, 53 Drawing Sheets

(56) References Cited

U.S. PATENT DOCUMENTS

| | | | |
|---|---|---|---|
| 9,678,012 | B2 | 6/2017 | Rothberg et al. |
| 9,678,068 | B2 | 6/2017 | Duffy et al. |
| 9,777,315 | B2 | 10/2017 | Fredriksson et al. |
| 9,829,456 | B1 | 11/2017 | Jin et al. |
| 9,921,157 | B2 | 3/2018 | Rothberg et al. |
| 9,926,566 | B2 | 3/2018 | Ochsner et al. |
| 9,938,314 | B2 | 4/2018 | Rohloff et al. |
| 9,987,609 | B2 | 6/2018 | Walavalkar et al. |
| 10,036,064 | B2 | 7/2018 | Merriman et al. |
| 10,221,207 | B2 | 3/2019 | Rohloff et al. |
| 10,221,421 | B2 | 3/2019 | Jarvis et al. |
| 10,239,908 | B2 | 3/2019 | Rohloff et al. |
| 10,316,321 | B2 | 6/2019 | Zichi et al. |
| 10,351,909 | B2 | 7/2019 | Drmanac et al. |
| 10,392,621 | B2 | 8/2019 | Ochsner et al. |
| 10,473,654 | B1 | 11/2019 | Mallick |
| 10,545,153 | B2 | 1/2020 | Marcotte et al. |
| 10,605,730 | B2 | 3/2020 | Rothberg et al. |
| 10,712,274 | B2 | 7/2020 | Rothberg et al. |
| 10,741,382 | B2 | 8/2020 | Sills et al. |
| 10,775,305 | B2 | 9/2020 | Rothberg et al. |
| 10,829,816 | B2 | 11/2020 | Staker et al. |
| 10,845,308 | B2 | 11/2020 | Rothberg et al. |
| 10,895,534 | B2 | 1/2021 | Finkelstein et al. |
| 11,203,612 | B2 | 12/2021 | Gremyachinskiy et al. |
| 11,282,586 | B2 | 3/2022 | Patel et al. |
| 11,505,796 | B2 | 11/2022 | Aksel et al. |
| 11,692,217 | B2 | 7/2023 | Aksel et al. |
| 11,935,311 | B2 | 3/2024 | Egertson et al. |
| 11,970,693 | B2 | 4/2024 | Mallick |
| 11,993,865 | B2 | 5/2024 | Klein et al. |
| 2003/0040020 | A1 | 2/2003 | Nguyen et al. |
| 2003/0054408 | A1 | 3/2003 | Ravi et al. |
| 2004/0023413 | A1 | 2/2004 | Opalsky |
| 2004/0067599 | A1 | 4/2004 | Katz et al. |
| 2004/0091931 | A1 | 5/2004 | Gold |
| 2004/0166106 | A1 | 8/2004 | Wang et al. |
| 2005/0148100 | A1 | 7/2005 | Su et al. |
| 2006/0160234 | A1 | 7/2006 | Lopez-Avila et al. |
| 2006/0263769 | A1 | 11/2006 | Luo et al. |
| 2009/0026082 | A1 | 1/2009 | Rothberg et al. |
| 2009/0127589 | A1 | 5/2009 | Rothberg et al. |
| 2009/0214591 | A1 | 8/2009 | Manucharyan et al. |
| 2009/0247414 | A1 | 10/2009 | Obradovic et al. |
| 2010/0111768 | A1 | 5/2010 | Banerjee et al. |
| 2010/0137143 | A1 | 6/2010 | Rothberg et al. |
| 2010/0282617 | A1 | 11/2010 | Rothberg et al. |
| 2011/0065807 | A1 | 3/2011 | Radovic-Moreno et al. |
| 2011/0263688 | A1 | 10/2011 | Barany et al. |
| 2012/0077688 | A1 | 3/2012 | Bergo et al. |
| 2013/0116153 | A1 | 5/2013 | Bowen et al. |
| 2015/0185199 | A1 | 7/2015 | Joo et al. |
| 2016/0102344 | A1 | 4/2016 | Niemeyer et al. |
| 2016/0310926 | A1 | 10/2016 | Sun et al. |
| 2017/0044245 | A1 | 2/2017 | Meng et al. |
| 2017/0191051 | A1 | 7/2017 | Nikiforov |
| 2017/0240962 | A1 | 8/2017 | Merriman et al. |
| 2017/0283868 | A1 | 10/2017 | Beechem et al. |
| 2018/0051316 | A1 | 2/2018 | Collins et al. |
| 2018/0112265 | A1 | 4/2018 | Boyanov et al. |
| 2018/0155773 | A1 | 6/2018 | Gunderson et al. |
| 2018/0305727 | A1 | 10/2018 | Merriman et al. |
| 2019/0145982 | A1 | 5/2019 | Chee et al. |
| 2020/0025752 | A1 | 1/2020 | Gopinath et al. |
| 2020/0025757 | A1 | 1/2020 | Gopinath et al. |
| 2020/0348307 | A1 | 11/2020 | Beierle et al. |
| 2020/0348308 | A1 | 11/2020 | Chee et al. |
| 2021/0355483 | A1 | 11/2021 | Chee et al. |
| 2023/0070896 | A1 | 3/2023 | Joly et al. |
| 2023/0090454 | A1 | 3/2023 | Kapp et al. |
| 2023/0114905 | A1 | 4/2023 | Egertson et al. |
| 2023/0149883 | A1 | 5/2023 | Indermuhle et al. |
| 2023/0167488 | A1 | 6/2023 | Robinson et al. |
| 2023/0287480 | A1 | 9/2023 | Stern et al. |
| 2023/0360732 | A1 | 11/2023 | Egertson et al. |

FOREIGN PATENT DOCUMENTS

| | | | | |
|---|---|---|---|---|
| EP | 2 872 898 | B1 | 12/2016 | |
| WO | 2001/046675 | A2 | 6/2001 | |
| WO | 2006/135527 | A2 | 12/2006 | |
| WO | 2007/117444 | A2 | 10/2007 | |
| WO | 2007/120208 | A2 | 10/2007 | |
| WO | 2007/123744 | A2 | 11/2007 | |
| WO | 2014/078855 | A1 | 5/2014 | |
| WO | 2015/097077 | A2 | 7/2015 | |
| WO | 2016/174525 | A1 | 11/2016 | |
| WO | 2017/127762 | A1 | 7/2017 | |
| WO | 2019/083856 | A1 | 5/2019 | |
| WO | 2019/236749 | A2 | 12/2019 | |
| WO | 2020/176793 | A1 | 9/2020 | |
| WO | 2020/223368 | A1 | 11/2020 | |
| WO | 2021/087402 | A1 | 5/2021 | |
| WO | 2022/159520 | A2 | 7/2022 | |
| WO | 2022/159663 | A1 | 7/2022 | |
| WO | 2022/271983 | A1 | 12/2022 | |
| WO | WO 2022271983 | * | 12/2022 | ............ G16B 30/00 |
| WO | 2023/122589 | A2 | 6/2023 | |
| WO | 2023/192917 | A1 | 10/2023 | |

OTHER PUBLICATIONS

Blatch et al., "The tetratricopeptide repeat: a structural motif mediating protein-protein interactions," Bioessays, Nov. 1999, vol. 21, No. 11, pp. 932-939.

Buenrostro et al., "Quantitative analysis of RNA-protein interactions on a massively parallel array reveals biophysical and evolutionary landscapes," Nature Biotechnology, Jun. 2014, vol. 32, No. 6, pp. 562-568.

Bunka et al., "Production and characterization of RNA aptamers specific for amyloid fibril epitopes," Journal of Biological Chemistry, Nov. 2007, vol. 282, No. 47, pp. 34500-34509.

Buus et al., "High-resolution mapping of linear antibody epitopes using ultrahigh-density peptide microarrays," Molecular & Cellular Proteomics, Dec. 2012, vol. 11, No. 12, pp. 1790-1800.

Chang, J. Y., "A novel Edman-type degradation: direct formation of the thiohydantoin ring in alkaline solution by reaction of Edman-type reagents with N-monomethyl amino acids," FEBS letters, Jul. 1978, vol. 91, No. 1, pp. 63-68.

Choung et al., "Determination of B-cell epitopes in patients with celiac disease: peptide microarrays," PLoS One, Jan. 2016, vol. 11, No. 1, pp. 1-16.

Domenyuk et al., "Plasma exosome profiling of cancer patients by a next generation systems biology approach," Scientific Reports, Feb. 2017, vol. 7, No. 1, pp. 1-15.

Egertson et al., "A theoretical framework for proteome-scale single-molecule protein identification using multi-affinity protein binding reagents," BioRxiv, Oct. 2021, 29 pages.

Fodor et al., "Light-directed, spatially addressable parallel chemical synthesis," Science, Feb. 1991, vol. 251, pp. 767-773.

Ford et al., "Degenerate recognition of T cell epitopes: impact of T cell receptor reserve and stability of peptide: MHC complexes," Molecular Immunology, Feb. 2004, vol. 40, Nos. 14-15, pp. 1019-1025.

Gheorghe et al., "Chapter 8: Deacetylation and internal cleavage of Proteins for N-terminal Sequence Analysis," in: Methods in Protein Structure Analysis, Springer, Boston, MA, 1995, pp. 81-86.

Ho et al., "Unification of protein abundance datasets yields a quantitative *Saccharomyces cerevisiae* proteome," Cell Systems, Feb. 2018. vol. 6, No. 2, pp. 192-205.

Huang et al., "Protein inference: a review," Briefings in Bioinformatics, Sep. 2012, vol. 13, No. 5, pp. 586-614.

Hung et al., "Large-area spatially ordered arrays of gold nanoparticles directed by lithographically confined DNA origami," Nature Nanotechnology, Feb. 2010, vol. 5, No. 2, pp. 121-126.

Hunniger et al., "Just in time-selection: A rapid semiautomated SELEX of DNA aptamers using magnetic separation and BEAMing," Analytical Chemistry, Nov. 2014, vol. 86, No. 21, pp. 10940-10947.

(56) References Cited

OTHER PUBLICATIONS

Kang, H., "The prevention and handling of the missing data," Korean Journal of Anesthesiology, May 2013, vol. 64, No. 5, pp. 402-406.
Laurenson et al., "Development of peptide aptamer microarrays for detection of HPV16 oncoproteins in cell extracts," Analytical Biochemistry, Mar. 2011, vol. 410, No. 2, pp. 161-170.
Lin et al., "Development of a novel peptide microarray for large-scale epitope mapping of food allergens," Journal of Allergy and Clinical Immunology, Aug. 2009, vol. 124, No. 2, pp. 315-322.
Lutz et al., "Efficient construction of therapeutics, bioconjugates, biomaterials and bioactive surfaces using azide- alkyne "click" chemistry," Advanced Drug Delivery Reviews, Jun. 2008, vol. 60, No. 9, pp. 958-970.
Mckay et al., "Click Chemistry in Complex Mixtures: Bioorthogonal Bioconjugation," Chemistry & Biology, Sep. 2014, vol. 21, No. 9, pp. 1075-1101.
Meldal et al., "Cu-Catalyzed Azide-Alkyne Cycloaddition," Chemical Reviews, Aug. 2008, vol. 108, No. 8, pp. 2952-3015.
Nonobe et al., "A tabu search approach to the constraint satisfaction problem as a general problem solver," European Journal of Operational Research, Apr. 1998, vol. 106, Nos. 2-3, pp. 599-623.
Patronov et al., "Peptide binding prediction for the human class II MHC allele HLA-DP2: a molecular docking approach," BMC Structural Biology, Dec. 2011, vol. 11, 10 pages.
Price et al., "On silico peptide microarrays for high-resolution mapping of antibody epitopes and diverse protein-protein interactions," Nature Medicine, Sep. 2012, vol. 18, No. 9, pp. 1434-1440.
Reineke et al., "Preface," in: Reineke et al., Epitope Mapping Protocols, New York, Humana Press, 2009, pp. v-vi.
Reyes et al., "Critical role of HLA-DRβ* binding peptides' peripheral flanking residues in fully-protective malaria vaccine development," Biochemical and Biophysical Research Communication, Jul. 2017, vol. 489, No. 3, pp. 339-345.
Riccelli et al., "Hybridization of single-stranded DNA targets to immobilized complementary DNA probes: comparison of hairpin versus linear capture probes," Nucleic Acids Research, Feb. 2001, vol. 29, No. 4, pp. 996-1004.
Richer et al., "Epitope identification from fixed-complexity random-sequence peptide microarrays," Molecular & Cellular Proteomics, Jan. 2015, vol. 14, No. 1, pp. 136-147.
Rothemund, P. W., "Folding DNA to create nanoscale shapes and patterns," Nature, Mar. 2006, vol. 440, No. 7082, pp. 297-302.
Rusmini et al., "Protein immobilization strategies for protein biochips," Biomacromolecules, Jun. 2007, vol. 8, No. 6, pp. 1775-1789.
Sant'Angelo et al., "Recognition of core and flanking amino acids of MHC class II-bound peptides by the T cell receptor," European Journal of Immunology, Sep. 2002, vol. 32, No. 9, pp. 2510-2520.
She et al., "Comprehensive and quantitative mapping of RNA-protein interactions across a transcribed eukaryotic genome," Proceedings of the National Academy of Sciences, Apr. 2017, vol. 114, No. 14, pp. 3619-3624.
Sjoberg et al., "Validation of affinity reagents using antigen microarrays," New Biotechnology, Jun. 2012, vol. 29, No. 5, pp. 555-563.
Speltz et al., "Design of protein-peptide interaction modules for assembling supramolecular structures in vivo and in vitro," ACS Chemical Biology, Sep. 2015, vol. 10, No. 9, pp. 2108-2115.
Stohr et al., "A 31-residue peptide induces aggregation of tau's microtubule-binding region in cells," Nature Chemistry, Sep. 2017, vol. 9, No. 9, pp. 874-881.
Swaminathan et al., "Highly parallel single-molecule identification of proteins in zeptomole-scale mixtures," Nature Biotechnology, Nov. 2018, vol. 36, No. 11, pp. 1076-1082.
Tessler, L. A., "Digital Protein Analysis: Technologies for Protein Diagnostics and Proteomics through Single-Molecule Detection," PhD diss., Washington University in St. Louis, Aug. 2011, 147 pages.
Wilson et al., "Single-step selection of bivalent aptamers validated by comparison with SELEX using high-throughput sequencing," PLoS One, Jun. 2014, vol. 9, No. 6, pp. 1-11.
Wisniewski et al., "A "proteomic ruler" for protein copy number and concentration estimation without spike-in standards," Molecular & Cellular Proteomics, Dec. 2014, vol. 13, No. 12, pp. 3497-3506.
Zandian et al., "Whole-proteome peptide microarrays for profiling autoantibody repertoires within multiple sclerosis and narcolepsy," Journal of Proteome Research, Mar. 2017, vol. 16, No. 3, pp. 1300-1314.
Zhao et al., "BagReg: Protein inference through machine learning," Computational Biology and Chemistry, Aug. 2015, vol. 57, pp. 12-20.

* cited by examiner

FLUIDIC MEDIA FOR SINGLE-ANALYTE ARRAYS

CROSS-REFERENCE TO RELATED APPLICATIONS

This application claims priority to U.S. Provisional Application No. 63/386,833, filed on Dec. 9, 2022, U.S. Provisional Application No. 63/508,618, filed on Jun. 16, 2023, and U.S. Provisional Application No. 63/584,288, filed on Sep. 21, 2023, each of which are incorporated herein by reference.

BACKGROUND

Fluidic media are often utilized in array-based processes or assays for various purposes, including transporting reagents to and from arrays, mediating interactions on the arrays, and facilitating interrogation of arrays for purposes such as quality control or data measurement. A fluidic medium may be formulated based upon its intended purpose in an array-based system. Formulation of a fluidic medium may be influenced, at least in part by the chemical properties of array components such as a solid support and surface chemistries disposed thereupon, as well as by the chemical properties (e.g., solubility, surface charge density, polarity, etc.) of a reagent contained within the fluidic medium.

A fluidic medium containing a type of reagent may be contacted to an array of analytes to facilitate formation of binding interactions between the reagent and analytes of the array of analytes. Of particular interest are fluidic media for facilitating binding of affinity agents or detectable binding reagents to analytes that are disposed on arrays, including arrays that are provided in single-analyte format. Arrays may be configured to facilitate formation of binding interactions of affinity agents or detectable binding reagents with analytes, and inhibit formation of binding interactions of affinity agents or detectable binding reagents with other array components, such as array sites or interstitial regions.

Binding interactions between binding reagents (e.g., affinity agents or detectable binding reagents) and an array may be broadly categorized as on-target binding interactions, off-target binding interactions, and orthogonal binding interactions. On-target binding interactions can refer to the favored, intended, or expected binding interactions of a binding reagent with an analyte or an epitope thereof. Off-target binding interactions can refer to disfavored, unintended, or unexpected binding interactions of a binding reagent with an analyte or an epitope thereof. Orthogonal binding interactions can refer to unwanted, unintended, or otherwise unexpected binding interactions of binding reagents with non-analyte array components, such as interstitial regions or array sites.

SUMMARY

In an aspect, provided herein is a method, comprising: a) binding binding reagents to an array of polypeptides, wherein the array of polypeptides comprises a plurality of sites, wherein individual sites of the plurality of sites each comprises one and only one polypeptide, wherein the individual sites are optically resolvable at single-molecule resolution, wherein binding the binding reagents to the array occurs in the presence of a binding reagent association medium, and wherein the binding reagent association medium comprises a non-polypeptide blocking agent, b) before dissociating the binding reagents from the array in the presence of a binding reagent dissociation medium, detecting at the individual sites presence or absence of a signal, wherein the detecting occurs in the presence of a binding reagent detection medium, and wherein the binding reagent detection medium comprises a reaction inhibitor species, and c) after the detecting, dissociating the binding reagents from the array of polypeptides, wherein the binding reagent dissociation fraction is at least 95%.

In another aspect, provided herein is a method, comprising: a) binding binding reagents to an array of polypeptides, wherein the array of polypeptides comprises a plurality of sites, wherein individual sites of the plurality of sites each comprises one and only one polypeptide, and wherein the individual sites are optically resolvable at single-molecule resolution, b) before dissociating the binding reagents from the array in the presence of a binding reagent dissociation medium, detecting at the individual sites presence or absence of a signal, wherein the detecting occurs in the presence of a binding reagent detection medium, and wherein the binding reagent detection medium comprises a reaction inhibitor species, and c) after the detecting, dissociating the binding reagents from the array of polypeptides, wherein dissociating the binding reagents from the array of polypeptides occurs in the presence of a binding reagent dissociation medium, and wherein the binding reagent dissociation fraction is at least 95%.

In another aspect, provided herein is a method, comprising: a) binding binding reagents to an array of polypeptides, wherein the array of polypeptides comprises a plurality of sites, wherein individual sites of the plurality of sites each comprises one and only one polypeptide, wherein the individual sites are optically resolvable at single-molecule resolution, wherein binding the binding reagents to the array occurs in the presence of a binding reagent association medium, and wherein the binding reagent association medium comprises a non-polypeptide blocking agent, b) before dissociating the binding reagents from the array in the presence of a binding reagent dissociation medium, detecting at the individual sites presence or absence of a signal, and c) after the detecting, dissociating the binding reagents from the array of polypeptides, wherein dissociating the binding reagents from the array of polypeptides occurs in the presence of a binding reagent dissociation medium, and wherein the binding reagent dissociation fraction is at least 95%.

In another aspect, provided herein is a method, comprising: a) binding binding reagents to an array of polypeptides, wherein the array of polypeptides comprises a plurality of sites, wherein individual sites of the plurality of sites each comprises one and only one polypeptide, wherein the individual sites are optically resolvable at single-molecule resolution, wherein binding the binding reagents to the array occurs in the presence of a binding reagent association medium, and wherein the binding reagent association medium comprises a non-polypeptide blocking agent, b) before dissociating the binding reagents from the array in the presence of a binding reagent dissociation medium, detecting at the individual sites presence or absence of a signal, wherein the detecting occurs in the presence of a binding reagent detection medium, and wherein the binding reagent detection medium comprises a reaction inhibitor species, and c) after the detecting, dissociating the binding reagents from the array of polypeptides, wherein dissociating the binding reagents from the array of polypeptides occurs in the presence of a binding reagent dissociation medium, and wherein the binding reagent dissociation fraction is at least 99%.

In another aspect, provided herein is a method, comprising: a) binding binding reagents to an array of polypeptides, wherein the array of polypeptides comprises a plurality of sites, wherein individual sites of the plurality of sites each comprises one and only one polypeptide, wherein the individual sites are optically resolvable at single-molecule resolution, wherein binding the binding reagents to the array occurs in the presence of a binding reagent association medium, and wherein the binding reagent association medium comprises a non-polypeptide blocking agent, b) before dissociating the binding reagents from the array in the presence of a binding reagent dissociation medium, detecting at the individual sites presence or absence of a signal, wherein the detecting occurs in the presence of a binding reagent detection medium, and wherein the binding reagent detection medium comprises a reaction inhibitor species, and c) after the detecting, dissociating the binding reagents from the array of polypeptides, wherein the binding anomaly fraction is no more than 5%.

In another aspect, provided herein is a method, comprising: a) binding binding reagents to an array of polypeptides, wherein the array of polypeptides comprises a plurality of sites, wherein individual sites of the plurality of sites each comprises one and only one polypeptide, and wherein the individual sites are optically resolvable at single-molecule resolution, b) before dissociating the binding reagents from the array in the presence of a binding reagent dissociation medium, detecting at the individual sites presence or absence of a signal, wherein the detecting occurs in the presence of a binding reagent detection medium, and wherein the binding reagent detection medium comprises a reaction inhibitor species, and c) after the detecting, dissociating the binding reagents from the array of polypeptides, wherein dissociating the binding reagents from the array of polypeptides occurs in the presence of a binding reagent dissociation medium, and wherein the binding anomaly fraction is no more than 5%.

In another aspect, provided herein is a method, comprising: a) binding binding reagents to an array of polypeptides, wherein the array of polypeptides comprises a plurality of sites, wherein individual sites of the plurality of sites each comprises one and only one polypeptide, wherein the individual sites are optically resolvable at single-molecule resolution, wherein binding the binding reagents to the array occurs in the presence of a binding reagent association medium, and wherein the binding reagent association medium comprises a non-polypeptide blocking agent, b) before dissociating the binding reagents from the array in the presence of a binding reagent dissociation medium, detecting at the individual sites presence or absence of a signal, and c) after the detecting, dissociating the binding reagents from the array of polypeptides, wherein dissociating the binding reagents from the array of polypeptides occurs in the presence of a binding reagent dissociation medium, and wherein the binding anomaly fraction is no more than 5%.

In another aspect, provided herein is a method, comprising: a) binding binding reagents to an array of polypeptides, wherein the array of polypeptides comprises a plurality of sites, wherein individual sites of the plurality of sites each comprises one and only one polypeptide, wherein the individual sites are optically resolvable at single-molecule resolution, wherein binding the binding reagents to the array occurs in the presence of a binding reagent association medium, and wherein the binding reagent association medium comprises a non-polypeptide blocking agent, b) before dissociating the binding reagents from the array in the presence of a binding reagent dissociation medium, detecting at the individual sites presence or absence of a signal, wherein the detecting occurs in the presence of a binding reagent detection medium, and wherein the binding reagent detection medium comprises a reaction inhibitor species, and c) after the detecting, dissociating the binding reagents from the array of polypeptides, wherein dissociating the binding reagents from the array of polypeptides occurs in the presence of a binding reagent dissociation medium, and wherein the binding anomaly fraction is no more than 1%.

In another aspect, provided herein is a method, comprising performing on a single-analyte array at least 50 cycles of a process, wherein each individual cycle of the process comprises the steps of: (a) binding, in the presence of a binding reagent association medium, binding reagents to analytes at sites of a plurality of sites of the single-analyte array, (b) detecting at each individual site of the plurality of sites a presence or an absence of a signal from a binding reagent of the binding reagents, and (c) dissociating, in the presence of a binding reagent dissociation medium, the binding reagents from the analytes at the sites of the plurality of sites, wherein the binding reagent association medium comprises a polymeric blocking reagent, wherein the binding reagent dissociation medium comprises a zwitterionic surfactant, and wherein at least one signal is detected at each individual site of at least 90% of sites of the plurality of sites during at least one cycle of the final 10 cycles of the at least 50 cycles of the process.

In another aspect, provided herein is a method, comprising performing on a single-analyte array at least 50 cycles of a process, wherein each individual cycle of the process comprises the steps of: (a) binding, in the presence of a binding reagent association medium, binding reagents to analytes at sites of a plurality of sites of the single-analyte array, (b) detecting at each individual site of the plurality of sites a presence or an absence of a signal from a binding reagent of the binding reagents, and (c) dissociating, in the presence of a binding reagent dissociation medium, the binding reagents from the analytes at the sites of the plurality of sites, wherein the binding reagent association medium comprises a polymeric blocking reagent, wherein the binding reagent dissociation medium comprises a zwitterionic surfactant, and wherein a signal is detected at each individual site of no more than 10% of sites of the plurality of sites during more than 2 consecutive cycles of the final 10 cycles of the at least 50 cycles of the process.

INCORPORATION BY REFERENCE

All publications, items of information available on the internet, patents, and patent applications cited in this specification are herein incorporated by reference to the same extent as if each individual publication, patent, or patent application was specifically and individually indicated to be incorporated by reference. To the extent publications, items of information available on the internet, patents, or patent applications incorporated by reference contradict the disclosure contained in the specification, the specification is intended to supersede and/or take precedence over any such contradictory material.

DETAILED DESCRIPTION

Figure 1:
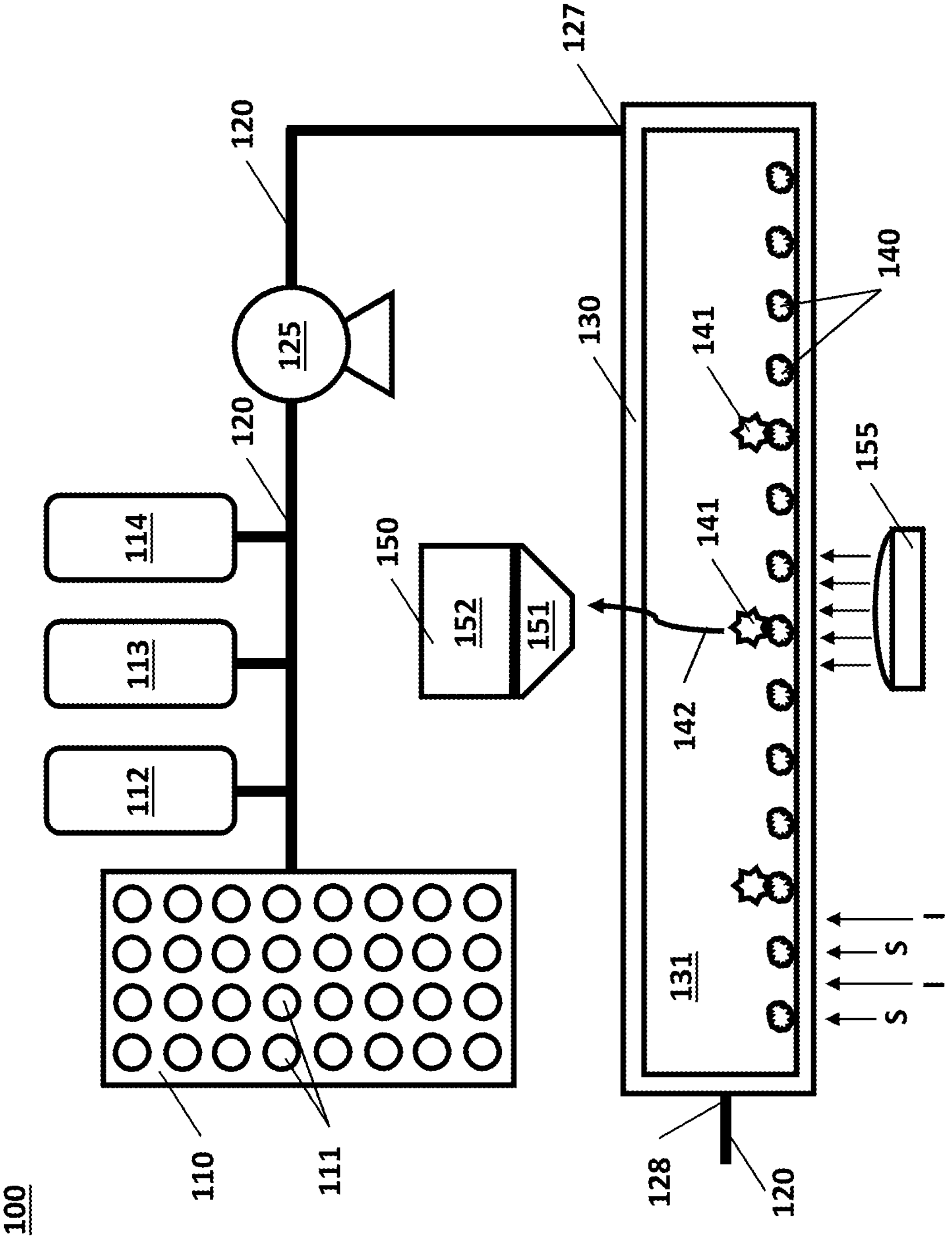
FIG. 1 illustrates a schematic of an array-based detection system comprising multiple fluidic reservoirs, in accordance with some embodiments.

A single-analyte array can describe an array that is structured to separate a plurality of analytes such that any given analyte on the array is sufficiently separated from each other analyte on the array to permit discrete interrogation of the given analyte without interference from surrounding analytes. As length scale decreases toward the nanoscale (the length scale of interest for most biomolecules such as polypeptides, nucleic acids, polysaccharides, etc.), achieving single-analyte deposition on an array can become increasingly challenging. Absent other factors, deposition of analytes on an array may achieve loading according to a Poisson distribution, suggesting single-molecule occupancy at about 37% of array sites, and a near-equal fraction of array sites having no analyte occupancy. Accordingly, methods of single-analyte array formation can utilize various approaches to achieving high single-analyte occupancy while minimizing multiple occupancy or no occupancy of array sites. One such approach is the use of anchoring moieties to facilitate coupling of a single analyte to a single array site while excluding the co-localization of other anchoring moieties and/or analytes to the same single array site. Anchoring moieties can be formed from any suitable material that is capable of attachment to an analyte and forming a binding interaction with a surface, including organic and/or inorganic nanoparticles as well as certain biomolecules such as polypeptides and nucleic acids. A particularly advantageous anchoring moiety may be formed from a nucleic acid nanoparticle given the tunable nature of nucleic acid conformations and the numerous types of covalent and non-covalent attachment strategies between nucleic acids and other molecules.

An advantage of providing analytes in single-analyte format is the ability to individually interrogate each analyte. Spatial separation afforded by arrays allows the interrogation and/or detection of each analyte independently of others. For example, performing biochemical assays in a single-molecule array format facilitates determination of characteristics or properties for each molecule on the array. A particular example that highlights the utility of single-analyte arrays is protein post-translational modification characterization. Bulk characterization of post-translational modifications (e.g., by mass spectrometry) can provide information on the abundance of certain modifications within a population of proteins, but cannot easily provide information on which post-translational modifications tend to occur on the same protein molecules. Single-molecule polypeptide analysis, on the other hand, can provide proteoform characterization for each molecule that is interrogated when proteins are provided as whole proteins.

In some processes or assays, analytes on an array are interrogated by detectable binding reagents (e.g., affinity agents). With respect to polypeptide analytes, affinity agents or binding reagents may be useful when applied to single-analyte assays for epitope mapping, polypeptide identification, proteoform identification, and peptide sequencing. Detectable binding interactions at individual array sites due to the binding of individual binding reagents to individual analytes can be utilized to determine characteristics of the individual analytes. In particular processes or assays, analyte characterization will include a sequence or set of cycles, each cycle including steps of: 1) coupling binding reagents to analytes on an array, 2) detecting addresses at which binding reagents are coupled to the array by binding interactions with analytes attached thereto, and 3) after detecting the coupled binding reagents at the addresses, removing the coupled binding reagents from the array. Optionally, after removing the coupled binding reagents, the array may again be interrogated to determine the absence of binding reagents at the addresses at which they were previously detected. The cycle can be repeated at least once, for example, using different binding reagents for respective cycles.

Affinity agents can be useful in assays that utilize a single-analyte format. Single-analyte assays may include any assay that involves detection of analytes with sufficient resolution to distinguish any analyte from any adjacent analytes. During a single-analyte assay, binding interactions of affinity agents with analytes may be detected, thereby providing information about each analyte given a presence or absence of binding of the affinity agent. Particular single-analyte assays may comprise cyclical detection of affinity agent binding interactions with analytes. For example, polypeptide analytes can be individually identified and/or characterized through development of binding profiles of multiple, differing affinity agents for each individual analyte. In another example, polypeptide analytes can be sequenced in a single-molecule format using an Edman-degradation type assay, in which terminal amino acids are identified by affinity agent binding. To perform an assay involving cyclical or sequential binding of affinity agents to analytes, it may be necessary to reliably dissociate bound affinity agents from analytes after each binding and/or detection event of the assay. The method of detection of affinity agent binding interactions and/or the method of interpreting detection data for affinity agent binding interactions may determine, at least in part, the extent of binding reagent dissociation necessary to acquire meaningful analyte information.

Single-analyte arrays may be formed for a purpose such as assaying of analytes, synthesis of analytes, modification of analytes, or combinations thereof. Many single-analyte assays or processes can be serial or cyclical in nature; given the stochastic nature of single-molecule interactions, repetition or sequencing of measurements or processes is an approach to overcoming the inherent uncertainty associated with any single measurement or process. Accordingly, single-analyte assays or processes can involve serial or cyclical formation and/or disruption of binding interactions between analytes, array constituents, and other reagents contacted with an array. In some instances, a single-analyte assay or process can involve serial or cyclical formation and/or disruption of a particular set of binding interactions, while maintaining other interactions without disruption. In particular instances, a single-analyte assay or process may maintain a particular binding interaction while disrupting a chemically-similar binding interaction at the same array site. For example, a single-analyte array may utilize anchoring moieties comprising nucleic acid nanoparticles, in which each nucleic acid nanoparticle comprises a network of hybridized oligonucleotides whose hybridization interactions maintain nanoparticle stability. Additionally, other molecules or moieties may be reversibly attached to nucleic acid nanoparticles by hybridization of linking nucleic acids to the nucleic acid nanoparticles. In such a system, it may be useful to identify a nanoparticle configuration and a dissociation condition that permits dehybridization of an attached molecule and linking nucleic acid without disrupting the nucleic acid nanoparticle itself.

Figure 22A:
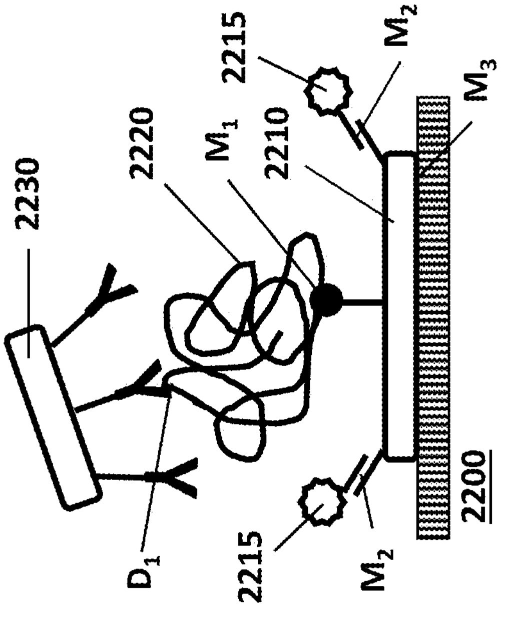
FIGS. 22A, 22B, 22C, 22D, 22E, 22F, and 22G show various configurations of single-analyte systems with associated detectable probes, in accordance with some embodiments.
Figure 22B:
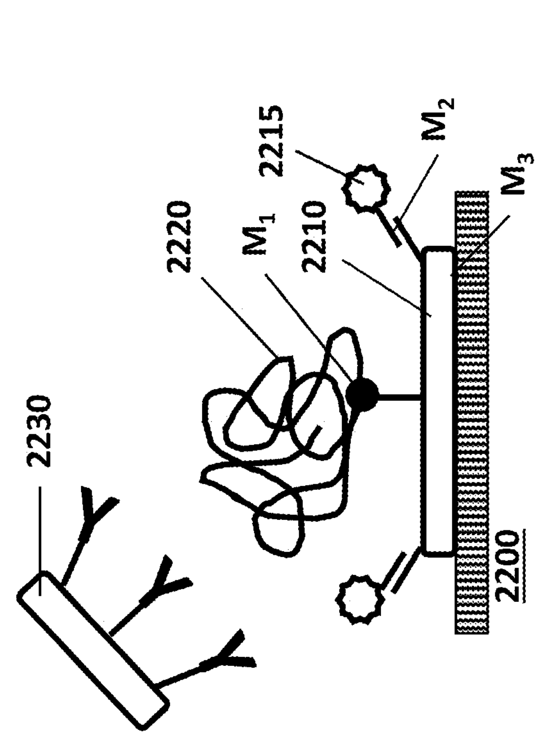

FIGS. 22A-22G depict examples of single-analyte systems that are configured to undergo an association or dissociation process without disrupting other binding interactions. FIGS. 22A-22B illustrate a single-analyte system with association and dissociation of a detectable binding reagent 2230 from a polypeptide analyte 2220. Such a system may be utilized for analyte identification and analysis. FIG. 22A depicts the single-analyte system in an associated state, in which the polypeptide analyte 2220 is coupled to a solid support 2200 by an anchoring moiety 2210. The anchoring moiety comprises at least two detectable labels 2215 (e.g., fluorophores) that facilitate detection of the anchoring moiety 2210 and/or analyte 2220 when associated to the anchoring moiety 2210. Several binding interactions may be present in the single-analyte system that are configured to be maintained throughout an array-based process or assay, including maintaining attachment $M_1$ (covalent and/or non-covalent) of the polypeptide analyte 2220 to the anchoring moiety 2210, maintaining attachments $M_2$, (covalent and/or non-covalent) of the detectable labels 2215 to the anchoring moiety 2210, and maintaining attachment $M_3$ (covalent and/or non-covalent) of the anchoring moiety 2210 to the solid support 2200. The system, in the associated state, also comprises at least one binding interaction $D_1$ between the detectable binding reagent 2230 and the polypeptide analyte 2220 that is configured to be disrupted, for example after detection of the detectable binding reagent 2230 co-localized with the analyte 2220. FIG. 22B depicts the single-analyte system in a dissociated state. Binding interaction $D_1$ has been disrupted, for example by a binding reagent dissociation condition as set forth herein, while binding interactions $M_1$, $M_2$, and $M_3$ have been maintained. The polypeptide analyte 2220 remains intact and coupled to the solid support 2200, thereby facilitating further analysis, for example with additional detectable binding reagents 2230.

Figure 22C:
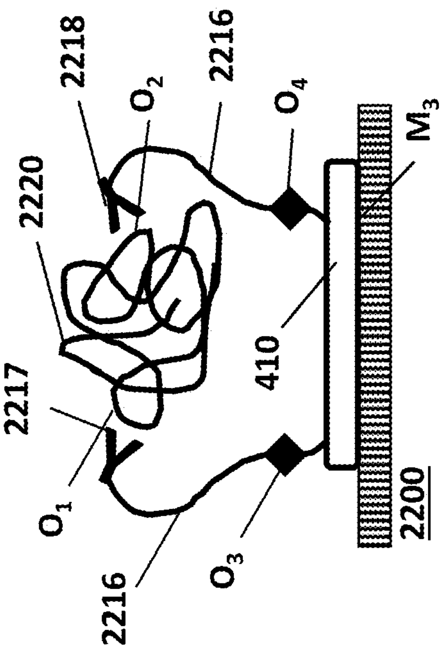
Figure 22D:
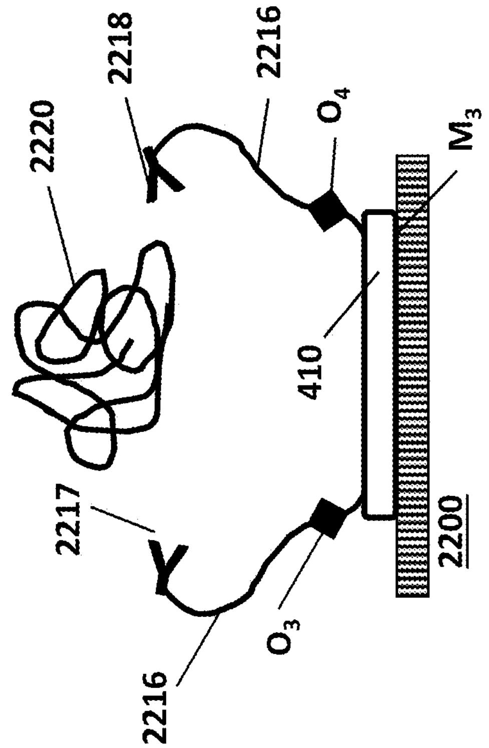
Figure 22E:
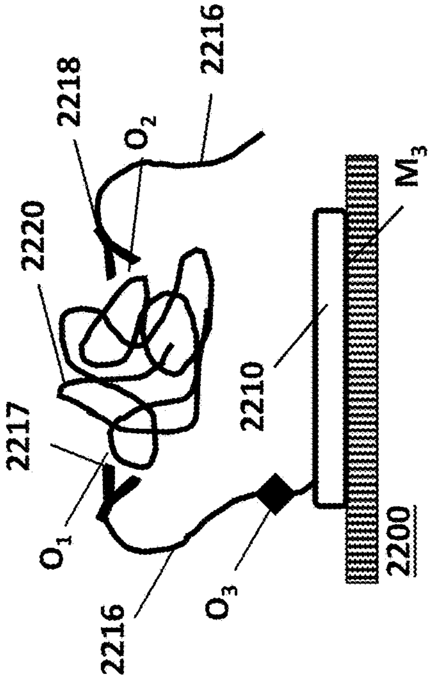

FIGS. 22C-22E illustrate a single-analyte system that is configured to perform a sandwich-type assay. Such a system may be utilized for analyte identification and analysis. FIG. 22C depicts an associated state of a complex, in which an analyte 2220 is coupled to an anchoring moiety 2210 by binding of a first affinity agent 2217 and a second affinity agent 2218. Affinity agents 2217 and 2218 are attached to the anchoring moiety 2210 by linkers 2216 (e.g., oligonucleotides, polymer chains). The anchoring moiety 2210 is coupled to a surface of a solid support 2200 by a binding interaction $M_3$ (covalent and/or non-covalent) that is configured to be maintained. The complex comprises several binding interactions, any of which may be dissociated depending upon a mode of use of the complex. For example, the analyte 2220 is coupled to the first affinity agent 2217 and the second affinity agent 2218 by binding interactions $O_1$ and $O_2$, respectively. Further, the first affinity agent 2217 and the second affinity agent 2218 may be attached (covalently or non-covalently) to the anchoring moiety 2210 by attachments $O_3$ and $O_4$, respectively. FIG. 22D depicts a first dissociated state in which the polypeptide analyte 2220 is dissociated from the first affinity agent 2217 and the second affinity agent 2218 while binding interactions $O_3$, $O_4$, and $M_3$ are maintained. FIG. 22E depicts a second dissociated state, in which the linker 2216 attached to affinity agent 2218 is dissociated from the anchoring moiety while binding interactions $O_1$, $O_2$, $O_3$, and $M_3$ are maintained.

Figure 22F:
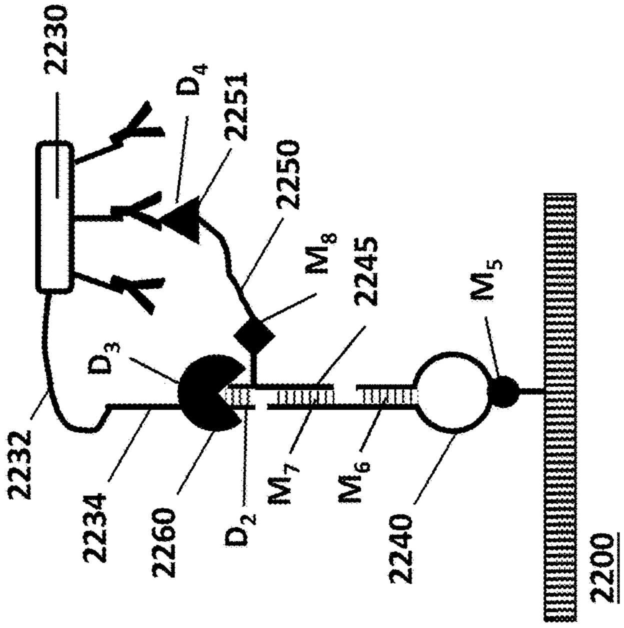
Figure 22G:
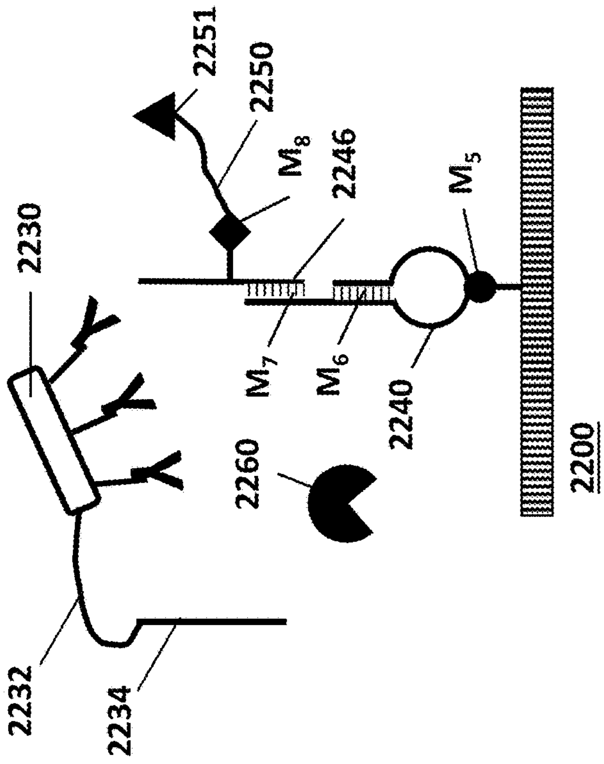

FIGS. 22F-22G illustrate a single-analyte system with association and dissociation of a detectable binding reagent 2230 from a terminal moiety 2251 of a peptide analyte 2250. Such a system may be utilized for Edman-type degradation sequencing assays. FIG. 22F depicts a fully associated state of the single-analyte system, in which a nucleic acid nanoparticle is formed by the hybridization of an analyte-attached oligonucleotide 2245 to a capture oligonucleotide 2240. The capture oligonucleotide 2240 may comprise internal complementarity. The peptide analyte 2250 is attached (covalently or non-covalently) to the analyte-attached oligonucleotide 2245. The terminal moiety 2251 of the analyte 2250 is bound by the detectable binding reagent 2230 which comprises a barcode oligonucleotide 2234 that is attached to the detectable binding reagent 2230 by a linker 2232. The barcode is coupled to the nucleic acid nanoparticle by hybridization, thereby permitting extension of a barcode sequence onto the analyte-attached oligonucleotide 2245 by an associated polymerization enzyme 2260 (e.g., a DNA polymerase, a reverse transcriptase, etc.). The single-analyte system contains several binding interactions that are configured to be maintained throughout an assay or process, including an attachment $M_5$ (covalent or non-covalent) of the capture oligonucleotide 2240 to a solid support 2200, self-hybridization $M_6$ of the capture oligonucleotide 2240, hybridization $M_7$ of the analyte-attached oligonucleotide 2245 to the capture oligonucleotide 2240, and attachment $M_8$ of the peptide analyte 2250 to the analyte-attached oligonucleotide 2245. The single-analyte system also contains several binding interactions that are configured to be disrupted, including hybridization $D_2$ of the barcoded oligonucleotide to the analyte-attached oligonucleotide 2245, binding $D_3$ of the polymerization enzyme 2260 to the nucleic acid nanoparticle, and binding $D_4$ of the detectable binding reagent 2230 to the terminal moiety 2251. FIG. 22G depicts the single-analyte system in a fully-dissociated state, in which binding interactions $D_2$, $D_3$, and $D_4$ have been dissociated while interactions $M_5$, $M_6$, $M_7$, and $M_8$ have been maintained.

Association and dissociation of a bound affinity agent from an analyte are complex phenomena that can be governed by one or more of: i) a chemical structure of the analyte, ii) a morphology of the analyte, iii) a chemical structure of the affinity agent, iv) a morphology of the affinity agent, v) kinetics of association/dissociation between the analyte and the affinity agent, and vi) a chemical environment in contact with the analyte and/or the affinity agent. For example, a change in the fluidic composition surrounding an affinity agent-analyte complex can trigger a conformational change in the analyte that facilitates association or dissociation of the affinity agent. In some cases, a binding interaction between an affinity agent and an analyte may be unlikely to naturally associate or dissociate within a timescale of an assay, thereby necessitating a process or method that triggers association or dissociation. For example, association or dissociation of an affinity agent from an analyte may be induced by introducing or altering the concentration of a chemical species such as a salt, a surfactant, a denaturant, or a combination thereof. A sufficient condition for associating or dissociating an affinity agent from an analyte may vary between two differing affinity agents. Moreover, certain association or dissociation reagents may chemically interact with assay components in a manner that is detrimental to the overall assay.

Compositions of analytes and/or affinity agents may affect association or dissociation phenomena of affinity agent-analyte complexes. In some cases, an analyte may comprise a chemical moiety that can form a covalent interaction with an analyte. For example, a polypeptide analyte can become cross-linked to an affinity agent (e.g., by a photochemical mechanism, by a catalyzed reaction, etc.). In other cases, during association or dissociation from an analyte, an affinity agent may become bound to a portion of a single-analyte array other than an analyte. For example, a binding reagent comprising an affinity agent may become bound to an interstitial region or a non-analyte portion of an analyte binding site of a single-analyte array.

Figure 19A:
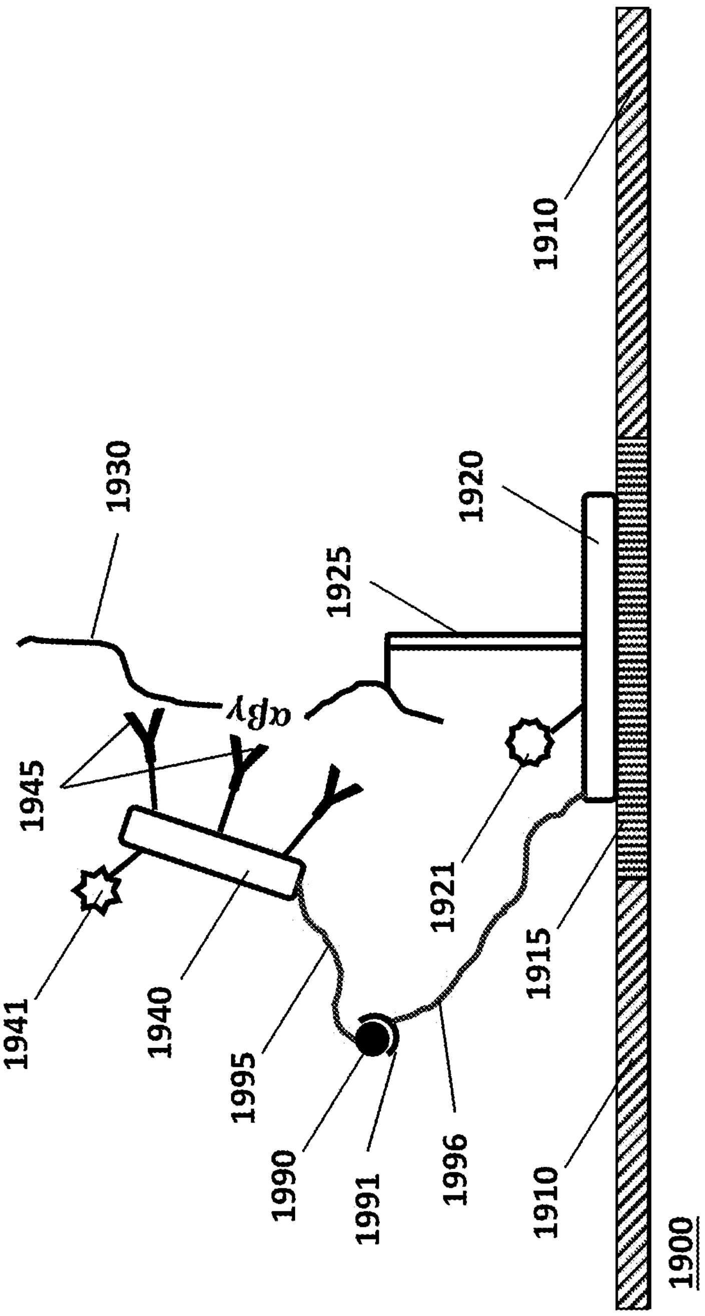
FIGS. 19A, 19B, 19C, 19D, and 19E depict potential probe dissociation events that could produce false negative or false positive detection, in accordance with some embodiments.
Figure 19B:
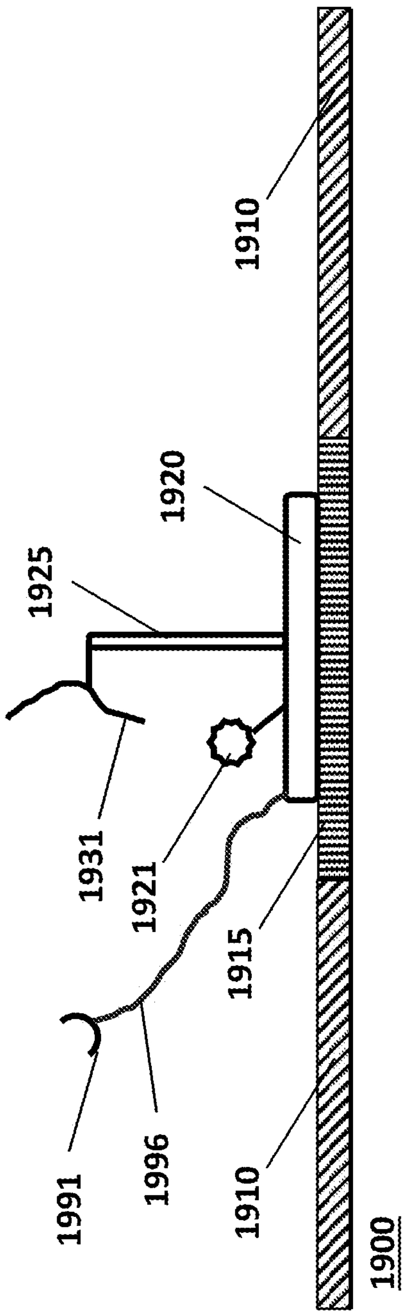
Figure 19C:
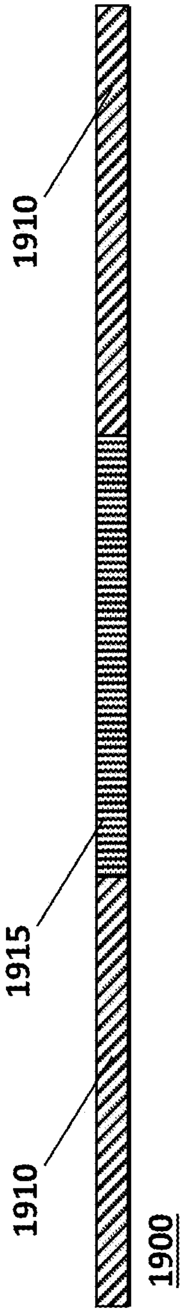
Figure 19D:
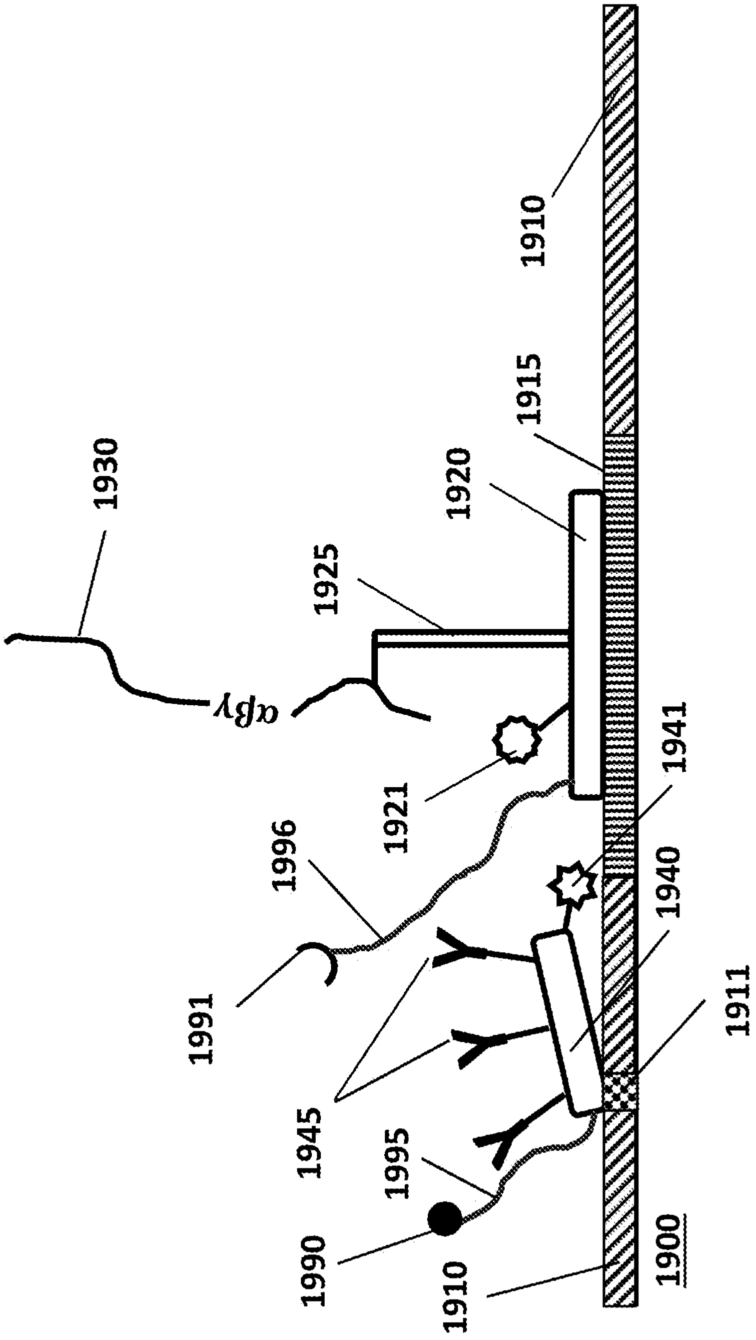
Figure 19E:
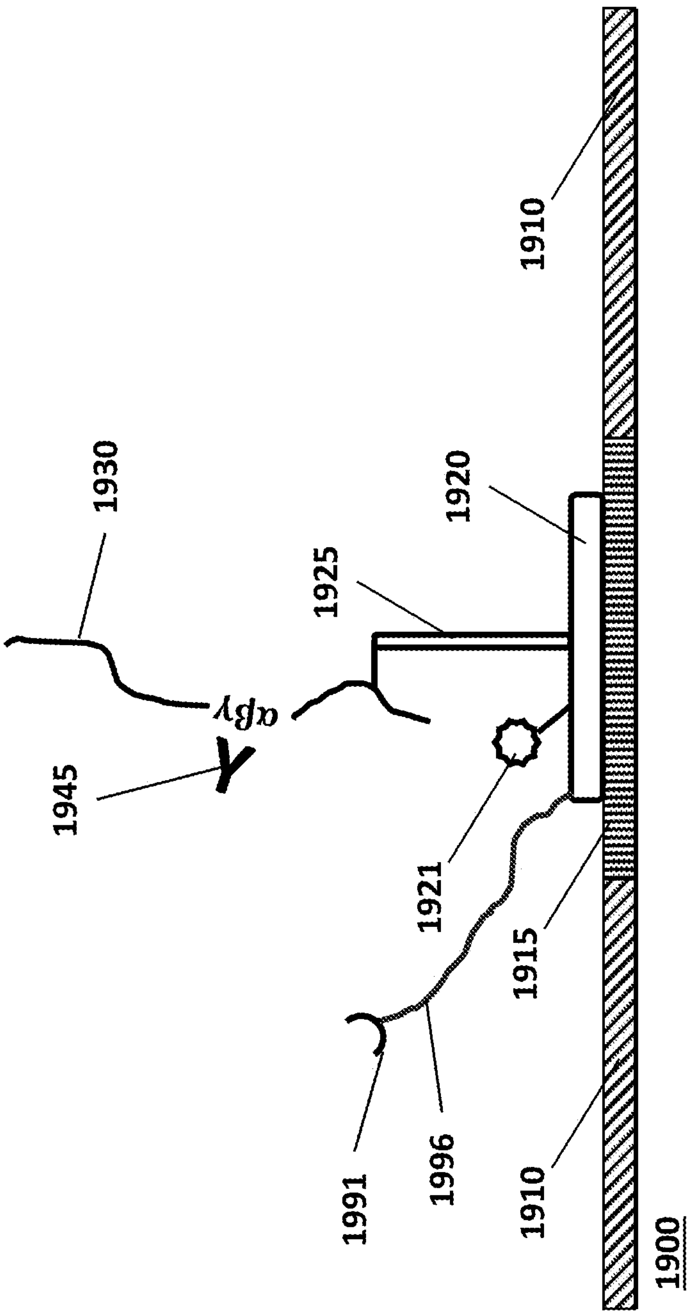

Identification of affinity agent dissociation in a single-analyte assay format involves the sequential identification of: 1) determining an address at which an affinity agent or a binding reagent comprising an affinity agent has bound to an analyte, and 2) after determining the address at which the affinity agent or binding reagent has bound the analyte, identifying an absence of the affinity agent or binding reagent at the address. False negative detection of affinity agents or binding reagents can lead to a false conclusion that the affinity agent or binding reagent has dissociated from an analyte to which it was bound. Such false negative detections can arise due to loss of a detectable signal from an affinity agent or detectable binding reagent (e.g., by photobleaching) or due to other phenomena, including false negative detection events induced by an affinity agent or binding reagent dissociation condition. FIG. 19A depicts a system in which a detectable binding reagent is bound to a polypeptide analyte. The affinity agent-analyte complex is formed on a solid support 1900 comprising interstitial surface layers 1910 that are configured to inhibit binding of affinity agents or binding reagents, and an analyte binding site surface layer 1915 that is configured to bind an analyte. An anchoring moiety 1920 is coupled to the analyte binding surface layer 1915. The anchoring moiety 1920 comprises a linker 1925 that provides separation between a surface of the solid support 1900 and a polypeptide analyte 1930. The anchoring moiety 1920 may further comprise a detectable label 1921. The detectable label 1921 may be configured to emit a signal that facilitates detection of the anchoring moiety and/or polypeptide analyte 1930 at an address of a single-analyte array. Alternatively, the detectable label 1921 may be coupled to the polypeptide analyte 1930 rather than the anchoring moiety 1920. The polypeptide analyte 1930 is coupled to the linker 1925 of the anchoring moiety 1920. The polypeptide analyte comprises an epitope αβγ that is coupled by a detectable binding reagent. The detectable binding reagent comprises a coupling moiety 1940 (e.g., a nanoparticle, a nucleic acid) that couples three affinity agents 1945, with each affinity agent having a binding specificity for epitope αβγ. The detectable binding reagent also comprises a detectable label 1941 that is coupled to the coupling moiety. The detectable label 1941 may be configured to emit a signal that facilitates detection of the detectable binding reagent at an address of a single-analyte array. Optionally, the detectable binding reagent may be further coupled to the array site by a coupled pair of avidity components. A first avidity component 1990 may be coupled to a detectable binding reagent (e.g., coupled to a coupling moiety 1940, coupled to an affinity agent 1945, etc.), optionally by a linking moiety 1995. A second avidity component 1991 may be coupled at the analyte binding site (e.g., coupled to a surface of the analyte binding site surface layer 1915, coupled to an anchoring moiety 1920, etc.), optionally by a linking moiety 1996. The coupling of the first avidity component 1990 to the second avidity component 1991 may provide an additional interaction that facilitates association of the detectable binding reagent to an analyte at an analyte binding site. FIGS. 19B-19E depict array configurations that may occur after a binding reagent dissociation condition is applied to the composition of FIG. 19A. FIGS. 19B-19E depict configurations that: 1) could produce a negative detection event at the analyte binding site, and 2) could disable the analyte from further analysis. FIG. 19B depicts a configuration in which the polypeptide analyte 1930 has become cleaved into fragment peptide 1931, causing loss of epitope αβγ. The loss of the epitope causes dissociation of the detectable binding reagent from the binding site, but also prevent analysis of the cleaved portion of the polypeptide analyte 1930. FIG. 19C depicts a configuration in which the entire anchoring moiety 1920 and polypeptide analyte 1930 has been dissociated from the solid support 1900, thereby causing a negative detection event due to absence of the detectable label 1921 and loss of the polypeptide analyte 1930 for subsequent analysis. FIG. 19D depicts a configuration that may produce a false positive detection. The affinity agent 1945 of the detectable binding reagent has dissociated from epitope αβγ, but the coupling moiety 1940 has become bound to a defect 1911 of the interstitial region surface layer 1910. Insufficient separation may exist between the location of the bound binding reagent and the analyte binding site to optically resolve whether the binding reagent is bound at the analyte binding site or the adjacent interstitial region. FIG. 19E depicts a configuration in which an affinity agent 1945 remains bound to epitope αβγ of the polypeptide analyte 1930 while the remainder of the detectable binding reagent has dissociated. The epitope αβγ may be occluded from binding other affinity agents, and the presence of the bound affinity agent 1945 may occlude binding of other affinity agents at adjacent epitopes. Configurations like those depicted in FIGS. 19B-19E may arise due to certain affinity agent dissociation conditions that damage or degrade single-analyte array components, such as presence of reactive conditions or harsh stripping conditions.

Accordingly, selection of dissociation conditions for an affinity agent-analyte complex during an assay may be based on one or more criteria including: 1) dissociation of a threshold quantity of bound affinity agents or binding reagents (e.g., at least 50%, 60%, 70%, 80%, 90%, 95%, or 99% of bound affinity agents), 2) retention of a threshold quantity of analytes (e.g., at least 90%, 95%, 99%, 99.9%, 99.99%, or 99.999% of analytes), and 3) minimal increase in orthogonal binding per round of affinity agent binding (e.g., no more than 10%, 5%, 1%, 0.5%, 0.1%, 0.05%, or 0.01% per cycle of affinity agent binding).

In some instances, one or more additional criteria may be applied in identifying a suitable binding reagent dissociation condition. A binding reagent dissociation condition may be selected based upon one or more criteria, including: 1) not causing substantial alteration of surface chemistry at analyte binding sites, 2) not causing substantial alteration of surface chemistry of interstitial regions of an array, 3) not causing substantial dissociation of an anchoring moiety from an analyte binding site, 4) not causing substantial dissociation of an analyte from an anchoring moiety, 5) maintaining one or more interactions that maintain structural integrity of an anchoring moiety, 6) maintaining one or more interactions that associate other components to an anchoring moiety (e.g., detectable labels, linking groups, etc.), 7) not causing substantial alteration of an analyte (e.g., cleavage, chemical alteration, etc.), 8) maintaining an analyte conformation that is capable of being bound by affinity agents or binding reagents, and 9) causing dissociation of an affinity agent or binding reagent from an analyte.

A challenge of obtaining high-confidence detection information from single-analyte arrays is the minimization and/or identification of unintended signals. Unintended signals can occur when a binding reagent has bound to an array site in an unwanted or unexpected fashion. In some cases, an unintended signal may be detected from off-target binding of a binding reagent to an analyte. For example, a promiscuous affinity agent may form a detectable binding interaction with an analyte with which it has a low probability of binding, thereby providing a signal at an array address at which it would not be expected to be detected. In other cases, an unintended signal may be detected from orthogonal binding of a binding reagent to an array component. For example, an affinity agent may bind to an interstitial region of an array, thereby providing a signal at an array address at which a signal is not supposed to be detected. In some cases, unintended signals may be easily detected duc to presence of a detected signal at an array address that is not configured to provide signals (e.g., an interstitial region). However, presence of unintended signals at array sites, especially those containing analytes, may be more challenging to determine.

Incomplete removal of binding reagents can also cause unintended detection in multi-cycle array-based processes or assays. Failure to remove a detectable reagent from an array site can cause signal detection at the address of the array site in subsequent detection steps. Accordingly, it is preferable to facilitate a maximal binding reagent removal rate from an array during each cycle of a multi-cycle array-based process or assay.

Moreover, array sites experiencing phenomena that cause unintended detection can become functionally disabled for a remaining duration of an assay or other process, or a portion thereof. For example, failed dissociation of a fluorescent binding reagent at an array site can produce fluorescent signals that are interpreted as false positives for subsequent detection steps, and/or the residual binding reagent can inhibit binding of other binding reagents. Further, there are multiple phenomena that functionally disable array sites or analytes attached thereto, with some causing permanent functional disabling of array sites or analytes attached thereto, and other causing temporary functional disabling of array sites or analytes attached thereto. Temporary or reversible disabling of array sites or analytes attached thereto may be a quasi-equilibrium phenomenon, with a first set of sites having become functionally disabled at a given moment, and a second set of sites having become functionally reactivated at the same moment. A primary technical challenge of temporary or reversible site-disabling may be identification of sites that have become disabled or sites that have become reactivated. Permanent disabling of array sites and/or analytes attached thereto causes attrition on an array. For example, if 0.1% of array sites become permanently disabled for each cycle of an array-based process, about 90% of array sites are still functional after 100 cycles, but if 1% of array sites become permanently disabled for each cycle of an array-based process, only about 36% of array sites are still functional after 100 cycles. A primary technical challenge of permanent or irreversible site-disabling may be minimizing the rate of attrition of array sites or analytes attach thereto.

Accordingly, it is advantageous to formulate an aligned set of reagents (e.g., binding reagents, fluidic media) and array chemistry (e.g., array site surface chemistry, interstitial chemistry, analyte chemistry) that maximize the quantity of functionally available or active array sites.

Although differing phenomena can lead to unintended signal detection on an array, there may be no discernible difference in the signals arising from the differing phenomena. Depending upon the mode of detection, signals due to on-target binding, off-target binding, or orthogonal binding of binding reagents can be substantially identical. Accordingly, it may be advantageous to provide fluidic media that can inhibit orthogonal binding, facilitate signal detection, and facilitate removal of bound binding reagents from an array.

Provided herein are systems of fluidic media that decrease a likelihood or occurrence rate of unintended signals during array-based processes or assays. Further provided herein are methods of utilizing the systems of fluidic media during array-based processes or assays to inhibit detection of unintended signals. In some cases, an array-based process or assay may utilize a binding or detection standard that facilitates determination of an on-target, off-target, or orthogonal binding rate. Further provided herein are methods of determining an on-target, off-target, or orthogonal binding rate based upon array detection data. Further provided herein are methods and systems for dissociating affinity agents or binding reagents comprising affinity agents from analytes on single-analyte arrays. Methods and systems set forth herein are compatible with combinations of system components that are utilized to maintain coupled single analytes to array sites when provided with binding reagent dissociation conditions that effect dissociation of binding reagents or affinity agents from analytes on the array. Some methods include the use of particular dissociation buffer formulations that effect efficient affinity agent dissociation without causing dissociation of analytes or other forms of degradation to the single-analyte array. Further disclosed herein are systems for analysis of single-analyte arrays that are configured to implement an affinity agent dissociation method, as set forth herein.

Definitions

Terms used herein will be understood to take on their ordinary meaning in the relevant art unless specified otherwise. Several terms used herein and their meanings are set forth below.

As used herein, the term "analyte" refers to a molecule, particle, or complex of molecules or particles that is coupled to an array site or an anchoring moiety. An analyte may comprise a target for an analytical method (e.g., sequencing, identification, quantification, etc.) or may comprise a functional element such as a binding ligand or a catalyst. An analyte may comprise a biomolecule, such as a polypeptide, polysaccharide, nucleic acid, lipid, metabolite, enzyme cofactor or a combination thereof. An analyte may comprise a non-biological molecule, such as a polymer, metal, metal oxide, ceramic, semiconductor, mineral, or a combination thereof. As used herein, the term "sample analyte" refers to an analyte derived from a sample collected from a biological or non-biological system. A sample analyte may be purified from at least one, some or all other substances, such as substances found in its native milieu, or unpurified from other substances, such as substances found in its native milieu. As used herein, the term "standard analyte" refers to a known or characterized analyte that is provided as a physical or chemical reference to a process. A standard analyte may comprise the same type of analyte as a sample analyte, or may differ from a sample analyte. For example, a polypeptide analyte process may utilize a polypeptide standard analyte with known characteristics. In another example, a polypeptide analyte process may utilize a non-polypeptide standard analyte with known characteristics.

As used herein, the term "avidity component" refers to a moiety of a first binding partner that is configured to interact with a moiety of a second binding partner to increase the rate of association between the first and second binding partners and/or to decrease the rate of dissociation the first and second binding partners. The first binding partner can further include a primary epitope moiety that interacts with a primary paratope moiety of the second binding partner, or vice versa. An avidity component can include a polymer, nucleic acid strand, nucleic acid duplex, nucleotide sequence, protein, affinity reagent, secondary epitope, secondary paratope, receptor, ligand or the like. A first avidity component can interact with a second avidity component via reversible binding, for example, via non-covalent binding or reversible covalent binding. As used herein, the term "binding specificity" refers to the tendency of a detectable probe, or an affinity reagent or avidity component thereof, to preferentially interact with an affinity target or avidity target, respectively. A detectable probe, or an affinity reagent or avidity component thereof, may have an observed, known, or predicted binding specificity for any possible binding partner, affinity target, or target moiety. Binding specificity may refer to selectivity for a single detectable probe, affinity target, or avidity target on an array over at least one other possible binding partner on the array. Moreover, binding specificity may refer to selectivity for a subset of affinity targets or avidity targets on an array over at least one other binding partner on the array.

As used herein, the term "binding affinity" refers to the strength or extent of binding between a detectable probe, or an affinity reagent or avidity component thereof, and a binding partner. In some cases, the binding affinity of a detectable probe, or an affinity reagent or avidity component thereof, for a binding partner may be vanishingly small or effectively zero. A binding affinity of a detectable probe, or an affinity reagent—or avidity component thereof, for a binding partner may be qualified as being a "high affinity," "medium affinity," or "low affinity." A binding affinity—of a detectable probe, or an affinity reagent or avidity component thereof, for a binding partner may be quantified as being "high affinity" if the interaction has a dissociation constant of less than about 100 nM, "medium affinity" if the interaction has a dissociation constant between about 100 nM and 1 mM, and "low affinity" if the interaction has a dissociation constant of greater than about 1 mM. Binding affinity—can be described in terms known in the art of biochemistry such as equilibrium dissociation constant ($K_D$), equilibrium association constant ($K_A$), association rate constant ($k_{on}$), dissociation rate constant ($k_{off}$) and the like. See, for example, Segel, Enzyme Kinetics John Wiley and Sons, New York (1975), which is incorporated herein by reference in its entirety.

As used herein, the term "rate," when used in reference to a plurality of detection events, refers to a quantity of detection events per a quantity of sites. For example, after detecting presence or absence of a detectable signal (e.g. from a signal producing binding reagent) at each individual site of a plurality of sites, a signal rate may be calculated as the total quantity of sites having a detectable signal divided by the total quantity of the plurality of sites. A rate can further include a temporal component (i.e., events per site per unit time); however, a rate need not necessarily include a temporal component.

As used herein, the term "binding reagent dissociation fraction," when used in reference to a plurality of detection events, refers to a quantity of sites having an apparent change in signal due to dissociation of a binding reagent per quantity of sites detected. The change in signal can be a decrease in signal or loss of signal, for example, due to dissociation or quenching of a label. Alternatively, the change in signal can be an increase in signal or gain of signal, for example, due to increased Forster resonance energy transfer or decreased signal quenching. A change in signal can be detected in real time or after a binding reagent dissociation step of an array-based method. A binding reagent dissociation rate can be determined after a dissociation step or can be inferred or imputed based upon prior characterizations. A binding reagent dissociation rate can be determined based upon measurements of binding reagent dissociation from sample analytes, standard analytes, or combinations thereof.

As used herein, the term "binding anomaly fraction" refers to a quantity of sites having a detected deviation in apparent binding per a quantity of sites detected by a detection device. A binding anomaly rate can be determined after an association step or a dissociation step, or can be inferred or imputed based upon prior characterizations. A binding anomaly rate can be determined based upon measurements of binding anomalies with sample analytes, standard analytes, or combinations thereof.

As used herein, the term "cycle" refers to a sequence of steps performed during an array-based process that comprises the steps of: i) associating at least one binding reagent to an analyte, and ii) dissociating the at least one binding reagent from the analyte. In some cases, a new cycle may be determined to have commenced when step i) has been repeated (i.e., each unique cycle must contain unique instances of performing steps i) and ii) together; alternatively, a single performance of step i) cannot be attributed to two different cycles). A process containing only one instance of steps i) and ii) may be considered a "single-cycle process." A process containing two or more instances of steps i) and ii) may be considered a "multi-cycle process." A cycle can further comprise additional steps, such as array formation steps (e.g., deposition of anchoring moieties, deposition of analytes, etc.), detection steps (e.g., detection of anchoring moieties, detection of analytes, detection of binding reagents), and other array-based procedures (e.g., rinsing, chemical or enzymatic treatment of array components, etc.). Steps i) and ii) of a cycle may be separated by one or more steps. Two consecutive cycles may be separated by one or more steps. Two cycles may comprise a differing sequence of steps, provided each cycle contains steps i) and ii). Aspects of steps i) and ii) may differ between different cycles. For example, a first cycle may comprise associating a first binding reagent to an analyte, and a second cycle may comprise associating a second binding reagent to the analyte, in which the first binding reagent differs from the second binding reagent.

As used herein, the term "detection event" refers to an interrogation of an array site by a detection device that produces a classifiable detection value regarding a presence or absence of a binding reagent at the array site. A classifiable detection value regarding presence or absence of a binding reagent at an array site may comprise a qualitative characterization, such as PRESENT/NOT PRESENT/UNCERTAIN, or EXPECTED/ANOMALOUS/UNCERTAIN. A classifiable detection value regarding presence or absence of a binding reagent at an array site may comprise a quantitative characterization, such as an average signal magnitude, peak signal intensity, signal lifetime, etc.

As used herein, the term "orthogonal binding", when used in reference to an array or a molecule, moiety, or particle contacted thereto, refers to any unwanted, unexpected, or contrary-to-design binding that is apparent at an array surface or array feature in the presence of a binding reagent. Orthogonal binding may arise, for example, due to binding interactions between the binding reagent and the array surface or due to binding interactions between the binding reagent and a moiety or substance at or near the array surface. Orthogonal binding phenomena may be qualitatively characterized as an apparent binding interaction that occurs in a system that has been engineered to prevent such a binding interaction (e.g., a hydrophilic molecule binding to a putatively hydrophobic surface). Orthogonal binding phenomena may be quantitatively characterized, for example, as measurable binding interactions occurring between an array surface or array feature (e.g., an interstitial region or an analyte binding site) and an unbound moiety that may become contacted with the array surface or feature, in which the measurable binding interactions occur at a rate and/or to an extent that exceeds a predicted rate and/or extent, such as a thermodynamic or kinetic prediction (e.g., a dissociation constant, a binding on-rate, a binding off-rate, etc.). For example, if an unbound moiety is characterized to bind to a surface-coupled passivating moiety (e.g., polyethylene glycol) with a kilomolar dissociation constant (a very weak binding interaction), then observing a millimolar binding dissociation constant between the unbound moiety and an array surface that is provided with a uniform layer of the surface-coupled passivating moiety would indicate an orthogonal binding phenomena (i.e., binding due to a mechanism other than the specific binding of the unbound moiety to the surface-coupling passivating moiety). Orthogonal binding phenomena may be characterized based upon a stochastic measure, such as spatial and/or temporal variations in unwanted, unexpected, or contrary-to-design binding phenomena.

As used herein, the term "non-orthogonal binding phenomena," when used in reference to an array or a molecule, moiety, or particle contacted thereto, refers to any wanted, expected, or designed binding interactions that occur at an array surface or array feature in the presence of a binding reagent. Examples of non-orthogonal binding interactions can include binding of an oligonucleotide to a complementary oligonucleotide, binding of a receptor to a ligand, binding of an affinity agent to an epitope for which the affinity agent has a binding specificity, and covalent binding of a Click-type reagent to a complementary Click-type reagent.

As used herein, the term "single-analyte resolution," when used in reference to a single-analyte array, refers to detection of a single-analyte under the conditions that: 1) the single-analyte is detected by a signal with a magnitude that exceeds the magnitude of background signals for the detection system, and 2) the single-analyte is detected by a signal at a location that is spatially separated from the location of a signal corresponding to a different single-analyte (i.e., a spatial minimum of signal magnitude exists between a first single-analyte and a second single-analyte for the two single-analytes to be spatially resolved). In some cases, a signal corresponding to a first single-analyte may be considered spatially resolved from a signal corresponding to a second single-analyte if a signal minimum occurs between the locations of the two single-analytes with a magnitude that is substantially less than an average or peak signal maximum of one or both signal maxima corresponding to the first and second single analytes. For example, a signal minimum between two signal maxima corresponding respectively to a first single analyte and a second single analyte may have a magnitude that is no more than about 95%, 90%, 80%, 70%, 60%, 50%, 40%, 30%, 20%, 10%, 5%, 1%, or less than 1% of an average or peak signal maximum of the two signal maxima. In some cases, signals corresponding to two or more analytes may be considered spatially resolved if a spatial resolution criterion is achieved, such as the Rayleigh Criterion. A signal magnitude (peak or average) corresponding to a single-analyte may have a signal-to-noise ratio relative to an average background signal of at least about 1.1:1, 1.5:1, 2:1, 2.5:1, 3:1, 4:1, 5:1, 10:1, 20:1, 50:1, 100:1 or more than 100:1.

As used herein, the term "channel," when used in reference to an optical sensor, refers to a portion of a sensor that is configured to detect a signal having particular characteristic(s) or lacking particular characteristic(s). A channel may be configured to detect photons with a characteristic wavelength, for example, at the exclusion of photon at other wavelengths. A channel may be configured to detect photons within a particular range of wavelengths, for example, at the exclusion of photon outside of the particular range of wavelengths. A channel may detect photons from within a region of the electromagnetic spectrum (e.g., far infrared, near infrared, visible, near-ultraviolet, or far ultraviolet) or subregions thereof (e.g., red wavelengths, orange wavelengths, yellow wavelengths, etc.), for example, at the exclusion of photons from outside the region of subregion. Alternatively, a channel may detect photons from outside those regions or subregions of the electromagnetic spectrum. A channel may comprise an array of light-sensing elements (e.g., CCD, CMOS), such as a pixel array. Each light-sensing element of an array of light-sensing elements of a channel may be configured to detect a signal with the same specific characteristic. An array of light-sensing elements of a channel may comprise a mixture of light-sensing elements with varying detection characteristics that combine to provide a range of detection characteristics to a channel. For example, a channel may comprise a mixture of red-sensing pixels (absorbing light with wavelengths between 620 nanometers (nm) and 750 nm) and orange-sensing pixels (absorbing light with wavelengths between 590 nm and 620 nm) to form a channel that detects light between 590 nm and 750 nm. A channel may comprise an array of light-sensing elements that is spatially separated from an array of light-sensing elements belonging to a separate channel. An array of light-sensing elements may comprise a mixture of different types of pixels, in which all pixels with the same detection properties comprise a channel. For example, a pixel array may comprise a patterned array of 3 types of light-sensing elements (e.g., red, yellow, blue, red, yellow, blue, etc.), in which a red-sensing channel comprises each of the red-sensing pixels, a blue-sensing channel comprises each of the blue-sensing pixels, and a yellow-sensing channel comprises each of the yellow-sensing pixels.

As used herein, the term "association," when used in reference to an array-based method or process, refers to a step of the method or process in which binding reagents are contacted to analytes, thereby facilitating binding of binding reagents to the analytes. Association may occur in the presence of binding reagent association medium. As used herein, the term "dissociation," when used in reference to an array-based method or process, refers to a step of the method or process in which bound binding reagents are separated from analytes to which the binding reagents are bound. Dissociation may occur in the presence of binding reagent dissociation medium.

As used herein, the term "binding anomaly" refers to a detection event or a sequence of detection events that deviates from an expected value of a signal or pattern of signals, respectively. For example, the presence of a signal from a binding reagent at an array site after a dissociation step can constitute a binding anomaly. In another example, the presence of a signal from a binding reagent at an array site for two or three consecutive detection events may comprise a binding anomaly.

As used herein, the term "on-target," when used in reference to binding of a binding reagent to an analyte, refers to the binding reagent binding to an epitope or set of epitopes of an analyte to which it has a highest characterized binding specificity. As used herein, the term "off-target," when used in reference to binding of a binding reagent to an analyte, refers to the binding reagent binding to an epitope of an analyte other than an epitope or set of epitopes to which it has a highest characterized binding specificity. Designations of on-target and off-target binding for a given binding reagent may be assigned with regard to a quantitative measure such as binding affinity. For example, a binding reagent may be characterized as having a nanomolar binding affinity for epitope A and a micromolar binding affinity for epitope B. Accordingly, binding to epitope A may be considered "on-target binding" and binding to epitope B may be considered "off-target binding" given the substantially higher affinity of the binding reagent for epitope A.

As used herein, the terms "blocking agent" or "blocking reagent" refer to a substance, material, molecule, particle, or moiety that inhibits orthogonal binding phenomena of a binding reagent or other assay reagent to an array component (e.g., an array site or a surface coating or layer attached thereto, an anchoring moiety, an analyte, an interstitial region or a surface coating or layer attached thereto) in a single-analyte array system. A blocking agent or blocking reagent may bind to a defect of an array or a surface thereof. A blocking agent or blocking reagent may be provided in a fluidic medium that is contacted to an array during an array-based method or process. A blocking agent or blocking reagent may be solvated, dissolved, suspended, or otherwise mobile within a fluidic medium. A blocking agent or blocking reagent may be bound to a surface of an array or bound to an array component (e.g., an array site or a surface coating or layer attached thereto, an anchoring moiety, an analyte, an interstitial region or a surface coating or layer attached thereto). A blocking agent or blocking reagent may comprise a polypeptide blocking agent or a non-polypeptide blocking agent. A blocking agent or blocking reagent may comprise an ionic polymer, a zwitterionic polymer, a non-ionic polymer, a cationic surfactant, an anionic surfactant, a non-ionic surfactant, a saccharide, a stabilizing agent, or an amphiphilic agent.

As used herein, the term "defect," when used in reference to a surface layer or coating (e.g., a passivating layer, a coupling layer) on an array or a surface thereof, refers to an address containing a chemical irregularity with respect to a bulk characteristic or structure of the surface layer. A chemical irregularity with respect to a passivating layer may include absence of a passivating molecule or moiety or a plurality thereof, absence of a coupling molecule or moiety or a plurality thereof, at an address of a surface that comprises the surface layer. A chemical irregularity with respect to a passivating layer may include an increased or decreased concentration of molecules at an address of a surface relative to an average concentration of molecules for a passivating layer. A defect may comprise a void in a passivating layer. For example, a passivating layer on a surface of a solid support may comprise a void (e.g., an absence of a molecule, particle, or moiety) that permits direct contact between an assay agent and the surface of the solid support. A defect may comprise a molecule, particle, or moiety whose chemical structure or characteristics differ from the bulk chemical structure or characteristics of the passivating layer. For example, a passivating layer of polyethylene glycol (PEG) molecules may comprise a defect containing a non-PEGylated molecule. A defect in a passivating layer may contain a molecule, particle, or moiety that facilitates binding of an assay agent to the passivating layer, such as a reactive species, an electrically-charged species, a magnetic species, a polar species, or a combination thereof. A defect may comprise a molecule, particle, or moiety that is covalently bound to a surface containing a passivating layer. A defect may comprise a molecule, particle, or moiety that is non-covalently bound to a surface containing a passivating layer. A defect may comprise a single molecule or moiety, or a complex of molecules or moieties that form an orthogonal binding interaction with an entity (e.g., an analyte, an anchoring moiety, a blocking reagent, an affinity agent, a detectable binding reagent, a detectable label, etc.) contacted with the defect. A defect may be co-located at an address comprising an interstitial region or a site, as set forth herein. A defect may have a length scale that differs significantly from a length scale of an interstitial region or site. A defect may have a characteristic size (e.g., length, width, diameter) of less than about 10 nanometers (nm), 5 nm, 4 nm, 3 nm, 2 nm, 1 nm, 0.5 nm, 0.1 nm, or less than 0.1 nm, while an interstitial region may have a characteristic size (e.g., length, width, diameter, pitch) of at least about 10 nm, 20 nm, 50 nm, 100 nm, 150 nm, 200 nm, 250 nm, 300 nm, 400 nm, 500 nm, 750 nm, 1 micron (μm), 2 μm, 5 μm, 10 μm, or more than 10 μm. A plurality of sites in an array may comprise a random or irregular spatial distribution such that a defect location can not be predicted based upon a location of any other address, site or defect in the array. A molecule, particle, or moiety on an array or a surface thereof can be considered a defect with respect to a binding context to which the array or array surface is exposed. For example, a surface layer that is intended to inhibit binding of an affinity agent may have a defect if an address of the layer binds an affinity agent. A layer, molecule, particle, or moiety of a defect can be hydrophobic, hydrophilic, polar, non-polar, positively-charged, negatively-charged, linear, branched, dendrimeric, or a combination thereof, depending upon a binding context or a chemical property of an assay agent.

As used herein, the term "nucleic acid nanoparticle," refers to a single- or multi-chain polynucleotide molecule comprising a compacted three-dimensional structure. The compacted three-dimensional structure can optionally have a characteristic tertiary structure. An exemplary nucleic acid nanostructure is a structured nucleic acid particle (SNAP). A SNAP can be configured to have an increased number of interactions between regions of a polynucleotide strand, less distance between the regions, increased number of bends in the strand, and/or more acute bends in the strand, as compared to the same nucleic acid molecule in a random coil or other non-structured state. Alternatively or additionally, the compacted three-dimensional structure of a nucleic acid nanostructure can optionally have a characteristic quaternary structure. For example, a nucleic acid nanostructure can be configured to have an increased number of interactions between polynucleotide strands or less distance between the strands, as compared to the same nucleic acid molecule in a random coil or other non-structured state. In some configurations, the tertiary structure (i.e. the helical twist or direction of the polynucleotide strand) of a nucleic acid nanostructure can be configured to be more dense than the same nucleic acid molecule in a random coil or other non-structured state. Nucleic acid nanostructures may include deoxyribonucleic acid (DNA), ribonucleic acid (RNA), peptide nucleic acid (PNA), other nucleic acid analogs, and combinations thereof. Nucleic acid nanostructures may have naturally-arising or engineered secondary, tertiary, or quaternary structures. A structured nucleic acid particle can contain at least one of: i) a moiety that is configured to couple an analyte to the nucleic acid nanostructure, ii) a moiety that is configured to couple the nucleic acid nanostructure to another object such as another SNAP, a solid support or a surface thereof, iii) a moiety that is configured to provide a chemical or physical property or characteristic to a nucleic acid nanostructure, or iv) a combination thereof. Exemplary SNAPs may include nucleic acid nanoballs (e.g. DNA nanoballs), nucleic acid nanotubes (e.g. DNA nanotubes), and nucleic acid origami (e.g. DNA origami). A SNAP may be functionalized to include one or more reactive handles or other moieties. A SNAP may comprise one or more incorporated residues that contain reactive handles or other moieties (e.g., modified nucleotides).

As used herein, the terms "type" or "species," when used in reference to a molecule, particle, or moiety, refer to a molecule, particle, or moiety with a unique, distinguishable chemical structure. For example, the term "type of anchoring moiety" can refer to an anchoring moiety with a unique, distinguishable binding characteristic, for example, as characterized by an anchoring moiety binding availability or anchoring moiety binding competency. A first anchoring moiety may have one or more structural dissimilarities, such as an absence of a detectable label or a damaged moiety, with respect to a second anchoring moiety and still be of the same type of anchoring moiety if the structural dissimilarities do not result in a difference in binding characteristic between the first anchoring moiety and the second anchoring moiety. Anchoring moiety variants with differences in quantity, location, orientation, and types of coupling moieties are different species from each other if the differences result in differences in a binding characteristic. For example, members of a "type of anchoring moiety" can have a unique, distinguishable structure that is common to the members compared to other anchoring moieties that lack the unique, distinguishable structure. Anchoring moiety types may be identified, for example, by common shape and/or conformation, number of coupling moieties, or type of coupling moieties.

As used herein, the term "array" refers to a population of sites that provide spatial separation of molecules, moieties, or analytes that are resolved such that the sites can be distinguished from each other. Accordingly, molecules, moieties or analytes at one site of an array can be resolved from molecules, moieties or analytes at other sites of the array. The sites can function as unique identifiers and/or the sites can be attached to unique identifiers. The term "array of analytes" refers to an array with a population of sites, in which a plurality of sites of the population of sites is occupied by analytes.

As used herein, the term "unique identifier" refers to a solid support (e.g., particle or bead), spatial address in an array, tag, label (e.g., luminophore), or barcode (e.g., nucleic acid barcode) that is attached to an analyte and that is distinct from other identifiers, throughout one or more steps of a process. The process can be an analytical process such as a method for detecting, identifying, characterizing or quantifying an analyte. Attachment to a unique identifier can be covalent or non-covalent (e.g., ionic bond, hydrogen bond, van der Waals forces etc.). A unique identifier can be exogenous to the analyte, for example, being synthetically attached to the analyte. Alternatively, a unique identifier can be endogenous to the analyte, for example, being attached or associated with the analyte in the native milieu of the analyte. An array can include different analytes that are each attached to different unique identifiers. For example, an array can include different molecules or analytes that are each located at different addresses on a solid support. Alternatively, an array can include separate solid supports each functioning as an address that bears a different molecule or analyte, where the different molecules or analytes can be identified according to the locations of the solid supports on a surface to which the solid supports are attached, or according to the locations of the solid supports in a liquid such as a fluid stream. The molecules or analytes of the array can be, for example, nucleic acids such as SNAPs, polypeptides, proteins, peptides, oligopeptides, enzymes, ligands, or receptors such as antibodies, functional fragments of antibodies or aptamers. The addresses of an array can optionally be optically observable and, in some configurations, adjacent addresses can be optically distinguishable when detected using a method or apparatus set forth herein.

As used herein, the terms "address," "binding site," and "site," when used in reference to an array, means a location in an array where a particular molecule or analyte is present. An address can contain only a single molecule or analyte, or it can contain a population of several molecules or analytes of the same species (i.e. an ensemble of the molecules). Alternatively, an address can include a plurality of molecules or analytes that are different species. Addresses of an array are typically discrete. Addresses can be optically resolvable. The discrete addresses can be contiguous, or they can have interstitial spaces between each other. An array useful herein can have, for example, addresses that are separated by less than 100 microns, 10 microns, 1 micron, 500 nm, 100 nm, 10 nm or less. Alternatively or additionally, an array can have addresses that are separated by at least 10 nm, 100 nm, 500 nm, 1 micron, 5 microns, 10 microns, 50 microns, 100 microns or more. The addresses can each have an area of less than 1 square millimeter, 500 square microns, 100 square microns, 25 square microns, 1 square micron or less. An array can include at least about $1\times10^4$, $1\times10^5$, $1\times10^6$, $1\times10^8$, $1\times10^{10}$, $1\times10^{12}$, or more addresses.

As used herein, the term "solid support" refers to a substrate that is insoluble in aqueous liquid. Optionally, the substrate can be rigid. The substrate can be non-porous or porous. The substrate can optionally be capable of taking up a liquid (e.g., due to porosity) but will typically, but not necessarily, be sufficiently rigid that the substrate does not swell substantially when taking up the liquid and does not contract substantially when the liquid is removed by drying. A nonporous solid support is generally impermeable to liquids or gases. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides etc.), nylon, ceramics, resins, Zeonor™, silica or silica-based materials including silicon and modified silicon, carbon, metals, metal oxides (e.g., zirconia, titania, alumina, etc.), inorganic glasses, optical fiber bundles, gels, and polymers.

As used herein, the terms "group" and "moiety" are intended to be synonymous when used in reference to the structure of a molecule. The terms refer to a component or part of the molecule. The terms do not necessarily denote the relative size of the component or part compared to the rest of the molecule, unless indicated otherwise. A group or moiety can contain one or more atom. As used herein, the term "coupling moiety" refers to a component or part of a molecule or particle that is configured to couple the molecule or particle to a second molecule or particle, or that couples the molecule or particle to the second molecule or particle. A coupling moiety may couple a molecule or particle to a second molecule or particle reversibly or irreversibly. A coupling moiety may couple a molecule or particle to a second molecule or particle covalently or non-covalently.

As used herein, the term "binding reagent" refers to an entity that is capable of reproducibly binding to a binding partner (e.g., an analyte) or other substance. A binding partner can comprise an affinity agent or a plurality thereof. A binding reagent may be detectable if one or more detectable labels (e.g., fluorophores, luminophores) are attached or otherwise incorporated with the binding reagent. A binding reagent can further comprise a linking group or linking moiety that couples components (e.g., affinity agents, detectable labels) of a binding reagent together. A linking group or linking moiety may comprise a nanoparticle, such as a nucleic acid nanoparticle, or a non-nucleic acid nanoparticle (e.g., a polymer nanoparticle, a semiconductor nanoparticle, a carbon nanoparticle, a metal nanoparticle). The terms "binding reagent" and "detectable binding reagent" is intended to be synonymous with the terms "probe" and "detectable probe" as used in U.S. Provisional Patent Application No. 63/386,833.

As used herein, the terms "affinity reagent" or "affinity agent" refer to a molecule or other discrete substance that is capable of specifically or reproducibly binding to a binding partner or other substance. Binding can optionally be used to identify, track, capture, alter, or influence the binding partner. The binding partner can optionally be larger than, smaller than or the same size as the affinity reagent. An affinity reagent may form a reversible or irreversible interaction with a binding partner. An affinity reagent may bind with a binding partner in a covalent or non-covalent manner. An affinity reagent may be configured to perform a chemical modification (e.g., ligation, cleavage, concatenation, etc.) that produces a detectable change in the larger molecule, thereby permitting observation of the interaction that occurred. Affinity reagents may include chemically reactive affinity reagents (e.g., kinases, ligases, proteases, nucleases, etc.) and chemically non-reactive affinity reagents (e.g., antibodies, antibody fragments, aptamers, DARPins, peptamers, etc.). An affinity reagent may comprise one or more known and/or characterized binding components or binding sites (e.g., complementarity-defining regions) that mediate or facilitate binding with a binding partner. Accordingly, an affinity reagent can be monovalent or multivalent (e.g. bivalent, trivalent, tetravalent, etc.). An affinity reagent is typically non-reactive and non-catalytic, thereby not permanently altering the chemical structure of a substance it binds in a method set forth herein.

As used herein, the terms "protein" and "polypeptide" are used interchangeably to refer to a molecule or analyte comprising two or more amino acids joined by a peptide bond. A polypeptide may refer to a peptide (e.g., a polypeptide with less than about 200, 150, 100, 75, 50, 40, 30, 20, 15, 10, or less than about 10 linked amino acids). A polypeptide may refer to a naturally-occurring molecule, or an artificial or synthetic molecule. A polypeptide may include one or more non-natural, modified amino acids, or non-amino acid linkers. A polypeptide may contain D-amino acid enantiomers, L-amino acid enantiomers or both. A polypeptide may be modified naturally or synthetically, such as by post-translational modifications.

As used herein, the term "label" or "detectable label" refers to a moiety of an affinity reagent or other substance that provides a detectable characteristic. The detectable characteristic can be, for example, an optical signal such as absorbance of radiation, luminescence or fluorescence emission, luminescence or fluorescence lifetime, luminescence or fluorescence polarization, or the like; Rayleigh and/or Mie scattering; binding affinity for a ligand or receptor; magnetic properties; electrical properties; charge; mass; radioactivity or the like. A label component can be a detectable chemical entity that is conjugated to or capable of being conjugated to another molecule or substance. Exemplary molecules that can be conjugated to a label component include an affinity reagent or a binding partner. A label component may produce a signal that is detected in real-time (e.g., fluorescence, luminescence or radioactivity). A label component may produce a signal that is detected off-line (e.g., a nucleic acid barcode) or in a time-resolved manner (e.g., time-resolved fluorescence). A label component may produce a signal with a characteristic frequency, intensity, polarity, duration, wavelength, sequence, or fingerprint. Exemplary labels include, without limitation, a fluorophore, luminophore, chromophore, nanoparticle (e.g., gold, silver or carbon nanotubes), heavy atom, radioactive isotope, mass label, charge label, spin label, receptor, ligand, nucleic acid barcode, polypeptide barcode, polysaccharide barcode, or the like.

As used herein, the term "nucleic acid origami" refers to a nucleic acid construct comprising an engineered secondary, tertiary or quaternary structure. A nucleic acid origami may include DNA, RNA, PNA, LNAs, other nucleic acid analog, modified or non-natural nucleic acids, or combinations thereof. A nucleic acid origami may comprise a plurality of oligonucleotides that hybridize via sequence complementarity to produce the engineered structuring of the origami particle. A nucleic acid origami may comprise sections of single-stranded or double-stranded nucleic acid, or combinations thereof. A nucleic acid origami may comprise one or more tertiary structures of a nucleic acid, such as A-DNA, B-DNA, C-DNA, L-DNA, M-DNA, Z-DNA, etc. A nucleic acid origami may comprise single-stranded nucleic acid, double-stranded nucleic acid, multi-stranded nucleic acid, or combinations thereof. Exemplary nucleic acid origami structures may include nanotubes, nanowires, cages, tiles, nanospheres, blocks, and combinations thereof.

As used herein, the term "nucleic acid nanoball" refers to a globular or spherical nucleic acid structure. A nucleic acid nanoball may comprise a concatemer of oligonucleotides that arranges in a globular structure. A nucleic acid nanoball may comprise one or more oligonucleotides, including oligonucleotides comprising self-complementary nucleic acid sequences. A nucleic acid nanoball may comprise a palindromic nucleic acid sequence. A nucleic acid nanoball may include DNA, RNA, PNA, LNAs, other nucleic acid analog, modified or non-natural nucleic acids, or combinations thereof.

As used herein, the term "oligonucleotide" refers to a molecule comprising two or more nucleotides joined by a phosphodiester bond or analog thereof. An oligonucleotide may comprise DNA, RNA, PNA, LNAs, other nucleic acid analog, modified nucleotides, non-natural nucleotides, or combinations thereof. An oligonucleotide may include a limited number of bonded nucleotides, such as, for example, less than about 10000, 8000, 6000, 5000, 4000, 3000, 2000, 1000, 750, 500, 400, 300, 250, 200, 190, 180, 170, 160, 150, 140, 130, 120, 110, 100, 90, 80, 70, 60, 50, 40, 30, 25, 20, 15, 10, or less than 5 nucleotides. An oligonucleotide may include a linking group or linking moiety at a terminal or intermediate position. For example, an oligonucleotide may comprise two nucleic acid strands that are joined by an intermediate PEG molecule. In another example, an oligonucleotide may comprise a cleavable linker (e.g., a photocleavable linker, an enzymatically-cleavable linker, a restriction site, etc.) that joins two portions of the oligonucleotide. The terms "polynucleotide" and "nucleic acid" are used herein synonymously with the term "oligonucleotide."

As used herein, the term "binding specificity" refers to the tendency of an affinity reagent to preferentially interact with a binding partner, affinity target, or target moiety relative to other binding partners, affinity targets, or target moieties. An affinity reagent may have a calculated, observed, known, or predicted binding specificity for any possible binding partner, affinity target, or target moiety. Binding specificity may refer to selectivity for a single binding partner, affinity target, or target moiety in a sample over at least one other analyte in the sample. Moreover, binding specificity may refer to selectivity for a subset of binding partners, affinity targets, or target moieties in a sample over at least one other analyte in the sample.

As used herein, the term "binding affinity" or "affinity" refers to the strength or extent of binding between an affinity reagent and a binding partner, affinity target or target moiety. In some cases, the binding affinity of an affinity reagent for a binding partner, affinity target, or target moiety may be vanishingly small or effectively zero. A binding affinity of an affinity reagent for a binding partner, affinity target, or target moiety may be qualified as being a "high affinity," "medium affinity," or "low affinity." A binding affinity of an affinity reagent for a binding partner, affinity target, or target moiety may be quantified as being "high affinity" if the interaction has a dissociation constant of less than about 100 nM, "medium affinity" if the interaction has a dissociation constant between about 100 nM and 1 mM, and "low affinity" if the interaction has a dissociation constant of greater than about 1 mM. Binding affinity can be described in terms known in the art of biochemistry such as equilibrium dissociation constant ($K_D$), equilibrium association constant ($K_A$), association rate constant ($k_{on}$), dissociation rate constant ($k_{off}$) and the like. See, for example, Segel, Enzyme Kinetics John Wiley and Sons, New York (1975), which is incorporated herein by reference in its entirety.

As used herein, the terms "coupled" and "attached" refer to the state of two entities being joined, fastened, adhered, connected, or bound to each other, thereby co-localizing the two entities. Two entities may be "directly coupled" if the two entities are contacted through a direct physical mechanism, such as covalent bonding, non-covalent bonding, electrostatic binding, or magnetic attraction. Two entities may be "indirectly coupled" if joining, fastening, adhesion, connection, or binding between the two entities is achieved through an intermediate entity. For example, an analyte, as set forth herein, may be coupled to a solid support, as set forth herein, by an anchoring moiety, in which the anchoring moiety is directly coupled to the solid support and in which the analyte is directly coupled to the anchoring moiety but does not physically contact the solid support. Coupling can be covalent or non-covalent. For example, a particle can be coupled to a protein by a covalent or non-covalent bond. A covalent bond is characterized by the sharing of pairs of electrons between atoms. A non-covalent bond is a chemical bond that does not involve the sharing of pairs of electrons and can include, for example, hydrogen bonds, ionic bonds, van der Waals forces, hydrophilic interactions, adhesion, adsorption, and hydrophobic interactions.

As used herein, the term "anchoring moiety" refers to a molecule or particle that serves as an intermediary attaching an analyte to a surface (e.g., on a solid support or a microbead). An anchoring group may be covalently or non-covalently attached to a surface and/or a polypeptide. An anchoring group may be a biomolecule, polymer, particle, nanoparticle, or any other entity that is capable of attaching to a surface or analyte. In some cases, an anchoring group may be a nucleic acid nanoparticle such as a SNAP.

As used herein, the term "unbound," when used in reference to a molecule, particle or moiety that is contacted with an array, refers to the molecule, particle, or moiety not being attached or bound to an analyte at an array site in an initial configuration. An unbound assay agent may include a molecule, particle, or moiety that is solvated, suspended, or otherwise mobile within a fluidic medium at the instant it is contacted with an array. As used herein, the term "bound" when used in reference to a molecule, particle or moiety that is contacted with an array, refers to the molecule, particle, or moiety being attached or coupled to an analyte at an array site. A bound molecule, particle, or moiety may be covalently or non-covalently coupled to an array site.

As used herein, the term "optically resolvable distance" refers to a distance on an array or a surface thereof at which two separate objects can be optically distinguished with respect to each other. The threshold for an optically resolvable distance can vary based upon the mechanism of detection and/or the physical apparatus used to perform an optical detection as well as the detectable species utilized for detection (e.g., single fluorophores, multiple fluorophores, nanoparticles, intercalated dyes, etc.). For example, when detecting two fluorescent objects on a surface via optical microscopy, an optically resolvable distance may depend upon an excitation wavelength of fluorophores, an emission wavelength of fluorophores, and optical characteristics of an optical microscope utilized to image the objects. An optically resolvable distance may be at least about 1 nanometer (nm), 5 nm, 10 nm, 25 nm, 50 nm, 75 nm, 100 nm, 125 nm, 150 nm, 200 nm, 300 nm, 400 nm, 500 nm, or more than 500 nm. Alternatively or additionally, an optically resolvable distance may be no more than about 500 nm, 400 nm, 300 nm, 200 nm, 150 nm, 125 nm, 100 nm, 75 nm, 50 nm, 25 nm, 10 nm, 5 nm, 1 nm, or less than 1 nm. In some cases, an optically resolvable distance may be determined with respect to a detection method (e.g., a pixel-based sensor). For example, two objects may be considered to be separated by an optically resolvable distance if a sensor-based detection produces two optical signal intensity maxima (corresponding to the two objects) and an optical signal intensity minimum between the two maxima, in which the optical signal intensity minimum has a magnitude that is no more than half of the average signal-to-noise ratio of the two optical signal intensity maxima. As used herein, the term "optically non-resolvable distance" refers to a distance on an array or a surface thereof which is less than an optically resolvable distance, as set forth herein. An optically non-resolvable distance may be a distance at which an optical signal from a first object can not be distinguished from an optical signal from a second object. For example, a first optical signal from a first object may be optically non-resolvable from a second optical signal from a second object if the first optical signal and the second optical signal are respectively detected by adjacent pixels of a pixel-based sensor.

As used herein, the term "epitope" refers to an affinity target within a protein, polypeptide or other analyte. Epitopes may include amino acid sequences that are sequentially adjacent in the primary structure of a protein. Epitopes may include amino acids that are structurally adjacent in the secondary, tertiary or quaternary structure of a protein despite being non-adjacent in the primary sequence of the protein. An epitope can be, or can include, a moiety of protein that arises due to a post-translational modification, such as a phosphate, phosphotyrosine, phosphoserine, phosphothreonine, or phosphohistidine. An epitope can optionally be recognized by or bound to an antibody. However, an epitope need not necessarily be recognized by any antibody, for example, instead being recognized by an aptamer, mini-protein or other affinity reagent. An epitope can optionally bind an antibody to elicit an immune response. However, an epitope need not necessarily participate in, nor be capable of, eliciting an immune response.

As used herein, the term "click-type reaction" refers to single-step, thermodynamically-favorable conjugation reaction utilizing biocompatible reagents. A click reaction may be configured to not utilize toxic or biologically incompatible reagents (e.g., acids, bases, heavy metals) or to not generate toxic or biologically incompatible byproducts. A click reaction may utilize an aqueous solvent or buffer (e.g., phosphate buffer solution, Tris buffer, saline buffer, MOPS, etc.). A click reaction may be thermodynamically favorable if it has a negative Gibbs free energy of reaction, for example a Gibbs free energy of reaction of less than about −5 kiloJoules/mole (KJ/mol), −10 KJ/mol, −25 KJ/mol, −100 KJ/mol, −250 KJ/mol, −500 KJ/mol, or less. Exemplary click reactions may include metal-catalyzed azide-alkyne cycloaddition, strain-promoted azide-alkyne cycloaddition, strain-promoted azide-nitrone cycloaddition, strained alkene reactions, thiol-ene reaction, Diels-Alder reaction, inverse electron demand Diels-Alder reaction (IEDDA), [3+2] cycloaddition, [4+1] cycloaddition, nucleophilic substitution, dihydroxylation, thiol-yne reaction, photoclick, nitrone dipole cycloaddition, norbornene cycloaddition, oxanobornadiene cycloaddition, tetrazine ligation, and tetrazole photoclick reactions. Exemplary reactive moieties utilized to perform click reactions may include alkenes, alkynes, azides, epoxides, amines, thiols, nitrones, isonitriles, isocyanides, aziridines, activated esters, and tetrazines. Other well-known click conjugation reactions may be used having complementary bioorthogonal reaction species, for example, where a first click component comprises a hydrazine moiety and a second click component comprises an aldehyde or ketone group, and where the product of such a reaction comprises a hydrazone functional group or equivalent. Exemplary bioorthogonal and click reactions are set forth in US Pat. App. Pub. No. 2021/0101930 A1, which is incorporated herein by reference.

As used herein, the terms "linker" and "linking moiety" refer synonymously to a moiety that connects two objects to each other. One or both objects can be a molecule, solid support, address, particle or bead. Both objects can be moieties of a molecule, solid support, address, particle or bead. The term can also refer to an atom, moiety or molecule that is configured to react with two objects to form a moiety that connects the two objects. The connection of a linker to one or both objects can be a covalent bond or non-covalent bond. A linker may be configured to provide a chemical or mechanical property to the moiety connecting two objects, such as hydrophobicity, hydrophilicity, electrical charge, polarity, rigidity, or flexibility. A linker may comprise two or more functional groups that facilitate coupling of the linker to the first and second objects. A linker may include a polyfunctional linker such as a homobifunctional linker, heterobifunctional linker, homopolyfunctional linker, or heteropolyfunctional linker. Exemplary compositions for linkers can include, but are not limited to, a polyethylene glycol (PEG), polyethylene oxide (PEO), amino acid, protein, nucleotide, nucleic acid, nucleic acid origami, dendrimer, protein nucleic acid (PNA), polysaccharide, carbon, nitrogen, oxygen, ether, sulfur, or disulfide. A linker can be a bead or particle such as a structured nucleic acid particle.

As used herein, the term "scaffold" refers to a molecule or complex of molecules having a structure that couples two or more entities to each other. A scaffold can form a structural basis for coupling binding components and/or labeling components to a binding reagent. A scaffold may comprise a plurality of attachment sites that permit the coupling or conjugation of binding reagent components to the scaffold. Scaffold attachment sites may include functional groups, active sites, binding ligands, binding receptors, nucleic acid sequences, or any other entity capable of forming a covalent or non-covalent attachment to a binding component, label component, or other binding reagent component. A scaffold may comprise an oligonucleotide molecule that serves as the primary structural unit for a nucleic acid origami. A scaffold may comprise single-stranded nucleic acids, double-stranded nucleic acids, or combinations thereof. A scaffold may be a circular oligonucleotide or a linear (i.e. non-circular) oligonucleotide. A scaffold may be derived from a natural source, such as a bacterial or viral genome (e.g., plasmid DNA or a phage genome). A circular scaffold may be formed by the ligation of a non-circular nucleic acid. A scaffold may comprise a particular number of nucleotides, for example, at least about 500, 1000, 1500, 2000, 2500, 3000, 3500, 4000, 4500, 5000, 5500, 6000, 6500, 7000, 7500, 8000, 8500, 9000, 9500, 10000, or more than 10000 oligonucleotides. A scaffold may comprise an organic or inorganic particle or nanoparticle. A scaffold may comprise a coating or layer applied to a particle or nanoparticle that permits attachment of detectable label components.

As used herein, the term "single," when used in reference to an object such as an analyte, means that the object is individually manipulated or distinguished from other objects. A single analyte can be a single molecule (e.g. single protein), a single complex of two or more molecules (e.g. a multimeric protein having two or more separable subunits, a single protein attached to a structured nucleic acid particle or a single protein attached to an affinity reagent), a single particle, or the like. Reference herein to a "single analyte" in the context of a composition, system or method herein does not necessarily exclude application of the composition, system or method to multiple single analytes that are manipulated or distinguished individually, unless indicated contextually or explicitly to the contrary.

As used herein, the term "structured nucleic acid particle" or "SNAP" refers to a single- or multi-chain polynucleotide molecule having a compacted three-dimensional structure. The compacted three-dimensional structure can optionally be characterized in terms of hydrodynamic radius or Stokes radius of the SNAP relative to a random coil or other non-structured state for a nucleic acid having the same sequence length as the SNAP. The compacted three-dimensional structure can optionally be characterized with regard to tertiary structure. For example, a SNAP can be configured to have an increased number of internal binding interactions between regions of a polynucleotide strand, less distance between the regions, increased number of bends in the strand, and/or more acute bends in the strand, as compared to a nucleic acid molecule of similar length in a random coil or other non-structured state. Alternatively or additionally, the compacted three-dimensional structure can optionally be characterized with regard to tertiary or quaternary structure. For example, a SNAP can be configured to have an increased number of interactions between polynucleotide strands or less distance between the strands, as compared to a nucleic acid molecule of similar length in a random coil or other non-structured state. In some configurations, the secondary structure of a SNAP can be configured to be more dense than a nucleic acid molecule of similar length in a random coil or other non-structured state. A SNAP may contain DNA, RNA, PNA, modified or non-natural nucleic acids, or combinations thereof. A SNAP may include a plurality of oligonucleotides that hybridize to form the SNAP structure. The plurality of oligonucleotides in a SNAP may include oligonucleotides that are attached to other molecules (e.g., binding reagents, analytes such as proteins, reactive moieties, or detectable labels) or are configured to be attached to other molecules (e.g., by functional groups). A SNAP may include engineered or rationally designed structures. Exemplary SNAPs include nucleic acid origami and nucleic acid nanoballs.

As used herein, the terms "reaction inhibitor" or "reaction inhibitor species," when used in reference to a fluidic medium, refer synonymously to a chemical species within the fluidic medium that inhibits or prevents a chemical reaction involving an entity bound to an array or an entity contacted to an array within the fluidic medium. A reaction inhibitor can prevent a single-species (e.g., an elimination reaction or lysis reaction) or a multi-species chemical reaction (e.g., an oxidation, reduction, or substitution reaction). A reaction inhibitor may inhibit or prevent a chemical reaction between a chemical species in a fluidic medium and an analyte or anchoring moiety that is contacted by the fluidic medium. A reaction inhibitor may inhibit or prevent a chemical reaction between a chemical species in a fluidic medium and an assay agent (e.g., a binding reagent or a component thereof) that is contacted by the fluidic medium or disposed within the fluidic medium. A reaction inhibitor may inhibit or prevent a chemical reaction between an analyte or anchoring moiety and an assay agent (e.g., a binding reagent or a component thereof) within a fluidic medium. A reaction inhibitor may inhibit or prevent a photon-mediated reaction, such as a photolysis reaction or a reaction between an array component or assay agent and a photon-generated chemical species (e.g., a reactive oxygen species, a radical species). A reaction inhibitor may be a radical scavenger, a reactive oxygen scavenger, or an antioxidant.

The term "comprising" is intended herein to be open-ended, including not only the recited elements, but further encompassing any additional elements.

As used herein, the term "each," when used in reference to a collection of items, is intended to identify an individual item in the collection but does not necessarily refer to every item in the collection. Exceptions can occur if explicit disclosure or context clearly dictates otherwise.

The embodiments set forth below and recited in the claims can be understood in view of the above definitions.

Methods of Dissociating Binding Reagents

In an aspect, provided herein is a method, comprising: a) providing a single-analyte array, in which the single-analyte array comprises a plurality of addresses, in which at least 37% of addresses of the plurality of addresses comprise one and only one coupled analyte of a plurality of analytes, b) identifying a first set of addresses of the plurality of addresses comprising at least one analyte of the plurality of analytes, c) contacting the single-analyte array with a plurality of binding reagents, in which a binding reagent of the plurality of binding reagents is configured to bind to at least one analyte of the plurality of analytes at an address of the first set of addresses, d) identifying a second set of addresses comprising a binding reagent of the plurality of binding reagents, in which the second set of addresses is a subset of the first set of addresses, and e) after identifying the second set of addresses, providing a binding reagent dissociation condition to the single-analyte array, in which the binding reagent dissociation condition produces a binding reagent dissociation rate of at least 70%, in which the binding reagent dissociation rate comprises a percentage of addresses of the second set of addresses comprising an absence of a binding reagent of the plurality of binding reagents after providing the binding reagent dissociation conditions, and in which the binding reagent dissociation conditions produces an analyte retention rate of at least 90%, in which the analyte retention rate comprises a percentage of addresses of the first set of addresses comprising a presence of an analyte of the plurality of analytes after providing the binding reagent dissociation condition.

Figure 20:
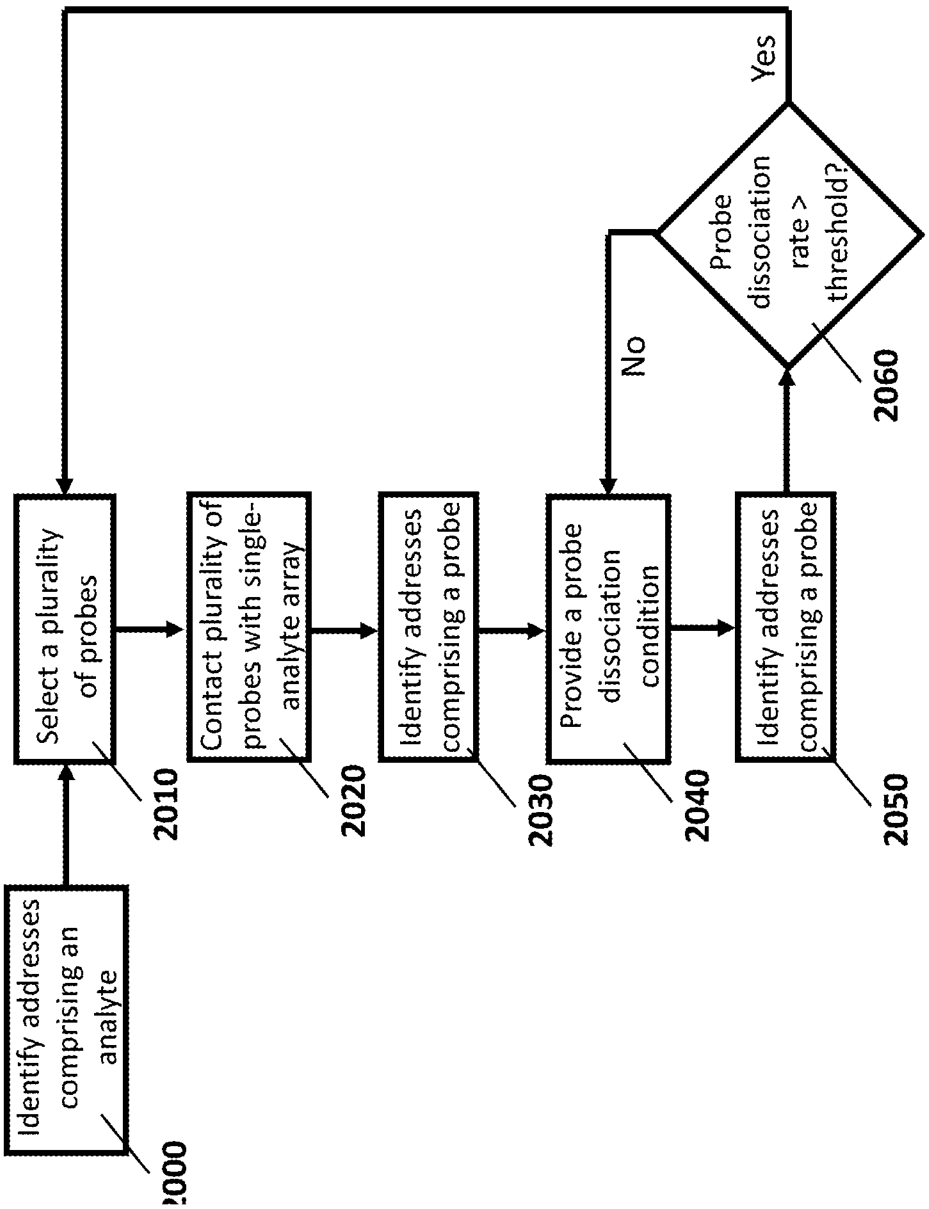
FIG. 20 illustrates a flow chart schematic for methods of performing a single-analyte assay comprising probe dissociation, in accordance with some embodiments.

FIG. 20 depicts a flow chart for a single-analyte array process, in accordance with some embodiments set forth herein. An initial step 2000 of a single-analyte process comprises determining which array addresses contain an analyte of a plurality of analytes. Alternatively, step 2000 may occur at any other time during the assay. Step 2010 comprises selecting a plurality of binding reagents that is to be contacted with a single-analyte array comprising a plurality of analytes. Subsequently, the selected plurality of binding reagents is contacted with the single-analyte array in step 2020, thereby binding binding reagents of the plurality of binding reagents to analytes of the plurality of analytes. In step 2030, addresses comprising binding reagents are identified (e.g., by optical microscopy). In step 2040, a binding reagent dissociation condition (e.g., a fluidic binding reagent dissociation medium, a pH change, a temperature change, etc.) is provided to the single-analyte array, thereby dissociating binding reagents from addresses of the single-analyte array. In step 2050, addresses comprising binding reagents are again identified. If binding reagent dissociation of binding reagents has occurred, fewer addresses will be identified as containing a binding reagent of the plurality of binding reagents. Based upon a difference in addresses comprising binding reagents before and after the binding reagent dissociation condition is provided in step 2040, a binding reagent dissociation rate may be determined. Decision 2060 comprises determining if the binding reagent dissociation rate meets or exceeds a threshold binding reagent dissociation rate (e.g., at least 50%, 60%, 70%, 80%, 90%, 95%, etc.). If the binding reagent dissociation rate exceeds the threshold rate, a new plurality of binding reagents may be selected and steps 2010 through 2060 may be repeated.

Figure 21:
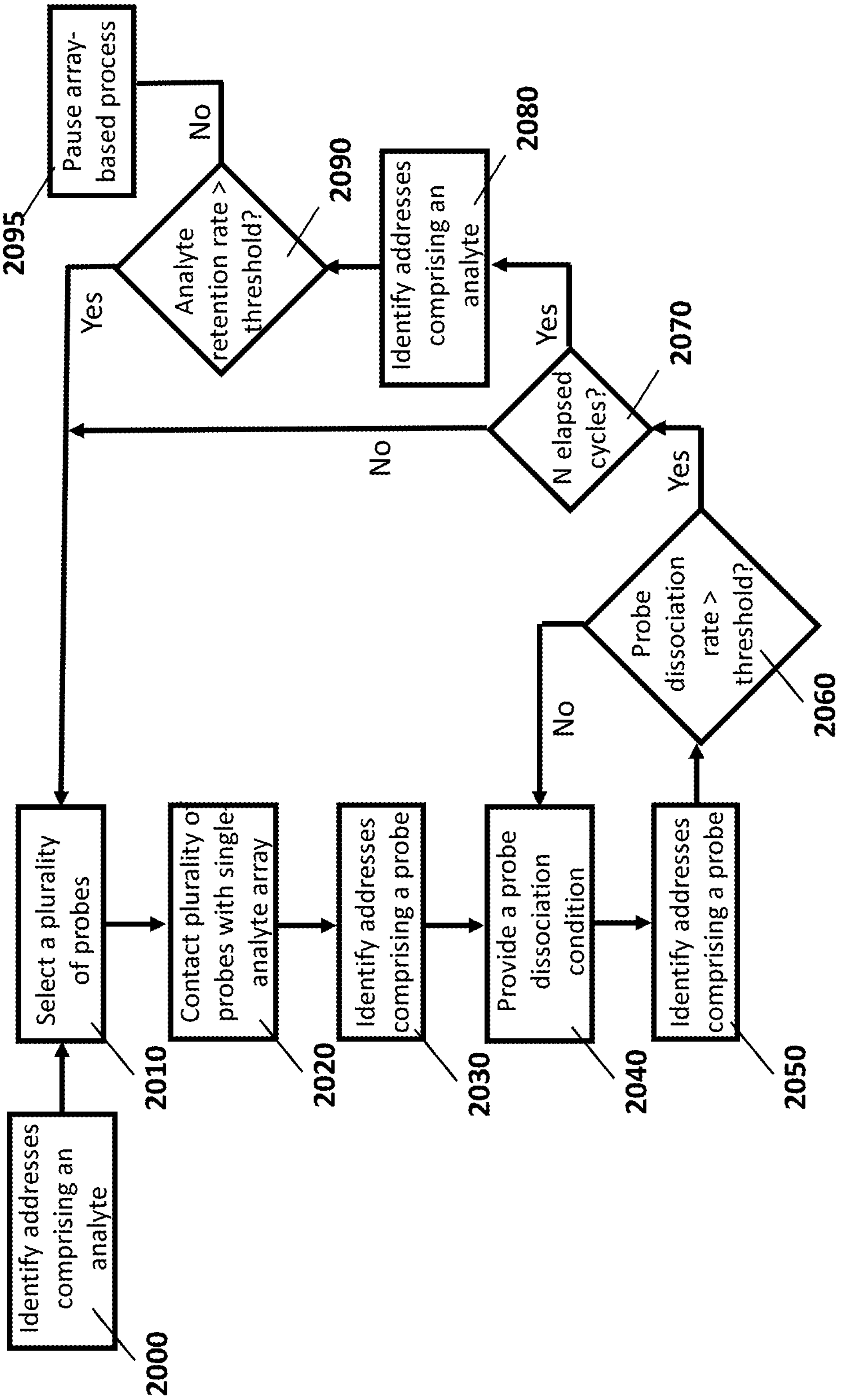
FIG. 21 illustrates a flow chart schematic for methods of performing a single-analyte assay comprising probe dissociation, in accordance with some embodiments.

FIG. 21 depicts a flow chart for a more complex single-analyte process, in accordance with some embodiments set forth herein. The depicted flow chart follows steps 2000 through 2060, as depicted in FIG. 20. After step 2060, an analyte retention rate may be determined. Such a determination may be made at frequency of about every N cycles, where N can be about every 1, 2, 3, 4, 5, 10, 15, 20, 25, 30, 40, 50, 75, 100, 150, 200, 250, or more than every 250 cycles. Decision 2070 may comprise determining if N cycles of the assay have elapsed. If not, steps 2010 through 2060 may be repeated until N cycles of the assay have occurred. If N cycles of the assay have occurred, optional step 2080 may comprise again identifying addresses comprising analytes of the plurality of analytes on the single-analyte array. Alternatively, a quantity of addresses comprising analytes may be inferred based upon binding reagent binding data. Based upon a quantity of addresses comprising an analyte before and after providing a binding reagent dissociation condition, a decision 2090 may be made if an analyte retention rate meets or exceeds a threshold analyte retention rate (e.g., at least 90%, 95%, 99%, 99.9%, 99.99%, etc.). If a threshold analyte retention rate is met or exceeds, the assay may proceed again to step 2010 and a new cycle may be initiated. If a threshold analyte retention rate is not met or exceeds, the assay may be paused to identify a cause of analyte dissociation. The skilled person will further recognize that FIGS. 20 and 21 can be modified to include multiple steps of binding binding reagents and/or detecting bound binding reagents before providing a binding reagent dissociation condition. For example, two pluralities of differing binding reagents may be bound to analytes and detected consecutively, followed thereafter by simultaneous dissociation of both pluralities of binding reagents.

Methods set forth herein may utilize a single-analyte array. A single-analyte array can comprise a plurality of analyte binding sites, in which each analyte binding site comprises an address that differs from each other analyte binding site. In some cases, an analyte binding site of a single-analyte array may be configured to bind or couple one and only one analyte. In some cases, an analyte of a plurality of analytes may be bound or coupled to one and only one analyte binding site. A single-analyte array may comprise a plurality of analyte binding sites, in which each analyte binding site of the plurality of analyte binding sites comprises a unique address, and in which each analyte binding site is configured to bind or couple one and only one analyte of a plurality of analytes. Optionally, each analyte of a plurality of analytes may be bound to one and only one analyte binding site of a plurality of analyte binding sites of a single-analyte array.

A single-analyte array may comprise a spatial distribution of analytes that differs from a Poisson distribution. It may be expected that, when distributing analytes to analyte binding sites, a first fraction of sites will have an occupancy of zero analytes, a second fraction of sites will have an occupancy of one analyte, and a remaining third fraction of sites will have an occupancy of two or more analytes. A Poisson distribution prediction for analyte binding site occupancy may predict ~37% of sites with an occupancy of zero analytes, ~37% of sites with an occupancy of one and only one analyte, and ~26% of sites with an occupancy of two or more analytes. A single-analyte array, as set forth herein, may be characterized as having an analyte occupancy distribution that diverges from a Poisson distribution. For example, less than 37% of all analyte binding sites may comprise an occupancy of zero analytes. In another example, less than 26% of all analyte binding sites may comprise an occupancy of two or more analytes.

A single-analyte array may have a characterized analyte occupancy distribution. In some cases, an analyte occupancy distribution may be determined with respect to all analyte binding sites of a single-analyte array. For example, a single-analyte array containing 1000000 analyte binding with about 50% of sites containing one and only one analyte would have about 500000 analyte binding sites with one and only one analyte. In other cases, an analyte occupancy distribution may be determined with respect to a fraction of all analyte binding sites of a single-analyte array. For example, an analyte occupancy distribution may be determined by observing occupancy in a set of regions of a single-analyte array (e.g., by optical microscopy), in which the set of regions contains less than all analyte binding sites of the single-analyte array. An analyte occupancy distribution of a single-analyte array may be characterized as comprising no more than about 37%, 35%, 30%, 25%, 20%, 15%, 10%, 5%, 1%, 0.5%, 0.1%, 0.01%, 0.001%, or less than 0.001% of analyte binding sites comprising zero analytes. Alternatively or additionally, an analyte occupancy distribution of a single-analyte array may be characterized as comprising at least about 0.001%, 0.01%, 0.1%, 0.5%, 1%, 5%, 10%, 15%, 20%, 25%, 30%, 35%, 37%, or more than 37% of analyte binding sites comprising zero analytes. An analyte occupancy distribution of a single-analyte array may be characterized as comprising at least about 37%, 40%, 50%, 60%, 70%, 80%, 85%, 90%, 95%, 99%, or more than 99% of analyte binding sites comprising one and only one analyte. Alternatively or additionally, an analyte occupancy distribution of a single-analyte array may be characterized as comprising no more than about 99%, 95%, 90%, 85%, 80%, 70%, 60%, 50%, 40%, 37%, or less than 37% of analyte binding sites comprising one and only one analyte. An analyte occupancy distribution of a single-analyte array may be characterized as comprising no more than about 26%, 25%, 20%, 15%, 10%, 5%, 1%, 0.5%, 0.1%, 0.01%, 0.001%, or less than 0.001% of analyte binding sites comprising two or more analytes. Alternatively or additionally, an analyte occupancy distribution of a single-analyte array may be characterized as comprising at least about 0.001%, 0.01%, 0.1%, 0.5%, 1%, 5%, 10%, 15%, 20%, 25%, 26%, or more than 26% of analyte binding sites comprising two or more analytes.

A single-analyte array may comprise a plurality of analyte binding sites, in which each analyte binding site of the plurality of analyte binding sites is located at a unique address of a plurality of addresses on the single-analyte array. In some cases, a single-analyte array may comprise a plurality of addresses, in which each address of the plurality of addresses comprises an analyte binding site, and in which each address of the plurality of addresses is located at a point of a patterned grid. A patterned grid may be characterized as having a substantially uniform spacing or separation between nearest adjacent addresses. A patterned grid of single-analyte array addresses may have a particular symmetry, such as a rectangular grid, a circular grid, a diagonal grid, or a hexagonal grid. In other cases, a single-analyte array may comprise a plurality of addresses, in which each address of the plurality of addresses comprises an analyte binding site, and in which each address of the plurality of addresses is located at a point of a non-patterned grid. A non-patterned grid may be characterized as having random or variable spacing or separation between nearest adjacent addresses. For example, a single-analyte array may comprise a first analyte binding site with a first separation distance from a nearest adjacent analyte binding site, and a second analyte binding site with a second separation distance from a nearest adjacent analyte binding site, in which the first separation distance varies from the second separation distance.

A single-analyte array may comprise a plurality of analyte binding sites, in which an analyte binding site of the plurality of analyte binding sites is separated from each adjacent analyte binding site by an interstitial region. An interstitial region may comprise a portion of a single-analyte array or a surface thereof that is configured to inhibit binding of analytes and/or other chemical moieties (e.g., a binding reagent). An interstitial region may comprise a surface layer that is configured to inhibit binding of analytes and/or other chemical moieties, for example by steric occlusion, hydrophobicity, hydrophilicity, electrical repulsion, or any other suitable physical mechanism. Exemplary materials for surfaces of interstitial regions may include polymers (e.g., polyethylene glycols, alkanes, fluorinated alkanes, etc.), biomolecules (e.g., polysaccharides, polypeptides, oligonucleotides, etc.), semiconductors, metals, and metal oxides.

A single-analyte array may comprise a plurality of analyte binding sites, in which each analyte binding site is located at a unique address of a plurality of addresses, and in which each address is separated from adjacent addresses of the plurality of addresses by an optically resolvable distance. An optically resolvable distance may comprise a distance at which a first detectable signal from a first address can be resolved as unique from a second detectable signal from a second address. An optically resolvable distance may be determined, in part by an optical detection system (e.g., an optical microscope) utilized to identify signals associated with a single-analyte array or an address thereof, as well as the nature of the signals associated with the single-analyte array (e.g., signal wavelength, signal intensity, etc.). An optically resolvable distance may be determined by a detection criterion, such as the Rayleigh Criterion. An optically resolvable distance may be at least about 10 nanometers (nm), 20 nm, 50 nm, 100 nm, 150 nm, 200 nm, 300 nm, 400 nm, 500 nm, 750 nm, 1 micron (μm), 1.5 μm, 2 μm, or more than 2 μm. Alternatively or additionally, an optically resolvable distance may be no more than about 2 μm, 1.5 μm, 1 μm, 750 nm, 500 nm, 400 nm, 300 nm, 200 nm, 150 nm, 100 nm, 50 nm, 20 nm, 10 nm, or less than 10 nm.

A method, as set forth herein, may comprise providing a single-analyte array comprising a plurality of addresses. Providing a single-analyte array may comprise a step of depositing on the single-analyte array a plurality of analytes. In some cases, depositing a plurality of analytes may comprise coupling one and only analyte of a plurality of analytes to an analyte binding site of a single-analyte array. In other cases, depositing a plurality of analytes may comprise coupling two or more analytes of a plurality of analytes to an analyte binding site of a single-analyte array. In some cases, depositing a plurality of analytes may comprise coupling an analyte of a plurality of analytes to one and only one analyte binding site of a single-analyte array.

Analytes may be deposited on a single-analyte array utilizing an anchoring moiety, in which the anchoring moiety couples an analyte to an analyte binding site. Depositing a plurality of analytes may comprise: i) coupling an analyte to an anchoring moiety, and ii) coupling an anchoring moiety to an analyte binding site of a single-analyte array. In some cases, an anchoring moiety may comprise a nucleic acid nanoparticle (e.g., a nucleic acid origami, a nucleic acid nanoball, etc.). In other cases, an anchoring moiety may comprise a non-nucleic acid particle (e.g., a polymer nanoparticle, an inorganic nanoparticle). An anchoring moiety (e.g., a nucleic acid nanoparticle) may be configured to remain structurally stable after providing a binding reagent dissociation condition. Structural stability of an anchoring moiety may comprise one or more of: i) remaining coupled to an analyte binding site of a single-analyte array, and ii) remaining coupled to an analyte of a plurality of analytes. In some cases, an anchoring moiety may be configured to inhibit dissociation of an analyte of a plurality of analytes from an address of a plurality of addresses of a single-analyte array after providing a binding reagent dissociation condition. In some cases, an anchoring moiety comprising a nucleic acid nanoparticle may comprise an intraparticle cross-link that maintains structural stability of the anchoring moiety. In other cases, an anchoring moiety may comprise a covalent linkage (e.g., via a Click-type reaction product) or a strong non-covalent linkage (e.g., via a receptor-ligand binding pair such as streptavidin-biotin, etc.) that maintains a coupling of the anchoring moiety to an address of a single-analyte array.

It may be useful to provide an avidity component at an array site to facilitate controlled binding of detectable probes to analytes at the array site. An avidity component may comprise any suitable moiety or ligand that has one or more properties of: i) facilitating binding of a first detectable probe at the array site, in which the first detectable probe comprises a mobile avidity component that is configured to bind to an immobilized avidity component, ii) inhibiting binding of a second detectable probe at the array site, in which the second detectable probe does not comprise an avidity component that is configured to bind to the avidity component, and iii) facilitating retention of an affinity agent of the first detectable probe at the array site until the presence of the first detectable probe has been detected.

Chart I presents pairs of complementary avidity components. An avidity component may be chosen from column A or B as an immobilized avidity component, and the complementary avidity component in the other column may be chosen as the mobile avidity component. An immobilized avidity component may be immobilized at an array site by covalent coupling to the array site (e.g., covalently coupled to a surface-coupled moiety of the array site), or by covalent coupling to an anchoring group or analyte attached to the array site. An immobilized avidity component may be immobilized at an array site by non-covalent coupling to the array site (e.g., non-covalently coupled to a surface-coupled moiety of the array site), or by non-covalent coupling to an anchoring group or analyte attached to the array site. In some cases, a non-covalently coupled immobilized avidity component may be configured to dissociate from an array site. For example, an immobilized avidity component may be dissociated from an array site by denaturation, change in pH, change in ionic strength, nucleic acid dehybridization, enzymatic cleavage, photocleavage, change in temperature, contact with a chemical denaturant, or any other suitable mechanism of disrupting the coupling of the immobilized avidity component to the array site. In some cases, after dissociating an immobilized a first avidity component from an array site, a second avidity component may be coupled to the array site.

CHART I

| Avidity Component | Complementary Avidity Component |
|---|---|
| Oligonucleotide | Partially- or fully-complementary oligonucleotide |
| Oligonucleotide | Single-stranded DNA-binding protein (e.g., SSB, transcription promoters, transcription repressors) |
| Double-stranded nucleic acid | Double-stranded DNA-binding protein (e.g., histones) |
| Short peptide (e.g., less than about 100, 75, 50, 25, 20, 15, 10, 5, 4, or 3 amino acids) | Short peptide-specific affinity agent (e.g., antibody, aptamer, etc.) |
| Antibody | Antibody-binding protein (e.g., Protein A, Protein G, Protein L, Gamma Fc Receptor, etc.) |
| Enzymatic protein | Tethered enzymatic substrate (i.e., substrate covalently coupled to a linking moiety) |
| First complexing protein (e.g., first procollagen) | Second complexing protein (e.g., second procollagen) |
| Polyelectrolyte brush molecule | Complementary protein molecule |
| Chemical cross-linking agent | Complementary chemical cross-linking agent |
| Photo-catalyzed cross-linking agent (e.g., thiol | Complementary photo-catalyzed cross-linking agent |

A first array site may be distinguished from a second array site by the presence of a first immobilized avidity component at the first array site and a differing second immobilized avidity component at the second array site. Accordingly, a first detectable probe may be configured to bind to the first array site by comprising a complementary mobile avidity component to the first immobilized avidity component, and a second detectable probe may be configured to bind to the second array site by comprising a complementary mobile avidity component to the second immobilized avidity component. In some cases, a first immobilized avidity component may differ from a second immobilized avidity component with respect to type of avidity component (e.g., selected from different rows of Chart I). For example, a first array site may comprise an immobilized polymer brush and a second array site may comprise an immobilized antibody-binding protein. In some cases, a first mobile avidity component may differ from a second mobile avidity component with respect to type of avidity component (e.g., selected from different rows of Chart I). For example, a first detectable probe may comprise a protein that is bound by a polymer brush, and a second detectable probe may comprise an antibody that is bound by an antibody-binding protein. In some cases, a first immobilized avidity component and a second avidity component may be the same type of avidity component, but may differ with respect to a characteristic of the type of avidity component, such as a residue sequence (e.g., amino acid sequence, nucleotide sequence), a secondary or tertiary structure, a binding affinity, a binding specificity, or a combination thereof. For example, a first array site may comprise an immobilized oligonucleotide with a first nucleotide sequence and a second array site may comprise an immobilized oligonucleotide with a second nucleotide sequence.

Detectable probes comprising an affinity agent and a mobile avidity component may be designed to have an effective binding affinity, effective association rate (i.e., on-rate), and/or effective dissociation rate (i.e., off-rate). Selection of a suitable mobile avidity component to pair with a particular affinity agent will depend, at least in part, on the binding characteristics of the affinity agent. To inhibit unwanted detection events of a detectable probe (e.g., due solely to binding of the mobile avidity component to an immobilized avidity component in the absence of binding of the affinity agent to an analyte), it may be preferable to select a mobile avidity component with less binding affinity for its complementary immobilized avidity component relative to the binding affinity of the affinity agent for its analyte target. In some cases, it may be preferable to form a detectable probe comprising an affinity agent and a mobile avidity component, in which the association rate and dissociation rate of the avidity component with its binding partner are slower than the association rate and dissociation rate of the affinity agent with its binding partner (i.e., the mobile avidity component is slower to form a binding interaction and slower to dissociate from its binding interaction). In some cases, it may be preferable to form a detectable probe comprising an affinity agent and a mobile avidity component, in which the association rate and dissociation rate of the avidity component with its binding partner are faster than the association rate and dissociation rate of the affinity agent with its binding partner (i.e., the mobile avidity component is faster to form a binding interaction and faster to dissociate from its binding interaction).

For an array comprising two or more differing immobilized avidity components, a binding characteristic (e.g., binding affinity, association rate, dissociation rate) of a first immobilized avidity component may differ from (e.g., greater than, less than) a binding characteristic of a second immobilized avidity component. Likewise, for a plurality of detectable probes containing two or more mobile avidity components, a binding characteristic (e.g., binding affinity, association rate, dissociation rate) of a first immobilized avidity component may differ from (e.g., greater than, less than) a binding characteristic of a second immobilized avidity component. In some cases, a binding affinity of a first mobile avidity component for a first immobilized avidity component is weaker than a binding affinity of a first affinity agent for a first analyte. In some cases, a binding affinity of a second mobile avidity component for the second immobilized avidity component is weaker than a binding affinity of a second affinity agent for a second analyte. In some cases, a binding affinity of a first mobile avidity component for a first immobilized avidity component is stronger than a binding affinity of a second mobile avidity component for a first immobilized avidity component. In some cases, a binding affinity of a second mobile avidity component for a second immobilized avidity component is stronger than a binding affinity of a first mobile avidity component for a second immobilized avidity component.

Accordingly, a suitable avidity component may increase an effective binding on-rate for a detectable probe, decrease an effective binding off-rate of a detectable probe, or decrease an effective dissociation constant of a detectable probe. Without wishing to be bound by theory, an avidity component may facilitate retention of a bound detectable probe at an array site by increasing the overall strength of binding interactions that must be overcome to release the detectable probe from the array site.

An immobilized avidity component may be located at an array site. An immobilized avidity component may be covalently coupled to an array site. An immobilized avidity component may be non-covalently coupled to an array site. An immobilized avidity component may co-located with an analyte at an array site. An immobilized avidity component may be co-located with an analyte at an array site by a covalent coupling of the immobilized avidity component to the analyte. An immobilized avidity component may be co-located with an analyte at an array site by a non-covalent coupling of the immobilized avidity component to the analyte. An immobilized avidity component may be co-located with an analyte at an array site by a covalent coupling of the immobilized avidity component to an anchoring group that is coupled to the array site. An immobilized avidity component may be co-located with an analyte at an array site by a non-covalent coupling of the immobilized avidity component to an anchoring group that is coupled to the array site.

A method may further comprise a step of associating a first avidity component to a second avidity component in the presence of a binding reagent association medium, as set forth herein. A method may further comprise a step of simultaneously associating i) a first avidity component to a second avidity component, and ii) a detectable binding reagent to an analyte in the presence of a binding reagent association medium, as set forth herein. A method may further comprise a step of dissociating a first avidity component from a second avidity component in the presence of a binding reagent dissociation medium, as set forth herein. A method may further comprise a step of simultaneously dissociating i) a first avidity component from a second avidity component, and ii) a detectable binding reagent from an analyte in the presence of a binding reagent dissociation medium, as set forth herein. Accordingly, a method of identifying an advantageous composition for a fluidic medium (e.g., a binding reagent association medium, a detection medium, a rinsing medium, a binding reagent dissociation medium) may be performed for single-analyte array systems containing avidity component pairs, as set forth herein.

A method, as set forth herein, may comprise a step of identifying on a single-analyte array a first set of addresses of a plurality of addresses, in which each address of the first set of addresses comprises at least one analyte of a plurality of analytes. Identifying a first set of addresses comprising at least one analyte may occur at any conceivable time of an array-based process, including: 1) at the beginning of an array-based process, 2) at the end of an array-based process, 3) at the beginning of a cycle or sequence of an array-based process, 4) at the end of a cycle or sequence of an array-based process, or 5) a combination thereof. In some cases, identifying a first set of addresses may comprise the steps of: i) at each address of a plurality of addresses, detecting presence or absence of a first signal from a first detectable label, and ii) identifying addresses comprising presence of the first signal to form the first set of addresses. In some cases, it may be advantageous to identify a first set of addresses comprising at least one analyte of a plurality of analytes before and after a step of identifying a second set of addresses comprising a binding reagent of a plurality of binding reagents due to a potential for loss of analytes from a single-analyte array during an array-based process.

A method, as set forth herein, may further comprise contacting a single-analyte array with a plurality of binding reagents, in which a binding reagent of the plurality of binding reagents is configured to bind to at least one analyte of the plurality of analytes at an address of the first set of addresses. A method may further comprise comprising binding a binding reagent of a plurality of binding reagents to an analyte of the plurality of analytes at an address of a second set of addresses, in which the second set of addresses is a subset of a first set of addresses comprising at least one analyte of a plurality of analytes. In some cases, identifying a second set of addresses comprising a binding reagent of a plurality of binding reagents may comprise: i) at each address of the first set of addresses, detecting presence or absence of a second signal from a second detectable label, and ii) identifying each address comprising presence of the second signal to form the second set of addresses, in which the second detectable label is coupled to the binding reagent of the plurality of binding reagents. In particular cases, identifying a second set of addresses may comprise, at each address of a plurality of addresses of a single-analyte array, detecting presence or absence of a second signal from a second detectable label. In other particular cases, a method may further comprise removing addresses from the second set of addresses that are not addresses of the first set of addresses (e.g., detection events caused by orthogonal binding of binding reagents to addresses comprising no analytes).

After identifying a second set of addresses comprising a binding reagent of a plurality of binding reagents, a binding reagent dissociation condition may be provided, thereby dissociating binding reagents from the single-analyte array. A binding reagent dissociation condition may comprise one or more or two or more conditions selected from the group consisting of: a) providing a fluidic binding reagent dissociation medium, b) altering a pH of a fluidic medium in contact with a single-analyte array, and c) heating the single-analyte array. Binding reagent dissociation conditions may be combined to increase the efficacy of any one condition. For example, heating a single-analyte array in the presence of a particular fluidic binding reagent dissociation medium may increase the likelihood of disassociating a binding reagent from an analyte.

polypeptide affinity agent (e.g., an antibody, an antibody fragment, etc.). Table I lists a group of potential chemical reagents that may be incorporated, alone or in combination, into a binding reagent dissociation composition. A fluidic binding reagent dissociation medium may comprise a fluidic medium comprising a binding reagent dissociation composition selected from the group consisting of: i) sodium iodide, ii) guanidinium hydrochloride, iii) urea, iv) sodium dodecyl sulfate (SDS), vi) methanol, vii) sodium hydroxide, viii) lithium chloride, ix) sodium chloride, x) sodium thiocyanate, and xi) magnesium chloride. In some cases, it may be preferable to contact a single-analyte array with a fluidic binding reagent dissociation medium comprising no more than one binding reagent dissociation composition. In other cases, it may be preferable to combine two or more binding reagent dissociation compositions to form a fluidic binding reagent dissociation medium. In particular cases, a binding reagent dissociation condition may comprise providing a fluidic binding reagent dissociation medium comprising an absence of magnesium ions. Such a composition may be advantageous for dissociating binding reagents comprising nucleic acids due to destabilization of nucleic acid secondary structure in an absence of magnesium ions. In some cases, a fluidic binding reagent dissociation medium may comprise a fluidic binding reagent dissociation composition and a reducing agent (e.g., DTT, TCEP, etc.).

TABLE I

| Binding Reagent Dissociation Reagents | | | | | | |
|---|---|---|---|---|---|---|
| Chaotropic/Denaturing | | | | | | |
| H-Bond Disruptors | Hydrophobic | Other | Reducing Agents | Low pH | High pH | Surfactants |
| $MgCl_2$ | Acetonitrile | Guanidinium Chloride | $HOCH_2CH_2SH$ | Glycine HCl | $N(CH_2CH_3)_3$ | Sodium dodecyl sulfate |
| LiCl | Methanol | Urea | DTT | Citric Acid | $N(CH_2CH_2OH)_3$ | Sodium 1-heptanesulfonate |
| NaI | Isopropanol | $LiClO_4$ | TCEP | HCl | $NH_4OH$ | TritonX-100 |
| NaSCN | N-butanol | $CH_3COOLi$ | | $CH_3COOH$ | NaOH | CTAB |
| NaCl | Ethanol | $C_6H_5OH$ | | Formamide | | CHAPS |
| | | 2-propanol | | | | |
| | | Thiourea | | | | |
| | | Deoxycholate | | | | |
| | | Dioxane | | | | |
| | | Ethylene glycol | | | | |
| | | Guanidinium Thiocyanate | | | | |

A concentration of a salt species, reducing agent, a denaturing species, a chaotropic species, and/or surfactant or detergent in a fluidic binding reagent dissociation medium may be chosen, at least in part, due to a reduced likelihood of causing orthogonal binding at array interstitial regions or analyte binding sites. A concentration of a salt species, reducing agent, a denaturing species, a chaotropic species, and/or surfactant or detergent in a fluidic binding reagent dissociation medium may be chosen, at least in part, due to a reduced likelihood of causing damage to an analyte.

A fluidic binding reagent dissociation medium may be formulated to dissociate a binding reagent of a plurality of binding reagents from an analyte of a plurality of analytes. In some cases, a fluidic binding reagent dissociation medium may be formulated to dissociate a binding reagent of a plurality of binding reagents from an analyte of a plurality of analytes, in which the binding reagent comprises a In some cases, a single-analyte array comprising a plurality of binding reagents bound to a plurality of analytes may be contacted with a fluidic binding reagent dissociation medium comprising a salt species, in which a binding reagent of the plurality of binding reagents comprises a polypeptide affinity agent (e.g., an antibody, an antibody fragment, etc.). In some cases, a plurality of binding reagents bound to a plurality of analytes may be contacted with a fluidic binding reagent dissociation medium comprising a surfactant or detergent species, in which a binding reagent of the plurality of binding reagents comprises a nucleic acid affinity agent (e.g., an aptamer).

In some cases, providing a binding reagent dissociation condition may comprise altering a pH of a fluidic medium in contact with a single-analyte array. Altering a pH of a fluidic medium in contact with a single-analyte array may comprise increasing the pH of the fluidic medium. Altering a pH of a fluidic medium in contact with a single-analyte array may comprise decreasing the pH of the fluidic medium. Altering a pH of a fluidic medium in contact with a single-analyte array may comprise exchanging or replacing a first fluidic medium comprising a first pH with a second fluidic medium comprising a second pH, in which the first pH differs from the second pH. Altering a pH of a fluidic medium in contact with a single-analyte array may comprise introducing an acidic species or a basic species to a fluidic medium, thereby altering the pH of the fluidic medium. A pH of a fluidic medium in contact with a single-analyte array may be increased or decreased by at least about 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, or more than 10 pH units. Alternatively or additionally, a pH of a fluidic medium in contact with a single-analyte array may be increased or decreased by no more than about 10, 9, 8, 7, 6, 5, 4.5, 4, 3.5, 3, 2.5, 2, 1.5, 1, 0.9, 0.8, 0.7, 0.6, 0.5, 0.4, 0.3, 0.2, 0.1, or less than about 0.1 pH units.

In some cases, a method may comprise heating a single-analyte array. A single-analyte array may be heated in the presence of a fluidic medium, as set forth herein (e.g., a binding reagent dissociation medium, a detection medium, a rinsing medium, a binding reagent dissociation medium). It may be preferable to heat a single-analyte array to facilitate dissociation of an interaction between a binding reagent and an analyte. Heating a single-analyte array may comprise heating a solid support of a single-analyte array, for example by conduction, convection, or radiative heat transfer. Heating a single-analyte array may comprise heating a fluidic medium that is contacted with the single-analyte array. For example, a surface of a single-analyte array may be contacted with a thermoelectric device that is configured to heat a single-analyte array or a fluidic medium contacted thereto. Heating a fluidic medium that is contacted with a single-analyte array may comprise exchanging or replacing a first fluidic medium with a second fluidic medium, in which a temperature of the second fluidic medium is greater than a temperature of the first fluidic medium. A single-analyte array or a fluidic medium contacted thereto may be heated by at least about 1, 5, 10, 15, 20, 25, 30, 35, 40, 45, 50, or more than 50 degrees Celsius (° C.). Alternatively or additionally, a single-analyte array or a fluidic medium contacted thereto may be heated by no more than about 50, 45, 40, 35, 30, 25, 20, 15, 10, 5, 1, or less than 1° C.

In some cases, a method may comprise cooling a single-analyte array. A single-analyte array may be cooled in the presence of a fluidic medium, as set forth herein (e.g., a binding reagent dissociation medium, a detection medium, a rinsing medium, a binding reagent dissociation medium). It may be preferable to cool a single-analyte array to facilitate association of an interaction between a binding reagent and an analyte, or to inhibit unwanted side reactions (e.g., cooling of a single-analyte array during photon-based detection may inhibit formation and/or reaction of phototoxic species such as free radicals or singlet oxygen). Cooling a single-analyte array may comprise cooling a solid support of a single-analyte array, for example by conduction, convection, or radiative heat transfer. Cooling a single-analyte array may comprise cooling a fluidic medium that is contacted with the single-analyte array. For example, a surface of a single-analyte array may be contacted with a thermoelectric device that is configured to cool a single-analyte array or a fluidic medium contacted thereto. Cooling a fluidic medium that is contacted with a single-analyte array may comprise exchanging or replacing a first fluidic medium with a second fluidic medium, in which a temperature of the second fluidic medium is less than a temperature of the first fluidic medium. A single-analyte array or a fluidic medium contacted thereto may be cooled by at least about 1, 5, 10, 15, 20, 25, 30, 35, 40, 45, 50, or more than 50 degrees Celsius (° C.). Alternatively or additionally, a single-analyte array or a fluidic medium contacted thereto may be cooled by no more than about 50, 45, 40, 35, 30, 25, 20, 15, 10, 5, 1, or less than 1° C.

A binding reagent dissociation condition may comprise introducing a binding competitor in a binding reagent dissociation fluidic medium. A binding competitor may comprise a binding target for a binding reagent. For example, binding reagents bound to a particular epitope of analytes on a single-analyte array may be dissociated from the analytes by introducing a binding competitor that comprises a binding target comprising the particular epitope. A binding competitor for polypeptides analytes may comprise peptides, in which the peptides comprise epitopes that are bound by binding reagents, as set forth herein. A binding competitor may be provided in a binding reagent dissociation fluidic medium at a concentration that exceeds an available concentration of a binding target on a single-analyte array.

A method, as set forth herein, may comprise providing two or more binding reagent dissociation conditions to a single-analyte array. In some cases, two or more binding reagent dissociation conditions may be provided sequentially. For example, a single-analyte array may be contacted with a fluidic binding reagent dissociation medium, and subsequently heated to dissociate a binding reagent from an analyte. In another example, a single-analyte array may be contacted with a first fluidic binding reagent dissociation medium, then subsequently contacted with a second fluidic binding reagent dissociation medium to dissociate a binding reagent from an analyte. In other cases, two or more binding reagent dissociation conditions may be provided simultaneously. For example, a fluidic medium contacted with a single-analyte array comprising bound binding reagents may be exchanged with a heated fluidic binding reagent dissociation medium, thereby dissociating a binding reagent from an analyte. In some cases, a single-analyte array may be provided a first binding reagent dissociation condition that dissociates a first fraction of binding reagents of a plurality of binding reagents and a second binding reagent dissociation condition that dissociates a second fraction of binding reagents of the plurality of binding reagents.

A method, as set forth herein, may comprise determining a binding reagent dissociation rate. A binding reagent dissociation rate may be calculated as a fraction or percentage of addresses of a first set of addresses that are characterized by: i) containing a binding reagent of a plurality of binding reagents after being contacted with the plurality of binding reagents and before being provided a binding reagent dissociation condition, and ii) not containing a binding reagent of a plurality of binding reagents after being provided a binding reagent dissociation condition. A binding reagent dissociation rate may be at least about 50%, 60%, 70%, 80%, 85%, 90%, 95%, 99%, 99.9%, 99.99%, 99.999%, 99.9999%, 99.99999%, 99.999999%, or more than 99.999999%. Alternatively or additionally, a binding reagent dissociation rate may be no more than about 99.999999%, 99.99999%, 99.9999%, 99.999%, 99.99%, 99.9%, 99%, 95%, 90%, 85%, 80%, 70%, 60%, 50%, or less than 50%. A method may comprise a step of, after providing a binding reagent dissociation condition, identifying a third set of addresses comprising a binding reagent of the plurality of binding reagents, in which the third set of addresses is a second subset of the first set of addresses. In some cases, identifying a third set of addresses comprising a binding reagent of a plurality of binding reagents may comprise: i) at each address of the first set of addresses, detecting presence or absence of a second signal from a second detectable label, and ii) identifying each address comprising presence of the second signal to form the third set of addresses, in which the second detectable label is coupled to the binding reagent of the plurality of binding reagents. A method may further comprise determining a binding reagent dissociation rate based upon a second set of addresses and a third set of addresses. In some cases, a binding reagent dissociation rate RP may be calculated as:

$$R_P = \frac{(N_2 - N_3)}{N_2} \times 100\% \quad (1)$$

in which $N_2$ is a total quantity of addresses in the second set of addresses and $N_3$ is a total quantity of addresses in the third set of addresses.

A method, as set forth herein, may comprise determining an analyte retention rate. An analyte retention rate may be calculated as a fraction or percentage of addresses of a first set of addresses that are characterized by: i) containing an analyte of a plurality of analytes after providing a single-analyte array comprising the plurality of analytes, and ii) containing the analyte of the plurality of analytes after being provided a binding reagent dissociation condition. An analyte retention rate may be at least about 50%, 60%, 70%, 80%, 85%, 90%, 95%, 99%, 99.9%, 99.99%, 99.999%, 99.9999%, 99.99999%, 99.999999%, or more than 99.999999%. Alternatively or additionally, a binding reagent dissociation rate may be no more than about 99.999999%, 99.99999%, 99.9999%, 99.999%, 99.99%, 99.9%, 99%, 95%, 90%, 85%, 80%, 70%, 60%, 50%, or less than 50%. A method may further comprise, after providing a binding reagent dissociation condition, identifying a fourth set of addresses comprising at least one analyte of a plurality of analytes, in which the fourth set of addresses is a third subset of the first plurality of addresses. In some cases, a fourth set of addresses may comprise each address of the first set of addresses (i.e., an analyte retention rate of 100%). In some cases, identifying a fourth set of addresses may comprise the steps of: i) at each address of a first set of addresses, detecting presence or absence of a first signal from a first detectable label, and ii) identifying addresses comprising presence of the first signal to form the fourth set of addresses. A method may further comprise determining an analyte retention rate based upon a fourth set of addresses and a first set of addresses. In some cases, an analyte retention rate RA may be calculated as:

$$R_A = \frac{(N_1 - N_4)}{N_1} \times 100\% \quad (2)$$

in which $N_1$ is a total quantity of addresses in the first set of addresses and $N_4$ is a total quantity of addresses in the fourth set of addresses.

In some cases, an analyte retention rate may be calculated at each cycle or sequence of steps of a single-analyte array process. In other cases, an analyte retention rate may be determined at a fixed or variable number of cycles, such as at least about every 1, 2, 3, 4, 5, 10, 15, 20, 25, 30, 40, 50, 75, 100, 150, 200, 250, 300, 400, 500, or more than 500 cycles. Alternatively or additionally, an analyte retention rate may be determined at no more than about every 500, 400, 300, 250, 200, 150, 100, 75, 50, 40, 30, 25, 20, 15, 10, 5, 4, 3, 2, or less than every 2 cycles. In some cases, an analyte retention rate may be determined by identifying addresses of a single-analyte array comprising an analyte of a plurality of analytes after providing a binding reagent dissociation condition to the single-analyte array. In other cases, an analyte retention rate may be inferred by binding reagent binding data. For example, diminished binding reagent binding rates may occur due to loss of analytes. If about 10% of analytes are expected to be bound by binding reagents on a 1000000 site array, it would be expected to detect binding reagents at about 100000 addresses after contacting the array with a plurality of binding reagents. If the binding reagent detection rate falls beneath an expected binding reagent detection rate (e.g., by at least about 1%, 5%, 10%, 20%, 25%, 50%, etc.) for a cycle or multiple cycles, it may be inferred that diminished detection is occurring due to loss of analytes. Accordingly, binding reagent detection rate data may be utilized to estimate an analyte retention rate.

A method, as set forth herein, may be configured to achieve a particular overall binding reagent dissociation rate or analyte retention rate (i.e., a rate calculated after completion of all cycles or steps of a sequence of steps) of a single-analyte process or assay. An overall binding reagent dissociation rate and/or analyte retention rate may be chosen based upon a desired or designed outcome of a single-analyte process or assay. For example, for an array comprising N sites, it may be intended to acquire high confidence analysis of at least 50%, 60%, 70%, 80%, 90%, 95%, 99%, 99.9%, or more than 99.9% of the N sites. In another example, a single-analyte process may be designed to achieve a dynamic range of analysis (e.g., identifying 1 analyte per a pool of 1000000 analytes provides a dynamic range factor of 1000000), such as a dynamic range factor of at least 1000, 10000, 100000, 1000000, 10000000, 100000000, 1000000000, or more than 1000000000. Given the stochastic nature of single-analyte processes, it may be necessary to analyze more than 1000000 array sites to identify a particular single analyte amongst the 1000000 sites to achieve a desired dynamic range. It may be necessary to achieve a number of analyzed sites by a factor of at least 1.1, 1.5, 2, 5, 10, 20, 50, 100, 250, 500, 1000, or more than 1000 to achieve a desired dynamic range on an array of N sites, where N is greater than the desired dynamic range factor. Accordingly, it may be preferable to acquire high confidence analysis of at least 50%, 60%, 70%, 80%, 90%, 95%, 99%, 99.9%, 99.99%, 99.999%, or more than 99.999% of the N sites to achieve a desired dynamic range factor.

Based upon a percentage of sites to be analyzed to achieve a desired extent of analysis, a minimum binding reagent dissociation rate or minimum analyte retention rate may be determined (on a per cycle or per sequence basis) as:

$$R=(r^n) \quad (3)$$

where R is the overall percentage of sites to be analyzed, r is the per cycle or per sequence binding reagent dissociation rate or analyte retention rate, and n is the total number of cycles or sequences of a single-analyte assay or process.

In some cases, a method may not include a step of determining an analyte retention rate. A binding reagent dissociation method may be characterized with respect to an analyte retention rate before it is utilized in a single-analyte assay, as set forth herein. In some cases, a method may comprise one or more steps of: i) before performing an assay on a single-analyte array, determining for a plurality of binding reagents bound to a plurality of analytes an analyte retention rate that meets or exceeds a threshold analyte retention rate for a binding reagent dissociation condition, ii) before performing the assay on the single-analyte array, determining for a plurality of binding reagents bound to a plurality of analytes a binding reagent dissociation rate that meets or exceeds a threshold binding reagent dissociation rate for the binding reagent dissociation condition, and iii) providing the binding reagent dissociation condition to the single-analyte array.

A binding reagent dissociation condition can inhibit a subsequent ability to detect an analyte. Detectable labels (e.g., fluorophores, luminophores, etc.) may be damaged or degraded by certain binding reagent dissociation conditions, thereby diminishing a signal provided by the detectable labels during detection of analytes. For example, strong acids or strong bases may react with certain fluorophores, thereby inhibiting emission of detectable signals from the fluorophores. Accordingly, loss of signal from a detectable label may inhibit an ability to detect an analyte at an address of a single-analyte array even if the analyte is still present at the address of the single-analyte array. In some cases, a binding reagent dissociation condition may be provided to a single-analyte array if it diminishes a signal intensity of a detectable label by no more than about 20%, 15%, 10%, 5%, 1%, 0.5%, 0.1%, 0.05%, 0.01%, 0.005%, 0.001%, or less than 0.001%.

A method, as set forth herein, may further comprise, after providing a first binding reagent dissociation condition: i) determining a binding reagent dissociation rate below a binding reagent dissociation rate criterium (e.g., a binding reagent dissociation rate of at least 50%, 60%, 70%, 80%, 90%, 95%, 99%, etc.), ii) after determining the binding reagent dissociation rate below the binding reagent dissociation rate criterium, providing a second binding reagent dissociation condition, and iii) after providing the second binding reagent dissociation condition, determining a binding reagent dissociation rate that meets or exceeds the binding reagent dissociation rate criterium. A method may further comprise, after providing a second binding reagent dissociation condition, identifying a fifth set of addresses comprising a binding reagent of the plurality of binding reagents, wherein the fifth set of addresses is a fourth subset of the first set of addresses. In some cases, identifying a fifth set of addresses comprising a binding reagent of a plurality of binding reagents may comprise: i) at each address of the first set of addresses, detecting presence or absence of a second signal from a second detectable label, and ii) identifying each address comprising presence of the second signal to form the fifth set of addresses, in which the second detectable label is coupled to the binding reagent of the plurality of binding reagents. In some cases, a method may comprise repeating steps i) and ii) until a binding reagent dissociation rate criterium is met or exceeded.

An array-based process may comprise repeatedly contacting a single-analyte array with a plurality of binding reagents. An array-based process may comprise cycles or sequences, in which a cycle or sequence of the process comprises the steps of: i) contacting a single-analyte array with a plurality of binding reagents, ii) identifying a set of addresses comprising a binding reagent of the plurality of binding reagents, and iii) providing a binding reagent dissociation condition, thereby dissociating binding reagents of the plurality of binding reagents. In some cases, a method may further comprise: f) contacting a single-analyte array with a second plurality of binding reagents, in which a binding reagent of the second plurality of binding reagents is configured to bind to at least one analyte of the plurality of analytes at an address of a first set of addresses, as set forth herein, g) identifying a sixth set of addresses comprising a binding reagent of the second plurality of binding reagents, in which the sixth set of addresses is a subset of the first set of addresses; and h) after identifying the sixth set of addresses, providing a third binding reagent dissociation condition, as set forth herein, to the single-analyte array. In some cases, a binding reagent of a second plurality of binding reagents may comprise a differing binding specificity from a binding reagent of a first plurality of binding reagents. Accordingly, a sixth set of addresses comprising a binding reagent of a second plurality of binding reagents may differ from a second set of addresses comprising a binding reagent of a first plurality of binding reagents. In some cases, a method may comprise performing one or more additional cycles of steps f) through h). In some cases, a method may comprise performing at least about 5, 10, 20, 30, 40, 50, 75, 100, 150, 200, 250, 300, 400, 500, or more than 500 cycles of steps f) through h).

A method may comprise a first step of contacting a single-analyte array with a first plurality of binding reagents, and a second step of contacting the single-analyte array with a second plurality of binding reagents. In some cases, a binding reagent of a first plurality of binding reagents may comprise a first affinity agent and a binding reagent of a second plurality of binding reagents may comprise a second affinity agent, in which the first affinity agent differs from the second affinity agent. A first affinity agent may differ from a second affinity agent with respect to a type of affinity agent (e.g., a first affinity agent comprises an antibody and a second affinity agent comprises an aptamer). A first affinity agent may differ from a second affinity agent with respect to a binding specificity (e.g., a first affinity agent binds to a first family of epitopes, and a second affinity agent binds to a second family of epitopes). In some cases, a first affinity agent may comprise a polypeptide affinity agent and a second affinity agent may comprise a nucleic acid affinity agent. In other cases, a first affinity agent may comprise a nucleic acid affinity agent and a second affinity agent may comprise a polypeptide affinity agent. In other cases, a first affinity agent may comprise a nucleic acid affinity agent and a second affinity agent may comprise a differing nucleic acid affinity agent. In other cases, a first affinity agent may comprise a polypeptide affinity agent and a second affinity agent may comprise a differing polypeptide affinity agent.

A method may comprise the steps of: i) contacting a single-analyte array with a first plurality of binding reagents, ii) after contacting the single-analyte array with the first plurality of binding reagents, providing a first binding reagent dissociation condition, iii) after providing the first binding reagent dissociation condition, contacting the single-analyte array with a second plurality of binding reagents, and iv) after contacting the single-analyte array with the second plurality of binding reagents, providing a second binding reagent dissociation condition. In some cases, a second binding reagent dissociation condition may differ from a first binding reagent dissociation condition. In particular cases, a difference between a second binding reagent dissociation condition and a first binding reagent dissociation condition may comprise one or more of a difference in composition of a fluidic binding reagent dissociation medium, a difference in pH of the fluidic binding reagent dissociation medium, and a difference in temperature of the fluidic binding reagent dissociation medium. For example, a first binding reagent dissociation condition may comprise contacting a single-analyte array with a first fluidic binding reagent dissociation medium and a second binding reagent dissociation condition may comprise contacting the single-analyte array with a second fluidic binding reagent dissociation medium, in which the first fluidic binding reagent dissociation medium differs in composition from the second fluidic binding reagent dissociation medium. In other cases, a second binding reagent dissociation condition may be the same as a first binding reagent dissociation condition. For example, binding reagents of a first plurality of binding reagents and binding reagents of a second plurality of binding reagents may be dissociated by the same fluidic binding reagent dissociation medium.

A method, as set forth herein, may comprise, after providing a binding reagent dissociation condition, providing an analyte regeneration condition. An analyte regeneration condition may comprise any conceivable process that enhances or restores an ability to bind a binding reagent to an analyte. An analyte regeneration condition may comprise altering a conformation of an analyte (e.g., altering a polypeptide secondary or tertiary structure). For example, a single-analyte array may be contacted with a fluidic analyte regeneration medium after providing a binding reagent dissociation condition. An analyte regeneration condition may comprise altering a chemical composition in contact with an analyte at an address of a single-analyte array. For example, a single-analyte array comprising nucleic acid anchoring moieties may be contacted with a fluidic analyte regeneration medium comprising an increased magnesium ion concentration after providing a binding reagent dissociation condition comprising providing a fluidic binding reagent dissociation medium comprising a diminished magnesium ion concentration. An analyte regeneration condition may comprise cooling a single-analyte array or a fluidic medium contacted therewith. An analyte regeneration condition may comprise contacting an analyte with a fluidic medium comprising a denaturing agent (e.g., acetic acid, trichloroacetic acid, sulfosalicylic acid, hydrochloric acid, nitric acid, sodium hydroxide, sodium bicarbonate, ethanol, urea, guanidinium hydrochloride, lithium perchlorate, sodium dodecyl sulfate, 2-mercaptoethanol, dithiothreitol, tris 2-carboxyethyl phosphine, dimethyl sulfoxide, formamide, propylene glycol, etc.). an analyte regeneration step may include mechanical agitation.

A method may be configured to selectively dissociate particular binding interactions while maintaining other binding interactions within a single-analyte array system, as set forth herein. The methods may be particularly advantageous for dissociating binding reagents from analytes that are coupled to single-analyte arrays, as set forth herein. In particular cases, analytes may be coupled to single-analyte arrays by one or more non-covalent interactions, and a binding reagent may be bound to an analyte by a non-covalent interaction. In such cases, a method set forth herein may be configured to dissociate the non-covalent interaction between the binding reagent and the analyte without causing dissociation of the analyte from the single-analyte array due to dissociation of at least a fraction of the one or more non-covalent interactions that couple the analyte to the array. In particular cases, analytes are coupled to a single-analyte array by nucleic acid nanoparticles, in which the nucleic acid nanoparticles comprises a network of binding interactions between a plurality of oligonucleotides, as well as one or more binding interactions to a solid support and a binding interaction to the analyte. In such cases, methods are provided for dissociating binding reagents from analytes without dissociating the analytes and/or nucleic acid nanoparticles from the solid support.

A method may comprise one or more steps of: 1) forming anchoring moieties, in which the anchoring moieties are optionally formed by coupling a plurality of molecules through binding interactions, 2) coupling single analytes to single anchoring moieties by a binding interaction, 3) coupling anchoring moieties to array binding sites by forming binding interactions between the anchoring moieties and the array binding sites, 4) coupling binding reagents to single analytes by binding interactions, 5) providing a binding reagent dissociation condition, and 6) dissociating binding reagents from analytes by disrupting the binding interactions between the binding reagents and the analytes, in which binding interactions between anchoring moieties and analytes and binding interactions between anchoring moieties and array binding sites are not dissociated.

In some cases, the methods set forth herein are particularly advantageous for dissociating binding reagents from analytes on arrays formed by deposition of analytes with nucleic acid nanoparticles. In an aspect, provided herein is a method comprising: a) forming an array of single-analyte complexes, wherein each single-analyte complex comprises: i) a nucleic acid nanoparticle comprising a first oligonucleotide and a second oligonucleotide, in which the first oligonucleotide is attached to a solid support by a first binding interaction, and in which the second oligonucleotide is attached to the first oligonucleotide by a second binding interaction, ii) a single analyte, in which the single analyte is coupled to the nucleic acid nanoparticle by a third binding interaction, and in which the single analyte is not attached to the solid support, and iii) a binding reagent, in which the binding reagent is coupled to the analyte by a fourth binding interaction, and in which the binding reagent is not attached to the solid support and the nucleic acid nanoparticle, and b) providing a binding reagent dissociation condition to the array of analyte complexes, thereby removing the binding reagent from the solid support via dissociation of the fourth binding interaction, in which the first binding interaction, the second binding interaction, and the third binding interaction retain the nucleic acid nanoparticle and the single analyte on the solid support. Binding interactions of a nucleic acid nanoparticle and a solid support, a nucleic acid nanoparticle and an analyte, and intra-particle binding interactions may comprise non-covalent binding, covalent binding, or combinations thereof. In some cases, a first binding interaction, a second binding interaction, or a third binding interaction can comprise a covalent binding interaction (e.g., a Click-type reaction product, an addition reaction product, a substitution reaction product, etc.). In some cases, a first binding interaction, a second binding interaction, or a third binding interaction may comprise a non-covalent binding interaction (e.g., nucleic acid hybridization, receptor-ligand binding, electrostatic adhesion, magnetic adhesion, etc.).

A first binding interaction may comprise a binding interaction that couples an oligonucleotide of a nucleic acid nanoparticle to a solid support. A first binding interaction may comprise a binding interaction that attaches an oligonucleotide of a nucleic acid nanoparticle to a solid support. In some cases, an oligonucleotide of a nucleic acid nanoparticle may be attached to a surface-coupled molecule or moiety, in which the surface-coupled molecule or moiety is attached to a solid support. For example, an oligonucleotide of a nucleic acid nanoparticle may be attached to a surface-coupled oligonucleotide by nucleic acid hybridization. In another example, an oligonucleotide of a nucleic acid nanoparticle may be attached to a surface-coupled molecule by a covalent bond between the oligonucleotide and the surface-coupled molecule. In some cases, a nucleic acid nanoparticle may be coupled to a surface by a plurality of first binding interactions, as set forth herein.

A second binding interaction may comprise a binding interaction that couples a first oligonucleotide of a nucleic acid nanoparticle to a second nucleic acid nanoparticle of the nucleic acid nanoparticle. In some cases, a first oligonucleotide of a nucleic acid nanoparticle may be coupled to a second nucleic acid nanoparticle of the nucleic acid nanoparticle by one or more non-covalent binding interactions. For example, a first oligonucleotide may be hybridized to a second oligonucleotide. In another example, a first oligonucleotide may be hybridized to a third oligonucleotide, in which the third oligonucleotide is hybridized to the second oligonucleotide. In some cases, a first oligonucleotide of a nucleic acid nanoparticle may be coupled to a second nucleic acid nanoparticle of the nucleic acid nanoparticle by one or more covalent binding interactions. For example, a first oligonucleotide may be coupled to a second oligonucleotide by a covalent cross-linking reagent (e.g., nitrogen mustards, cisplatin, chloro-ethyl nitroso urea, psoralens, mitomycin C, nitrous acid, bifunctional aldehydes, formaldehyde, or combinations thereof). A nucleic acid nanoparticle may comprise a plurality of oligonucleotides, in which the plurality of oligonucleotides comprises the first oligonucleotide and the second oligonucleotide, and in which the nucleic acid nanoparticle comprises a plurality of second binding interactions, as set forth herein.

A third binding interaction may comprise a binding interaction that couples a nucleic acid nanoparticle to an analyte. A third binding interaction may comprise a binding interaction that couples a first oligonucleotide of a nucleic acid nanoparticle to an analyte. A third binding interaction may comprise a binding interaction that couples a second oligonucleotide of a nucleic acid nanoparticle to an analyte. A third binding interaction may comprise a non-covalent binding interaction between a nucleic acid nanoparticle and an analyte. For example, an analyte may be attached to an oligonucleotide, in which the oligonucleotide attached to the analyte is attached to an oligonucleotide of the nucleic acid nanoparticle. A third binding interaction may comprise a covalent binding interaction between a nucleic acid nanoparticle and an analyte. For example, an analyte may be covalently attached to an oligonucleotide of a nucleic acid nanoparticle by a covalent bond (e.g., a Click-type reaction product, an addition reaction product, a substitution reaction product, etc.).

In some cases, a nucleic acid nanoparticle may comprise a plurality of oligonucleotides, such as at least about 5, 10, 20, 25, 30, 40, 50, 75, 100, 125, 150, 175, 200, or more than 200 oligonucleotides, in which the plurality of oligonucleotides comprises a first oligonucleotide and a second oligonucleotide, as set forth herein. A nucleic acid nanoparticle may comprise a plurality of oligonucleotides, in which each oligonucleotide of the plurality of oligonucleotides is coupled to each other oligonucleotide of the plurality of oligonucleotides. A nucleic acid nanoparticle may comprise a plurality of oligonucleotides, in which each oligonucleotide of the plurality of oligonucleotides is at least partially hybridized to another oligonucleotide of the plurality of oligonucleotides. A nucleic acid nanoparticle may comprise a plurality of oligonucleotides, in which an oligonucleotide of the plurality of oligonucleotides is covalently cross-linked to another oligonucleotide of the plurality of oligonucleotides.

A nucleic acid nanoparticle may comprise a second binding interaction that couples a first oligonucleotide to a second oligonucleotide. A nucleic acid nanoparticle may comprise a plurality of second binding interactions, as set forth herein. A nucleic acid nanoparticle may comprise at least as many second binding interactions as a quantity of oligonucleotides of a plurality of oligonucleotides of the nucleic acid nanoparticle. A nucleic acid nanoparticle may comprise more second binding interactions than a quantity of oligonucleotides of a plurality of oligonucleotides of the nucleic acid nanoparticle. For example, a second oligonucleotide may comprise a first sequence and a second sequence, in which the first sequence hybridizes with a complementary first sequence of a first oligonucleotide, and in which the second sequence hybridizes with a complementary second sequence of the first oligonucleotide. A nucleic acid nanoparticle may comprise at least about 5, 10, 20, 25, 30, 40, 50, 75, 100, 125, 150, 175, 200, 250, 300, 400, or more than 400 second binding interactions. Alternatively or additionally, a nucleic acid nanoparticle may comprise no more than about 400, 300, 250, 200, 175, 150, 125, 100, 75, 50, 40, 30, 25, 20, 10, 5, or less than 5 second binding interactions.

A method may comprise contacting a single-analyte array, as set forth herein, with a plurality of binding reagents. A binding reagent may comprise an affinity agent and a detectable label, wherein the detectable label is coupled to the affinity agent. In some cases, a binding reagent may comprise a nanoparticle (e.g., a nucleic acid nanoparticle, an organic nanoparticle, an inorganic nanoparticle), in which an affinity agent is coupled to the nanoparticle, and in which a binding reagent is coupled to the nanoparticle. In a particularly advantageous case, a binding reagent may comprise a nanoparticle, in which a plurality of affinity agents is coupled to the nanoparticle, and in which a detectable is coupled to the nanoparticle.

A binding reagent may comprise an affinity agent that is configured to couple to an analyte that is coupled to a single-analyte array. A plurality of binding reagents may be configured to bind to a subset of analytes of a single-analyte array. For example, binding reagents of a plurality of binding reagents may bind to analytes comprising a specific epitope (e.g., a trimer, tetramer, pentamer, hexamer, etc. with a known amino acid sequence) or a group of epitopes. A plurality of binding reagents may comprise two or more differing binding reagents, in which the two or more differing binding reagents differ with respect to binding specificity. For example, a plurality of binding reagents may comprise a first binding reagent with a binding specificity for a first epitope or group of epitopes, and a may further comprise a second binding reagent with a binding specificity for a second epitope or group of epitopes. For such a plurality of binding reagents, the first binding reagent may comprise a first detectable label and the second binding reagent may comprise a second detectable label, in which the first detectable label is distinguishable from the second detectable label (e.g., by fluorophore emission wavelength, by luminescence lifetime, etc.). Accordingly, a single-analyte array may comprise binding reagents coupled to analytes, in which first binding reagents are coupled to a first subset of analytes, and in which second binding reagents are coupled to a second subset of analytes.

A fourth binding interaction may comprise non-covalent binding of an affinity agent of a binding reagent to a single analyte. Given the differing types of affinity agents that may be incorporated into a binding reagent, the skilled person will readily recognize the nature of the binding interactions between such affinity agents and analytes (e.g., polypeptides, nucleic acids, polysaccharides, etc.). For example, antibody or aptamer affinity agents may bind to a target epitope through Van der Waals or hydrogen bonding interactions. A fourth binding interaction may not comprise non-covalent binding or covalent binding of a constituent of a binding reagent other than an affinity agent to a single analyte. For example, a binding reagent comprising fluorescent moieties may be configured to prevent orthogonal binding of the fluorescent moieties to a single analyte.

In some cases, a binding reagent of a plurality of binding reagents may comprise a nucleic acid nanoparticle. A nucleic acid nanoparticle may be advantageous due to the tunability of orientation of binding reagent constituents (e.g., affinity agents, detectable labels, linking moieties, etc.) and a flexible architecture that facilitates binding reagent dissociation from single analytes. In some cases, a method may comprise dissociating a fourth binding interaction between a binding reagent, as set forth herein, and a single analyte, in which dissociating the fourth binding interaction comprises: i) dissociating a detectable label from an affinity agent of the binding reagent, and ii) after dissociating the detectable label, dissociating the affinity agent from the single analyte.

Figure 23:
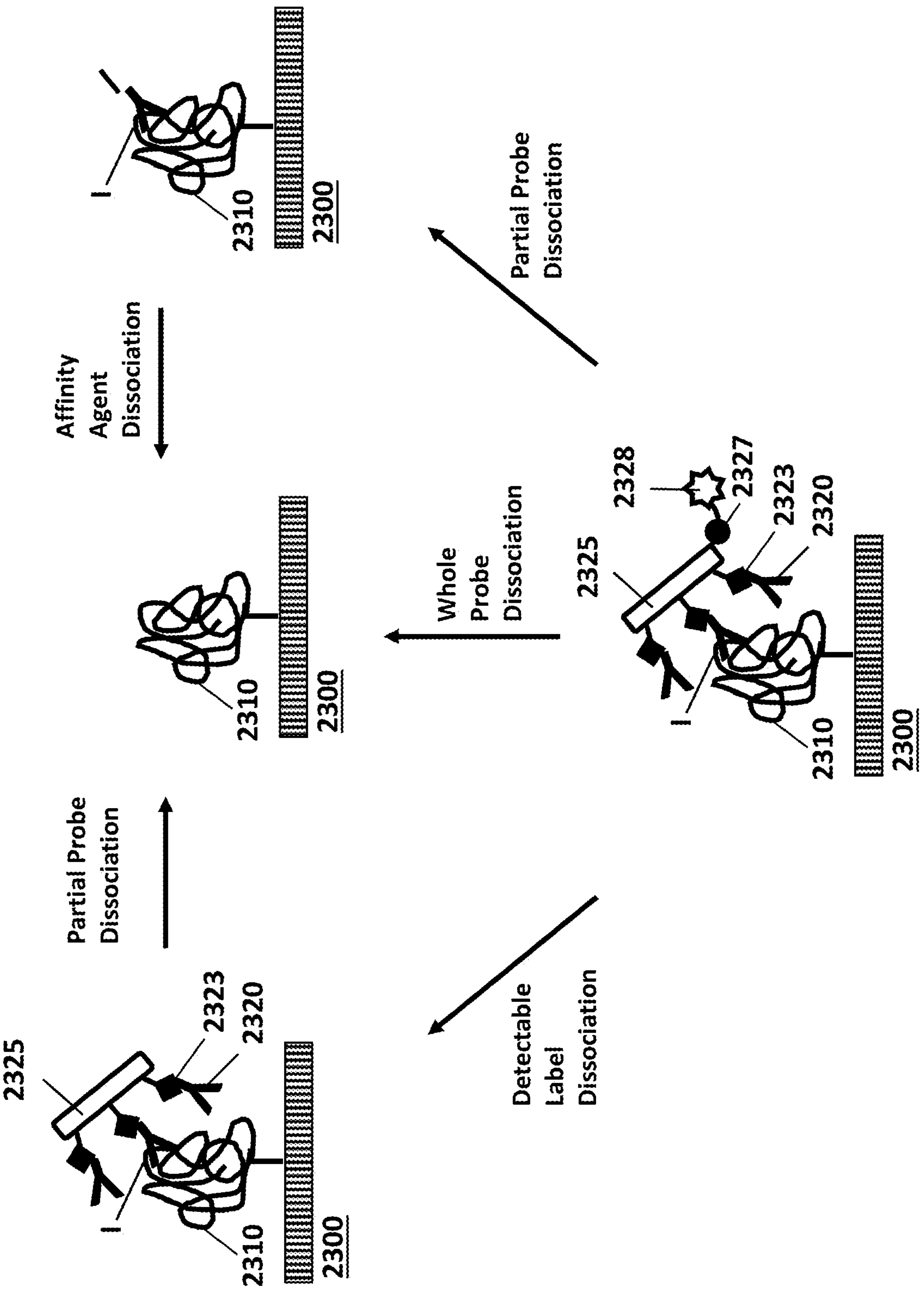
FIG. 23 displays various pathways for detectable probe dissociation from an analyte, in accordance with some embodiments.

FIG. 23 illustrates various methods for dissociating a detectable binding reagent, as set forth herein, from a single analyte. The lowermost configuration depicts a single analyte 2310 (e.g., a polypeptide) coupled to a solid support 2300. A detectable binding reagent is bound to the single analyte 2310 by a fourth binding interaction, I. The detectable binding reagent comprises an affinity agent 2320 (optionally a plurality of affinity agents 2320) that is coupled to an optional nanoparticle 2325 (e.g., a nucleic acid nanoparticle). The detectable binding reagent further comprises a detectable label 2328 (e.g., a fluorophore) that is coupled to the affinity agent 2320. Optionally, the detectable binding reagent may further comprise cleavable bonds 2323 (e.g., photocleavable linkers, chemically-cleavable linkers) that couple affinity agents 2320 to a nanoparticle 2325, and cleavable bonds 2327 that couple a detectable label 2328 to the nanoparticle 2325. In a first (central) dissociation pathway, the detectable binding reagent may be dissociated from the single analyte 2310 by whole binding reagent dissociation, in which the entire binding reagent is dissociated from the single analyte 2310 simultaneously, for example by providing a binding reagent dissociation medium, as set forth herein, or heating the binding reagent-analyte complex. In a second (left) pathway, the detectable binding reagent may be dissociated from the single analyte 2310 by first dissociating the detectable label 2328 from the detectable binding reagent, for example by cleaving the cleavable bond 2327 or dehybridizing an oligonucleotide that couples the detectable label 2328 to the nucleic acid nanoparticle 2325. After dissociating the detectable label 2328, the remaining portion of the detectable binding reagent may be dissociated passively or dissociated by a binding reagent dissociation condition, as set forth herein. The second pathway may be advantageous by inhibiting detectability of the detectable binding reagent, thereby permitting additional cycles of binding reagent binding and detection to proceed while the remaining first detectable binding reagent to dissociate. In a third (right) pathway, the detectable binding reagent may be dissociated from the single analyte 2310 by first dissociating the bound affinity agent 2320 from the detectable binding reagent, for example by cleaving the cleavable bond 2323 or dehybridizing an oligonucleotide that couples the affinity agent 2320 to the nucleic acid nanoparticle 2325. After dissociating the bound affinity agent 2320, the remaining affinity agent 2320 may be dissociated passively or dissociated by a binding reagent dissociation condition, as set forth herein. The third pathway may be advantageous due to removing the detectable portion of the detectable binding reagent as well as reducing a steric size of the remaining binding reagent constituents still bound to the single analyte 2310, thereby facilitating subsequent detection if the affinity agent 2320 has not dissociated.

A binding reagent may comprise a nucleic acid nanoparticle, as set forth herein. A nucleic acid nanoparticle may be configured to facilitate binding reagent dissociation. A binding reagent may comprise one or more oligonucleotides whose melting temperatures are sufficiently low to permit dehybridization when the binding reagent is heated. In some cases, thermal dehybridization of an oligonucleotide may dissociate an affinity agent from a nucleic acid nanoparticle comprising the oligonucleotide. In some cases, thermal dehybridization of an oligonucleotide may dissociate a detectable label from a nucleic acid nanoparticle comprising the oligonucleotide. In some cases, thermal dehybridization of a plurality of oligonucleotides of a nucleic acid nanoparticle may substantially decompose the nucleic acid nanoparticle structure, thereby making the binding reagent undetectable. In some cases, an oligonucleotide (e.g., coupled to an affinity agent, coupled to a detectable label) of a nucleic acid nanoparticle may be dehybridized by a binding reagent dissociation medium, as set forth herein. In some cases, an oligonucleotide (e.g., coupled to an affinity agent, coupled to a detectable label) of a nucleic acid nanoparticle may be dehybridized by a reduction of an ion concentration (e.g., magnesium ions) in a medium contacted with the nucleic acid nanoparticle, as set forth herein. In some cases, a binding reagent constituent (e.g., an affinity agent, a detectable label, an intraparticle cross-link) may be cleaved by providing a cleavage condition (e.g., providing irradiation by light of a cleavage wavelength, providing a chemical dissociation agent, etc.).

A binding reagent dissociation condition may comprise applying a mechanical force. In some cases, a binding reagent dissociation condition may comprise contacting a binding reagent-analyte complex with an interface (e.g., a liquid/air interface, a liquid/liquid interface), thereby dissociating a binding reagent from a single analyte. In some cases, a binding reagent dissociation condition may comprise contacting a binding reagent-analyte complex with a mechanical stress (e.g., a shear stress, a compressional stress, a rotational stress), for example by fluidic mixing or agitation. In some cases, a binding reagent dissociation condition may comprise dissociating a binding reagent from a single analyte by generating a force on the binding reagent. For example, additional matter may be coupled to a binding reagent, thereby dissociating the binding reagent from a single analyte by a gravitational stress in a quiescent medium or a centripetal stress in a non-quiescent medium. In another example, a binding reagent may be coupled to electrically-charged or magnetic particles, thereby producing a dissociating force when an electrical field or magnetic field, respectively, is applied.

It is recognized that disclosed methods for single-analyte assays and processes include assays and processes that utilize multiple cycles or sequences of steps to achieve single-analyte analysis or detection. Accordingly, disclosed methods may include the use of pluralities of affinity agents, in which each cycle can utilize a differing plurality of affinity agents relative to a prior or posterior cycle or step (e.g., differing with respect to analytes bound, differing with respect to epitopes bound, etc.). Moreover, disclosed methods may include a cycle or step in which two differing binding reagents (e.g., differing with respect to analytes or epitopes bound) are simultaneously bound to analytes (i.e., multiplexed detection). In some cases, a method may utilize a same binding reagent dissociation condition for each cycle or sequence of steps of a single-analyte process or assay. For example, a single-analyte array system, as set forth herein, may comprise a single binding reagent dissociation fluidic medium that is utilized in all binding reagent dissociation steps. In other cases, a method may utilize two or more binding reagent dissociation conditions, in which a binding reagent dissociation condition of the two or more binding reagent dissociation conditions is chosen for each cycle or sequence of steps (e.g., depending upon a type of binding reagent used for a particular cycle or sequence of steps). In some cases, a multiplexed single-analyte assay method may comprising coupling two differing binding reagents to a single-analyte array, as set forth herein, in which the two differing binding reagents are dissociated by the same binding reagent dissociation condition.

Methods set forth herein may utilize nucleic acid nanoparticles for one or more functions during a single-analyte assay or process. It may be advantageous to utilize nucleic acid nanoparticles as anchoring moieties to achieve controlled coupling of analytes to analyte binding sites of a single-analyte array. It may also be advantageous to utilize nucleic acid nanoparticles as retaining components for binding reagents, especially for binding reagents that comprise multiple affinity agents per binding reagent. Aspects of nucleic acid nanoparticle design for anchoring moieties and binding reagents are set forth in U.S. Pat. App. No. 20220290130A1 and U.S. Pat. App. No. 20220162684A1, each of which is herein incorporated by reference. Functionally, it will be recognized that anchoring moieties may be intended to remain associated with an analyte binding site and a single analyte when provided with a binding reagent dissociation condition, as set forth herein, whereas binding reagents may be intended to dissociate from an analyte when provided the same binding reagent dissociation condition. Accordingly, a structure of a nucleic acid nanoparticle of an anchoring moiety may differ in certain respects from a structure of a nucleic acid nanoparticle of a binding reagent. Set forth herein are aspects of nucleic acid nanoparticle design that can impact behavior and function in a single-analyte array system, as set forth herein.

A nucleic acid nanoparticle may comprise two or more oligonucleotides that form a structure of the nucleic acid nanoparticle through base-pair hybridization interactions. Two-dimensional and/or three-dimensional structures associated with nucleic acid nanostructures may arise, in part, due to self-complementarity hybridization interactions of a single oligonucleotide within the nucleic acid nanostructure. Additionally or alternatively, two-dimensional and/or three-dimensional structures associated with nucleic acid nanostructures may arise, in part, due to hybridization interactions between two or more oligonucleotides of a nucleic acid nanoparticle. In some cases, two-dimensional and/or three-dimensional structures associated with nucleic acid nanostructures may arise, in part, due to hybridization interactions between a first oligonucleotide and two or more non-contiguous nucleotide sequences of a second oligonucleotide. For example, nucleic acid origami may be formed by repeated folding of a scaffold oligonucleotide due to hybridization of staple oligonucleotides, in which staple oligonucleotides bind to at least two non-contiguous sequences of the scaffold oligonucleotide. In some cases, a two-dimensional and/or three-dimensional structures associated with nucleic acid nanostructures may arise, in part, due to hybridization interactions between a first oligonucleotide and part of a second oligonucleotide. For example, pendant single-stranded oligonucleotide may be formed by partial hybridization of a first oligonucleotide to a second oligonucleotide, in which a terminal nucleotide sequence or an intermediate nucleotide sequence of the first oligonucleotide is of sufficient length to form a pendant single stranded nucleic acid. In some cases, a nucleic acid nanoparticle may comprise a single oligonucleotide, in which a structure of the nucleic acid nanoparticle arises due to internal self-complementarity of nucleotide sequences for complementary nucleic acid sequences of the single oligonucleotide (e.g., a nucleic acid nanoball comprising a concatemer of a self-complementary nucleotide sequence).

A nucleic acid nanoparticle may comprise at least two oligonucleotides. A nucleic acid nanoparticle may comprise a plurality of oligonucleotides, in which each oligonucleotide is at least partially hybridized to at least one other oligonucleotide of the plurality of oligonucleotides. A nucleic acid nanoparticle may comprise at least about 2, 3, 4, 5, 10, 20, 25, 30, 40, 50, 75, 100, 125, 150, 175, 200, 250, 500, or more than 500 oligonucleotides. Alternatively or additionally, a nucleic acid nanoparticle may comprise no more than about 500, 250, 200, 175, 150, 125, 100, 75, 50, 40, 30, 25, 20, 10, 5, 4, 3, 2, or less than 2 oligonucleotides.

In some cases, a nucleic acid nanoparticle may comprise a scaffold oligonucleotide. A scaffold oligonucleotide may be hybridized to a plurality of staple oligonucleotides to form a particular two-dimensional or three-dimensional structure of a nucleic acid nanoparticle. A scaffold oligonucleotide may be modified, for example by the inclusion of non-natural or modified nucleotides, thereby permitting attachment of entities (e.g., a single analyte, a solid support, a surface-coupled moiety) to the scaffold oligonucleotide. A scaffold oligonucleotide may be modified to alter a conformation of a nucleic acid nanoparticle.

A nucleic acid nanoparticle may comprise a plurality of staple oligonucleotides. A staple oligonucleotide may comprise any oligonucleotide that is hybridized with, or configured to hybridize with, a nucleic acid scaffold, other staples, or a combination thereof. A staple oligonucleotide may be modified to include additional chemical entities, such as binding components, label components, chemically-reactive groups or handles, or other groups (e.g., polyethylene glycol (PEG) moieties). A staple oligonucleotide may comprise linear or circular nucleic acids. A staple oligonucleotide may comprise one or more single-stranded regions, double-stranded regions, or combinations thereof. A staple oligonucleotide may be hybridized with, or configured to hybridize with, a scaffold strand or one or more other staples, for example, via complementary base pair hybridization (e.g., Watson-Crick hybridization). A staple oligonucleotide may be hybridized with other nucleic acids by complementary base pair hybridization or ligation. A staple oligonucleotide may be configured to act as a primer for a complementary nucleic acid strand and the primer staple may be extended by an enzyme (e.g., a polymerase) to form lengthened regions of double-stranded nucleic acid, for example, using a scaffold, staple or other strand as a template. In some cases, the primer need not be hybridized to a template when extended. For example, a primer can be extended by template-free addition of one or more nucleotides by a terminal transferase enzyme, by template-free addition of one or more oligonucleotides by a ligase enzyme or template-free addition of nucleotide(s) or oligonucleotide(s) by non-enzymatic chemical reaction. A staple oligonucleotide may include one or more modified nucleotides. A modified nucleotide may include a linking group or a reactive handle (e.g., a functional group configured to perform a click-type reaction). A modified staple oligonucleotide may facilitate attachment of entities (e.g., a single analyte, a solid support, a surface-coupled moiety) to the staple oligonucleotide.

A staple oligonucleotide may be any length depending upon the design of the SNAP. A staple oligonucleotide may be designed by a software package, such as caDNAno2, ATHENA, OR DAEDALUS. A staple oligonucleotide may have a length of at least about 10, 25, 50, 100, 150, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2500, 3000, 3500, 4000, 4500, 5000, or more than 5000 nucleotides. Alternatively or additionally, a staple may have a length of no more than about 5000, 4500, 4000, 3500, 3000, 2500, 2000, 1900, 1800, 1700, 1600, 1500, 1400, 1300, 1200, 1100, 1000, 950, 900, 850, 800, 750, 700, 650, 600, 550, 500, 450, 400, 350, 300, 250, 200, 150, 100, 50, 25, 10, or less than 10 nucleotides.

A nucleic acid nanoparticle may be formed by hybridization of two or more oligonucleotides. A stability of any hybridization interaction within a nucleic acid nanoparticle may depend at least in part on factors such as a total number of base-paired nucleotides, presence of non-paired nucleotides within a base-paired nucleotide sequence, and GC content of a base-paired nucleotide sequence. Nucleic acid melting temperature may be a useful proxy for relative stability of a nucleic acid hybridization interaction. Typically, a higher nucleic acid melting temperature suggests a more stable binding interaction. A binding interaction within a nucleic acid nanoparticle may be designed facilitate or inhibit dissociation of the binding interaction. For example, a binding reagent may comprise a nucleic acid nanoparticle, in which a detectable label is coupled to the nucleic acid nanoparticle by oligonucleotide hybridization, and in which the oligonucleotide comprising the detectable label is configured to have a lower melting temperature than an average melting temperature of the nucleic acid nanoparticle. In another example, an anchoring moiety may comprise a plurality of pendant single-stranded nucleic acids, in which the pendant single-stranded nucleic acids attach to surface-coupled oligonucleotides, and in which an average melting temperature of hybridization interactions of pendant single-stranded nucleic acids with surface-coupled oligonucleotides is at least as high as an average melting temperature of the nucleic acid nanoparticle. In some cases, a higher melting temperature of a nucleic acid hybridization interaction may suggest a more stable binding interaction during a binding reagent dissociation condition, as set forth herein.

A nucleic acid nanoparticle may comprise a first oligonucleotide attached to a second oligonucleotide by a hybridization interaction, in which the hybridization interaction has a characterized melting temperature. A hybridization interaction between a first oligonucleotide and a second oligonucleotide may have a melting temperature of at least about 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., or more than 90° C. Alternatively or additionally, a hybridization interaction between a first oligonucleotide and a second oligonucleotide may have a melting temperature of no more than about 90° C., 89° C., 88° C., 87° C., 86° C., 85° C., 84° C., 83° C., 82° C., 81° C., 80° C., 79° C., 78° C., 77° C., 76° C., 75° C., 74° C., 73° C., 72° C., 71° C., 70° C., 69° C., 68° C., 67° C., 66° C., 65° C., 64° C., 63° C., 62° C., 61° C., 60° C., 59° C., 58° C., 57° C., 56° C., 55° C., 54° C., 53° C., 52° C., 51° C., 50° C., 49° C., 48° C., or less than 48° C.

A nucleic acid nanoparticle may comprise a plurality of nucleic acid hybridization interactions, in which the plurality of nucleic acid hybridization interactions comprise an average characterized melting temperature. A plurality of hybridization interactions may have an average melting temperature of at least about 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., or more than 90° C. Alternatively or additionally, a plurality of hybridization interaction may have an average melting temperature of no more than about 90° C., 89° C., 88° C., 87° C., 86° C., 85° C., 84° C., 83° C., 82° C., 81° C., 80° C., 79° C., 78° C., 77° C., 76° C., 75° C., 74° C., 73° C., 72° C., 71° C., 70° C., 69° C., 68° C., 67° C., 66° C., 65° C., 64° C., 63° C., 62° C., 61° C., 60° C., 59° C., 58° C., 57° C., 56° C., 55° C., 54° C., 53° C., 52° C., 51° C., 50° C., 49° C., 48° C., or less than 48° C.

Methods set forth herein may involve dissociation of binding reagents from a binding interaction with an analyte, including binding reagents comprising nucleic acid nanoparticles. Accordingly, it may be advantageous to alter a stability of particular hybridization interactions that form a binding reagent or a constituent thereof (e.g., a nucleic acid nanoparticle). For example, a binding reagent may comprise an affinity agent coupled to a detectable label by nucleic acid hybridization. In such a binding reagent composition, it may be advantageous to dissociate the detectable label by dehybridizing an oligonucleotide comprising the detectable label, thereby making the affinity agent undetectable. The affinity agent can subsequently dissociate independently of the detectable label. In some cases, a detectable label may be incorporated into a binding reagent by attachment to an oligonucleotide that couples to the binding reagent by a dissociable hybridization interaction. In some cases, an affinity agent may be incorporated into a binding reagent by attachment to an oligonucleotide that couples to the binding reagent by a dissociable hybridization interaction.

Methods set forth herein may involve association of anchoring moieties to an analyte binding site and/or an analyte, including anchoring moieties comprising nucleic acid nanoparticles. Accordingly, it may be advantageous to alter a stability of particular hybridization interactions that form an anchoring moiety or a constituent thereof (e.g., a nucleic acid nanoparticle). For example, an analyte may be attached to an oligonucleotide that is coupled to a nucleic acid nanoparticle by a hybridization interaction, in which the hybridization interaction must remain stable to prevent dissociation of the analyte throughout a single-analyte process or assay. In another example, an anchoring moiety comprising a nucleic acid nanoparticle may be coupled to an analyte binding site by hybridization interactions of pendant single stranded nucleic acids of the nucleic acid nanoparticle to surface-coupled oligonucleotides of the analyte binding site, in which a sufficient quantity of hybridization interactions must remain stable to prevent dissociation of the anchoring moiety from the analyte binding site.

Accordingly, a particular nucleic acid hybridization interaction may be designed to have increased or decreased stability with respect to another nucleic acid hybridization interaction or another network of nucleic acid hybridization interactions. In some cases, a first nucleic acid hybridization interaction within a binding reagent or a constituent thereof may be more stable or less stable than a second nucleic acid hybridization interaction within a binding reagent or a constituent thereof. In some cases, a nucleic acid hybridization interaction within a binding reagent or a constituent thereof may be more stable or less stable than a nucleic acid hybridization interaction within an anchoring moiety or a constituent thereof. In some cases, a first nucleic acid hybridization interaction within an anchoring moiety or a constituent thereof may be more stable or less stable than a second nucleic acid hybridization interaction within an anchoring moiety or a constituent thereof. In some cases, a nucleic acid hybridization interaction within an anchoring moiety or a constituent thereof may be more stable or less stable than a nucleic acid hybridization interaction within a binding reagent or a constituent thereof. In some cases, a first nucleic acid hybridization interaction and a second nucleic acid hybridization interaction or network thereof may be designed to have a similar stability, for example as characterized by nucleic acid melting temperature.

A difference in stability between a particular nucleic acid hybridization interaction and another nucleic acid hybridization interaction or network thereof may be characterized by a differential in melting temperatures. In some cases, a differential in melting temperatures may be calculated as a difference in melting temperatures between a first hybridization interaction and a second hybridization interaction. In other cases, a differential in melting temperatures may be calculated as a difference in melting temperatures between a first hybridization interaction and an average of a plurality of hybridization interactions. A differential in melting temperatures may have an absolute value of at least about 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., or more than 30° C. Alternatively or additionally, a differential in melting temperatures may have an absolute value of no more than about 30° C., 29° C., 28° C., 27° C., 26° C., 25° C., 24° C., 23° C., 22° C., 21° C., 20° C., 19° C., 18° C., 17° C., 16° C., 15° C., 14° C., 13° C., 12° C., 11° C., 10° C., 9° C., 8° C., 7° C., 6° C., 5° C., 4° C., 3° C., 2° C., 1° C., or less than 1° C.

A nucleic acid nanoparticle may comprise one or more faces that provide a structural feature and/or perform a function for the nucleic acid nanoparticle. A nucleic acid nanoparticle may comprise one or more of: 1) a display face; 2) a capture face; 3) a coupling face; and 4) a utility face. A display face may comprise a capture moiety that couples, or is configured to couple, a nucleic acid nanoparticle to an analyte. A capture face may comprise a capture moiety that couples, or is configured to couple, a nucleic acid nanoparticle to a surface or interface of a solid support. A coupling face may comprise a coupling moiety that couples, or is configured to couple, a first nucleic acid nanoparticle to a second nucleic acid nanoparticle. A utility face may comprise a utility moiety that provides an additional utility to a nucleic acid nanoparticle, such as providing structure, providing stability, altering an interaction (e.g., attraction or repulsion, steric hindrance, etc.) between a nucleic acid nanoparticle and another entity (e.g., a second nucleic acid nanoparticle, a surface, etc.), or altering a physical property of a nucleic acid nanoparticle (e.g., a utility moiety may comprise an electrical, magnetic, or optical material, etc.). A nucleic acid nanoparticle may comprise a face with more than one function. For example, a coupling face may also comprise a utility face. In another example, a display face may also comprise a utility face or a capture face. A nucleic acid nanoparticle may comprise a face that is comprised of one or more other types of faces. For example, a display face may comprise portions or regions that are utility faces comprising steric blocking groups (e.g., PEG, PEO, dextrans, etc.). In some configurations, a multi-function face may be counted as a single face. For example, a cube-like nanoparticle may comprise about six distinct faces, with each of the six faces comprising one or more functions, e.g., a display face and a utility face on one of the six sides.

A nucleic acid nanoparticle may have a particular number of faces. A nucleic acid nanoparticle may have at least about 1, 2, 3, 4, 5, 6, 7, 8, 9, 10, 11, 12, 13, 14, 15, 16, 17, 18, 19, 20, or more than 20 faces. Additionally or alternatively, a nucleic acid nanoparticle may have no more than about 20, 19, 18, 17, 16, 15, 14, 13, 12, 11, 10, 9, 8, 7, 6, 5, 4, 3, 2 or less than 2 faces. The number of faces of a nucleic acid nanoparticle may be chosen to match a functionality for the nucleic acid nanoparticle. For example, a nucleic acid nanoparticle that is configured to couple an analyte to a solid support may necessitate at least 2 faces (a display face and a coupling face), with additional faces added based upon other design considerations (e.g., utility faces). An orientation of a first face may be determined with respect to an orientation of a second face based upon an angular offset between a first vector that is normal to a plane defining an average spatial location of the first face and a second vector that is normal to a plane defining an average spatial location of the second face. In other configurations, an orientation of a first face may be offset from an orientation of a second face by at least about 90°. In other configurations, an orientation of a first face may be offset from an orientation of a second face by about 180°. A nucleic acid nanoparticle may comprise a first face and a second face with an angular offset of at least about 10°, 20°, 30°, 40°, 50°, 60°, 70°, 80°, 90°, 100°, 110°, 120°, 130°, 140°, 150°, 160°, 170°, 180°, 190°, 200°, 210°, 220°, 230°, 240°, 250°, 260°, 270°, 280°, 290°, 300°, 310°, 320°, 330°, 340°, 350° or more than 350°. Alternatively or additionally, a nucleic acid nanoparticle may comprise a first face and a second face with an angular offset of no more than about 360°, 350°, 340°, 330°, 320°, 310°, 300°, 290°, 280°, 270°, 260°, 250°, 240°, 230°, 220°, 210°, 200°, 190°, 180°, 170°, 160°, 150°, 140°, 130°, 120°, 110°, 100°, 90°, 80°, 70°, 60°, 50°, 40°, 30°, 20°, 10°, or less than 10°.

Stability of nucleic acid nanoparticles may be influenced by a presence of covalent cross-linking. In some cases, covalent cross-linking may occur between a first oligonucleotide of a nucleic acid nanoparticle and a second oligonucleotide of a nucleic acid nanoparticle (i.e., inter-strand cross-linking). In some cases, covalent cross-linking may occur within a single oligonucleotide of a nucleic acid nanoparticle (i.e., intra-strand cross-linking). Covalent cross-linking may occur due to contact of a nucleic acid cross-linking reagent, as set forth herein, with a nucleic acid or a nucleic acid nanoparticle. In some cases, a nucleic acid nanoparticle may comprise at least as many covalent cross-links as a quantity of oligonucleotides within the nucleic acid nanoparticle. In other cases, a nucleic acid nanoparticle may comprise fewer covalent cross-links than a quantity of oligonucleotides within the nucleic acid nanoparticle. Covalent cross-linking may be particularly advantageous for nucleic acid nanoparticles of anchoring moieties due to a need to maintain stability of the nucleic acid nanoparticles to prevent dissociation from analyte binding sites.

Stability of nucleic acid nanoparticles may be influenced by a presence of cleavable linkers (e.g., photocleavable linkers, chemically-cleavable linkers, etc.). In some cases, cleavable linkers may be incorporated into nucleic acid nanoparticles to facilitate decomposition of the nucleic acid nanoparticle. In some cases, a cleavable linker may be incorporated into nucleic acid nanoparticles to facilitate dissociation of a particular component or moiety from the nucleic acid nanoparticle (e.g., a detectable label, an affinity agent). A cleavable linker may be dissociated by contacting a nucleic acid nanoparticle with a cleaving condition, such as light irradiation (for photocleavable linkers), contacting with a chemical cleaving agent (for chemically-cleavable linkers), or enzymatic digestion (e.g., restriction enzyme digestion). Incorporation of cleavable linkers may be particularly advantageous for binding reagents, whereby dissociation of binding reagents from analytes can be accomplished, at least in part, by decomposition of the binding reagent or dissociation of components from the binding reagents.

A nucleic acid nanoparticle may comprise one or more pendant moieties, such as single-stranded nucleic acids, polymeric chains (e.g., PEG, alkane chains, etc.), components of a receptor-ligand binding pair (e.g., streptavidin-biotin, SpyCatcher-SpyTag, SnoopCatcher-SnoopTag, etc.), or covalent reactive groups (e.g., NHS esters, Click-type reagents, etc.). A pendant moiety may be configured to couple a nucleic acid nanoparticle to a solid support. In some cases, a nucleic acid nanoparticle may be coupled to a solid support by binding interactions of a plurality of pendant moieties. In particular cases, pendant moieties may form non-covalent binding interactions, covalent binding interactions, or combinations thereof with a solid support or moieties attached thereto. It may be particularly advantageous to couple an anchoring moiety to an analyte binding site by at least one covalent binding interaction, thereby inhibiting dissociation of the anchoring moiety and/or analyte from the analyte binding site. A pendant moiety may be configured to couple a detectable label to a nucleic acid nanoparticle. For example, a nucleic acid nanoparticle of a binding reagent or an anchoring moiety may comprise a pendant single-stranded nucleic acid that forms a hybridization interaction with an oligonucleotide comprising a detectable label. It may be particularly advantageous to couple a detectable label to a pendant moiety of a binding reagent to facilitate dissociation of the detectable label. In some cases, a detectable label may not be coupled to a pendant moiety of a nucleic acid nanoparticle. For example, fluorophore may be incorporated into internal portions of a nucleic acid nanoparticle of an anchoring moiety to decrease a likelihood of dissociation.

A method may further comprise a step of forming a binding profile for each individual site of a plurality of sites, in which the binding profile for each individual site of the plurality of sites comprises presence or absence of a signal from a binding reagent for a subset of cycles of at least 10 cycles of an array-based process. In some cases, the subset of cycles can comprise a cycle of the at least 10 cycles of the array-based process. In some cases, the subset of cycles can comprise one and only one cycle of the at least 10 cycles of the array-based process. In some cases, the subset of cycles can comprise each individual cycle of the at least 10 cycles of the process. In some cases, the subset of cycles can comprise N cycles (e.g., N=1, 2, 3, 4, 5, 6, 7, 8, 9, 10, 15, 20, 25, 30, 40, 50, 75, 100, etc.) of the at least M cycles (e.g., N=10, 20, 25, 30, 40, 50, 75, 100, 150, 200, 250, 300, 400, 500, 1000, etc.) of the array-based process. In some cases, a subset of cycles can comprise two consecutive cycles of an array-based process. In some cases, a subset of cycles can comprise a particular subset of cycles (e.g., the first N cycles, the last N cycles, the middle N cycles, etc. where N=1, 2, 3, 4, 5, 6, 7, 8, 9, 10, etc.).

In some cases, a method may further comprise a step of determining a characteristic for at least 50% (e.g., for at least 60%, at least 70%, at least 80%, at least 90%, at least 95%, at least 99%, at least 99.9%, etc.) of analytes of the single-analyte array based upon a binding profile for each individual site of the plurality of sites. The determined characteristic of an analyte may comprise an identity, an isoform, a species, a type, a physiochemical property (e.g., molecular weight, isoelectric point, hydrodynamic radius, etc.), or a combination thereof.

Figure 25B:
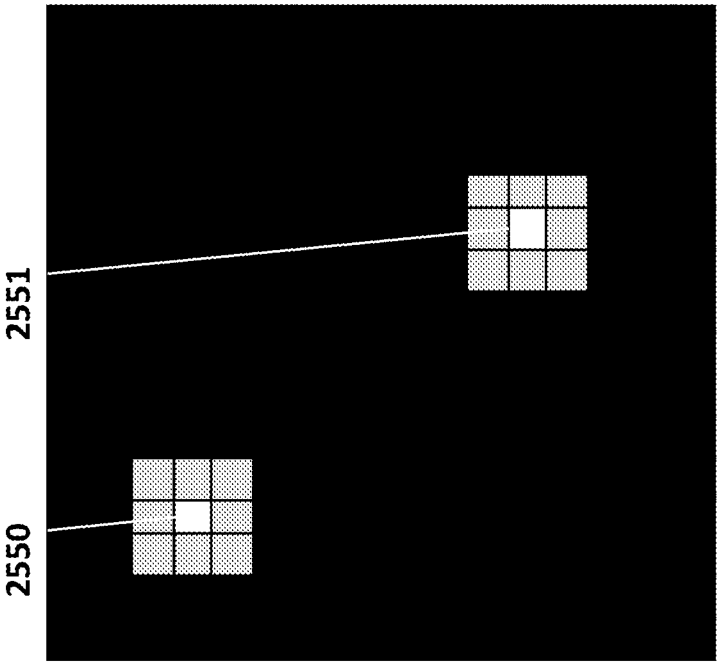
FIG. 25B shows a simulated image of detected signals from the array-bound detectable binding reagents shown in FIG. 25A.
Figure 25A:
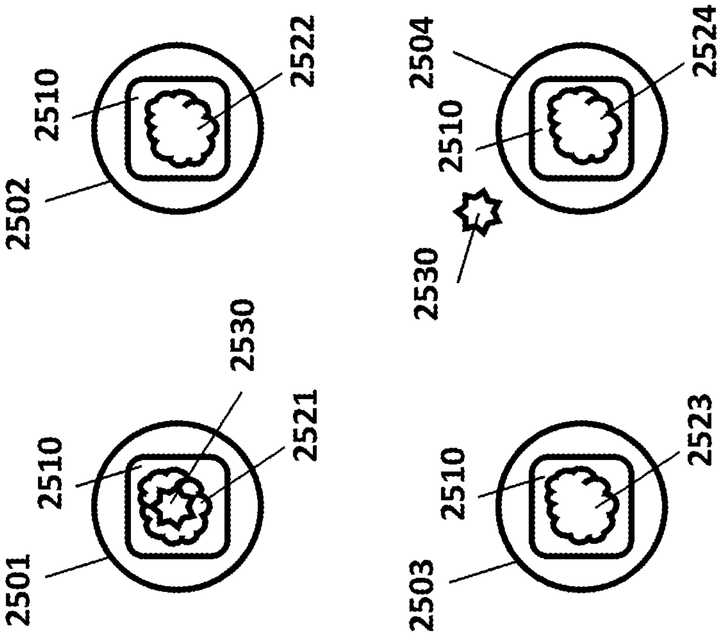
FIG. 25A illustrates a configuration of an array of analytes with a detectable binding reagent bound to an analyte and a detectable binding reagent bound to an interstitial region of the array.

A method may further comprise a step of detecting binding of a binding reagent to an interstitial region of an array. Signals produced by binding reagents bound to interstitial regions can produce cross-talk during signal detection that produces unintended signals at addresses corresponding to array sites. FIG. 25A depicts a configuration of an array containing a detectable binding reagent bound to an interstitial region of the array. The array comprises sites 2501, 2502, 2503, and 2504. The sites are separated from each other by interstitial region 2505. Each individual array site contains an anchoring moiety 2510 that mediates attachment of an analyte to the array site. Array sites 2501, 2502, 2503, and 2504 contain analytes 2521, 2522, 2523, and 2524, respectively. Optionally, one or more analytes of the array may differ from one or more other analytes of the array (e.g., with respect to species, with respect to isoform, with respect to state, etc.). A first detectable binding reagent 2530 is bound to analyte 2521 at array site 2501. A second detectable binding reagent 2530 is bound to the interstitial region 2505 adjacent to array site 2504. FIG. 25B depicts a simulated image (e.g., a confocal fluorescent microscope image collected on a pixel-based array) of signals emitted from the array by detectable binding reagents. A first signal 2550 is detected at addresses (e.g., pixels) associated with array site 2501. A second signal 2551 is detected at addresses associated with array site 2504 and the interstitial region 2505. Accordingly, signal 2551 may be detected as a false detection event (i.e., a signal detected at array site 2504 despite no detectable binding reagent bound to analyte 2524). Cross-talk due to binding reagents bound to interstitial regions or adjacent to array sites may increase a binding reagent anomaly fraction or false detection fraction at low signal occupancy (e.g., signals detected at less than 25%, less than 20%, less than 15%, less than 10%, less than 5%, less than 1%, etc. of addresses associated with array sites) due to uncertainty caused by sparse mapping of array site addresses.

In some cases, a method may comprise a step of detecting at each individual interstitial region of one or more interstitial regions a presence or an absence of a signal from a binding reagent of a plurality of binding reagents. In some cases, at least one individual cycle (e.g., two or more individual cycles) of at least 50 cycles further comprises a step of: (d) detecting at each individual interstitial region of one or more interstitial regions a presence or an absence of a signal from a binding reagent of a plurality of binding reagents. In some cases, each individual cycle of at least 50 cycles further comprises a step of: (d) detecting at each individual interstitial region of one or more interstitial regions a presence or an absence of a signal from a binding reagent of a plurality of binding reagents.

The fluidic media set forth herein may be further advantageous for inhibiting binding of binding reagents at interstitial regions or facilitating removal of binding reagents bound to the interstitial regions. In some cases, for any two consecutive cycles of an array-based process, a presence of a signal may be detected from individual addresses of the one or more interstitial regions during the first cycle of the two consecutive cycles, and wherein an absence of a signal is detected from at least 50% (e.g., at least 60%, at least 70%, at least 75%, at least 80%, at least 90%, at least 95%, at least 99%, at least 99.9%, etc.) of the individual addresses during the second cycle of the at least two consecutive cycles. In some cases, a total quantity of signals detected at the one or more interstitial regions of an array during any cycle of an array-based process is no more than 50% (e.g., no more than 40%, no more than 30%, no more than 25%, no more than 20%, no more than 10%, no more than 5%, no more than 1%, no more than 0.1%, etc.) of a total quantity of sites of the plurality of sites of a single-analyte array. In some cases, a total quantity of signals detected at the one or more interstitial regions during any individual cycle of the last 10 cycles, first 10 cycles, or middle 10 cycles of an array-based process is no more than 50% (e.g., no more than 40%, no more than 30%, no more than 25%, no more than 20%, no more than 10%, no more than 5%, no more than 1%, no more than 0.1%, etc.) of a total quantity of sites of the plurality of sites of the single-analyte array.

In another aspect, provided herein is a method, comprising: (a) binding in the presence of a first binding reagent association medium a first plurality of binding reagents to analytes at sites of a plurality of sites of the single-analyte array, (b) dissociating in the presence of a first binding reagent dissociation medium the first plurality of binding reagents from the analytes at the sites of the plurality of sites, (c) binding in the presence of a second binding reagent association medium a second plurality of binding reagents to analytes at sites of a plurality of sites of the single-analyte array, and (d) dissociating in the presence of a second binding reagent dissociation medium the second plurality of binding reagents from the analytes at the sites of the plurality of sites. In some cases, the first plurality of binding reagents can differ (e.g., with respect to binding specificity, with respect to type of binding reagent, with respect to type of particle or nanoparticle, with respect to binding reagent amount or concentration, etc.) from the second plurality of binding reagents. In other cases, the first plurality of binding reagents may be the same (e.g., with respect to binding specificity, with respect to type of binding reagent, with respect to type of particle or nanoparticle, with respect to binding reagent amount or concentration, etc.) as the second plurality of binding reagents.

In some cases, a method may comprise separate steps of providing a first plurality of binding reagents and providing a second plurality of binding reagents, in which binding reagents of the first plurality of binding reagents are attached to a first type of particle, and binding reagents of the second plurality of binding reagents are attached to a second type of particle. In some cases, the first type of particle and the second type of particle both comprise nucleic acid nanoparticles. In some cases, each individual nucleic acid nanoparticle comprises three or more hybridized oligonucleotides. In particular cases, the three or more hybridized oligonucleotides of the first type of particle differ from the three or more hybridized oligonucleotides of the second type of particle with respect to nucleotide sequences of the three or more oligonucleotides. In some cases, the first type of particle differs from the second type of particle with respect to particle morphology. For example, types of particles may differ with respect to hydrodynamic ratio, aspect ratio, curvature, surface area, etc.). In some cases, the first type of particle or the second type of particle may be substantially devoid of nucleic acid.

In some cases, a method may comprise binding a first plurality of binding reagents and a second plurality of binding reagents at separate times. In some cases, the first plurality of binding reagents may be bound in the presence of a first binding reagent association medium, and the second plurality of binding reagents may be bound in the presence of a second binding reagent association medium, in which the first binding reagent association medium and the second binding reagent association medium may have the same or substantially similar compositions. In other cases, the first plurality of binding reagents may be bound in the presence of a first binding reagent association medium, and the second plurality of binding reagents may be bound in the presence of a second binding reagent association medium, in which the first binding reagent association medium and the second binding reagent association medium may have differing compositions. In some cases, the first plurality of binding reagents may be dissociated in the presence of a first binding reagent dissociation medium, and the second plurality of binding reagents may be dissociated in the presence of a second binding reagent dissociation medium, in which the first binding reagent dissociation medium and the second binding reagent dissociation medium may have the same or substantially similar compositions. In other cases, the first plurality of binding reagents may be dissociated in the presence of a first binding reagent dissociation medium, and the second plurality of binding reagents may be dissociated in the presence of a second binding reagent dissociation medium, in which the first binding reagent dissociation medium and the second binding reagent dissociation medium may have differing compositions. The suitability of a binding reagent association medium or binding reagent dissociation medium for a particular binding reagent may be determined by a method set forth herein.

Systems of Fluidic Media

In an aspect, provided herein is a method, comprising performing on a single-analyte array at least 10 cycles (e.g., at least 20 cycles, at least 30 cycles, at least 40 cycles, at least 50 cycles, at least 75 cycles, at least 100 cycles, at least 150 cycles, at least 200 cycles, at least 250 cycles, at least 500 cycles, etc.) of a process, in which each individual cycle of the at least 10 cycles comprises the steps of: (a) binding in the presence of a binding reagent association medium binding reagents to analytes at sites of a plurality of sites of the single-analyte array, (b) detecting at each individual site of the plurality of sites a presence or an absence of a signal from a binding reagent of the binding reagents, and (c) dissociating in the presence of a binding reagent dissociation medium the binding reagents from the analytes at the sites of the plurality of sites, in which at least one signal is detected at each individual site of at least 90% (e.g., at least 95%, at least 99%, at least 99.5%, at least 99.9%, etc.) of sites of the plurality of sites during at least one cycle of the final N cycles (e.g., N=1, 2, 3, 4, 5, 6, 7, 8, 9, 10, etc) of the at least 10 cycles (e.g., at least 20 cycles, at least 30 cycles, at least 40 cycles, at least 50 cycles, at least 75 cycles, at least 100 cycles, at least 150 cycles, at least 200 cycles, at least 250 cycles, at least 500 cycles, etc.) of the process.

In another aspect, provided herein is a method, comprising performing on a single-analyte array at least 10 cycles (e.g., at least 20 cycles, at least 30 cycles, at least 40 cycles, at least 50 cycles, at least 75 cycles, at least 100 cycles, at least 150 cycles, at least 200 cycles, at least 250 cycles, at least 500 cycles, etc.) of a process, in which each individual cycle of the at least 10 cycles comprises the steps of: (a) binding in the presence of a binding reagent association medium binding reagents to analytes at sites of a plurality of sites of the single-analyte array, (b) detecting at each individual site of the plurality of sites a presence or an absence of a signal from a binding reagent of the binding reagents, and (c) dissociating in the presence of a binding reagent dissociation medium the binding reagents from the analytes at the sites of the plurality of sites, in which a binding anomaly is identified at no more than 20% (e.g., no more than 15%, no more than 10%, no more than 5%, no more than 1%, no more than 0.5%, no more than 0.1%, etc.) of individual sites of the plurality of sites during the final N cycles (e.g., N=1, 2, 3, 4, 5, 6, 7, 8, 9, 10, etc.) of the at least 10 cycles (e.g., at least 20 cycles, at least 30 cycles, at least 40 cycles, at least 50 cycles, at least 75 cycles, at least 100 cycles, at least 150 cycles, at least 200 cycles, at least 250 cycles, at least 500 cycles, etc.) of the process.

In another aspect, provided herein is a method, comprising performing on a single-analyte array at least 10 cycles (e.g., at least 20 cycles, at least 30 cycles, at least 40 cycles, at least 50 cycles, at least 75 cycles, at least 100 cycles, at least 150 cycles, at least 200 cycles, at least 250 cycles, at least 500 cycles, etc.) of a process, in which each individual cycle of the at least 10 cycles comprises the steps of: (a) binding in the presence of a binding reagent association medium binding reagents to analytes at sites of a plurality of sites of the single-analyte array, (b) detecting at each individual site of the plurality of sites a presence or an absence of a signal from a binding reagent of the binding reagents, and (c) dissociating in the presence of a binding reagent dissociation medium the binding reagents from the analytes at the sites of the plurality of sites, in which a binding anomaly is identified at no more than 10% (e.g., no more than 5%, no more than 1%, no more than 0.5%, no more than 0.1%) of individual sites of the plurality of sites during any individual cycle of the final N cycles (e.g., N=1, 2, 3, 4, 5, 6, 7, 8, 9, 10, etc.) of the at least 10 cycles (e.g., at least 20 cycles, at least 30 cycles, at least 40 cycles, at least 50 cycles, at least 75 cycles, at least 100 cycles, at least 150 cycles, at least 200 cycles, at least 250 cycles, at least 500 cycles, etc.) of the process.

In another aspect, provided herein is a method, comprising performing on a single-analyte array at least 10 cycles (e.g., at least 20 cycles, at least 30 cycles, at least 40 cycles, at least 50 cycles, at least 75 cycles, at least 100 cycles, at least 150 cycles, at least 200 cycles, at least 250 cycles, at least 500 cycles, etc.) of a process, in which each individual cycle of the at least 10 cycles comprises the steps of: (a) binding in the presence of a binding reagent association medium binding reagents to analytes at sites of a plurality of sites of the single-analyte array, (b) detecting at each individual site of the plurality of sites a presence or an absence of a signal from a binding reagent of the binding reagents, and (c) dissociating in the presence of a binding reagent dissociation medium the binding reagents from the analytes at the sites of the plurality of sites, in which, for any two consecutive cycles of the at least 10 cycles, a presence of a signal is detected from each individual site of a first subset of sites of the plurality of sites during the first cycle of the two consecutive cycles, and in which an absence of a signal is detected from at least 90% (e.g., at least 95%, at least 99%, at least 99.5%, at least 99.9%, etc.) of individual sites of the first subset of sites during the second cycle of the at least two consecutive cycles.

In another aspect, provided herein is a method, comprising performing on a single-analyte array at least 10 cycles (e.g., at least 20 cycles, at least 30 cycles, at least 40 cycles, at least 50 cycles, at least 75 cycles, at least 100 cycles, at least 150 cycles, at least 200 cycles, at least 250 cycles, at least 500 cycles, etc.) of a process, wherein each individual cycle of the process comprises the steps of: (a) binding, in the presence of a binding reagent association medium, binding reagents to analytes at sites of a plurality of sites of the single-analyte array, (b) detecting at each individual site of the plurality of sites a presence or an absence of a signal from a binding reagent of the binding reagents, and (c) dissociating, in the presence of a binding reagent dissociation medium, the binding reagents from the analytes at the sites of the plurality of sites, in which the binding reagent association medium comprises a polymeric blocking reagent, in which the binding reagent dissociation medium comprises a zwitterionic surfactant, and in which a signal is detected at each individual site of no more than 10% of sites (e.g., no more than 9%, 8%, 7%, 6%, 5%, 4%, 3%, 2%, 1%, 0.5%, 0.1%, 0.01%, or less than 0.01%) of the plurality of sites during more than 2 consecutive cycles (e.g., 3, 4, 5 consecutive cycles) of the final 10 cycles of the at least 10 cycles of the process.

A signal can refer to a detection event by a detection system that exceeds a background level or magnitude. For example, a pixel-based array for optical detection can be expected to have some amount of background noise that produces a spatially- or temporally-variable background signal. A signal may refer to a spatially- and/or temporally-localized detection event that exceeds this background signal.

In some cases, a signal may be considered to be located at a site if a signal is detected in a region of interest that contains the site. For example, when optical signals are detected by a pixel-based array, individual pixels of the pixel-based array may be aligned with a surface of an array of analytes such that the individual pixels map to discrete regions of interest of the surface of the array of analytes. Accordingly, emission of a signal from a region of interest of an array of analytes (e.g., a signal emitted from a detectable binding reagent bound at an array site) can be detected at a particular pixel or set of pixels of a pixel-based array that map to the region of interest. In cases where site pitch of an array of analytes and absolute position of a signal detection system relative to the array of analytes is known, detection of a signal or signals at a region of interest can be considered to correspond to detection of a signal or signals at a site within the region of interest.

FIG. 1 depicts a schematic diagram of a system 100 for detecting binding interactions of binding reagents with analytes of an array of analytes. The system 100 contains a fluidic cartridge or flow cell 130 comprising a volume or chamber 131. Disposed on a surface of the volume or chamber 131 is an array of analytes 140. The array of analytes 140 could be disposed on a separate solid support that is incorporated into the fluidic cartridge or flow cell 130, or could be disposed on a surface of the body of the fluidic cartridge or flow cell 130. In some cases, the analytes 140 may be substantially homogeneous (e.g., with respect to a type, species, isoform, size, or other property). For example, a plurality of analytes 140 may be substantially all polypeptides, or may be substantially a single species of polypeptides. In other cases, the analytes 140 may be substantially heterogeneous (e.g., with respect to a type, species, isoform, size, or other property). For example, a plurality of analytes 140 may be a mixture of polypeptides, lipids, and polysaccharides, or may be a mixture of polypeptide species (such as proteomic or sub-proteomic sample). In some cases, the analytes 140 may be bound to sites S that are separated by interstitial regions I. In some cases, the sites S may be ordered or patterned such that the sites S have a substantially uniform spacing or pitch between sites S, and/or a substantially uniform characteristic dimension (e.g., diameter, length, width, height, etc.). In other cases, the sites S may be disordered or unpatterned. Binding reagents 141 may be bound to analytes 140. The binding reagents 141 may be bound to analytes 140 with a random spatial distribution (i.e., the sites S at which binding reagents 141 are detectable lack a regular or repeating spatial pattern). The binding reagents 141 may be configured to produce a detectable signal 142 such that a physical address containing a binding reagent 141 can be detected by a detection device 150.

Continuing with FIG. 1, the fluidic cartridge or flow cell 130 may be in fluidic communication with a fluidic system comprising various fluidic components (e.g., fluid transfer conduits 120, fluid displacement devices 125, and various fluid reservoirs 112, 113, and 114). The fluid transfer conduits 120 may inject or withdraw fluid into the fluidic cartridge or flow cell 130 through a first port 127 or a second port 128. The system 100 depicted in FIG. 1 is configured for fluid injection through the first port 127, and fluid discharge through the second port 128, but the system can be reconfigured for bidirectional fluid transfer, for example by connecting a fluid transfer conduit 120 to both the first port 127 and the second port 128. In some configurations, fluidic communication may be provided by a fixed fluidic conduit 120 (e.g., a plumbed pipe or tube connected to the fluidic cartridge or flow cell 130). In other configurations, fluidic communication may be provided by a discontinuous fluidic connection (e.g., a robotic, automated, or manual pipetting apparatus). In some configurations, a fluidic cartridge or flow cell 130 may comprise a manifold (not pictured in FIG. 1) that facilitates fluid transfer into and/or out of the fluidic cartridge or flow cell 130.

Continuing with FIG. 1, a fluidic system of a system 100 may comprise reservoirs containing various fluidic media, as set forth herein. FIG. 1 depicts reservoirs 112, 113, and 114, each of which is in fluidic communication with a fluidic conduit 120. The system 100 may, for example, contain a first reservoir 112 containing a detection medium, a second reservoir 113 containing a rinsing medium, and a third reservoir 114 containing a binding reagent dissociation medium. The fluidic system may also comprise a fluidic library 110 comprising a plurality of reservoirs 111. In some configurations, each reservoir of the plurality of reservoirs 111 may comprise a plurality of binding reagents in a binding reagent association medium. In particular configurations, each reservoir of the plurality of reservoirs 111 may comprise a plurality of binding reagents 141 in a binding reagent association medium, in which each plurality of binding reagents 141 is distinguished from other pluralities of binding reagents 141 by a binding specificity of the plurality of binding reagents. For example, a first reservoir may contain a plurality of binding reagents 141 with a binding specificity for a first polypeptide epitope, and a second reservoir may contain a plurality of binding reagents 141 with a binding specificity for a second polypeptide epitope.

Continuing with FIG. 1, a system 100 may further comprise a detection device 150. The detection device may comprise an optical detection device containing optical components 151 (e.g., an objective lens, a tube lens, a dichroic mirror, etc.) and a sensing device (e.g., a pixel-based array, a camera, etc.). The detection device 150 may be configured to detect a signal 142 provided by a binding reagent 141. In some configurations, a system 100 may further comprise a signal stimulation device 155. FIG. 1 depicts a signal stimulation device 155 that emits a light field for fluorescent signal generation (e.g., a laser, an LED, a bulb, a filament, etc.). In other configurations, a signal stimulation device 155 could be used, for example, to stimulate a chemiluminescent signal (e.g., a device that transfer a luminogenic substrate into the fluidic cartridge or flow cell 130 through the fluidic system) or a thermoluminescent signal (e.g., a temperature-modulating device that alters a temperature of the environment within the fluidic cartridge or flow cell 130).

Figure 2:
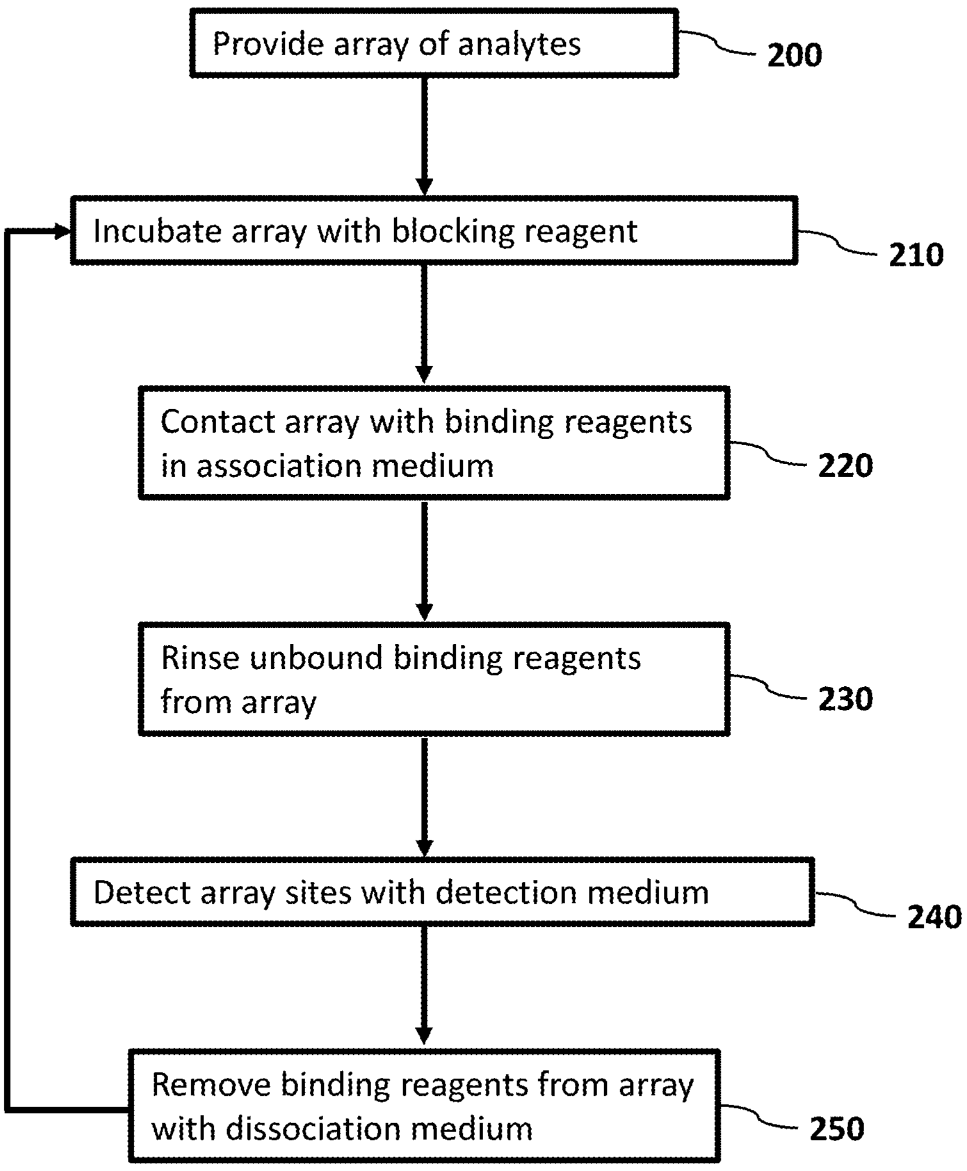
FIG. 2 shows a flow chart describing steps of an array-based process utilizing multiple fluidic media, in accordance with some embodiments.

Turning to FIG. 2, the depicted flow chart represents an array-based process that can be performed, for example, on the system 100 of FIG. 1. In a first step 200, an array of analytes 140 may be provided to a system 100. In a preferable configuration, the array of analytes 140 may be provided such that analytes 140 of the array of analytes 140 are bound at individual addresses such that each analyte can be individually interrogated. In another preferable configuration, the array of analytes 140 may be provided such that the array comprises a plurality of sites, in which each individual site of the plurality of sites is resolvable at single-analyte resolution, and in which each individual site of the plurality of sites comprises one and only one analyte 140.

Continuing with FIG. 2, a second step 210 of a method may comprise incubating the array of analytes 140 with a blocking reagent. A blocking reagent may comprise a molecule, particle, or moiety that binds to a defect of an array, fluidic cartridge, flow cell 130, or a surface thereof. In some cases, incubating with a blocking reagent 210 may occur before analytes 140 have been deposited at array sites. In other cases, incubation with a blocking reagent may occur after analytes 140 have been deposited at array sites. FIG. 2 depicts a cyclical, array-based method, in which a series or sequence of steps may be repeated. In some cyclical methods, the incubating step 210 may be performed during a first cycle, and omitted during subsequent cycles. In some cases, the incubating step 210 may be performed during each cycle of a cyclical method. In other cases, the incubating step 210 may be performed at a regular or recurring interval, such as once about every 2 cycles, 5 cycles, 10 cycles, 20 cycles, etc. In yet other cases, the incubating step 210 may be performed at a random or irregular interval. A frequency of performing the incubating step 210 may be determined, at least in part, on detection of one or more signal anomalies that suggest a presence and/or increasing rate of orthogonal binding of binding reagents 141 to the array or a surface thereof. Incubating with a blocking reagent 210 may comprise contacting the array of analytes 140 with a fluidic medium comprising the blocking reagent. Optionally, the fluidic medium containing the blocking reagent may be substantially devoid of binding reagents during the incubating step 210. Optionally, the fluidic medium containing the blocking reagent may comprise a binding anomaly detection standard, as set forth herein.

Continuing with FIG. 2, a third step 220 may comprise contacting the array of analytes 140 with a binding reagent association medium containing a plurality of binding reagents 141. In a preferable embodiment, the binding reagent association medium may comprise: i) the plurality of binding reagents 141, and ii) a blocking reagent. Optionally, the binding reagent association medium may further comprise a binding anomaly detection standard, as set forth herein. Contacting the binding reagent association medium 220 with the array of analytes 140 may occur for at least about 1 second (s), 15 s, 30 s, 1 minute (min), 2 mins, 5 mins, 10 mins, 15 mins, 20 mins, 30 mins, 1 hour, or more than 1 hour. Alternatively or additionally, contacting the binding reagent association medium 220 with the array of analytes 140 may occur for no more than about 1 hour, 30 mins, 20 mins, 15 mins, 10 mins, 5 mins, 2 mins, 1 min, 30 s, 15 s, 1 s, or less than 1 s.

Continuing with FIG. 2, a fourth step 230 may comprise rinsing unbound binding reagents 141 from the array of analytes 140. In some cases, rinsing 230 unbound binding reagents 141 from the array of analytes 140 may be repeated one or more times. In some cases, rinsing 230 unbound binding reagents 141 from the array of analytes 140 may comprise displacing a volume of binding reagent association medium from an array of analytes 140 or chamber 131 of a fluidic cartridge or flow cell 130. Rinsing 230 unbound binding reagents 141 from the array of analytes 140 may comprise utilizing a volume of a rinsing medium in a ratio to a volume of a chamber 131 of at least about 0.1, 0.5, 1, 1.5, 2, 3, 4, 5, 10, 15, 20, or more than 20. Alternatively or additionally, rinsing 230 unbound binding reagents 141 from the array of analytes 140 may comprise utilizing a volume of a rinsing medium in a ratio to a volume of a chamber 131 of no more than about 20, 15, 10, 5, 4, 3, 2, 1, 1.5, 1, 0.5, 0.1, or less than 0.1. Optionally, a rinsing medium may comprise: i) a blocking reagent, and ii) a binding anomaly detection standard, as set forth herein. Additional rinsing steps may be performed during an array-based method, such as after a detecting step 240, or after a removing or dissociating step 250. Optionally, a rinsing step may be omitted. For example, a detection medium may be displaced from a fluidic cartridge or flow cell 130 by a binding reagent dissociation medium rather than a rinsing medium. Contacting the detection medium 240 with the array of analytes 140 may occur for at least about 1 second (s), 15 s, 30 s, 1 minute (min), 2 mins, 5 mins, 10 mins, 15 mins, 20 mins, 30 mins, 1 hour, or more than 1 hour. Alternatively or additionally, contacting the detection medium 240 with the array of analytes 140 may occur for no more than about 1 hour, 30 mins, 20 mins, 15 mins, 10 mins, 5 mins, 2 mins, 1 min, 30 s, 15 s, 1 s, or less than 1 s. The time length for contact of a detection medium with an array of analytes 140 may be determined by a detection rate or speed of a detection device 150.

Continuing with FIG. 2, a fifth step 240 may comprise detecting a presence or absence of binding reagents 141 at array sites of a plurality of array sites of an array of analytes 140. Detecting 240 the presence or absence of binding reagents 141 at array sites may comprise contacting the array of analytes 140 with a detection medium. The detection medium may comprise one or more of: i) a photodamage inhibitor, as set forth herein, ii) a blocking reagent, and iii) a binding anomaly detection standard. Detecting 240 the presence or absence of binding reagents 141 at array sites may further comprise contacting the array of analytes with light from a signal stimulation device 155 (e.g., a light field containing light of a fluorescent excitation wavelength of a binding reagent 141). Detecting 240 the presence or absence of binding reagents 141 at array sites may comprise detecting a presence or absence of signals 142 from binding reagents 141 at addresses corresponding to the array sites of the array of analyte 140. In some cases, detecting 240 the presence or absence of binding reagents 141 at array sites may comprise detecting at each individual site of a plurality of sites a presence or absence of an individual binding reagent 141. In some cases, detecting 240 the presence or absence of binding reagents 141 at array sites may comprise detecting at an array site presence of two or more binding reagents 141.

Continuing with FIG. 2, a sixth step 250 may comprise removing or dissociating binding reagents 141 from the array of analytes 140 in the presence of a binding reagent dissociation medium. A binding reagent dissociation medium may comprise one or more of: i) a binding reagent disruption agent (e.g., a chaotrope, a denaturant, etc.), ii) a blocking reagent, and iii) a binding anomaly detection standard. Removing or dissociating 250 binding reagents 141 from the array of analytes 140 may comprise contacting the array of analytes with the binding reagent dissociation medium. Contacting the binding reagent dissociation medium 220 with the array of analytes 140 may occur for at least about 1 second (s), 15 s, 30 s, 1 minute (min), 2 mins, 5 mins, 10 mins, 15 mins, 20 mins, 30 mins, 1 hour, or more than 1 hour. Alternatively or additionally, contacting the binding reagent dissociation medium 220 with the array of analytes 140 may occur for no more than about 1 hour, 30 mins, 20 mins, 15 mins, 10 mins, 5 mins, 2 mins, 1 min, 30 s, 15 s, 1 s, or less than 1 s.

The skilled person will readily recognize numerous variations to the array-based method of FIG. 2. Optionally, individual steps can differ between cycles. For example, each cycle can be performed by contacting the array with a different binding reagent, respectively. Moreover, blocking agents can differ from one cycle to another, rinse medium can differ from one cycle to another or detection medium can differ from one cycle to another. Other variations between cycles can include differences in duration, temperature or other condition for a given step, or differences in detector configurations. It will be understood that, in at least some cases, two or more cycles can be repeated using the same binding reagent or same conditions. In some cases, a method may comprise a sequence or cycle of steps. For example, a method may comprise a cycle of contacting 220 binding reagents 141 with an array of analytes 140, detecting 240 binding reagents 141, and dissociating 250 binding reagents 141, in which each cycle comprises contacting 220 a differing plurality of binding reagents with the array of analytes 140 (e.g., as distinguished by binding specificity of each plurality of binding reagents 141 contacted to the array of analytes 140).

Figure 9A:
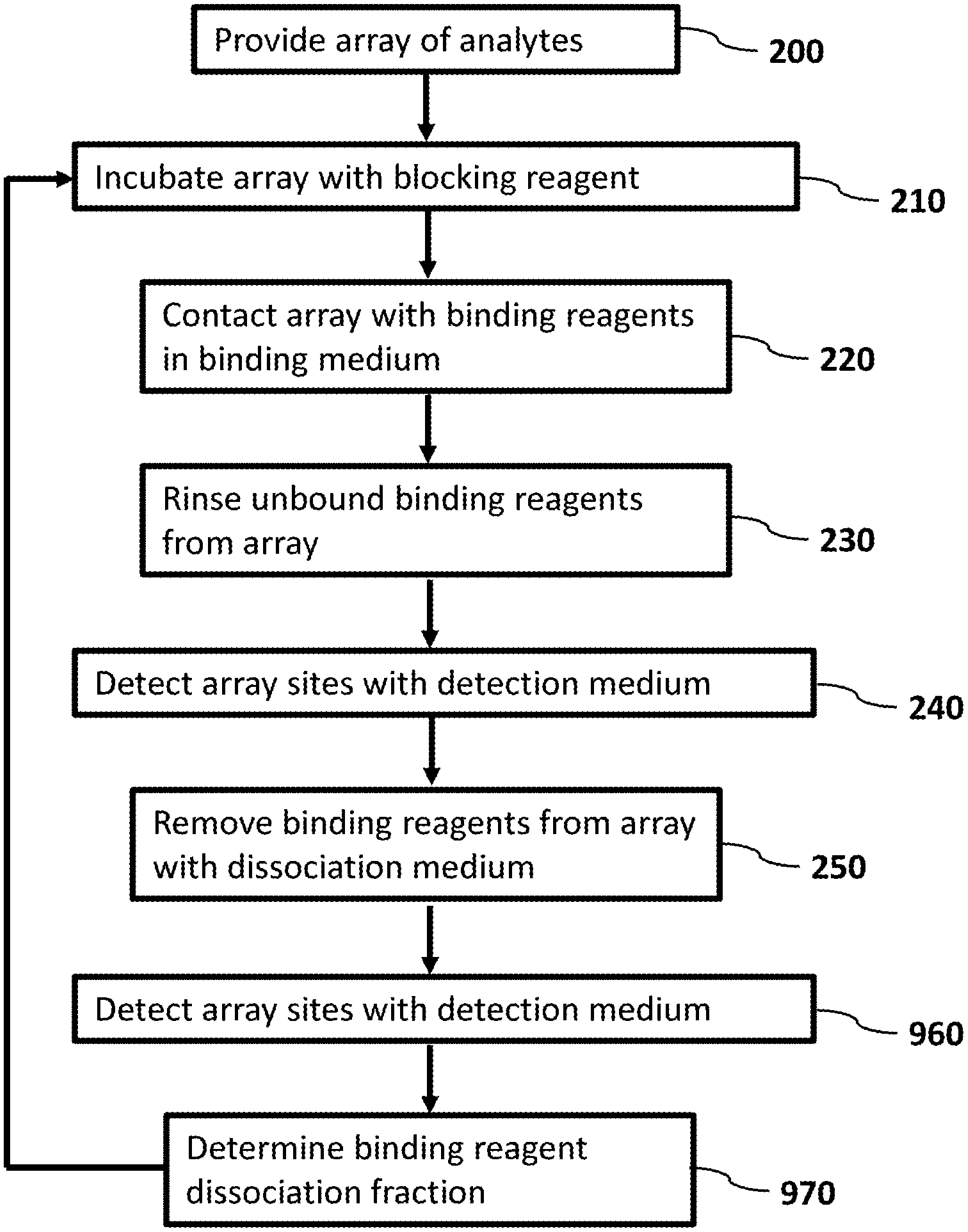
FIGS. 9A and 9B illustrate methods for determining binding anomaly fractions or binding reagent dissociation fractions, in accordance with some embodiments.
Figure 9B:
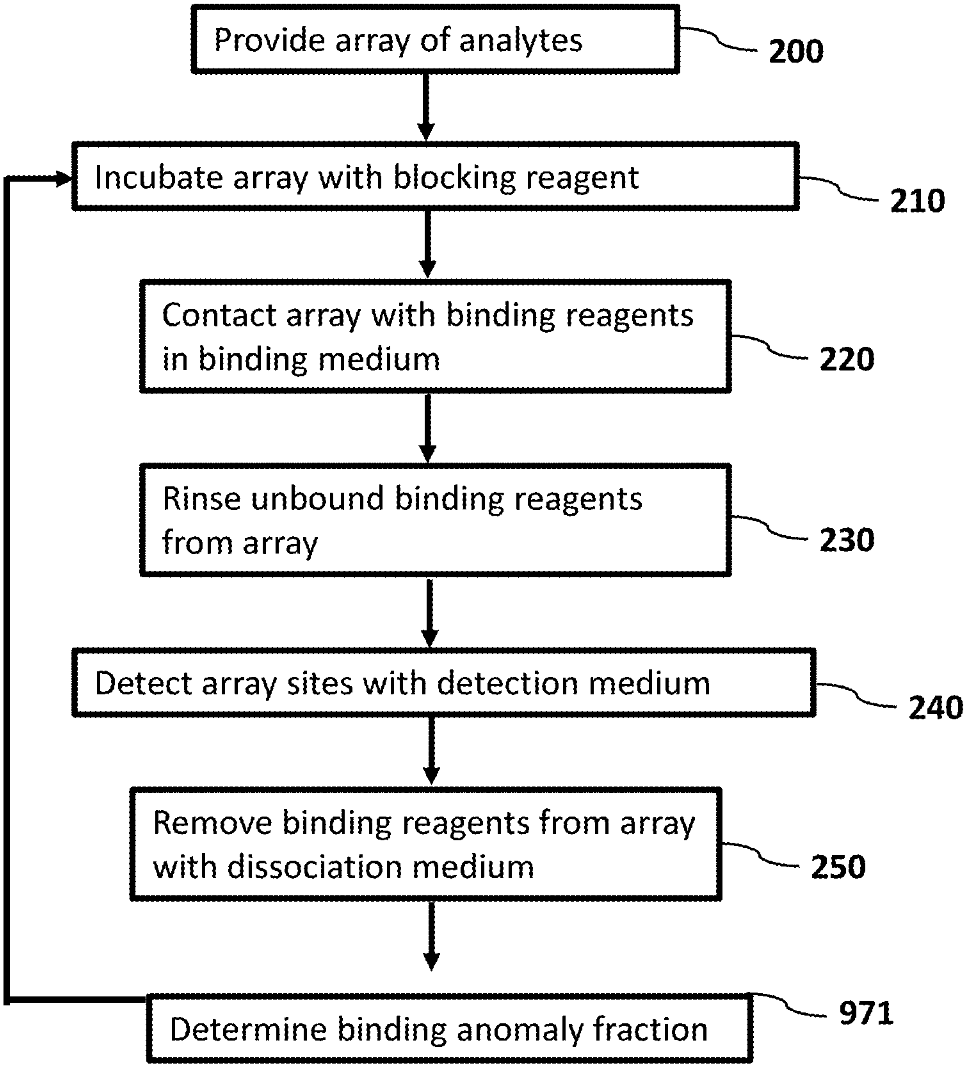

FIGS. 9A and 9B depict methods similar to the methods depicted in FIG. 2, but further including determination of a quantifiable binding behavior (e.g., a binding reagent dissociation fraction, a binding anomaly fraction). FIG. 9A depicts a method that includes steps 200 to 250 of FIG. 2. After providing the binding reagent dissociation medium, a second detecting step 960 is performed to determine a presence or absence of a signal from a binding reagent at each individual site of the plurality of sites. After the second detecting step 960, a binding reagent dissociation fraction may be determined 970 utilizing signal data determined from the first detection step 240 and the second detection step 960. Optionally, one or more steps may be repeated (e.g., performing the cycle with a different binding reagent) after determining the binding reagent dissociation fraction 970. Alternatively, a binding anomaly fraction may be determined in step 970. FIG. 9B depicts a method that includes steps 200 to 250 of FIG. 2. After providing the binding reagent dissociation medium, a binding anomaly fraction may be determined 971 utilizing signal data from the detection step 240. In some cases, a binding anomaly fraction may further utilize signal data from a detection step of a previous cycle or sequence of steps. For example, if detection is performed only after a binding reagent association step (i.e., excluding detection after a binding reagent dissociation step), a binding anomaly may be identified from a presence of a signal at an array site for 2, 3, 4, or more than 4 consecutive detection steps.

The systems provided herein may contain a set or sequence of buffers that collectively inhibit and/or minimize sources of unintended signals during an array-based process. Alternatively, systems provided herein may contain a set or sequence of buffers, in which each buffer is configured to inhibit and/or minimize one or more sources of signals during an array-based process. A method performed on a system set forth herein may include characterizing or quantifying a rate associated with unintended signal detection, such as a binding reagent dissociation fraction or a binding anomaly fraction. In particular, characterization or quantification of a rate associated with unintended signal detection can be based on measurements of signals at single-analyte resolution (i.e., detection of presence or absence of signals at each individual site of a plurality of sites of a single-analyte array).

A rate of unintended signal detection as a basis for characterizing and/or quantifying system behavior or performance in a single-analyte array system may be based on the configuration of the system and the chosen method of use. For example, some methods may include detection steps after both a step of coupling binding reagents to analytes and a step of removing the coupled binding reagents from the analytes. Accordingly, a binding reagent dissociation fraction may be quantified directly from a quantity of sites providing a signal after coupling binding reagents and a quantity of sites providing a signal after removing the binding reagents. In another example, some methods may exclude a detection step after removing binding reagents from analytes (e.g., to minimize photodegradation processes like photodamage and photobleaching due to excessive light exposure). Accordingly, a binding reagent dissociation fraction may not be directly quantifiable, but may be inferred by methods such as the use of standard analytes or by a proxy measurement such as a binding anomaly fraction that can be correlated to a binding reagent dissociation fraction. The skilled person will readily recognize how variations in array configuration and methodology may impact analysis of system performance based upon availability of signal detection information.

In an aspect, provided herein is a method, comprising: a) binding binding reagents to an array of polypeptides, wherein the array of polypeptides comprises a plurality of sites, wherein each individual site of the plurality of sites comprises one and only one polypeptide, wherein each individual site of the plurality of sites is optically resolvable at single-molecule resolution, wherein binding the binding reagents to the array occurs in the presence of a binding reagent association medium, and wherein the binding reagent association medium comprises a non-polypeptide blocking agent, b) before dissociating the binding reagents from the array in the presence of a binding reagent dissociation medium, detecting at each individual site of the plurality of sites a presence or absence of a signal, wherein detecting the presence or absence of the signal occurs in the presence of a binding reagent detection medium, and wherein the binding reagent detection medium comprises an reaction inhibitor species; and c) after detecting at each individual site of the plurality of sites the presence or absence of the signal, dissociating the binding reagents from the array of polypeptides, wherein the binding reagent dissociation fraction is at least 95%.

In another aspect, provided herein is a method, comprising: a) binding binding reagents to an array of polypeptides, wherein the array of polypeptides comprises a plurality of sites, wherein each individual site of the plurality of sites comprises one and only one polypeptide, and wherein each individual site of the plurality of sites is optically resolvable at single-molecule resolution, b) before dissociating the binding reagents from the array in the presence of a binding reagent dissociation medium, detecting at each individual site of the plurality of sites a presence or absence of a signal, wherein detecting the presence or absence of the signal occurs in the presence of a binding reagent detection medium, and wherein the binding reagent detection medium comprises a reaction inhibitor species, and c) after detecting at each individual site of the plurality of sites the presence or absence of the signal, dissociating the binding reagents from the array of polypeptides, wherein dissociating the binding reagents from the array of polypeptides occurs in the presence of a binding reagent dissociation medium, and wherein the binding reagent dissociation fraction is at least 95%.

In another aspect, provided herein is a method, comprising: a) binding binding reagents to an array of polypeptides, wherein the array of polypeptides comprises a plurality of sites, wherein each individual site of the plurality of sites comprises one and only one polypeptide, wherein each individual site of the plurality of sites is optically resolvable at single-molecule resolution, wherein binding the binding reagents to the array occurs in the presence of a binding reagent association medium, and wherein the binding reagent association medium comprises a non-polypeptide blocking agent, b) before dissociating the binding reagents from the array in the presence of a binding reagent dissociation medium, detecting at each individual site of the plurality of sites a presence or absence of a signal, and c) after detecting at each individual site of the plurality of sites the presence or absence of the signal, dissociating the binding reagents from the array of polypeptides, wherein dissociating the binding reagents from the array of polypeptides occurs in the presence of a binding reagent dissociation medium, and wherein the binding reagent dissociation fraction is at least 95%.

In another aspect, provided herein is a method, comprising: a) binding binding reagents to an array of polypeptides, wherein the array of polypeptides comprises a plurality of sites, wherein each individual site of the plurality of sites comprises one and only one polypeptide, wherein each individual site of the plurality of sites is optically resolvable at single-molecule resolution, wherein binding the binding reagents to the array occurs in the presence of a binding reagent association medium, and wherein the binding reagent association medium comprises a non-polypeptide blocking agent, b) before dissociating the binding reagents from the array in the presence of a binding reagent dissociation medium, detecting at each individual site of the plurality of sites a presence or absence of a signal, wherein detecting the presence or absence of the signal occurs in the presence of a binding reagent detection medium, and wherein the binding reagent detection medium comprises a reaction inhibitor species, and c) after detecting at each individual site of the plurality of sites the presence or absence of the signal, dissociating the binding reagents from the array of polypeptides, wherein dissociating the binding reagents from the array of polypeptides occurs in the presence of a binding reagent dissociation medium, and wherein the binding reagent dissociation fraction is at least 99%.

In another aspect, provided herein is a method, comprising: a) binding binding reagents to an array of polypeptides, wherein the array of polypeptides comprises a plurality of sites, wherein each individual site of the plurality of sites comprises one and only one polypeptide, wherein each individual site of the plurality of sites is optically resolvable at single-molecule resolution, wherein binding the binding reagents to the array occurs in the presence of a binding reagent association medium, and wherein the binding reagent association medium comprises a non-polypeptide blocking agent, b) before dissociating the binding reagents from the array in the presence of a binding reagent dissociation medium, detecting at each individual site of the plurality of sites a presence or absence of a signal, wherein detecting the presence or absence of the signal occurs in the presence of a binding reagent detection medium, and wherein the binding reagent detection medium comprises a reaction inhibitor species; and c) after detecting at each individual site of the plurality of sites the presence or absence of the signal, dissociating the binding reagents from the array of polypeptides, wherein the binding anomaly fraction is no more than 5%.

In another aspect, provided herein is a method, comprising: a) binding binding reagents to an array of polypeptides, wherein the array of polypeptides comprises a plurality of sites, wherein each individual site of the plurality of sites comprises one and only one polypeptide, and wherein each individual site of the plurality of sites is optically resolvable at single-molecule resolution, b) before dissociating the binding reagents from the array in the presence of a binding reagent dissociation medium, detecting at each individual site of the plurality of sites a presence or absence of a signal, wherein detecting the presence or absence of the signal occurs in the presence of a binding reagent detection medium, and wherein the binding reagent detection medium comprises a reaction inhibitor species, and c) after detecting at each individual site of the plurality of sites the presence or absence of the signal, dissociating the binding reagents from the array of polypeptides, wherein dissociating the binding reagents from the array of polypeptides occurs in the presence of a binding reagent dissociation medium, and wherein the wherein the binding anomaly fraction is no more than 5%.

In another aspect, provided herein is a method, comprising: a) binding binding reagents to an array of polypeptides, wherein the array of polypeptides comprises a plurality of sites, wherein each individual site of the plurality of sites comprises one and only one polypeptide, wherein each individual site of the plurality of sites is optically resolvable at single-molecule resolution, wherein binding the binding reagents to the array occurs in the presence of a binding reagent association medium, and wherein the binding reagent association medium comprises a non-polypeptide blocking agent, b) before dissociating the binding reagents from the array in the presence of a binding reagent dissociation medium, detecting at each individual site of the plurality of sites a presence or absence of a signal, and c) after detecting at each individual site of the plurality of sites the presence or absence of the signal, dissociating the binding reagents from the array of polypeptides, wherein dissociating the binding reagents from the array of polypeptides occurs in the presence of a binding reagent dissociation medium, and wherein the wherein the binding anomaly fraction is no more than 5%.

In another aspect, provided herein is a method, comprising: a) binding binding reagents to an array of polypeptides, wherein the array of polypeptides comprises a plurality of sites, wherein each individual site of the plurality of sites comprises one and only one polypeptide, wherein each individual site of the plurality of sites is optically resolvable at single-molecule resolution, wherein binding the binding reagents to the array occurs in the presence of a binding reagent association medium, and wherein the binding reagent association medium comprises a non-polypeptide blocking agent, b) before dissociating the binding reagents from the array in the presence of a binding reagent dissociation medium, detecting at each individual site of the plurality of sites a presence or absence of a signal, wherein detecting the presence or absence of the signal occurs in the presence of a binding reagent detection medium, and wherein the binding reagent detection medium comprises a reaction inhibitor species, and c) after detecting at each individual site of the plurality of sites the presence or absence of the signal, dissociating the binding reagents from the array of polypeptides, wherein dissociating the binding reagents from the array of polypeptides occurs in the presence of a binding reagent dissociation medium, and wherein the wherein the binding anomaly fraction is no more than 1%.

A fluidic medium set forth herein, such as a binding reagent association medium, a detection medium, a binding reagent dissociation medium, or a rinsing medium, may comprise a blocking reagent. Choice of blocking reagent may be guided, in whole or in part, by the chemical nature of analytes on an array of analytes. For example, it may be preferable to use a non-polypeptide blocking reagent for an assay utilizing a polypeptide array. Likewise, it may be preferable to use a non-polysaccharide blocking reagent for an assay utilizing a polysaccharide array. In some cases, the blocking reagent may comprise a polypeptide blocking reagent (e.g., bovine serum albumin, human serum albumin, etc.). In some cases, the blocking reagent may comprise a non-polypeptide blocking reagent (e.g., a polysaccharide blocking reagent, a polymeric blocking reagent, a cationic blocking reagent, an anionic blocking reagent, a zwitterionic blocking reagent, a non-ionic blocking reagent). In some cases, the blocking reagent may comprise a non-polysaccharide blocking reagent. In some cases, the blocking reagent may comprise a non-nucleic acid blocking reagent. In some cases, a fluidic medium, as set forth herein, may be substantially devoid of a polypeptide blocking reagent (e.g., bovine serum albumin, human serum albumin, or an engineered variant thereof). In some cases, a fluidic medium, as set forth herein, may be substantially devoid of a polysaccharide blocking reagent (e.g., dextran sulfate, dextran carboxylate, etc.). In some cases, a fluidic medium, as set forth herein, may be substantially devoid of a nucleic acid blocking reagent (e.g., sheared salmon DNA). In some cases, a fluidic medium may comprise a polypeptide blocking agent (e.g., bovine serum albumin, human serum albumin, or an engineered variant thereof). In some cases, a fluidic medium may comprise a polypeptide blocking agent and a non-polypeptide blocking agent (e.g., a medium comprising bovine serum albumin and a polymer blocking agent such as polyvinylpyrrolidone, PF-127, or a dextran compound).

In some cases, a fluidic medium set forth herein, such as a binding reagent association medium, a detection medium, a binding reagent dissociation medium, or a rinsing medium, may comprise two or more blocking reagents. Two or more non-polypeptide blocking agents can be selected independently from the group consisting of an ionic polymer, a zwitterionic polymer, a non-ionic polymer, a cationic surfactant, an anionic surfactant, a non-ionic surfactant, a saccharide, a stabilizing agent, and an amphiphilic agent. In some cases, a non-polypeptide blocking agent of the two or more non-polypeptide blocking agents can be a cationic polymer or an anionic polymer. In some cases, a non-polypeptide blocking agent of the two or more non-polypeptide blocking agents is a nucleic acid (e.g., a DNA, RNA, PNA, LNA, a combination thereof, or a modified version thereof). In some cases, a first non-polypeptide blocking reagent of two or more non-polypeptide blocking reagents may comprise a non-ionic polymer and a second non-polypeptide blocking reagent of two or more non-polypeptide blocking reagents may comprise an anionic polymer or a cationic polymer.

A plurality of binding reagents may be contacted to an array of analytes, as set forth herein. A plurality of binding reagents may be disposed within a binding reagent association medium, as set forth herein. In some cases, contacting a plurality of binding reagents to an array of analytes may comprise contacting a binding reagent association medium containing the plurality of binding reagents with the array of analytes. In some cases, contacting a plurality of binding reagents to an array of analytes may comprise: i) contacting a first binding reagent association medium containing the plurality of binding reagents with the array of analytes, and ii) contacting a second binding reagent association medium with the array of analytes, in which the second binding reagent association medium is substantially devoid of binding reagents. For example, a method may comprise the steps of first contacting a plurality of binding reagents with an array of analytes in a first binding reagent association medium with a first fluid property (e.g., pH, ionic strength, temperature, concentration, etc.), then contacting the array of analytes with a second binding reagent association medium with a second fluid property (e.g., a differing pH, ionic strength, temperature, concentration, etc.). In a preferable configuration, a binding reagent association medium may comprise one or more of: i) a blocking reagent, and ii) a binding anomaly detection standard.

A method may comprise a step of detecting presence or absence of a binding reagent at a site of a plurality of sites in the presence of a detection medium. A detection medium may comprise a reactive inhibitor species or a photodamage inhibitor. A reactive inhibitor species or photodamage inhibitor may be configured to prevent false detection events, for example by inhibiting photo-catalyzed cross-linking of binding reagents to analytes or other array components, or by inhibiting photo-catalyzed formation of defects on an array or a surface thereof. A reactive inhibitor species or photodamage inhibitor may comprise a radical scavenger species, an antioxidant, or a reactive oxygen scavenger species. In some cases, a detection medium may comprise two or more reactive inhibitor species or photodamage inhibitors. It may be advantageous to provide two or more reactive inhibitor species or photodamage inhibitors, in which the two or more reactive inhibitor species or photodamage inhibitors inhibit or prevent different reactive pathways. For example, a detection medium may comprise an antioxidant and a reactive oxygen scavenger (e.g., ascorbic acid or a suitable antioxidant replacement thereof, and sodium sulfite, a reactive oxygen scavenger). In some cases, a detection medium may comprise a blocking reagent, such as a non-polypeptide blocking reagent. In other cases, a detection medium may be substantially devoid of a blocking reagent.

A reactive inhibitor species or photodamage inhibitor may comprise a reactive oxygen scavenger. A reactive oxygen scavenger may comprise any chemical species that is capable of reacting with a reactive oxygen species (e.g., singlet oxygen, oxygen-containing radicals such as hydroxyl radical or peroxyl radical, nitric oxide species, oxygenated anions such as peroxynitrite or superoxide anion, etc.) in a fluidic medium. Exemplary reactive oxygen scavengers can include sodium pyruvate, N,N-dimethylthiourea (DMTU), mannitol, dimethyl sulfoxide (DMSO), carboxy-PTIO, 6-hydroxy-2,5,7,8-tetramethylchroman-2-carboxylic acid, alpha-tocopherol, 2-phenyl-1,2-benzisoselenazol-3(2H)-one, uric acid, sodium azide, manganese(III)-tetrakis(4-benzoic acid)porphyrin (MnTBAP), 4,5-dihydroxybenzene-1,3-disulfonate, and combinations thereof. In some cases, a fluidic medium may comprise two or more species of reactive oxygen scavengers.

A reactive inhibitor species or photodamage inhibitor may comprise a free radical scavenger. A free radical scavenger may comprise any chemical species that is capable of reacting with a free radical species in a fluidic medium. Exemplary free radical scavengers can include enzymatic free radical scavengers (e.g., catalase, superoxide dismutase, glutathione peroxidase) and non-enzymatic free radical scavengers (e.g., ascorbic acid, tocopherols, tocotrienols, beta-carotene, glutathione, melatonin, and uric acid). In some cases, a fluidic medium may comprise two or more species of free radical scavengers.

A method may comprise detecting at each individual site of a plurality of sites presence or absence of a signal from a binding reagent. In some cases, a signal from a binding reagent may comprise a fluorescence signal, a luminescence signal, or a luminescence lifetime signal. In some cases, detecting at each individual site of the plurality of sites the presence or the absence of the signal from the binding reagent comprises contacting an individual site of the plurality of sites with electromagnetic radiation (e.g., light from a signal stimulation device). In some cases, contacting the individual site of the plurality of sites with electromagnetic radiation comprises contacting two or more individual sites of the plurality of sites with electromagnetic radiation. For example, a method may comprise illuminating a subset of sites, a subarray of sites, or all sites of a plurality of sites of an array of analytes.

In some cases, illuminating each individual site with light may comprise providing each individual site with a dosage of light having an amount of energy (i.e., as determined by an average number of photons provided to each individual site). Illuminating each individual site with light may comprise providing each individual site with at least about $1\times10^{-18}$ Joules (J), $1\times10^{-15}$ J, $1\times10^{-12}$ J, $1\times10^{-9}$ J, $1\times10^{-8}$ J, $1\times10^{-7}$ J, $1\times10^{-6}$ J, $1\times10^{-5}$ J, $1\times10^{-4}$ J, $1\times10^{-3}$ J, or more than $1\times10^{-3}$ J of light to each individual site. Alternatively or additionally, illuminating each individual site with light may comprise providing each individual site with no more than about $1\times10^{-3}$ J, $1\times10^{-4}$ J, $1\times10^{-5}$ J, $1\times10^{-6}$ J, $1\times10^{-7}$ J, $1\times10^{-8}$ J, $1\times10^{-9}$ J, $1\times10^{-12}$ J, $1\times10^{-15}$ J, $1\times10^{-18}$ J, or less than $1\times10^{-18}$ J of light to each individual site. The photon energy provided to an individual site may be an amount of energy provided during a single cycle of a single-analyte array process. Alternatively, the photon energy provided to an individual site may be a cumulative amount of energy provided over a cumulative number of cycles of a single-analyte array process. (e.g., providing $1\times10^{-9}$ J to a site for each individual cycle of 100 cycles will lead to a cumulative energy input of $1\times10^{-7}$ J for the site).

In some cases, illuminating each individual site with light may comprise providing light of a first wavelength during a first cycle, and providing light of a second wavelength during a second cycle. For example, a method may comprise a first step comprising illuminating a site with 488 nm light, and a second step comprising illuminating a site with 647 nm light. In some cases, illuminating each individual site with light may comprise providing light of a first wavelength and light of a second wavelength during a single cycle. For example, a method may comprise a step comprising illuminating a site with 488 nm light, and a subsequently illuminating the site with 647 nm light during the same cycle. Two or more wavelengths of light may be utilized during a single cycle for multiplex detection of multiple types of binding reagents, or distinguishing labels associated with anchoring moieties from labels associated with binding reagents.

In some cases, contacting an individual site of a plurality of sites with electromagnetic radiation can comprise contacting the site with electromagnetic radiation with a wavelength of at least about 200 nanometers (nm), 250 nm, 300 nm, 350 nm, 400 nm, 420 nm, 440 nm, 460 nm, 480 nm, 500 nm, 520 nm, 540 nm, 560 nm, 580 nm, 600 nm, 620 nm, 640 nm, 660 nm, 680 nm, 700 nm, 750 nm, 800 nm, 900 nm, 1000 nm, or more than 1000 nm. Alternatively or additionally, contacting an individual site of a plurality of sites with electromagnetic radiation can comprise contacting the site with electromagnetic radiation with a wavelength of no more than about 1000 nm, 950 nm, 900 nm, 850 nm, 800 nm, 750 nm, 700 nm, 680 nm, 660 nm, 640 nm, 620 nm, 600 nm, 580 nm, 560 nm, 540 nm, 520 nm, 500 nm, 480 nm, 460 nm, 440 nm, 420 nm, 400 nm, 350 nm, 300 nm, 250 nm, 200 nm, or less than 200 nm.

In some cases, a method may comprise two or more steps of contacting an individual site of a plurality of sites with electromagnetic radiation, in which a first step comprises contacting the individual site with light of a first wavelength, and a second step comprises contacting the individual site with light of a second wavelength, in which the first wavelength and the second wavelength differ. In some cases, a first photo-generated reactive species (e.g., free radicals, reactive oxygen species, etc.) may be generated by light of a first wavelength, and a second photo-generated reactive species may be generated by light of a second wavelength, in which the first wavelength and the second wavelength differ, and in which the first photo-generated reactive species and the second photo-generated reactive species differ. Accordingly, a first fluidic medium comprising a first photodamage inhibitor or reactive species inhibitor may be provided when utilizing light of the first wavelength, and a second fluidic medium comprising a second photodamage inhibitor or reactive species inhibitor may be provided when utilizing light of the second wavelength.

A method may comprise a step of determining a binding reagent dissociation fraction. A binding reagent dissociation fraction can refer to a percentage or fraction of sites of an array of analytes having an absence of a signal after a binding reagent dissociation step of an array-based method. For example, an array containing $10^6$ sites may have a binding reagent dissociation fraction of at least 90% if at least $9\times10^5$ sites have no detectable signal after a binding reagent dissociation step. Alternatively, a binding reagent dissociation fraction can refer to a percentage or fraction of sites of an array of analytes having an absence of a signal after a binding reagent dissociation step of an array-based method relative to a quantity of sites having a signal after a binding reagent association step of the array-based method. For example, if a signal from a binding reagent is detected at $10^6$ sites after contacting the binding reagents to analytes of a single-analyte array, a binding reagent dissociation fraction may be at least 90% for the single-analyte array if no signal is detected after a binding reagent dissociation process for at least $9\times10^5$ sites of the $10^6$ sites.

Determining a binding reagent dissociation fraction may comprise detecting at each individual site of a plurality of sites presence or absence of a signal. In some cases, a binding reagent dissociation fraction may be determined utilizing a quantity of sites, such as all sites of an array, a subset of sites of an array (e.g., at least about 0.1%, 1%, 5%, 10%, 20%, 25%, 50%, or more than 50% of all sites of an array), or a subarray of an array (e.g., a subdivision of sites of an array comprising a contiguous cluster of sites). In some cases, a plurality of sites utilized to determine a binding reagent dissociation fraction may have a random spatial distribution. In other cases, a plurality of sites utilized to determine a binding reagent dissociation fraction may have a non-random spatial distribution.

Determining a binding reagent dissociation fraction may comprise detecting at each individual site of a plurality of sites presence or absence of a signal in the presence of a binding reagent detection medium. In some cases, a binding reagent detection medium utilized for binding reagent detection after a binding reagent dissociation step may have the same composition as a detection medium utilized for binding reagent detection after a binding reagent association step. In other cases, a binding reagent detection medium utilized for binding reagent detection after a binding reagent dissociation step may have a differing composition compared to a detection medium utilized for binding reagent detection after a binding reagent association step (e.g., with respect to a blocking reagent, with respect to a photodamage inhibitor, etc.).

In some cases, a binding reagent dissociation fraction may be determined after each step of contacting a plurality of binding reagents to an array of analytes. For example, for a method comprising 10 cycles of associating, detecting, and dissociating binding reagents to analytes, a binding reagent dissociation fraction may be determined for each cycle of the 10 cycles. In other cases, a binding reagent dissociation fraction may be determined at a fixed, sequenced, or random interval. For example, a binding reagent dissociation fraction may be determined at least once every about 2, 3, 5, 10, 20, 25, 50, or more than every 50 steps of contacting a plurality of binding reagents to an array of analytes. Alternatively or additionally, a binding reagent dissociation fraction may be determined no more than every about 50, 25, 20, 10, 5, 3, or less than every 3 steps of contacting a plurality of binding reagents to an array of analytes.

Determination of binding reagent dissociation fraction may occur at least in part due to the detection and analysis of one or more phenomena related to unintended detection events (i.e., detection of signal associated with a binding reagent at a site after a binding reagent dissociation step). Phenomena that may cause unintended detection events include orthogonal binding (e.g., binding of binding reagents to array components other than analytes), off-target binding (e.g., unexpected or low probability binding of binding reagents to analytes), and binding reagent dissociation failure (e.g., cross-linking of a binding reagent to an analyte, failure to disrupt a non-covalent interaction between an analyte and a binding reagent). A binding reagent dissociation fraction may be determined directly (e.g., via presence or absence of signals from binding reagents after a binding reagent dissociation step) or may be imputed, inferred, or otherwise determined during an array-based process (e.g., by presence or absence of signal from binding reagents at addresses associated with standard analytes). A binding reagent dissociation fraction may be a function of one or more contributing rates, such as an orthogonal binding rate, an off-target binding rate, or a binding reagent dissociation failure rate. Accordingly, a method may comprise a step of determining an orthogonal binding rate, an off-target binding rate, or a binding reagent dissociation failure rate by a method set forth herein.

A method set forth herein may have a characterized or quantified binding reagent dissociation fraction of at least about 50%, 60%, 70%, 80%, 85%, 90%, 95%, 96%, 97%, 98%, 99%, 99.5%, 99.9%, 99.99%, 99.999%, or more than 99.999%. Alternatively or additionally, a method set forth herein may have a characterized or quantified binding reagent dissociation fraction of no more than about 99.999%, 99.99%, 99.9%, 99.5%, 99%, 98%, 97%, 96%, 95%, 90%, 85%, 80%, 70%, 60%, 50%, or less than 50%. A method set forth herein may have a characterized or quantified binding reagent dissociation fraction of at least about 50%, 60%, 70%, 80%, 85%, 90%, 95%, 96%, 97%, 98%, 99%, 99.5%, 99.9%, 99.99%, 99.999%, or more than 99.999% when a particular fluidic medium (e.g., a binding reagent association medium, a detection medium, a binding reagent dissociation medium) is utilized during the method. Alternatively or additionally, a method set forth herein may have a characterized or quantified binding reagent dissociation fraction of no more than about 99.999%, 99.99%, 99.9%, 99.5%, 99%, 98%, 97%, 96%, 95%, 90%, 85%, 80%, 70%, 60%, 50%, or less than 50% when a particular fluidic medium (e.g., a binding reagent association medium, a detection medium, a binding reagent dissociation medium) is utilized during the method.

A method may comprise a step of determining a binding anomaly fraction. A binding anomaly fraction can refer to a measured or inferred rate of false signal detection (i.e., detection of a signal at an address at which a signal should not occur). Examples of unintended signal detection can include signal detection due to orthogonal binding interactions, signal detection due to off-target binding interactions, and signal detection due to binding reagent dissociation failure. Identification of binding anomalies and determination of binding anomaly fractions is discussed further in the section titled "Determination of Anomaly Occurrence Rates."

A method set forth herein may have a characterized or quantified binding anomaly fraction of no more than about 10%, 5%, 1%, 0.5%, 0.1%, 0.05%, 0.01%, 0.005%, 0.001%, 0.0001%, 0.00001%, 0.000001%, or less than 0.000001%. Alternatively or additionally, a method set forth herein may have a characterized or quantified binding anomaly fraction of at least about 0.000001%, 0.00001%, 0.0001%, 0.001%, 0.005%, 0.01%, 0.05%, 0.1%, 0.5%, 1%, 5%, 10%, or more than 10%. A method set forth herein may have a characterized or quantified binding anomaly fraction of no more than about 10%, 5%, 1%, 0.5%, 0.1%, 0.05%, 0.01%, 0.005%, 0.001%, 0.0001%, 0.00001%, 0.000001%, or less than 0.000001% when a particular fluidic medium (e.g., a binding reagent association medium, a detection medium, a binding reagent dissociation medium) is utilized during the method. Alternatively or additionally, a method set forth herein may have a characterized or quantified binding anomaly fraction of at least about 0.000001%, 0.00001%, 0.0001%, 0.001%, 0.005%, 0.01%, 0.05%, 0.1%, 0.5%, 1%, 5%, 10%, or more than 10% when a particular fluidic medium (e.g., a binding reagent association medium, a detection medium, a binding reagent dissociation medium) is utilized during the method.

Prior to utilization in an array-based process, binding reagents may be characterized to determine a binding behavior, for example as characterized or quantified by a binding reagent dissociation fraction or a binding anomaly fraction. Accordingly, observing a significant difference between a prior characterized binding behavior and what is observed during an array-based process can result in an assay being considered low confidence, modifying its execution plan (i.e., a sequence of steps), stop the process entirely, or perform other actions. A method may comprise, before contacting a plurality of binding reagents with an array, determining a binding reagent dissociation fraction or a binding anomaly fraction for the plurality of binding reagents. In some cases, such a method may exclude a step of determining a binding reagent dissociation fraction or a binding anomaly fraction during an array-based process. For example, if a binding behavior of a plurality of binding reagents has been determined before an array-based process, measurement of the binding behavior may be assumed to behave accordingly during an array-based process if similar fluidic media and/or array configurations are utilized. In other cases, a method may include a step of determining a binding reagent dissociation fraction or a binding anomaly fraction during an array-based process. For example, a binding behavior (e.g., a binding reagent dissociation fraction, a binding anomaly fraction) may be measured or quantified by detecting coupling of binding reagents to a plurality of standard analytes, as set forth herein, or by detecting coupling of binding reagents to a plurality of sample analytes.

In some cases, a first binding behavior (e.g., a binding reagent dissociation fraction, a binding anomaly fraction) may be correlated or otherwise associated to a second binding behavior. For example, before an array-based process, a binding dissociation rate behavior and a binding anomaly fraction behavior may be characterized or measured for a plurality of binding reagents, thereby determining a quantitative correlation between the two rates. Accordingly, during an array-based process, measurement of a binding anomaly fraction of the plurality of binding reagents to sample analytes or standard analytes may be utilized to infer or impute a binding reagent dissociation fraction of the binding reagents.

Determination of unintended detection events, as characterized by measures such as binding reagent dissociation fraction and/or binding anomaly fraction, can impact an array-based process in several ways, including: 1) providing a measure of data uncertainty when characterizing sample analytes, and 2) providing a measure of system performance during the array-based process. Accordingly, providing a fluidic medium or a set of fluidic media, as set forth herein, that are configured to inhibit or otherwise minimize unintended detection events may affect an array-based process by: 1) facilitating characterization of a maximal or optimal quantity of sample analytes, and/or 2) facilitating alteration of one or more steps of a method to reduce unintended detection events.

Figure 10A:
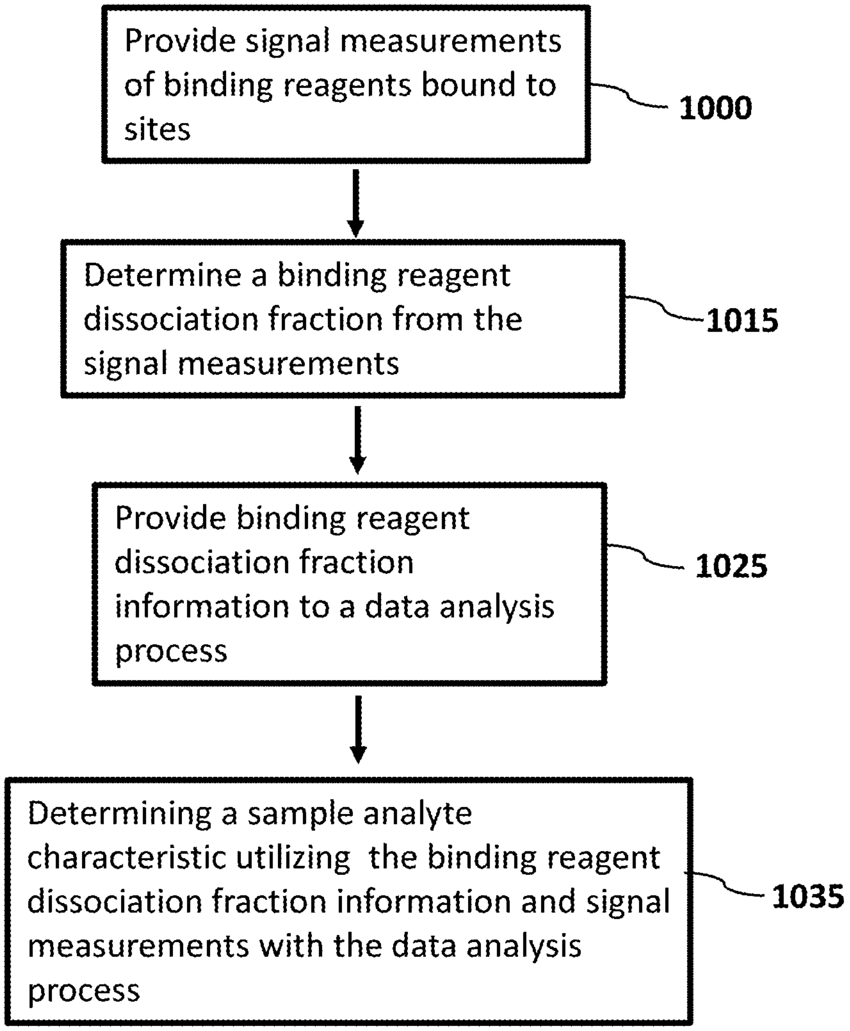
FIGS. 10A and 10B show methods of utilizing binding anomaly fractions or binding reagent dissociation fractions for data analysis, in accordance with some embodiments.
Figure 10B:
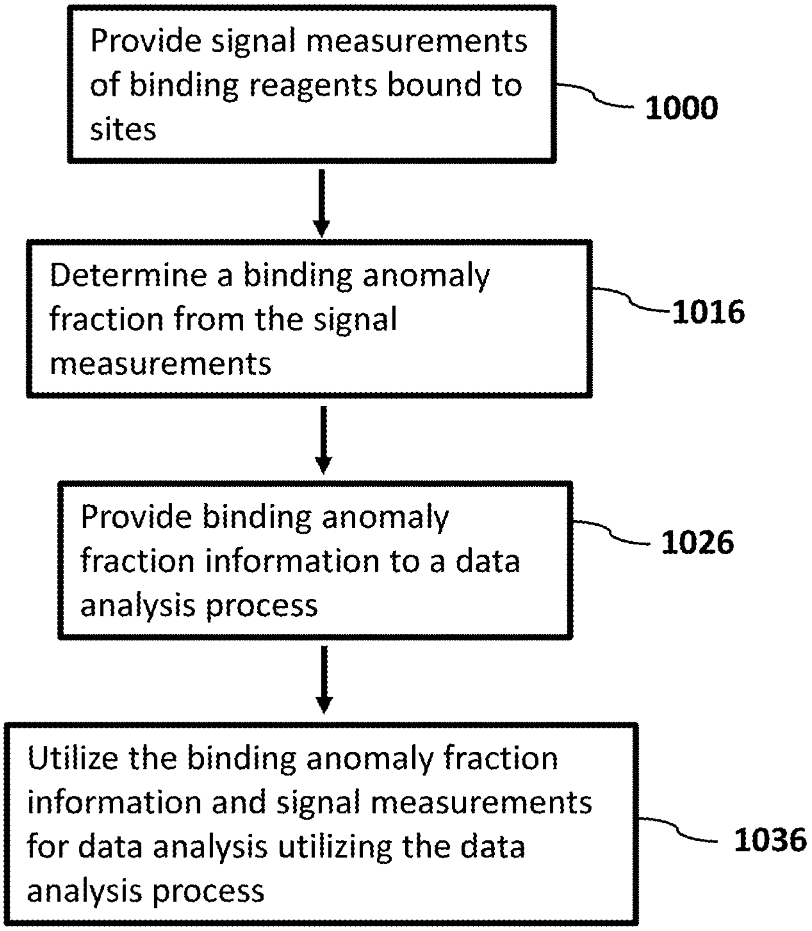

FIGS. 10A and 10B illustrate methods of utilizing signal data from an array-based process for the characterization of sample analytes. A method of characterizing sample analytes may be combined with a method of detecting an array of sample analytes, such as methods depicted in FIGS. 2, 9A, and 9B. In some cases, a method of characterization of sample analytes may occur concurrently with a method of detecting an array. For example, signal data acquired by detection of an array may be provided to a computer or processor in real-time as the signal data is collected by a detection device. In other cases, a method of characterization of sample analytes may occur iteratively with a method of detecting an array. For example, signal data acquired by detection of an array may be provided to a computer or processor after each detection step, or after a plurality of detection steps. In some cases, a method of characterization of sample analytes may occur after completing a method of detecting an array.

Turning to FIG. 10A, a first step of a method of characterizing sample analytes may comprise providing 1000 to a computer or processor signal measurements comprising presences or absences of bound binding reagents at a plurality of sites of a single-analyte array. In some cases, the signal measurements may be provided to an image or detection analysis process. An image analysis process may perform one or more data analysis steps, including: i) compiling signal measurements, ii) performing data transformation processes on signal measurements (e.g., filtering, rotation, contrast enhancement, etc.), iii) classifying signal measurements (e.g., assigning values such as BOUND/NOT BOUND/UNCERTAIN, etc.), and iv) preparing signal measurements for further data analysis processes (e.g., tabulating assigned data classifications according to a site or address of an array). Signal measurements processed by an image or detection analysis process may be provided to a data analysis process after the image or detection analysis process. In other cases, signal measurements may be provided to a data analysis process that includes an image or detection analysis process.

Returning to FIG. 10A, a second step of a method of characterizing sample analytes may comprise determining 1015 a binding reagent dissociation fraction from the provided signal measurements. In some cases, the binding reagent dissociation fraction may be determined based upon signal measurements of binding reagents bound to sample analytes. In other cases, a binding reagent dissociation fraction may be determined based upon signal measurements of binding reagents bound to standard analytes. Alternatively, signal measurements may include metadata that is utilized to determine a binding reagent dissociation fraction. For example, if binding reagent dissociation fraction has been characterized as a function of assay conditions prior to an array-based process, signal measurement data may include metadata concerning assay conditions (e.g., fluidic media utilized, time length of contacting of fluidic media to the array, etc.) that are utilized to infer or impute a binding reagent dissociation fraction.

Returning to FIG. 10A, a third step of a method of characterizing sample analytes may comprise providing 1025 the binding reagent dissociation fraction information and the signal measurements to a data analysis process. The binding reagent dissociation fraction information and the signal measurements may be provided to a data analysis process that determines a characteristic of a sample analyte at a site of a plurality of sites based upon one or more of: i) presence or absence of a signal of a binding reagent at the site, and ii) a binding reagent dissociation fraction. A data analysis process may comprise a statistical or probabilistic model that utilizes a binding reagent dissociation fraction. A data analysis process may comprise a trained data analysis process or a machine learning process. Additional details of data analysis processes are described in U.S. Pat. No. 11,282,586, U.S. Patent Publication No. 20210390705, and U.S. patent application Ser. No. 18/192,606, each of which is incorporated by reference herein in its entirety.

Returning to FIG. 10A, a fourth step of a method of characterizing sample analytes may comprise determining 1035 a characteristic of a sample analyte or a standard analyte utilizing the data analysis process that has been provided the signal measurements and/or the binding reagent dissociation fraction. In some cases, determining 1035 a characteristic of a sample analyte or a standard analyte utilizing the data analysis process may comprise determining characteristics of a plurality of sample analytes and/or standard analytes. In some cases, determining 1035 a characteristic of a sample analyte or a standard analyte utilizing the data analysis process may comprise determining characteristics of a plurality of sample analytes and/or standard analytes, in which the sample analytes and/or standard analytes have a diversity of analytes based upon a diversity metric such as quantity of species, quantity of isoforms, or dynamic range. Additional aspects of analyte diversity, as exemplified with respect to polypeptides, are described below in the section titled "Polypeptide assays."

Turning to FIG. 10B, an alternative method is shown for determining analyte characteristics. The steps of the method may be analogous to the steps shown for FIG. 10A, with a second step replaced with a step of determining 1016 a binding anomaly fraction based upon the signal measurements provided to a computer or processor. In some cases, the binding anomaly fraction may be determined based upon signal measurements of binding reagents bound to sample analytes. In other cases, a binding anomaly fraction may be determined based upon signal measurements of binding reagents bound to standard analytes. Alternatively, signal measurements may include metadata that is utilized to determine a binding anomaly fraction. For example, if binding anomaly fraction has been characterized as a function of assay conditions prior to an array-based process, signal measurement data may include metadata concerning assay conditions (e.g., fluidic media utilized, time length of contacting of fluidic media to the array, etc.) that are utilized to infer or impute a binding anomaly fraction.

Returning to FIG. 10B, after determining a binding anomaly fraction, the method may proceed analogously to the method of FIG. 10A, with a binding anomaly fraction substituted for the binding reagent dissociation fraction. Accordingly, the method may include a third step of providing 1026 the binding anomaly fraction information and the signal measurements to a data analysis process, and a fourth step of determining 1036 a characteristic of a sample analyte or a standard analyte utilizing the data analysis process that has been provided the signal measurements and/or the binding reagent dissociation fraction. The skilled person will readily recognize that in some cases, a data analysis process may utilize a binding reagent dissociation fraction and a binding anomaly fraction for determining analyte characteristics.

Figure 12A:
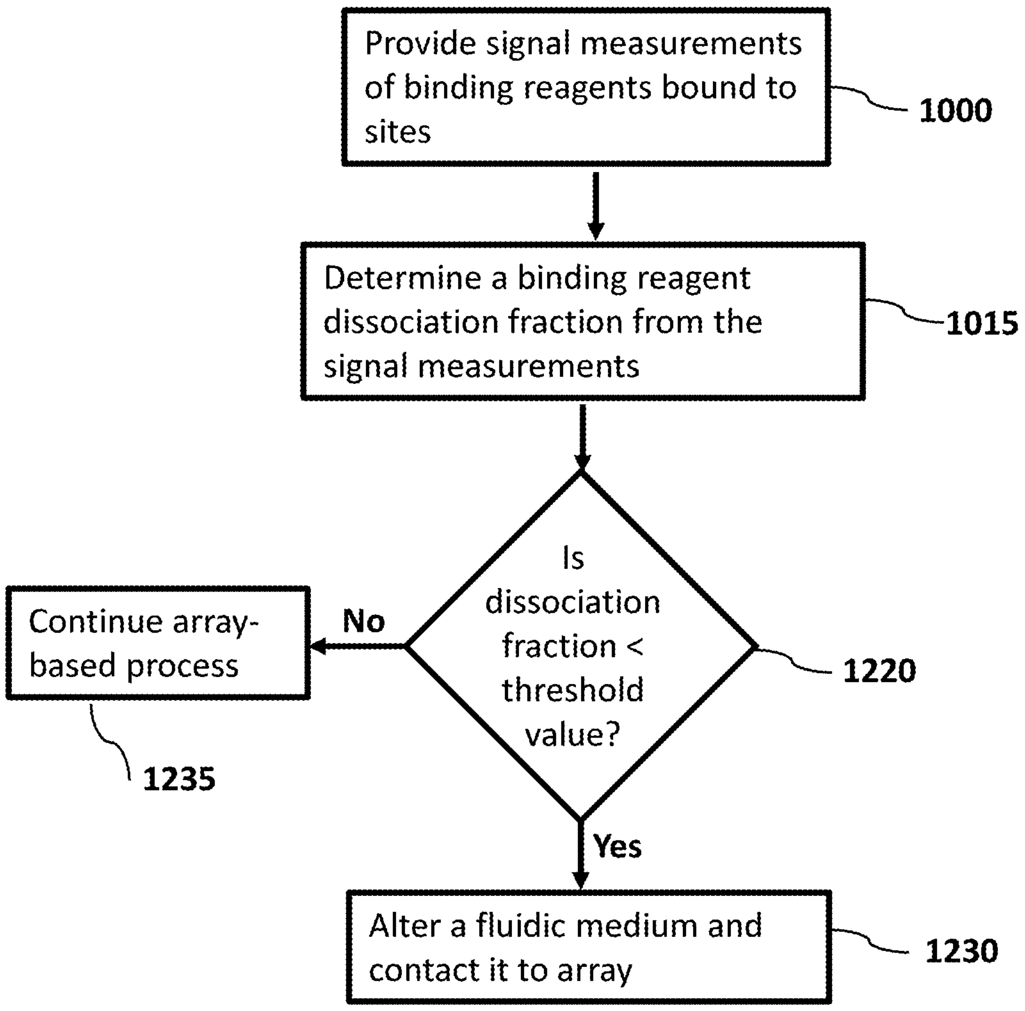
FIGS. 12A and 12B depict flow charts for performing array-based processes, in accordance with some embodiments.
Figure 12B:
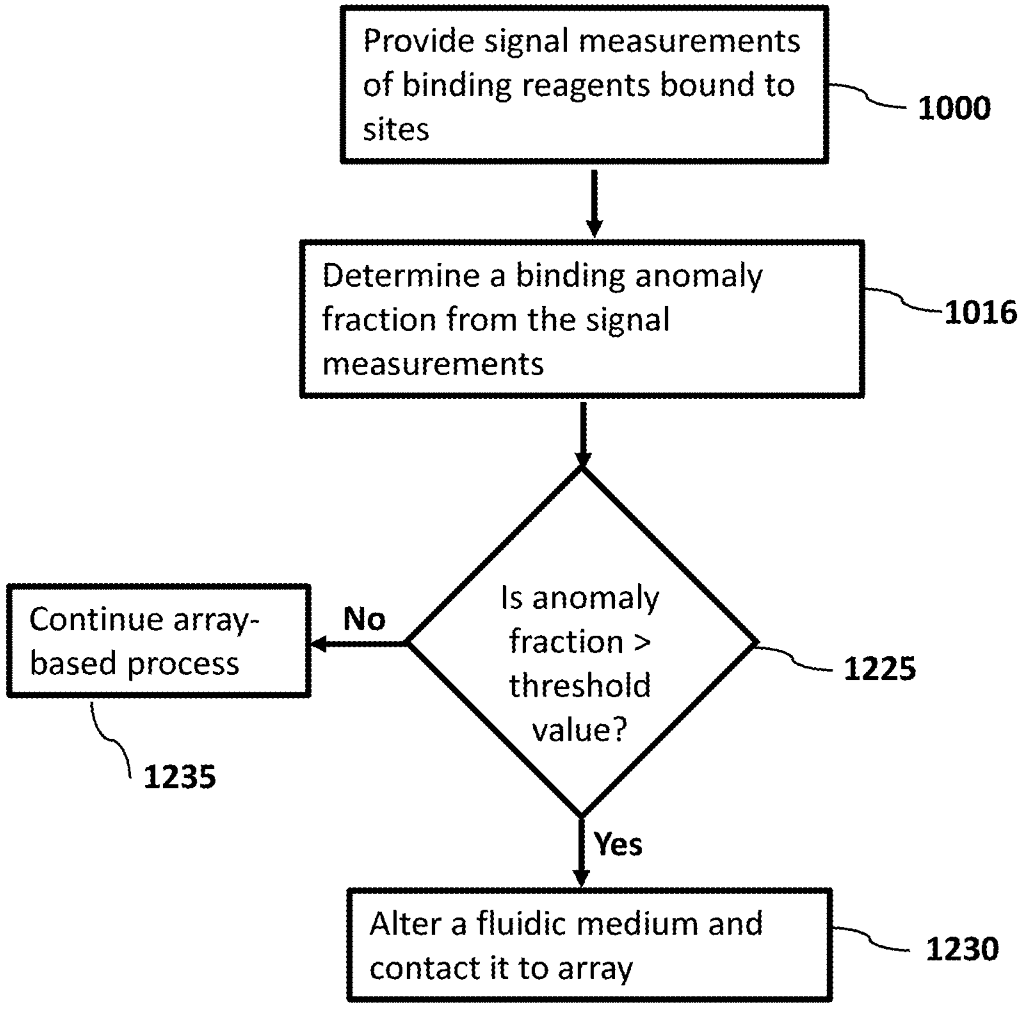

FIGS. 12A and 12B depict methods of altering an array-based process based upon determination of a binding behavior (e.g., as determined by a binding dissociation fraction or a binding anomaly fraction). A method of altering an array-based process based upon determination of a binding behavior may be combined with a method of detecting an array of sample analytes, such as methods depicted in FIGS. 2, 9A, and 9B. In some cases, a method of altering an array-based process based upon determination of a binding behavior may occur concurrently with a method of detecting an array. For example, compositions and/or incubation times of one or more fluidic media utilized during an array-based process may be altered one or more times during the array-based assay based upon measured binding reagent dissociation fractions and/or bind anomaly fractions. In other cases, a method of altering an array-based process based upon determination of a binding behavior may occur iteratively with a method of detecting an array. For example, compositions and/or incubation times of one or more fluidic media utilized during an array-based process may be altered at a fixed interval (e.g., after N cycles) or a random interval during the array-based assay based upon measured binding reagent dissociation fractions and/or bind anomaly fractions. In some cases, a method of altering an array-based process based upon determination of a binding behavior may occur after completing a method of detecting an array.

Turning to FIG. 12A, a method of altering an array-based process based upon determination of a binding behavior may proceed analogously to steps 1000 and 1015 of FIG. 10A. Signal measurements processed by an image or detection analysis process may be provided to an instrument control process after the image or detection analysis process. In other cases, signal measurements may be provided to an instrument control process that includes an image or detection analysis process.

Returning to FIG. 12A, a third step of a method of altering an array-based process based upon determination of a binding behavior may comprise determining 1220 if the binding reagent dissociation fraction is less than a threshold value (e.g., less than about 99.99999%, 99.9999%, 99.999%, 99.99%, 99.9%, 99.5%, 99%, 98%, 97%, 96%, 95%, 90%, or less than 90%). If the binding reagent dissociation fraction is greater than or equal to the threshold value, the instrument control process may proceed with a fourth step of continuing 1235 an array-based process, as set forth herein. If the binding reagent dissociation fraction is less than the threshold value, the instrument control process may provide an instruction that is executed by the array-based system of altering 1230 a condition of a fluidic medium that is contacted to the array. Altering a fluidic medium may include adding a chemical species to the fluidic medium, removing a chemical species from the fluidic medium, increasing or decreasing a concentration of a chemical species in the fluidic medium (e.g., a concentration of a species such as a blocking agent, antioxidant, surfactant, chaotrope, photodamage inhibitor, etc.), increasing or decreasing an incubation time with the array of the fluidic medium, adding or removing fluid-contacting steps from an assay, or increasing or decreasing a temperature of a fluidic medium.

Turning to FIG. 12B, a method of altering an array-based process based upon determination of a binding behavior may proceed analogously to steps 1000 and 1016 of FIG. 10B. After determining 1016 a binding anomaly fraction, a third step of a method of altering an array-based process based upon determination of a binding behavior may comprise determining 1225 if the binding anomaly fraction is greater than a threshold value (e.g., more than about 0.00001%, 0.0001%, 0.001%, 0.01%, 0.1%, 0.5%, 1%, 2%, 3%, 4%, 5%, 10%, or more than 10%). If the binding anomaly fraction is less than the threshold value, the instrument control process may proceed with a fourth step of continuing 1235 an array-based process, as set forth herein. If the binding anomaly fraction is greater than or equal to the threshold value, the instrument control process may provide an instruction that is executed by the array-based system of altering 1230 a condition of a fluidic medium that is contacted to the array. In some cases, an instrument control process may utilize the binding reagent dissociation fraction and the binding anomaly fraction to determine if it is necessary to alter a condition of a fluidic medium.

A method, as set forth herein, may further include one or more steps of characterizing sample analytes of a plurality of sample analytes. Characterization of sample analytes can include identification of sample analytes, measurement of physical and/or chemical properties of sample analytes, measurement of interactions of sample analytes (e.g., binding to small molecules or other ligands, reactivity to molecules or other ligands), and any other conceivable form of interrogation of sample analytes. A method of characterizing a plurality of sample analytes may comprise one or more steps of: i) providing signal data (e.g., a processed image, an unprocessed image, a tabulated signal set) to a computer or processor, ii) on the computer or processor, determining a presence or absence of a signal at each individual site of a plurality of sites of an array, iii) on the computer or processor, determining a presence or absence of a binding anomaly at each individual site of the plurality of sites of the array, iv) based upon the presence or absence of the signal at each individual site of the plurality of sites of the array, determining a binding reagent dissociation fraction, v) based upon the presence or absence of the binding anomaly at each individual site of the plurality of sites of the array, determining a binding anomaly fraction, vi) providing the signal data and one or more of the binding reagent dissociation fraction and the binding anomaly fraction to a sample analyte characterization process on the computer or processor, and vii) determining with the sample analyte characterization process a characteristic (e.g., an identity, a property, a binding specificity, etc.) for at least about 50% (e.g., at least about 60%, 70%, 75%, 80%, 85%, 90%, 95%, 96%, 97%, 98%, 99%, 99.5%, 99.9%, 99.99%, 99.999%, 99.9999%, 99.99999%, or more than 99.99999%) of sample analytes of a plurality of sample analytes. Additional details regarding methods of characterizing sample analytes, as exemplified with regard to polypeptides, is provided below in the section titled "Polypeptide assays." Additional details regarding processing and analysis of signal data can be found in U.S. Patent Publication No. 20210390705 and U.S. patent application Ser. No. 18/192,606, each of which is herein incorporated by reference in its entirety.

A method, as set forth herein, may comprise a step of providing an array of analytes (e.g., sample analytes, standard analytes). A method may further comprise a step of forming the array of analytes. A method of forming an array of analytes may comprise the steps of: i) providing a solid support comprising a plurality of sites, and ii) depositing at each individual site of the plurality of sites one and only one analyte of a plurality of analytes (e.g., sample analytes, standard analytes, or combinations thereof). Preferably, each individual site of the plurality of sites is optically resolvable at single-analyte resolution. In some cases, a plurality of analytes may be attached to anchoring moieties (e.g., nucleic acid nanoparticles, polymeric nanoparticles, etc.), as set forth herein, in which each individual analyte is attached to one and only one anchoring moiety, and optionally in which each anchoring moiety is attached to one and only one analyte. In some cases, a plurality of analytes may be attached to a plurality of anchoring moieties before depositing the plurality of analytes and anchoring moieties at the plurality of sites of the single-analyte array. In other cases, a plurality of anchoring moieties may be coupled to the plurality of sites, then the plurality of analytes may be attached to the plurality of anchoring moieties. Methods of forming single-analyte arrays are known in the art. Methods of forming arrays, including arrays containing standard and/or control analytes are described in U.S. Pat. Nos. 11,203,612, 11,505,796, and U.S. Patent Publication No. 20220227890A1, each of which is incorporated by reference in its entirety.

A method, as set forth herein, may further comprise one or more washing or rinsing steps. A washing or rinsing step may be included in an array-based process to displace a fluidic medium (e.g., a binding reagent association medium, a detection medium, a binding reagent dissociation medium) from an array, as set forth herein, and/or to displace a bound or unbound moiety (e.g., a binding reagent, a surfactant, a denaturing species, a crowding agent, an ionic species, an analyte, an anchoring moiety, etc.) from an array, as set forth herein. The skilled person will readily recognize that an array-based process may comprise a plurality of washing or rinsing steps. For example, a cycle of a multi-cycle array-based process may comprise one or more washing or rinsing steps after a binding reagent association step and/or a binding reagent dissociation step to remove unbound or weakly bound binding reagents.

A washing or rinsing step may comprise contacting a rinsing medium to an array, as set forth herein, or an array component (e.g., an anchoring moiety, an analyte, a binding reagent, a surface-coupled moiety, a surface-coupling moiety, etc.). A rinsing medium may comprise one or more species that are configured to alter a binding interaction between two or more array components (e.g., strengthening binding of an anchoring moiety to an array surface, strengthening binding of an analyte to an anchoring moiety, weakening binding of a binding reagent to an analyte, weakening binding of a binding reagent to an array surface, etc.). A rinsing medium may comprise one or more of an ionic species, a surfactant species, a denaturing species, a chaotropic species, a reducing agent, a reaction inhibitor species, or a combination thereof. A rinsing medium may comprise an ionic species, a surfactant species, a denaturing species, a chaotropic species, a reducing agent, or a reaction inhibitor species set forth herein for another fluidic medium (e.g., a binding reagent association medium, a binding reagent dissociation medium, a detection medium, etc.).

A rinsing medium may be provided with a fluidic property (e.g., ionic strength, pH, concentration of a species, etc.) that facilitates dissociation or displacement of a moiety (e.g., a binding reagent, an analyte, an anchoring moiety, an ionic species, a surfactant species, a denaturing species, etc.) from an array or a component thereof. Formulation of a rinsing medium may depend upon preceding and/or following steps of an array-based process. For example, a rinsing step that occurs after a binding reagent association step and before a detection step may be facilitated by a rinsing medium that inhibits dissociation of analytes, anchoring moieties, and/or binding reagents. In another example, a rinsing step that occurs after a binding reagent dissociation step may be facilitated by a rinsing medium that facilitates dissociation of binding reagents and inhibits dissociation of analytes and/or anchoring moieties. Accordingly, a rinsing medium may be formulated with a fluidic property (e.g., ionic strength, pH, concentration of a species, etc.) that differs from another fluidic medium of an array-based process (e.g., binding reagent association medium, detection medium, binding reagent dissociation medium). In some cases, a rinsing medium may have an increased ionic strength, pH, or concentration of a species relative to a binding reagent association medium, detection medium, or binding reagent dissociation medium. In other cases, a rinsing medium may have a decreased ionic strength, pH, or concentration of a species relative to a binding reagent association medium, detection medium, or binding reagent dissociation medium. In some cases, two or more rinsing media may be utilized during an array-based process, in which a first rinsing medium of the two or more rinsing media differs from a second rinsing medium of the two or more rinsing media (e.g., with respect to ionic strength, pH, presence or absence of a species, concentration of a species, etc.).

One or more steps of an array-based process (e.g., binding reagent association, detection of bound binding reagents, binding reagent dissociation, rinsing), as set forth herein, may occur in the presence of a chemical species that alters a physical state or configuration of an analyte or other array component (e.g., anchoring moiety, surface-coupling moiety, surface-coupled moiety, binding reagent). For example, a polypeptide array may be contacted with a denaturant, chaotrope, or reducing agent to disrupt a native folding state of a polypeptide, or induce re-folding of the polypeptide. In another example, a nucleic acid may be contacted with an ionic species that enhances or inhibits enzymatic (e.g., polymerase, ligase, exonuclease, endonuclease, etc.) binding and/or processivity of the nucleic acid. Accordingly, a fluidic medium (e.g., a binding reagent association medium, a binding reagent detection medium, a binding reagent dissociation medium, a rinsing medium) may comprise a chemical species that alters a physical state or configuration of an analyte or other array component (e.g., a denaturant, chaotrope, or reducing agent). Alternatively, a fluidic medium may be substantially devoid of a chemical species that alters a physical state or configuration of an analyte or other array component.

In some cases, a method may comprise: i) performing a first method step, as set forth herein, in which performing the first method step comprises providing a fluidic medium comprising a chemical species that alters a physical state or configuration of an analyte or other array component, and ii) after performing the first method step, performing a second method step, as set forth herein, in which performing the second method step comprises providing a fluidic medium that is substantially devoid of a chemical species that alters a physical state or configuration of an analyte or other array component. For example, denaturing species or reducing agents may be excluded during binding reagent association or binding reagent detection of antibody-based binding reagents due to possible denaturing/inactivation of the binding reagents.

In some cases, a method may comprise: i) performing a first method step, as set forth herein, in which performing the first method step comprises providing a fluidic medium comprising a first chemical species that alters a physical state or configuration of an analyte or other array component, and ii) after performing the first method step, performing a second method step, as set forth herein, in which performing the second method step comprises providing a fluidic medium comprising a second chemical species that alters a physical state or configuration of an analyte or other array component, in which the first chemical species differs from the second chemical species. For example, a method may comprise a first step of contacting an array of polypeptides with a fluidic medium (e.g., a rinsing medium) comprising a strongly denaturing species (e.g., guanidinium chloride), and a second step of contacting the array of polypeptides with a binding reagent association medium comprising a weakly denaturing species (e.g., dilute acetic acid).

In some cases, a method may comprise: i) performing a first method step, as set forth herein, in which performing the first method step comprises providing a first fluidic medium comprising a chemical species that alters a physical state or configuration of an analyte or other array component, and ii) after performing the first method step, performing a second method step, as set forth herein, in which performing the second method step comprises providing a second fluidic medium comprising a chemical species that alters a physical state or configuration of an analyte or other array component, in which the first fluidic medium differs from the second fluidic medium with respect to a fluidic property (e.g., presence or absence of a denaturing species, presence or absence of additional denaturing species, concentration of a denaturing species, etc.). For example, a method may comprise a first step of contacting an array of polypeptides with a fluidic medium (e.g., a rinsing medium) comprising guanidinium chloride (a chaotropic denaturant) and dithiothreitol (a disulfide bond reducer), and a second step of contacting the array of polypeptides with a binding reagent association medium comprising a lower concentration of guanidinium chloride (relative to the rinsing medium) and substantially no dithiothreitol.

An array, as set forth herein, may comprise a plurality of sites. A plurality of sites of an array may comprise at least about 10, $10^2$, $10^3$, $10^4$, $10^5$, $10^6$, $10^7$, $10^8$, $10^9$, $10^{10}$, $10^{11}$, $10^{12}$, or more than $10^{12}$ sites. Alternatively or additionally, a plurality of sites of an array may comprise no more than about $10^{12}$, $10^{11}$, $10^{10}$, $10^9$, $10^8$, $10^7$, $10^6$, $10^5$, $10^4$, $10^3$, $10^2$, 10, or less than 10 sites. A total quantity of a plurality of sites may be provided on a solid support to ensure a depth of sample analysis according to a measure of analyte diversity, such as total analyte species, total analyte isoforms, analyte dynamic range, or a combination thereof. For example, if a dynamic range between analyte species A and analyte species B is $10^6$, an array may be provided with at least $10^7$ sites to ensure that species B can be characterized during an array-based process.

A fluidic medium (e.g., a binding reagent association medium, a detection medium, a rinsing medium, a binding reagent dissociation medium) for an array-based method or process may comprise any of a variety of components, such as a solvent species, pH buffering species, a cationic species, an anionic species, a surfactant species, a denaturing species, a crowding agent, an antioxidant, or a combination thereof. Advantageous compositions of differing fluidic media are described in more detail throughout the present disclosure. A solvent species may include water, acetic acid, methanol, ethanol, n-propanol, isopropyl alcohol, n-butanol, formic acid, ammonia, propylene carbonate, nitromethane, dimethyl sulfoxide, acetonitrile, dimethylformamide, acetone, ethyl acetate, tetrahydrofuran, dichloromethane, chloroform, carbon tetrachloride, dimethyl ether, diethyl ether, 1-4, dioxane, toluene, benzene, cyclohexane, hexane, cyclopentane, pentane, or combinations thereof. A fluidic medium may include a buffering species including, but not limited to, MES, Tris, Bis-tris, Bis-tris propane, ADA, ACES, PIPES, MOPSO, MOPS, BES, TES, HEPES, HEPBS, HEPPSO, DIPSO, MOBS, TAPSO, TAPS, TABS, POPSO, TEA, EPPS, Tricine, Gly-Gly, Bicine, AMPD, AMPSO, AMP, CHES, phosphate buffer solution (PBS), CAPSO, CAPS, and CABS. A fluidic medium may include cationic species such as Na+, K+, Ag+, Cu+, NH4+, Mg2+, Ca2+, Cu2+, Cd2+, Zn2+, Fe2+, Co2+, Ni2+, Cr2+, Mn2+, Ge2+, Sn2+, Al3+, Cr3+, Fe3+, Co3+, Ni3+, Ti3+, Mn3+, Si4+, V4+, Ti4+, Mn4+, Ge4+, Se4+, V5+, Mn5+, Mn6+, Se6+, and combinations thereof. A fluidic medium may include anionic species such as F—, Cl—, Br—, ClO3-, H2PO4-, HCO3-, HSO4-, OH—, I—, NO3-, NO2-, MnO4-, SCN—, CO32-, CrO42-, Cr2O72-, HPO42-, SO42-, SO32-, PO43-, and combinations thereof. A fluidic medium may include a surfactant species, such as a cationic surfactant, an anionic surfactant, a zwitterionic surfactant (e.g., a sultaine, a betaine), or an amphoteric surfactant. A fluidic medium may include a surfactant species including, but not limited to, stearic acid, lauric acid, oleic acid, sodium dodecyl sulfate, sodium dodecyl benzene sulfonate, dodecylamine hydrochloride, hexadecyltrimethylammonium bromide, polyethylene oxide, nonylphenyl ethoxylates, Triton X, pentapropylene glycol monododecyl ether, octapropylene glycol monododecyl ether, pentaethylene glycol monododecyl ether, octaethylene glycol monododecyl ether, lauramide monocthylamine, lauramide diethylamine, octyl glucoside, decyl glucoside, lauryl glucoside, Tween 20, Tween 80, n-dodecyl-β-D-maltoside, nonoxynol 9, glycerol monolaurate, polyethoxylated tallow amine, poloxamer, digitonin, zonyl FSO, 2,5-dimethyl-3-hexyne-2,5-diol, Igepal CA630, Aerosol-OT, tricthylamine hydrochloride, cetrimonium bromide, benzethonium chloride, octenidine dihydrochloride, cetylpyridinium chloride, adogen, dimethyldioctadecylammonium chloride, CHAPS, CHAPSO, cocamidopropyl betaine, amidosulfobetaine-16, cocoamphoacetate, cocoamidopropyl hydroxysultaine, lauryl-N,N-(dimethylammonio)butyrate, lauryl-N,N-(dimethyl)-glycinebetaine, hexadecyl phosphocholine, lauryldimethylamine N-oxide, lauryl-N,N-(dimethyl)-propanesulfonate, 3-(1-pyridinio)-1-propanesulfonate, 3-(4-tert-butyl-1-pyridinio)-1-propanesulfonate, N-laurylsarcosine, and combinations thereof. A fluidic medium may comprise a denaturing species including, but not limited to, acetic acid, trichloroacetic acid, sulfosalicylic acid, sodium bicarbonate, ethanol, ethylenediamine tetraacetic acid (EDTA), urea, guanidinium chloride, lithium perchlorate, sodium dodecyl sulfate, 2-mercaptoethanol, dithiothreitol, and tris(2-carboxyethyl) phosphine (TCEP). A fluidic medium may comprise a crowding agent, including but not limited to, carbonate ion, sulfate ion, phosphate ion, magnesium ion, lithium ion, zinc ion, aluminum ion, trehalose, glucose, proline, tert-butanol, polyethylene glycol, and combinations thereof.

A fluidic medium (e.g., a binding reagent association medium, a detection medium, a rinsing medium, a binding reagent dissociation medium) for an array-based method or process may comprise an excipient species. An excipient species may be provided to preserve or promote a function or state of an assay agent (e.g., an analyte, binding reagent, or anchoring moiety). Exemplary types of excipient agents can include cryoprotectants, biocidal agents, chaotropes and/or denaturants, reactive species inhibitors, anti-aggregants, enzymatic inhibitors, and molecular stability promoters.

In some cases, an excipient agent may be provided in a fluidic medium (e.g., a binding reagent association medium, a detection medium, a rinsing medium, a binding reagent dissociation medium). In other cases, an excipient agent may be mixed or diluted into a fluidic medium (e.g., a binding reagent association medium, a detection medium, a rinsing medium, a binding reagent dissociation medium). For example, a method may comprise the steps of: i) providing a binding reagent in a first fluidic medium comprising an excipient agent, ii) mixing the first fluidic medium with a second fluidic medium (e.g., a binding reagent association medium) to form a third fluidic medium, and iii) contacting the third fluidic medium to an array, as set forth herein.

An excipient agent may comprise a cryoprotectant. A cryoprotectant may comprise one or more chemical species that prevent damage to an assay agent (e.g., a binding reagent, an analyte, an anchoring moiety) during storage or assay processes that occur at reduced temperatures (e.g., less than 10° C., 0° C., −10° C., etc.). Exemplary cryoprotectants can include dextrans, ethylene glycol, glycerol, glycerol-3-phosphate, dimethyl sulfoxide (DMSO), 2-methyl-2,4 propanediol (MPD), erythritol, xylitol, trehalose, sucrose, sorbitol, formamide, proline, polymers, and combinations thereof. An excipient agent may comprise a biocidal agent. A biocidal agent may comprise one or more chemical species that inhibit growth of single-cell or multi-cell biological organisms. A biocidal agent can include an antibiotic agent (e.g., proclin), an antifungal agent, an antiprotozoal agent, an anti-parasitic agent, and a combination thereof. An excipient agent may comprise an anti-aggregant. An anti-aggregant may prevent aggregation of macromolecules (e.g., polypeptides, nucleic acids, polysaccharides, combinations thereof). Exemplary anti-aggregants can include histidine, glutamine, arginine, sucrose, glycerol, trimethylamine N-oxide (TMAO), and combinations thereof. An excipient agent may comprise an enzymatic inhibitor. An enzymatic inhibitor can include any species that inhibits enzymatic activity, such as protease inhibitors and/or nuclease inhibitors. An excipient agent may comprise a molecular stability promoter. A nucleic acid stability promoter may comprise a chemical species that inhibits dehybridization of double-stranded nucleic acids. Exemplary nucleic acid stability promoters can include nucleic acid stability promoters, such as magnesium ions and polyamines (putrescine, spermine, spermidine, etc.), and other biomolecular stability promoters such as sugars (e.g., sucrose, maltodextrin, raffinose, trehalose, sorbitol, etc.), dextrans, cyclodextrins (e.g., nonadecacylic caged compounds, methyl cellulose,cellulose derivatives, alpha-cyclodextrins, beta-cyclodextrins, gamma-cyclodextrins, etc.), polyols (e.g., polyethylene glycol), betaines, and combinations thereof.

A fluidic medium (e.g., a binding reagent association medium, a detection medium, a rinsing medium, a binding reagent dissociation medium) may be formulated with any combination of a solvent species, a pH buffering species, a cationic species, an anionic species, or a surfactant species. The components of a fluidic medium may be formulated in amounts to optimize the deposition of anchoring groups or polypeptide composites to a solid support, to optimize the association of binding reagents to analytes, and/or to optimize the dissociation of binding reagents from analytes. A fluidic medium may be formulated to be a homogeneous liquid medium. A fluidic medium may be formulated to be a single-phase liquid medium. A fluidic medium may be formulated to be a multi-phase liquid medium, such as an oil-in-water emulsion or a water-in-oil emulsion. For a fluidic medium formulated as an emulsion, anchoring groups or polypeptide composites may be solvated or suspended within the dissolved phase.

A species (e.g., a solvent species, pH buffering species, a cationic species, an anionic species, a zwitterionic species, a surfactant species, a denaturing species, a crowding agent, an antioxidant) may be formulated in a fluidic medium (e.g., a binding reagent association medium, a detection medium, a rinsing medium, a binding reagent dissociation medium) in any quantity. A species may be present in a fluidic medium at a concentration of at least about 0.0001M, 0.001M, 0.01M, 0.02M, 0.03M, 0.04M, 0.05M, 0.06M, 0.07M, 0.08M, 0.09M, 0.1M, 0.2M, 0.3M, 0.4M, 0.5M, 0.6M, 0.7M, 0.8M, 0.9M, 1M, 1.1M, 1.2M, 1.3M, 1.4M, 1.5M, 1.6M, 1.7M, 1.8M, 1.9M, 2M, 2.1M, 2.2M, 2.3M, 2.4M, 2.5M, 2.6M, 2.7M, 2.8M, 2.9M, 3M, 3.1M, 3.2M, 3.3M, 3.4M, 3.5M, 3.6M, 3.7M, 3.8M, 3.9M, 4M, 4.1M, 4.2M, 4.3M, 4.4M, 4.5M, 4.6M, 4.7M, 4.8M, 4.9M, 5M, 5.1M, 5.2M, 5.3M, 5.4M, 5.5M, 5.6M, 5.7M, 5.8M, 5.9M, 6M, 7M, 8M, 9M or more than 10M. Alternatively or additionally, a species may be present in a fluidic medium at a concentration of no more than about 10M, 9M, 8M, 7M, 6M, 5.9M, 5.8M, 5.7M, 5.6M, 5.5M, 5.4M, 5.3M, 5.2M, 5.1M, 5.0M, 4.9M, 4.8M, 4.7M, 4.6M, 4.5M, 4.4M, 4.3M, 4.2M, 4.1M, 4.0M, 3.9M, 3.8M, 3.7M, 3.6M, 3.5M, 3.4M, 3.3M, 3.2M, 3.1M, 3.0M, 2.9M, 2.8M, 2.7M, 2.6M, 2.5M, 2.4M, 2.3M, 2.2M, 2.1M, 2.0M, 1.9M, 1.8M, 1.7M, 1.6M, 1.5M, 1.4M, 1.3M, 1.2M, 1.1M, 1.0M, 0.9M, 0.8M, 0.7M, 0.6M, 0.5M, 0.4M, 0.3M, 0.2M, 0.1M, 0.09M, 0.08M, 0.07M, 0.06M, 0.05M, 0.04M, 0.03M, 0.02M, 0.01M, 0.001M, 0.001M, or less than about 0.001M.

A species (e.g., a solvent species, pH buffering species, a cationic species, an anionic species, a surfactant species, a denaturing species, a crowding agent, an antioxidant) may be formulated in a fluidic medium (e.g., a binding reagent association medium, a detection medium, a rinsing medium, a binding reagent dissociation medium) in a weight percentage of at least about 0.0001 weight percent (wt %), 0.001 wt %, 0.002 wt %, 0.003 wt %, 0.004 wt %, 0.005 wt %, 0.006 wt %, 0.007 wt %, 0.008 wt %, 0.009 wt %, 0.01 wt %, 0.02 wt %, 0.03 wt %, 0.04 wt %, 0.05 wt %, 0.06 wt %, 0.07 wt %, 0.08 wt %, 0.09 wt %, 0.1 wt %, 0.2 wt %, 0.3 wt %, 0.4 wt %, 0.5 wt %, 0.6 wt %, 0.7 wt %, 0.8 wt %, 0.9 wt %, 1.0 wt %, 1.1 wt %, 1.2 wt %, 1.3 wt %, 1.4 wt %, 1.5 wt %, 1.6 wt %, 1.7 wt %, 1.8 wt %, 1.9 wt %, 2 wt %, 2.1 wt %, 2.2 wt %, 2.3 wt %, 2.4 wt %, 2.5 wt %, 2.6 wt %, 2.7 wt %, 2.8 wt %, 2.9 wt %, 3 wt %, 3.1 wt %, 3.2 wt %, 3.3 wt %, 3.4 wt %, 3.5 wt %, 3.6 wt %, 3.7 wt %, 3.8 wt %, 3.9 wt %, 4 wt %, 4.1 wt %, 4.2 wt %, 4.3 wt %, 4.4 wt %, 4.5 wt %, 4.6 wt %, 4.7 wt %, 4.8 wt %, 4.9 wt %, 5 wt %, 6 wt %, 7 wt %, 8 wt %, 9 wt %, 10 wt %, 20 wt %, 30 wt %, 40 wt %, 50 wt %, 60 wt %, 70 wt %, 80 wt %, 90 wt %, 95 wt %, 99 wt %, 99.9 wt %, or more than 99.9 wt %. Alternatively or additionally, a species may be present in a fluidic medium in a weight percentage of no more than about 99.9 wt %, 99 wt %, 95 wt %, 90 wt %, 80 wt %, 70 wt %, 60 wt %, 50 wt %, 40 wt %, 30 wt %, 20 wt %, 10 wt %, 9 wt %, 8 wt %, 7 wt %, 6 wt %, 5 wt %, 4.9 wt %, 4.8 wt %, 4.7 wt %, 4.6 wt %, 4.5 wt %, 4.4 wt %, 4.3 wt %, 4.2 wt %, 4.1 wt %, 4.0 wt %, 3.9 wt %, 3.8 wt %, 3.7 wt %, 3.6 wt %, 3.5 wt %, 3.4 wt %, 3.3 wt %, 3.2 wt %, 3.1 wt %, 3.0 wt %, 2.9 wt %, 2.8 wt %, 2.7 wt %, 2.6 wt %, 2.5 wt %, 2.4 wt %, 2.3 wt %, 2.2 wt %, 2.1 wt %, 2.0 wt %, 1.9 wt %, 1.8 wt %, 1.7 wt %, 1.6 wt %, 1.5 wt %, 1.4 wt %, 1.3 wt %, 1.2 wt %, 1.1 wt %, 1.0 wt %, 0.9 wt %, 0.8 wt %, 0.7 wt %, 0.6 wt %, 0.5 wt %, 0.4 wt %, 0.3 wt %, 0.2 wt %, 0.1 wt %, 0.09 wt %, 0.08 wt %, 0.07 wt %, 0.06 wt %, 0.05 wt %, 0.04 wt %, 0.03 wt %, 0.02 wt %, 0.01 wt %, 0.009 wt %, 0.008 wt %, 0.007 wt %, 0.006 wt %, 0.005 wt %, 0.004 wt %, 0.003 wt %, 0.002 wt %, 0.001 wt %, 0.0001 wt %, or less than 0.0001 wt %.

A fluidic medium may comprise one or more ionic species that provide the fluidic medium an ionic strength. Ionic strength of a fluidic medium may be formulated with respect to a single ionic species or with respect to a total ionic species content. For example, a fluidic medium comprising sodium chloride and magnesium chloride may be provided with an ionic strength of 0.05M with respect to the magnesium chloride and 0.5M of total ionic strength from both salt species. A fluidic medium (e.g., a binding reagent association medium, a detection medium, a rinsing medium, a binding reagent dissociation medium) may be formulated to have an ionic strength (with respect to a single ionic species or with respect to a total ionic species content) of at least about 0.000001M, 0.00001M, 0.0001M, 0.001M, 0.01M, 0.02M, 0.03M, 0.04M, 0.05M, 0.06M, 0.07M, 0.08M, 0.09M, 0.1M, 0.2M, 0.3M, 0.4M, 0.5M, 0.6M, 0.7M, 0.8M, 0.9M, 1M, 1.1M, 1.2M, 1.3M, 1.4M, 1.5M, 1.6M, 1.7M, 1.8M, 1.9M, 2M, 2.1M, 2.2M, 2.3M, 2.4M, 2.5M, 2.6M, 2.7M, 2.8M, 2.9M, 3M, 3.1M, 3.2M, 3.3M, 3.4M, 3.5M, 3.6M, 3.7M, 3.8M, 3.9M, 4M, 4.1M, 4.2M, 4.3M, 4.4M, 4.5M, 4.6M, 4.7M, 4.8M, 4.9M, 5M, 5.1M, 5.2M, 5.3M, 5.4M, 5.5M, 5.6M, 5.7M, 5.8M, 5.9M, 6M, 7M, 8M, 9M or more than 10M. Alternatively or additionally, a fluidic medium may be formulated to have an ionic strength (with respect to a single ionic species or with respect to a total ionic species content) of no more than about 10M, 9M, 8M, 7M, 6M, 5.9M, 5.8M, 5.7M, 5.6M, 5.5M, 5.4M, 5.3M, 5.2M, 5.1M, 5.0M, 4.9M, 4.8M, 4.7M, 4.6M, 4.5M, 4.4M, 4.3M, 4.2M, 4.1M, 4.0M, 3.9M, 3.8M, 3.7M, 3.6M, 3.5M, 3.4M, 3.3M, 3.2M, 3.1M, 3.0M, 2.9M, 2.8M, 2.7M, 2.6M, 2.5M, 2.4M, 2.3M, 2.2M, 2.1M, 2.0M, 1.9M, 1.8M, 1.7M, 1.6M, 1.5M, 1.4M, 1.3M, 1.2M, 1.1M, 1.0M, 0.9M, 0.8M, 0.7M, 0.6M, 0.5M, 0.4M, 0.3M, 0.2M, 0.1M, 0.09M, 0.08M, 0.07M, 0.06M, 0.05M, 0.04M, 0.03M, 0.02M, 0.01M, 0.001M, 0.001M, 0.0001M, 0.00001M, 0.000001M, or less than about 0.000001M.

A fluidic medium (e.g., a binding reagent association medium, a detection medium, a rinsing medium, a binding reagent dissociation medium) may be formulated to have a pH at a value or within a range of values. A fluidic medium may have a pH of about 0, 0.1, 0.2, 0.3, 0.4, 0.5, 0.6, 0.7, 0.8, 0.9, 1.0, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, or about 14.0. A fluidic medium may have a pH of at least about 0, 0.1, 0.2, 0.3, 0.4, 0.5, 0.6, 0.7, 0.8, 0.9, 1.0, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0 or more than about 14.0. Alternatively or additionally, a fluidic medium may have a pH of no more than about 14.0, 13.9, 13.8, 13.7, 13.6, 13.5, 13.4, 13.3, 13.2, 13.1, 13.0, 12.9, 12.8, 12.7, 12.6, 12.5, 12.4, 12.3, 12.2, 12.1, 12.0, 11.9, 11.8, 11.7, 11.6, 11.5, 11.4, 11.3, 11.2, 11.1, 11.0, 10.9, 10.8, 10.7, 10.6, 10.5, 10.4, 10.3, 10.2, 10.1, 10.0, 9.9, 9.8, 9.7, 9.6, 9.5, 9.4, 9.3, 9.2, 9.1, 9.0, 8.9, 8.8, 8.7, 8.6, 8.5, 8.4, 8.3, 8.2, 8.1, 8.0, 7.9, 7.8, 7.7, 7.6, 7.5, 7.4, 7.3, 7.2, 7.1, 7.0, 6.9, 6.8, 6.7, 6.6, 6.5, 6.4, 6.3, 6.2, 6.1, 6.0, 5.9, 5.8, 5.7, 5.6, 5.5, 5.4, 5.3, 5.2, 5.1, 5.0, 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, 0.1, 0, or less than about 0. A fluidic medium may have a pH in a range from about 0 to about 2, about 0 to about 4, about 0 to about 6, about 0 to about 8, about 0 to about 10, about 0 to about 12, about 0 to about 14, about 2 to about 4, about 2 to about 6, about 2 to about 8, about 2 to about 10, about 2 to about 12, about 2 to about 14, about 4 to about 6, about 4 to about 8, about 4 to about 10, about 4 to about 12, about 4 to about 14, about 6 to about 8, about 6 to about 10, about 6 to about 12, about 6 to about 14, about 8 to about 10, about 8 to about 12, about 8 to about 14, about 10 to about 12, about 10 to about 14, or about 12 to about 14.

A method, as set forth herein, may comprise contacting an array with a fluidic medium (e.g., a binding reagent association medium, a detection medium, a rinsing medium, a binding reagent dissociation medium) for a sufficient amount of time. A fluid contacting step may occur for a sufficient amount of time to form a binding interaction between array components (e.g., an anchoring moiety with an array site or a moiety attached thereto, an analyte with an anchoring moiety, a binding reagent with an analyte, etc.). A fluid contacting step may occur for at least enough time to remove unbound or weakly bound species from an array, a component thereof, or a surface thereof. Alternatively or additionally, a time length of a fluid contacting step may be limited to prevent unwanted dissociation or degradation of array components (e.g., anchoring moieties, analytes, surface-coupling moieties, surface-coupled moieties, etc.) A fluid contacting step may occur for a sufficient time to detect presence or absence of binding reagents at a plurality of array sites. A fluid contacting step may comprise contacting an array or a component thereof with a fluidic medium for at least about 1 second (s), 15 s, 30 s, 1 minute (min), 2 mins, 5 mins, 10 mins, 15 mins, 30 mins, 1 hour (hr), 2 hrs, 3 hrs, 6 hrs, 12 hrs, or more than 12 hrs. Alternatively or additionally, a fluid contacting step may comprise contacting an array or a component thereof with a fluidic medium for no more than about 12 hrs, 6 hrs, 3 hrs, 2 hrs, 1 hr, 30 mins, 15 mins, 10 mins, 5 mins, 2 mins, 1 min, 30 s, 15 s, 1 s, or less than 1 s.

A fluidic medium (e.g., a binding reagent association medium, a detection medium, a rinsing medium, a binding reagent dissociation medium) may be provided at a particular temperature when contacted with an array or a component thereof. In some cases, a fluidic medium may be heated or cooled to the particular temperature before being contacted to the array or the component thereof. In other cases, a fluidic medium may be contacted to the array or component thereof, then subsequently heated or cooled to the particular temperature. A temperature of a fluidic medium contacted to an array or a component thereof may be at least about −80° C., −50° C., −10° C., −5° C., 0° C., 5° C., 10° C., 15° C., 20° C., 25° C., 30° C., 35° C., 40° C., 45° C., 50° C., 60° C., 70° C., 80° C., 90° C., 95° C., or more than 95° C. Alternatively or additionally, a temperature of a fluidic medium contacted to an array or a component thereof may be no more than about 95° C., 90° C., 80° C., 70° C., 60° C., 50° C., 45° C., 40° C., 35° C., 30° C., 25° C., 20° C., 15° C., 10° C., 5° C., 0° C., −5° C., −10° C., −50° C., −80° C., or less than −80° C.

A fluidic medium (e.g., a binding reagent association medium, a detection medium, a rinsing medium, a binding reagent dissociation medium) may be provided to an array with a volume sufficient to perform a step of a method, as set forth herein. A volume of a fluidic medium that is contacted to an array may depend upon a size of a channel, void, reservoir, or chamber within which the array is disposed. In an advantageous configuration, an array, as set forth herein, may be disposed within a flow cell or fluidic cartridge, in which the flow cell or fluidic cartridge contains a channel, void, reservoir, or chamber of a known volume within which an array, as set forth herein, is disposed. A volume of a fluidic medium provided to the channel, void, reservoir, or chamber within which the array is disposed may be provided in proportion to the volume of the channel, void, reservoir, or chamber. For example, a ratio of a volume of fluid provided to a channel, void, reservoir, or chamber relative to the volume of the channel, void, reservoir, or chamber may be at least 2, if at least twice as much fluid is provided as the volume of the channel, void, reservoir, or chamber. A fluidic medium may be provided to a channel, void, reservoir, or chamber within which an array is disposed in a ratio of at least about 0.01, 0.1, 0.5, 1, 1.5, 2, 2.5, 3, 4, 5, 10, 20, 25, 50, 100, or more than 100. Alternatively or additionally, a fluidic medium may be provided to a channel, void, reservoir, or chamber within which an array is disposed in a ratio of no more than 100, 50, 25, 20, 10, 5, 4, 3, 2.5, 2, 1.5, 1, 0.5, 0.1, 0.01, or less than 0.01.

It may be advantageous to provide a fluidic medium to an array in a fashion that facilitates or enhances mass transfer of fluid components. Various steps that occur during an array-based process involve movement of moieties into, out of, or through a fluidic medium. For example, deposition of analytes and/or anchoring moieties on arrays, binding of binding reagents to analytes, dissociation of binding reagents from analytes, and rinsing of binding reagents from arrays all involve mass transfer processes mediated by a fluidic medium.

A method may comprise a series of steps, in which two or more steps comprises contacting an array, as set forth herein, with a fluidic medium (e.g., a binding reagent association medium, a detection medium, a rinsing medium, a binding reagent dissociation medium). For example, a method may comprise the steps of: i) contacting an array with a binding reagent association medium, ii) contacting an array with a detection medium, iii) contacting an array with a binding reagent dissociation medium, and iv) optionally contacting an array with a rinsing medium. Each individual contacting between an array and a fluidic medium may facilitate a different physical process (e.g., a binding reagent association medium to facilitate binding of a binding reagent to an analyte, a binding reagent dissociation medium to facilitate dissociation of a binding reagent from an analyte, etc.). Accordingly, compositions of fluidic media may be formulated to the specific aspects of each fluid-related step of the method. In some cases, two or more fluidic media of a series of fluidic media may comprise a same reagent (e.g., a same blocking reagent, a same surfactant, a same photodamage inhibitor, a same denaturant or chaotrope, a same excipient species, etc.). In particular cases, two or more fluidic media of a series of fluidic media may comprise a same reagent, but vary with respect to a concentration of the reagent. In some cases, two or more fluidic media of a series of fluidic media may comprise a same type of reagent (e.g., a same type of blocking reagent, a same type of surfactant, a same type of photodamage inhibitor, a same type of denaturant or chaotrope, a same type of excipient species, etc.), but differ with respect to the species of the type of reagent. For example, a binding reagent association medium may comprise a first species of denaturant, and a binding reagent dissociation medium may comprise a second species of denaturant.

Signal Analysis Standards

The present disclosure provides an array of analytes comprising one or more signal analysis standard analytes. A signal analysis standard analyte may refer to a molecule, particle, or moiety that is provided on an array for the purpose of identifying and/or quantitating signal detection during an array-based process. In some cases, a signal analysis standard analyte may comprise a standard for identifying and/or quantitating a binding reagent dissociation fraction. In some cases, a signal analysis standard analyte may comprise a standard for identifying and/or quantitating an anomaly occurrence rate.

An array of analytes may be provided with a plurality of standard analytes. A plurality of standard analytes may be deposited on an array before a plurality of analytes are deposited on the array. A plurality of standard analytes may be deposited on an array after a plurality of analytes are deposited on the array. A plurality of standard analytes and a plurality of analytes may be deposited on an array simultaneously. For example, a plurality of standard analytes may be combined with a plurality of analytes to form a combined deposition mixture, then the deposition mixture may be contacted with an array, thereby depositing the plurality of standard analytes and the plurality of analytes on the array to form the array of analytes. In some cases, an array may be provided with standard analytes deposited prior to utilization of the array. Methods of forming arrays, including arrays containing standard and/or control analytes are described in U.S. Pat. Nos. 11,203,612, 11,505,796, and U.S. Patent Publication No. 20220227890A1, each of which is incorporated by reference in its entirety.

Figure 3B:
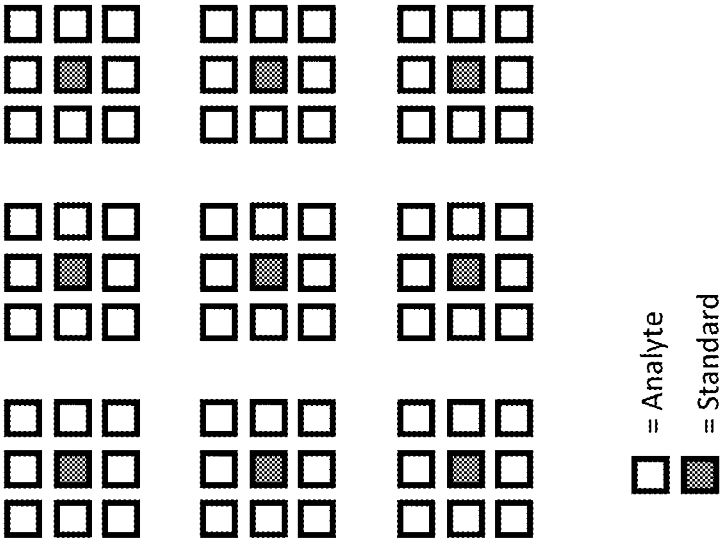
FIGS. 3A, 3B, and 3C display array configurations with differing spatial distributions of standard analytes, in accordance with some embodiments.
Figure 3A:
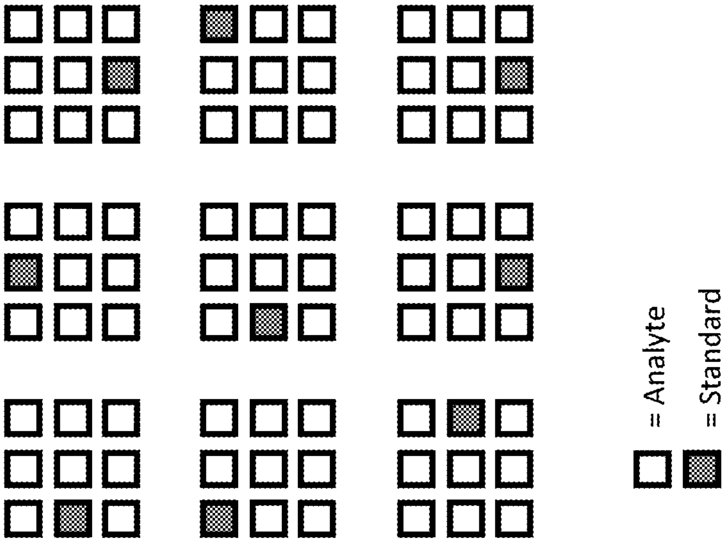
Figure 3C:
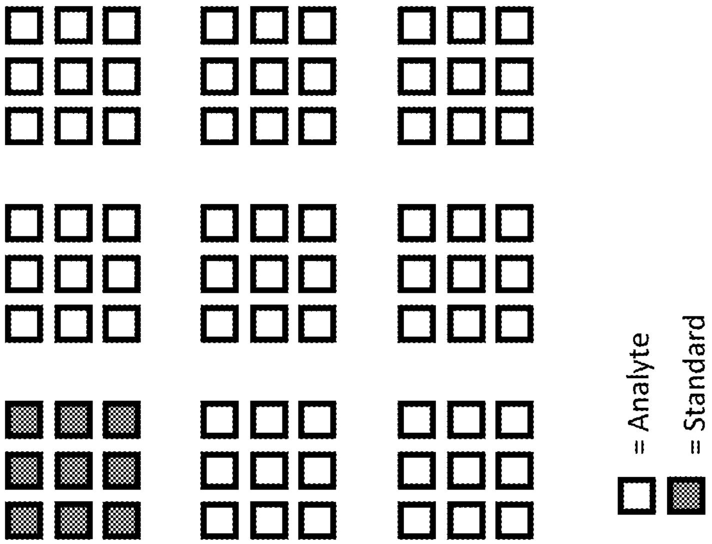

Standard analytes may be distributed on an array in various spatial arrangements that facilitate utilization of the standard analytes for data analysis and interpretation. FIGS. 3A-3C depict various arrangements of standard analytes on an array containing a plurality of sites. FIG. 3A depicts an array containing 9 subarrays, with each subarray having 9 sites arranged in a square grid. The grey sites indicate sites containing a standard analyte and the white sites indicate sites containing target analytes for a given assay. The standard analytes are arranged in a random spatial distribution (i.e., an address containing an analyte cannot be predicted for any randomly chosen subarray). Such a spatial arrangement may be advantageous for identifying spatial differences in binding anomalies (e.g., binding reagent dissociation failure, off-target binding interactions, orthogonal binding interactions). FIG. 3B depicts a similar spatial configuration of array sites as shown in FIG. 3A, with standard analytes located at a predictable or non-random address of each subarray. Such a spatial arrangement may be advantageous for rapidly identifying sites containing standard analytes. FIG. 3C depicts a similar spatial configuration of array sites as shown in FIG. 3A, with standard analytes located within a single subarray. Such a spatial arrangement (especially when standard analytes are deposited prior to analytes) may be advantageous for ensuring sufficient standard analytes are available during an array-based method. In some cases, standard analytes may be provided at array addresses that deviate from a pattern or gridding of array sites (e.g., at addresses in interstitial regions of an array). The skilled person will readily recognize numerous variations of spatially arranging standard analytes on an array.

A signal analysis standard analyte may be provided to facilitate determination of a binding reagent dissociation fraction during an array-based method. In some cases, a standard analyte for determining a binding reagent dissociation fraction may comprise any molecule, particle, or moiety that is orthogonal to binding specificity of a binding reagent that is contacted to the standard analyte. In particular cases, a standard analyte for determining a binding reagent dissociation fraction may comprise any molecule, particle, or moiety that is orthogonal to binding specificities of two or more binding reagents that are contacted to the standard analyte. For example, a standard analyte may exclude any epitope for which a binding reagent has a binding specificity. It may be particularly advantageous to provide a standard analyte that is orthogonal to binding specificities of all binding reagents that are contacted to the standard analyte. A standard analyte that is orthogonal to a binding specificity of a binding reagent may have the detection properties of: i) not producing a signal at an address containing the standard analyte after being contacted with the binding reagent, and ii) not producing a signal at the address containing the standard analyte after a step of dissociating binding reagents from the array.

A standard analyte that is orthogonal to the binding specificity of a binding reagent may be useful for determining an off-target binding rate. An off-target binding rate may refer to a percentage or fraction of sites of a plurality of sites having a bound binding reagent present in the absence of an epitope to which the binding reagent has a binding specificity. Determining an off-target binding rate may comprise one or more steps of: i) coupling binding reagents to standard analytes at sites of a plurality of sites, in which each individual site of the plurality of sites contains a standard analyte, ii) after coupling the binding reagents to the standard analytes, detecting a presence or absence of a signal at each individual site of the plurality of sites, thereby determining a quantity of bound binding reagents, and iii) based upon the quantity of bound binding reagents and a quantity of sites of the plurality of sites, determining an off-target binding rate. An off-target binding rate may be determined as:

$$R_T = \frac{N_1}{Q_s} \tag{4}$$

in which $R_T$ is the off-target binding rate, $N_1$ is a quantity of bound binding reagents, and $Q_s$ is the quantity of sites containing a standard analyte of the plurality of sites.

In other cases, a standard analyte for determining a binding reagent dissociation fraction may comprise any molecule, particle, or moiety that contains an epitope that can bind a binding reagent when the binding reagent is contacted to the standard analyte. In particular cases, a standard analyte for determining a binding reagent dissociation fraction may comprise any molecule, particle, or moiety that contains two or more epitopes that can bind two or more binding reagents when the binding reagents are contacted to the standard analyte. It may be particularly advantageous to provide a standard analyte that contains a plurality of epitopes, in which the plurality of epitopes contains the complete diversity of the epitopes that are bound by all binding reagents utilized during an array-based method. In another advantageous embodiment, a plurality of standard analytes may be provided, in which the plurality of standard analytes contains the complete diversity of epitopes that are bound by all binding reagents utilized during an array-based method. For example, a sequence of ten different binding reagents, in which each binding reagent has a binding specificity for a differing epitope, a plurality of standard analytes may comprise ten different standard analytes, in which each standard analyte contains one of the ten differing epitopes.

Determining a binding reagent dissociation fraction may comprise one or more steps of: i) coupling binding reagents to analytes or standard analytes at sites of a plurality of sites, ii) after coupling the binding reagents to the analytes or standard analytes, detecting presence or absence of a signal at each individual site of the plurality of sites, thereby determining a first quantity of bound binding reagents, iii) providing a binding reagent dissociation condition, iv) after providing the binding reagent dissociation condition, detecting presence or absence of a signal at each individual site of the plurality of sites, thereby determining a second quantity of bound binding reagents, and v) based upon the first quantity of bound binding reagents and the second quantity of bound binding reagents, determining a binding reagent dissociation fraction. A binding reagent dissociation fraction may be calculated as:

$$R_D = \frac{(N_1 - N_2)}{N_1} \tag{5}$$

in which $R_D$ is the binding reagent dissociation fraction, $N_1$ is the first quantity of bound binding reagents, and $N_2$ is the second quantity of bound binding reagents.

Alternatively, determining a binding reagent dissociation fraction may comprise one or more steps of: i) providing a binding reagent dissociation condition, ii) after providing the binding reagent dissociation condition, detecting presence or absence of a signal at each individual site of a plurality of sites, thereby determining a quantity of bound binding reagents, and iii) based upon the quantity of bound binding reagents and a quantity of sites of the plurality of sites, determining a binding reagent dissociation fraction. A binding reagent dissociation fraction may be calculated as:

$$R_D = \frac{N_1}{Q_s} \tag{6}$$

in which $R_D$ is the binding reagent dissociation fraction, $N_1$ is the quantity of bound binding reagents, and $Q_s$ is the quantity of sites of the plurality of sites.

Figure 4A:
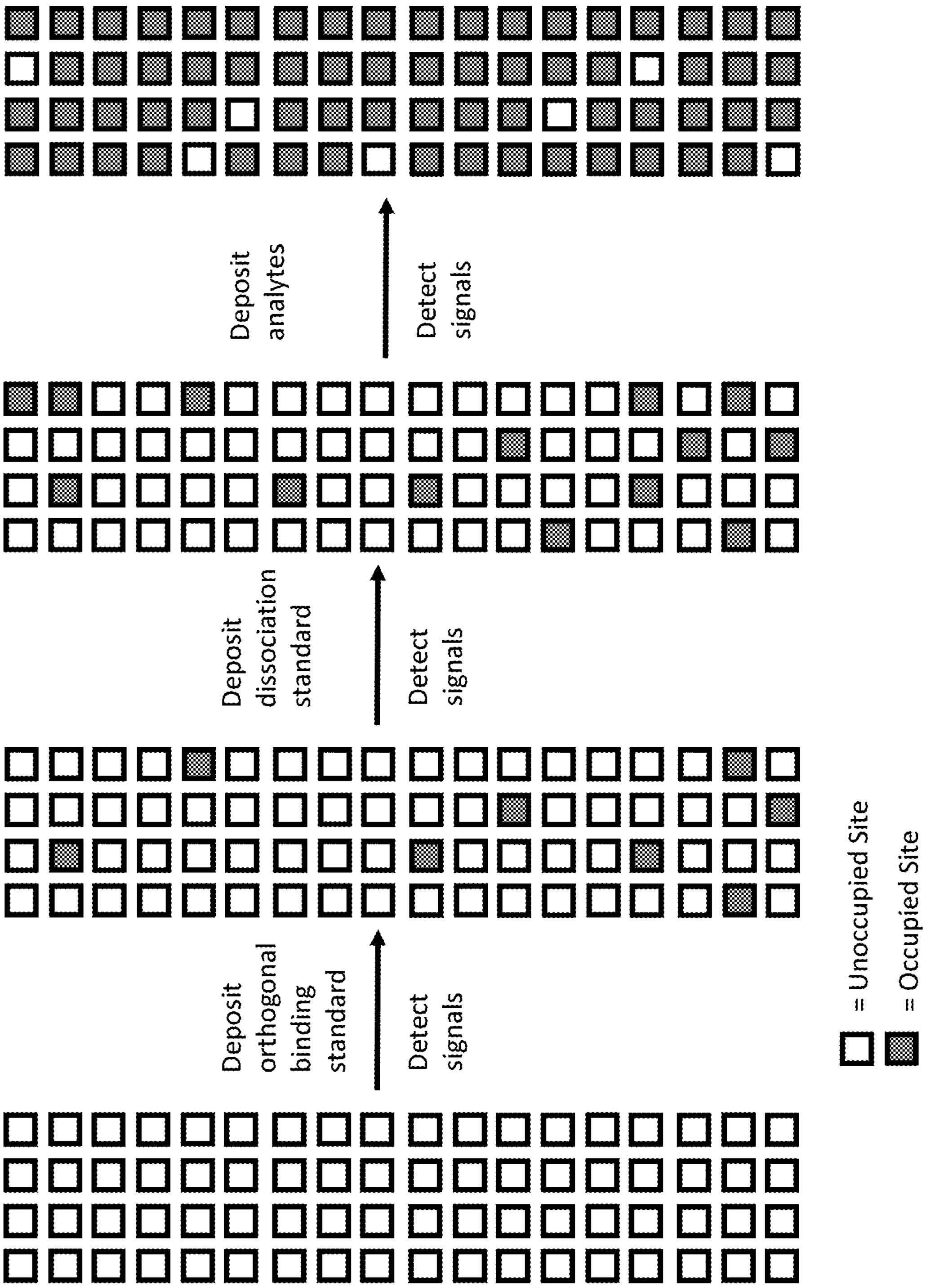
FIGS. 4A and 4B depict methods of forming arrays with analytes and standard analytes, in accordance with some embodiments.
Figure 4B:
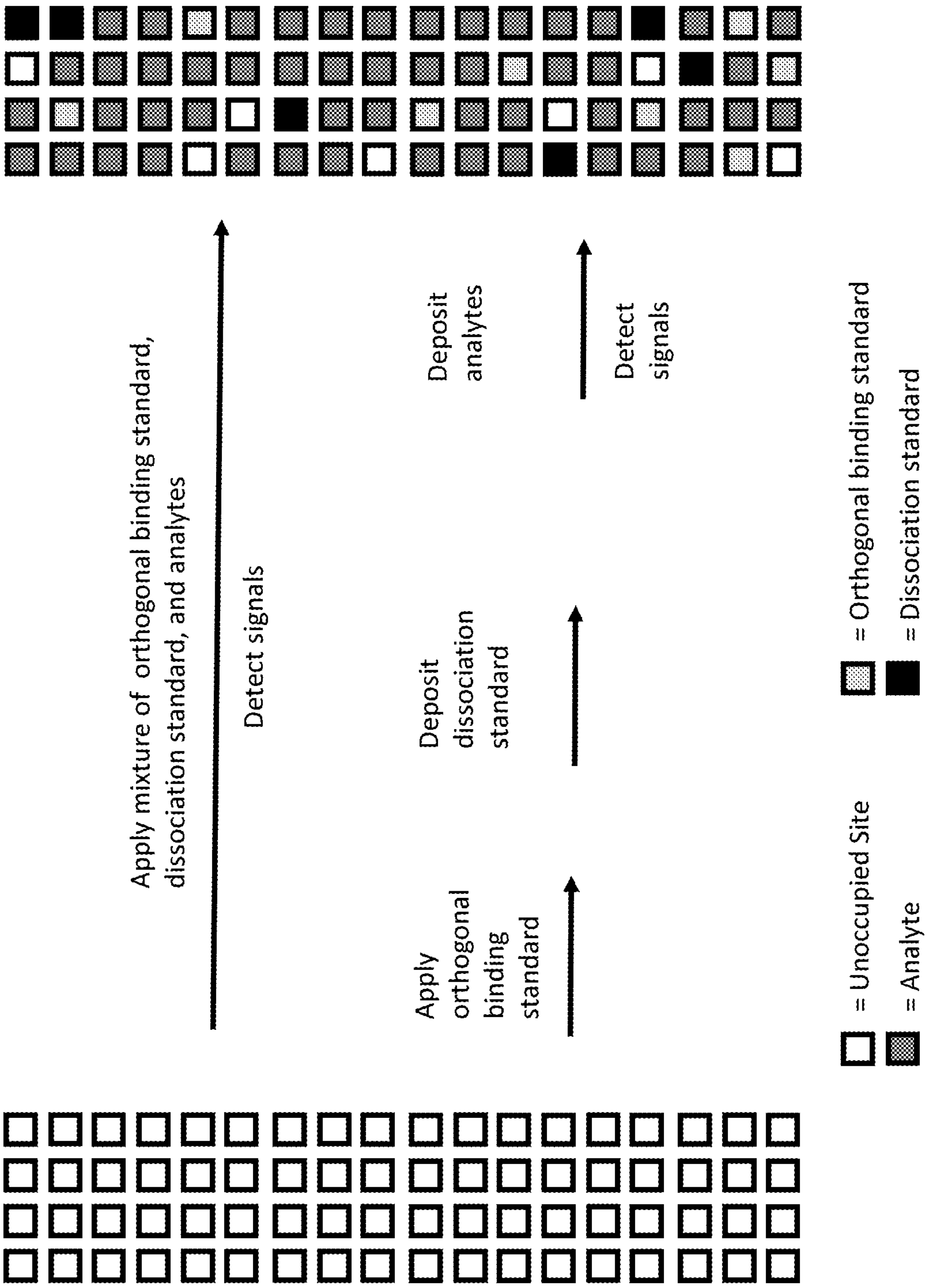

It may be advantageous to provide arrays for which the sites containing standard analytes are known. FIG. 3C depicts a configuration in which the standard analytes are clustered in a localized region of an array (e.g., a subarray). Alternatively, standard analytes may be distributed across an array, for example, in a random or non-random spatial distribution. FIGS. 4A and 4B depict methods for forming arrays containing analytes and standard analytes, in which sites containing the standard analytes are known or identifiable. FIG. 4A depicts a sequential method of identifying addresses containing a standard analyte utilizing a single detectable label. Initially, an array of sites is provided. In a first step, a first standard analyte is deposited (e.g., an orthogonal binding standard) then detected (e.g., via fluorescence) to identify sites containing the first standard analyte. In a second step, a second standard analyte is deposited (e.g., a dissociation standard) then detected to identify sites containing the second standard analyte. This method may be continued for as many standard analytes as necessary for an array-based method. After standard analytes have been deposited, analytes (e.g., polypeptides, nucleic acids, polysaccharides, lipids, metabolites, etc.) may be deposited and detected to identify sites containing the analytes. Each analyte and standard analyte can be coupled to a same detectable label (e.g., a fluorophore or plurality thereof). A detectable label can be coupled to an analyte or a detectable label (e.g., covalently or non-covalently coupled). A detectable label can be coupled to an anchoring moiety (e.g., a nucleic acid nanoparticle, a polymer nanoparticle, or any other suitable nanoparticle), in which the anchoring moiety is coupled to an analyte or a standard analyte.

FIG. 4B depicts methods of identifying addresses containing analytes or standard analytes utilizing different detectable labels. In a first embodiment of the method, a plurality of analytes may be combined with one or more standard analytes (e.g., orthogonal binding standards, dissociation standards, off-target binding standards, etc.) to form a combined analyte mixture. Each individual species of standard analyte and the plurality of analytes may be labeled with differing detectable labels. The combined analyte mixture may be deposited on the array in a single step, then detected at each array site to determine a presence or absence of a moiety at each array site, in which the type of moiety can be identified by the sensed detectable label. Alternatively, the deposition of analytes and standard analytes may proceed in a step-wise fashion, with detection occurring after each deposition step or after the final deposition step. The skilled person will readily recognize that the methods of FIGS. 4A and 4B can be varied, for example with regard to ordering of deposition steps or detection steps. For example, a method can be configured to utilize both sequential deposition of different types of standard analytes (e.g. as depicted in FIG. 4A) and differential labeling of respective types of standard analytes (e.g. as depicted in FIG. 4B).

In some cases, a standard analyte for determining a binding reagent dissociation fraction may comprise the same type of molecule, moiety, or particle as an analyte of an array of analytes. For example, an array of polypeptides may comprise a polypeptide standard analyte. In other cases, a standard analyte for determining a binding reagent dissociation fraction may comprise a differing type of molecule, moiety, or particle compared to an analyte of an array of analytes. For example, an array of polypeptides may comprise a non-polypeptide standard analyte (e.g., a nucleic acid analyte, a polysaccharide analyte, a polymer molecule, etc.).

A signal analysis standard analyte may be utilized to characterize one or more aspects of array performance, such as binding reagent dissociation fraction, off-target binding rate, orthogonal binding rate, and/or binding reagent dissociation failure rate. It may be preferable to measure, quantify, or otherwise characterize a behavior (e.g., a binding reagent dissociation fraction, off-target binding rate, orthogonal binding rate, or binding reagent dissociation failure rate) of a signal analysis standard analyte.

Figure 5A:
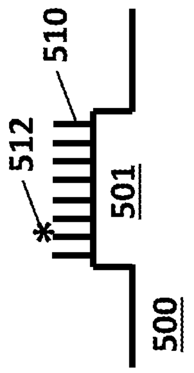
FIGS. 5A, 5B, 5C, 5D, 5E, 5F, 5G, 5H, 5I, and 5J illustrate differing embodiments of standard analytes, in accordance with some embodiments.
Figure 5B:
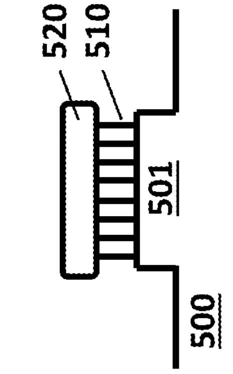
Figure 5C:
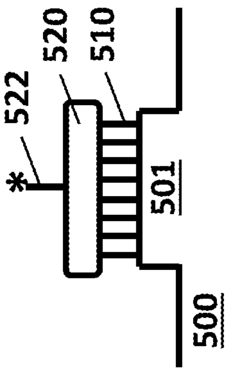

FIGS. 5A-5J illustrate examples of structures for signal analysis standards. FIGS. 5A-5C depict examples of signal analysis standards that do not contain a standard analyte. Such standards may be useful for identifying binding anomalies associated with dysfunctional or non-functional array sites or array components attached thereto. For example, an array site or a component attached thereto (e.g., coupling moieties) may comprise a defect (e.g., an unreacted functional group, a damaged or degraded moiety, an impurity, etc.) that facilitates orthogonal binding of a binding reagent to the array site. In another example, an array component (e.g., an anchoring moiety) may comprise a defect (e.g., a manufacturing defect, a damaged or degraded moiety, etc.) that facilitates orthogonal binding of a binding reagent to the array component. FIG. 5A depicts a solid support 500 comprising an array site 501, in which the array site 501 is unoccupied (e.g., by an analyte, by an anchoring moiety), and in which the unoccupied array site 501 comprises a signal analysis standard. The array site 501 may comprise a coating or surface layer 510 (e.g., a plurality of coupling moieties, a plurality of passivating moieties), in which the coating or surface layer 510 comprises a defect 512. Detection of a signal from a binding reagent at an unoccupied array site 501 may provide a measure of orthogonal binding rate associated with array sites 501. In some cases, unoccupied array sites 501 may be formed intrinsically during deposition of sample analytes or standard analytes due to incomplete deposition at all array sites 501 of a plurality of array sites. In other cases, unoccupied array sites 501 may be formed by: i) blocking array sites (e.g., with a blocking particle or a blocking chemical group or layer), ii) depositing sample analytes and/or standard analytes at sites excluding the blocked array sites, and iii) unblocking the blocked array sites (e.g., via chemical or enzymatic digestion, via photocatalyzed degradation of blocking groups, via photodegradation of blocking particles). FIG. 5B depicts a solid support 500 comprising an array site 501, in which a coating or surface layer 510 of the array site 501 is coupled to an anchoring moiety 520. The anchoring moiety 520 may be covalently or non-covalently attached to the coating or surface layer 510. Detection of a signal from a binding reagent at an array site 501 containing an anchoring moiety 520 and no sample analyte or standard analyte may provide a measure of orthogonal binding rate associated with anchoring moieties 520. Moreover, utilization of a plurality of standard analytes as shown in FIG. 5B will provide a unique pattern of sites that are known to provide no non-orthogonal binding, thereby providing information on the orthogonal binding fraction during an array-based process. FIG. 5C depicts a similar configuration to FIG. 5B, with an anchoring moiety 520 comprising an uncoupled analyte-coupling moiety 522 (i.e., a moiety that is configured to couple a sample analyte or a standard analyte to the anchoring moiety 520). Detection of a signal from a binding reagent at an array site 501 containing an anchoring moiety 520 with an uncoupled analyte-coupling moiety 522 may provide a measure of orthogonal binding rate associated with anchoring moieties 520 that did not couple a sample analyte or standard analyte during an analyte preparation process, or became dissociated from the sample analyte or standard analyte before or during an array-based process.

Figure 5D:
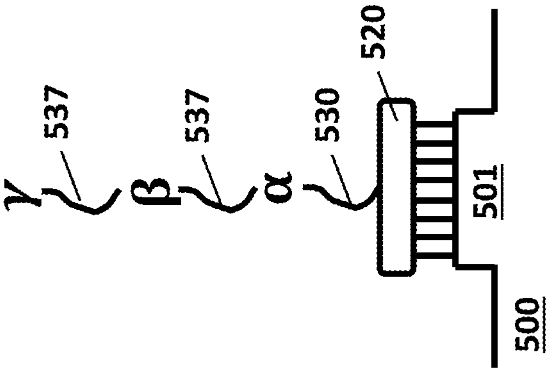
Figure 5E:
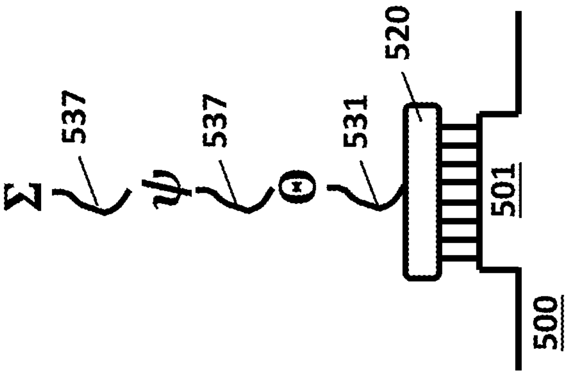

FIGS. 5D and 5E depict examples of signal analysis standard analytes. FIG. 5D depicts a solid support 500 comprising an array site 501, in which the array site 501 is occupied by a standard analyte 530 that is attached to an anchoring moiety 520, and in which the anchoring moiety 520 is coupled to the array site 501. The standard analyte 530 contains epitopes α, β, and γ, which are optionally separated by linking moictics 537 (e.g., a polypeptide linking moiety, a non-polypeptide linking moiety such as polyethylene glycol, a nucleic acid linking moiety, etc.). Epitopes α, β, and γ may be chosen with a same structure (e.g., a residue sequence) as epitopes targeted for binding by binding reagents utilized during an array-based process. A standard analyte 530 may contain all epitopes targeted by binding reagents during an array-based process, or a subset thereof (e.g., at least about 1%, 5%, 10%, 20%, 25%, 30%, 50%, or more than 50% of targeted epitopes). Detection of presence and/or absence of a signal (depending upon after an association or dissociation step) from a binding reagent at an array site 501 containing a standard analyte 530 may provide a measure of on-target (i.e., binding to an epitope for which a binding reagent has binding specificity) binding rate for a binding reagent, or a measure of binding reagent dissociation fraction between the standard analyte 530 and a binding reagent attached thereto. FIG. 5E depicts a solid support 500 comprising an array site 501, in which the array site 501 is occupied by a standard analyte 531 that is attached to an anchoring moiety 520, and in which the anchoring moiety 520 is coupled to the array site 501. The standard analyte 531 contains epitopes Θ, ψ, and Σ, which are optionally separated by linking moieties 537. Epitopes Θ, ψ, and Σ may be chosen with a differing structure from epitopes targeted for binding by binding reagents utilized during an array-based process. Detection of presence and/or absence of a signal (depending upon after an association or dissociation step) from a binding reagent at an array site 501 containing a standard analyte 531 may provide a measure of off-target (i.e., binding to an epitope for which a binding reagent does not have binding specificity) binding rate for a binding reagent, or a measure of binding reagent dissociation fraction between the standard analyte 530 and a binding reagent attached thereto.

Figure 5F:
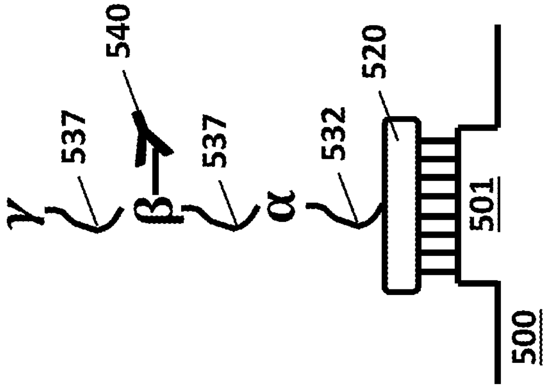
Figure 5G:
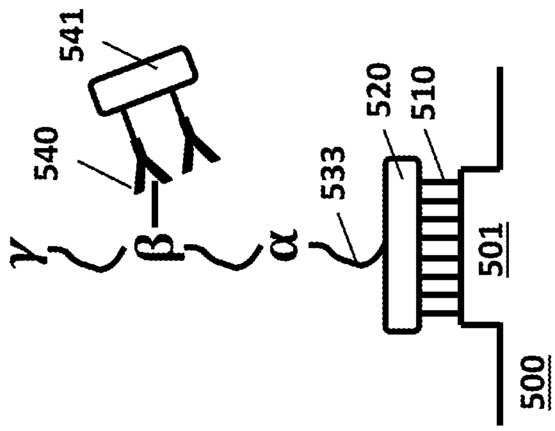
Figure 5H:
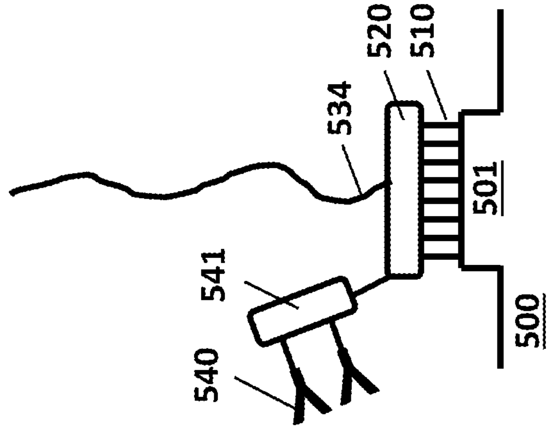

FIGS. 5F-5H illustrate signal analysis standard analytes that may be advantageous for identifying and/or measuring binding anomalies associated with binding reagent dissociation failure. FIG. 5F depicts a solid support 500 comprising an array site 501, in which the array site 501 is occupied by a standard analyte 532 that is attached to an anchoring moiety 520, and in which the anchoring moiety 520 is coupled to the array site 501. The standard analyte 532 has a similar structure to standard analyte 530, but with an affinity agent 540 attached (e.g., via a cross-linking or a covalent bond) to a residue of epitope β. The presence of the affinity agent 540 would likely occlude further binding of binding reagents to epitope β, and could inhibit binding to other epitopes, such as epitopes α and γ. Accordingly, detection of a signal from a binding reagent that has a binding specificity for epitope β, or a proximal epitope may suggest binding due to orthogonal binding rather than binding of the binding reagent to the standard analyte 532. FIG. 5G depicts a standard analyte 533 that is structurally similar to standard analyte 532, but with a more complex binding reagent. The binding reagent of FIG. 5G may comprise a retaining component 541 (e.g., a nanoparticle, a polymer particle, a nucleic acid nanoparticle) that is coupled to a plurality of affinity agents 540. The standard analyte of configuration of FIG. 5G may be expected to behave similarly to the configuration of FIG. 5F, although the larger multivalent binding reagent may more effectively cause steric occlusion of other binding reagents, thereby further inhibiting binding to other epitopes of the standard analyte 533. FIG. 5H depicts a solid support 500 comprising an array site 501, in which the array site 501 is occupied by a standard analyte 534 that is attached to an anchoring moiety 520, and in which the anchoring moiety 520 is coupled to the array site 501. A binding reagent similar to the binding reagent of FIG. 5G may be coupled to the anchoring moiety 520. Such a configuration may partially occlude binding of binding reagents to the standard analyte 534, although binding may still be possible. It may be advantageous to provide a mixture of standard analytes similar to FIGS. 5F-5H to characterize binding anomalies associated with different types of binding reagent dissociation failure during an array-based process.

Figure 5I:
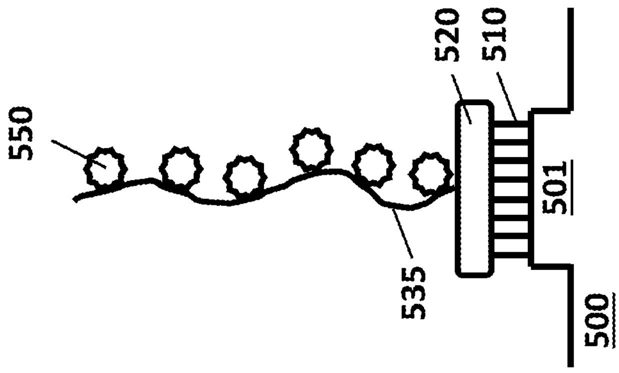
Figure 5J:
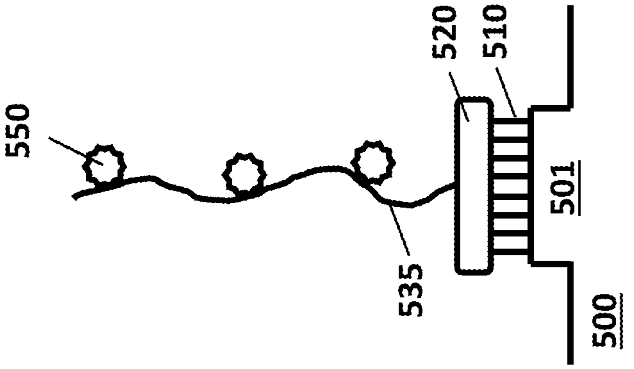

FIGS. 5I-5J illustrate standard analytes that may be useful for measuring signals associated with photobleaching in an array system. Detectable labels of a binding reagent that is retained on an array due to binding reagent dissociation failure may photobleach over successive detection steps due to repeated exposure to light. Accordingly, the discrete or continuous decrease of signal magnitude from a retained binding reagent due to photobleaching may be useful characteristic for identifying signal anomalies associated with retained binding reagents. FIG. 5I depicts a solid support 500 comprising an array site 501, in which the array site 501 is occupied by a standard analyte 535 that is attached to an anchoring moiety 520, and in which the anchoring moiety 520 is coupled to the array site 501. The standard analyte 535 comprises a plurality of detectable labels 550 (e.g., fluorophores, luminophores). FIG. 5J depicts a similar configuration to the configuration of FIG. 5I, but with fewer detectable labels 550 coupled to the standard analyte 535. It may be advantageous to provide a gradient of standard analytes 535 over a plurality of sites, wherein the gradient is based upon differing quantities of detectable labels 550 at respective sites in the plurality of sites, thereby facilitating quantitation of photobleaching rate as a function of number of fluorophores available at an array site.

Figure 7A:
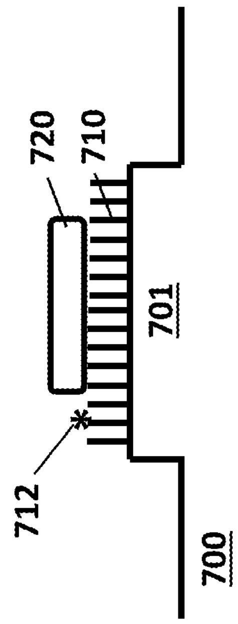
FIGS. 7A and 7B display detection of a surface defect utilizing a standard analyte, in accordance with some embodiments.
Figure 7B:
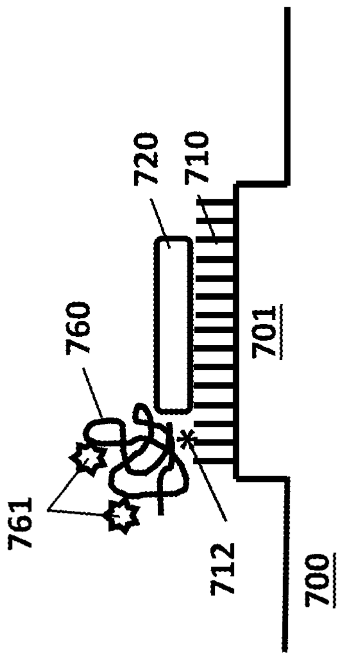

An array containing a plurality of sites may comprise a plurality of defects that facilitate orthogonal binding of binding reagents to array sites. Accordingly, a signal detected at an array site can be caused by orthogonal binding of a binding reagent, on-target binding of the binding reagent, or a combination thereof. It may be advantageous to provide a standard analyte that facilitates spatial identification of an array site that contains a defect, or is within a spatially non-resolvable proximity to a defect. FIGS. 7A-7B depict aspects of utilizing signal analysis standards to detect array defects. FIG. 7A depicts a solid support 700 comprising an array site 701, in which a coating or surface layer 710 of the array site 701 is coupled to an anchoring moiety 720. The coating or surface layer 710 comprises a defect 712 that is not fully occluded by the presence of the anchoring moiety 720. FIG. 7B depicts an array configuration in which a blocking agent 760, as set forth herein, has been coupled to the defect 712 of the coating or surface layer 710. The blocking agent comprises one or more detectable labels 761, thereby facilitating detection of the blocking agent at the array site 701.

Figure 8:
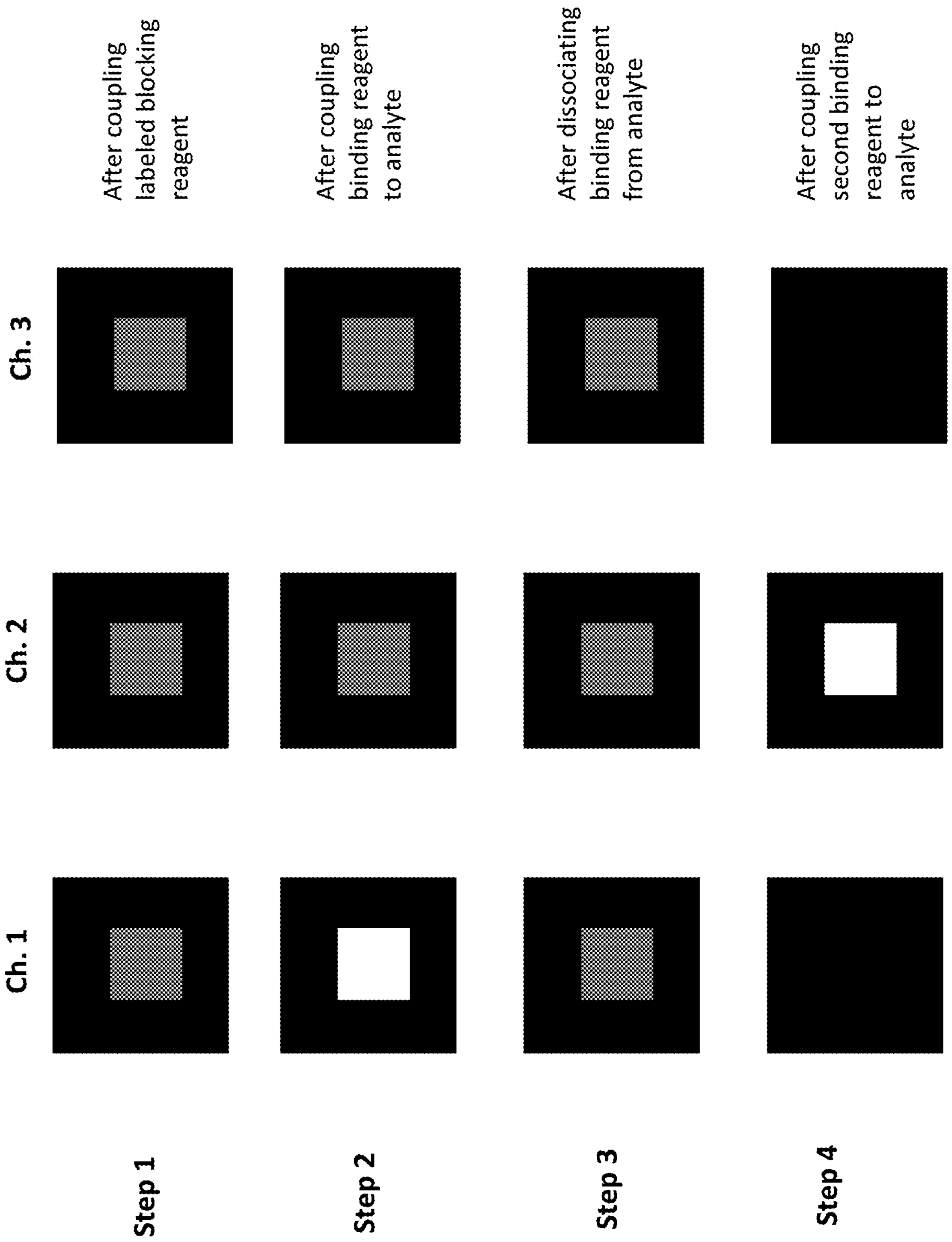
FIG. 8 depicts steps for identifying a binding anomaly utilizing a standard analyte, in accordance with some embodiments.

In a particularly advantageous embodiment of the signal analysis standard of FIG. 7B, the blocking agent 760 may be provided with two or more species of detectable label 761 (e.g., as distinguished by fluorophore excitation and/or emission wavelength). For example, a blocking agent 760 may be coupled to two or three different species of fluorophores, in which each fluorophore is present at a quantity that is minimally sufficient for detection (e.g. no more than about 10, 9, 8, 7, 6, 5, 4, 3, 2, or less than 2 fluorophores per species of fluorophore). Such a configuration may be advantageous for providing an unambiguous signal when the blocking agent 760 is bound at or adjacent to an array site 701. FIG. 8 depicts exemplary signal detection images at an array site containing a defect after a blocking agent has been contacted to the array site. Presence or absence of a signal is detected in three different channels corresponding to differing emission wavelengths of the three species of fluorophores coupled to a blocking agent. In a first detection step that occurs after contacting a plurality of labeled blocking agents to an array, dim signals are observed in channels 1, 2, and 3, thereby indicating presence of the blocking agent at the detected array site. Prior to a second detection step, a binding reagent that is detectable in channel 1 can be contacted to the array. During detection step 2, a strong signal is observed in channel 1, suggesting presence of a bound binding reagent at the array site, and dimmer signals are still observed in channels 2 and 3, suggesting retention of the labeled blocking agent at the array site. Prior to a third detection step, a binding reagent dissociation condition is provided (e.g., contacting a binding reagent dissociation medium to the array). In the third detection step, dimmer signals are observed in channels 1, 2, and 3, suggesting that the binding reagent has been dissociated and the blocking agent remains associated at the array site. Prior to a fourth step, a binding reagent that is detectable in channel 2 can be contacted to the array. During the fourth detection step, a strong signal is observed in channel 2, suggesting presence of a bound binding reagent at the array site, but no signals are detected in channels 1 and 3, suggesting the blocking reagent has dissociated from the array site. Accordingly, detection of the first binding reagent at the array site may be assigned a greater confidence than detection of the second binding reagent because absence of the blocking agent in the fourth detection step increases the likelihood that the detection event of the second binding reagent was due to orthogonal binding. In some cases, a method may comprise: i) providing signal data from detection of presence or absence of a labeled blocking agent at an array site to a computer or processor, and ii) based upon the signal data, assigning a measure of confidence to a detection event at the array site.

Determination of Binding Anomaly Fractions

Detection of single-analyte arrays at single-analyte resolution can involve detection of binding events at potentially millions or billions of individual array sites. Amongst so many detection events, observation of binding anomalies is likely to occur. Binding anomalies can arise due to array-based binding phenomena, such as orthogonal binding interactions, off-target binding interactions, and binding reagent dissociation failure, as well as sensor-based phenomena, such as failure to reset or discharge accumulated charge from a pixel of a pixel-based sensor. Identification and quantification of array-based binding anomalies may facilitate an array-based process by providing a measurable reference for efficacy of fluidic media systems utilized during an array-based assay.

A binding anomaly can refer to a detectable signal that deviates with respect to one or more signal characteristics from a signal associated with a binding reagent. Signal characteristics that may be useful for identification of binding anomalies can include spatial signal characteristics (e.g., signal morphology, signal magnitude, signal address) and temporal characteristics (e.g., signal lifetime, signal decay rate, signal growth rate, signal blinking rate, signal presence at improper time during a method). Accordingly, detectable binding anomalies can include: i) aberrant signal morphology, ii) high signal magnitude, iii) low signal magnitude, iv) improper signal location, v) unexpectedly long signal lifetime, vi) unexpectedly short signal lifetime, vii) unexpectedly slow signal decay rate, viii) unexpectedly fast signal decay rate, ix) unexpectedly fast signal growth rate, x) unexpectedly slow signal growth rate, xi) absence of a signal at a particular method step, xii) presence of a signal at a particular method step, xiii) persistence of a signal over consecutive method steps, xiv) absence of a signal over consecutive method steps, and combinations thereof.

Detection of signals from binding reagents at sites of a plurality of sites can be performed in numerous ways, thereby providing different types of signal information. Accordingly, configuration of signal detection steps during an array-based process may affect which signals are interpreted as corresponding to binding anomalies. For example, in a method involving association of binding reagents to analytes followed dissociation of the binding reagents from the analytes, a signal may be present or absent at a site after the association step depending upon whether a binding reagent bound an analyte at the site, but the signal will always be expected to be absent after a dissociation step that is configured to dissociate the binding reagent from the analyte at the site. Accordingly, if signals of binding reagents bound to analytes at sites are detected after an association step and after a dissociation step, expected sets of signal values at a given site (shown as [association value, dissociation value]) can be [PRESENT, NOT PRESENT] or [NOT PRESENT, NOT PRESENT], and anomalous signal values at the given site can be [NOT PRESENT, PRESENT] or [PRESENT, PRESENT]. Likewise, if signals of binding reagents bound to analytes at sites are detected only after association steps, classification of expected or anomalous values may be determined by presence or absence of signals after consecutive association steps. Table II depicts possible signal detection patterns for a site containing an analyte during three consecutive binding reagent association steps. The sequence of binding reagents that are contacted with the analyte at the site is chosen such that it is unlikely that the analyte would bind a binding reagent during two consecutive steps. Accordingly, signal patterns are assigned classification values of EXPECTED, POSSIBLY ANOMALOUS (2 consecutive detections), or ANOMALOUS (3 consecutive detections).

TABLE II

Classification of Signal Patterns

| Association Step | | | Signal |
|---|---|---|---|
| Step 1 | Step 2 | Step 3 | Classification |
| Signal | No Signal | No Signal | EXPECTED |
| Signal | Signal | No Signal | POSSIBLY ANOMALOUS |
| Signal | Signal | Signal | ANOMALOUS |
| No Signal | Signal | Signal | POSSIBLY ANOMALOUS |
| No Signal | Signal | No Signal | EXPECTED |
| No Signal | Signal | Signal | POSSIBLY ANOMALOUS |
| No Signal | No Signal | Signal | EXPECTED |
| No Signal | No Signal | No Signal | EXPECTED |

In some cases, a less stringent signal classification criterium can be applied, such as permitting 2 consecutive detected signals, but classifying 3 or more consecutive signals as a binding anomaly.

The skilled person will readily recognize that other methods of signal detection (e.g., luminescence or fluorescence lifetime detection) will have differing types of binding anomalies. For example, luminescence or fluorescence lifetime detection may produce anomalous signals that have sudden decreases in signal magnitude, sudden increases in signal magnitude, or other temporal anomalies such as signal blinking. Although methods set forth herein are exemplified with respect to discrete signal measurements in the temporal domain (i.e., taken at fixed points in time), the methods can be assumed to extend to continuous signal measurements (and detection of anomalies in such data) such as those associated with luminescence or fluorescence lifetime.

Figure 11A:
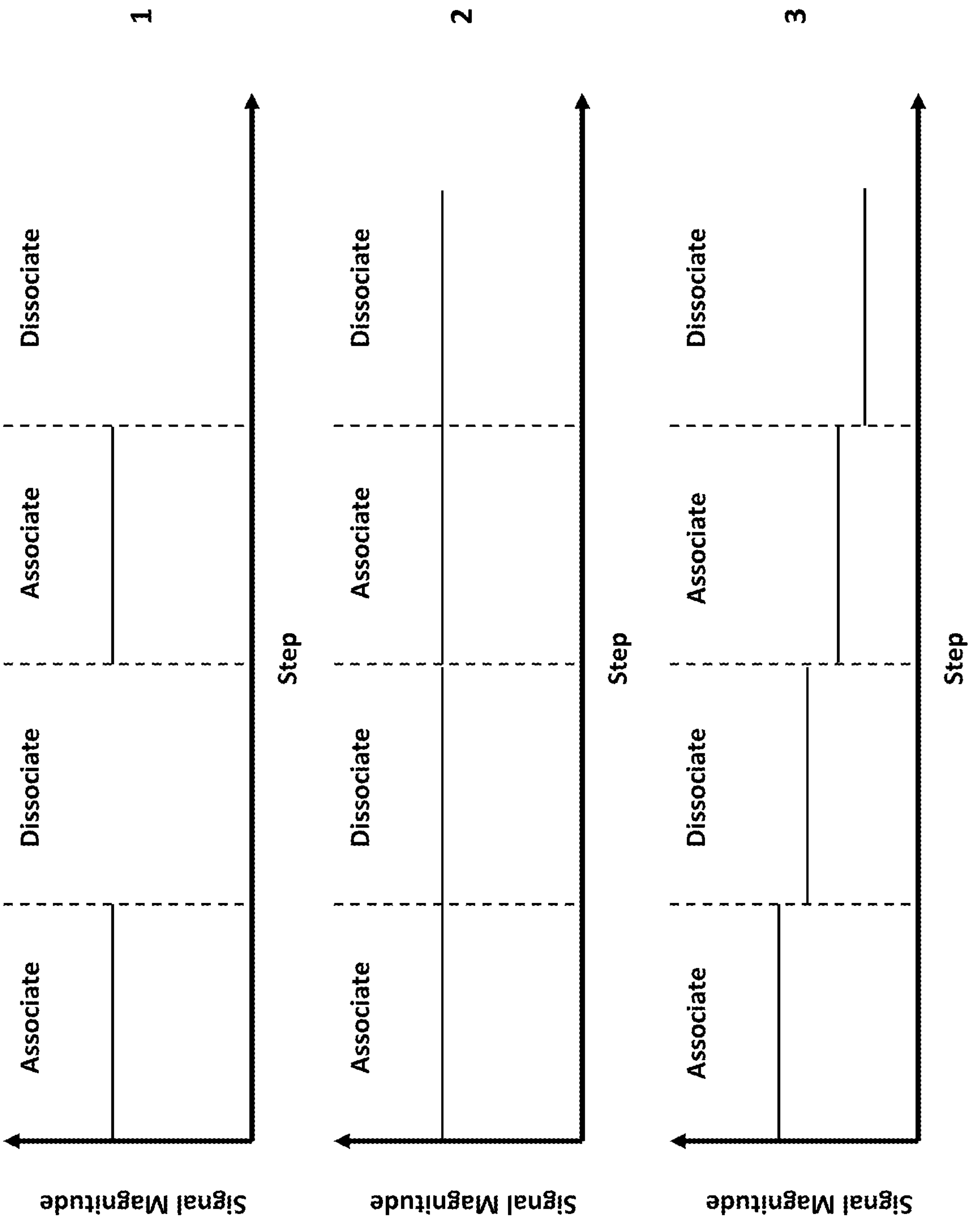
FIGS. 11A and 11B display signal patterns suggesting a binding anomaly, in accordance with some embodiments.
Figure 11B:
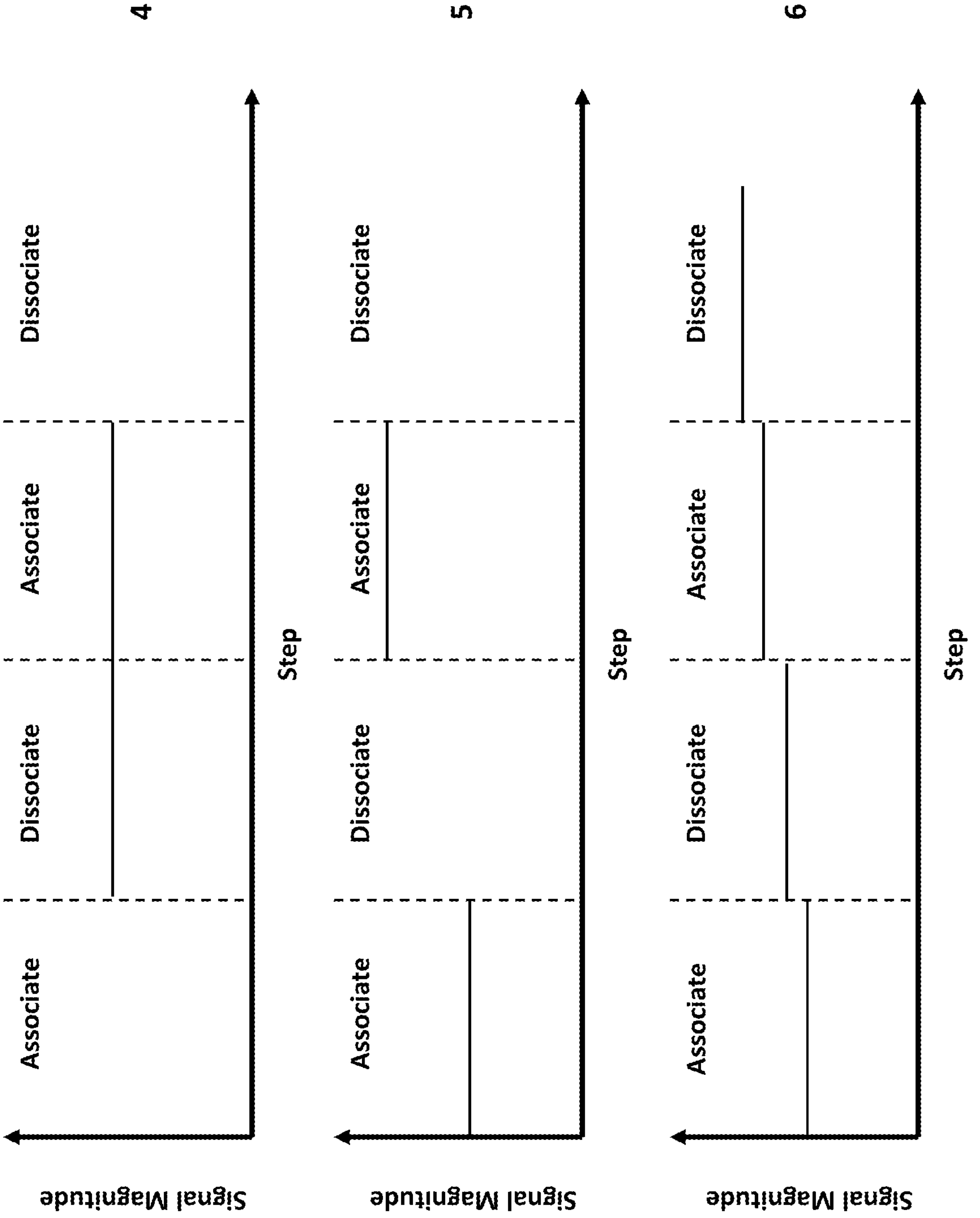

FIGS. 11A and 11B depict examples of signal patterns that may be identified as expected or anomalous. The plots depict detected signal magnitudes at an array site over successive steps of associating and dissociating binding reagents to the site. Plot 1 of FIG. 11A depicts an expected detection signal pattern. A measurable signal magnitude is detected during the two association steps, and low or no signal magnitude is detected during the two dissociation steps. This pattern suggests co-location of binding reagents at the site during the association steps, and dissociation of the binding reagents during the dissociation steps. Plot 2 of FIG. 11A depicts an anomalous signal pattern in which no change in signal magnitude is observed between association and dissociation steps. Such a signal pattern may be associated with orthogonal binding of a binding reagent at the array site or failure of a binding reagent dissociation process. Plot 3 of FIG. 11A depicts an anomalous signal pattern in which the signal magnitude decreases at a steady rate with each successive detection step. Such a signal pattern may be associated with a photodegradation process such as photobleaching of an orthogonally-bound or non-dissociated binding reagent, thereby causing the anomalous signals. Plot 4 of FIG. 11B depicts an anomalous signal pattern in which no signal is present during the first association detection step, but a signal appears during the first dissociation detection step. Such a signal pattern might suggest incidental orthogonal binding of a dissociated binding reagent from a different site during the dissociation step. Plot 5 of FIG. 11B depicts a signal pattern similar to Plot 1 of FIG. 11A, but with differing signal magnitudes between the first association step and the second association step. Such a signal pattern might be expected if there is variance in signal intensities between binding reagents, or may be anomalous if the difference in signal magnitude exceeds the variance (e.g., due to co-location of multiple binding reagents at the site). Plot 6 of FIG. 11B depicts an anomalous signal pattern in which the signal magnitude increases with each consecutive detection step. Such a pattern could arise due to aggregation of binding reagents at the site.

In some cases, a plurality of signal analysis standards may be utilized to identify a binding anomaly or a binding anomaly fraction. A method may comprise the steps of: i) contacting binding reagents to a plurality of sites, in which each individual site of the plurality of sites contains a signal analysis standard, ii) detecting presence or absence of a signal from a binding reagent at each individual site of the plurality of sites, and iii) identifying a binding anomaly at a site of the plurality of sites, in which the site contains a signal analysis standard. In some cases, step iii) may comprise identifying a plurality of binding anomalies at sites of the plurality of sites. In some cases, a method may further comprise, based upon identifying the plurality of binding anomalies at sites of the plurality of sites, determining a binding anomaly fraction.

Figure 6A:
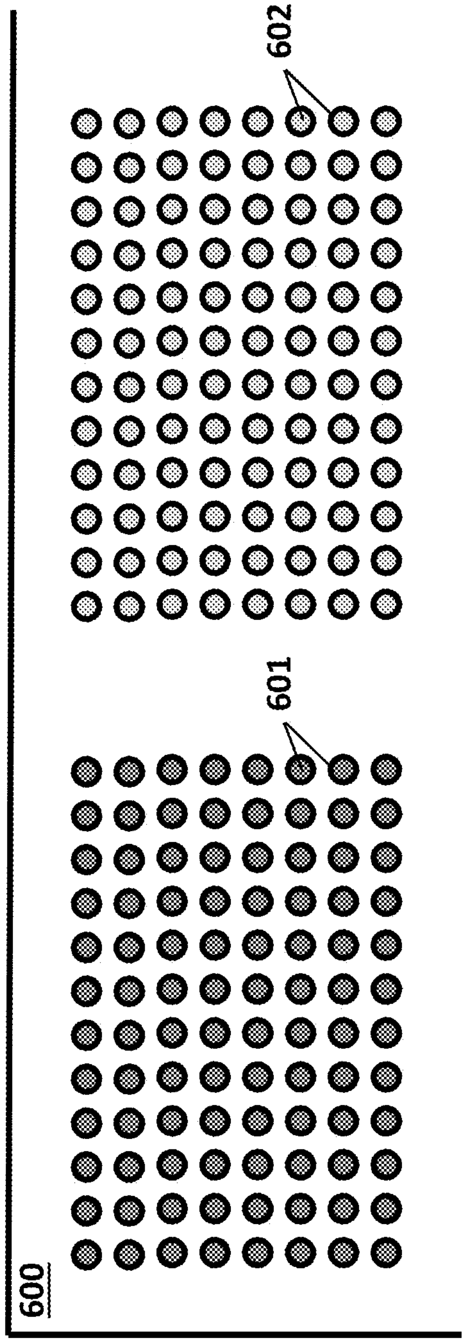
FIG. 6A shows a configuration of an array containing analytes and standard analytes, in accordance with some embodiments.
Figure 6B:
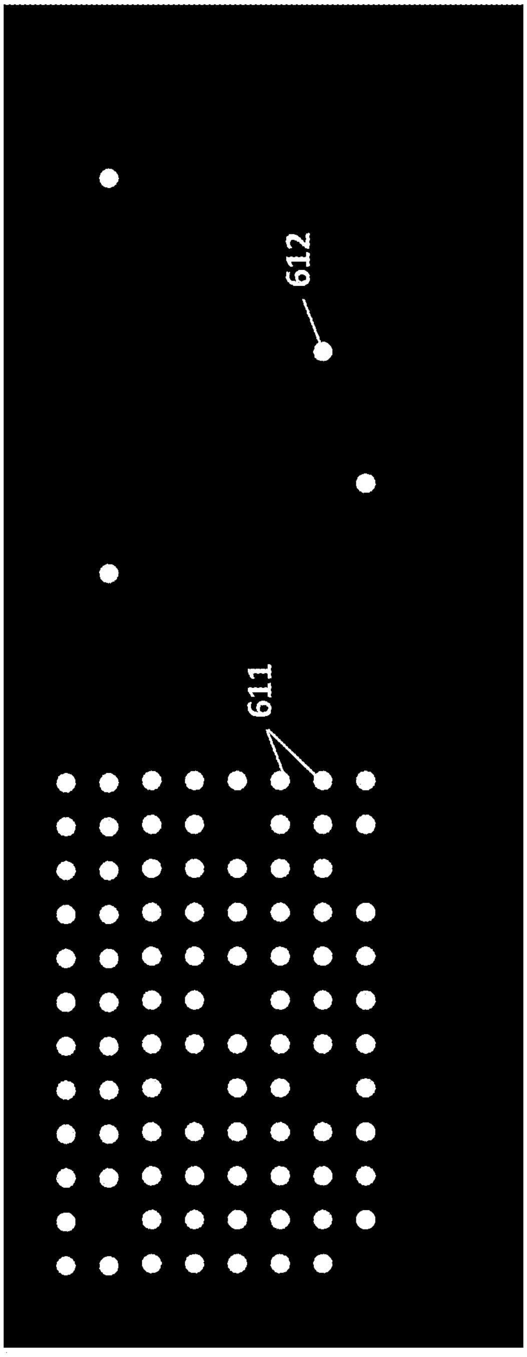
FIGS. 6B, 6C, and 6D show detection of binding events on the array of FIG. 6A under differing binding conditions, in accordance with some embodiments.
Figure 6C:
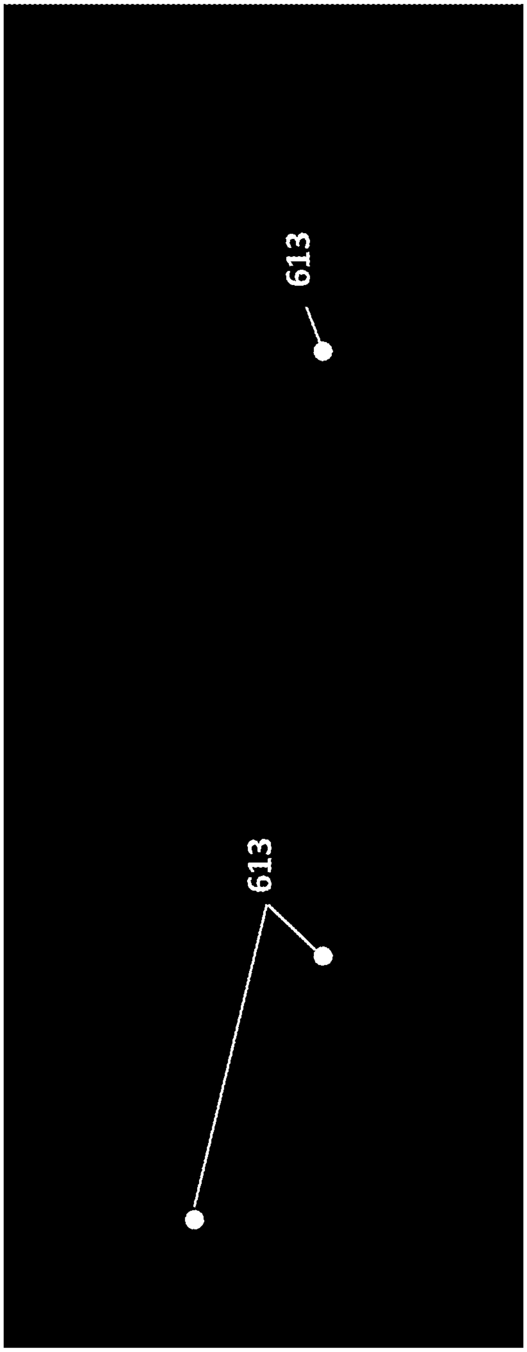
Figure 6D:
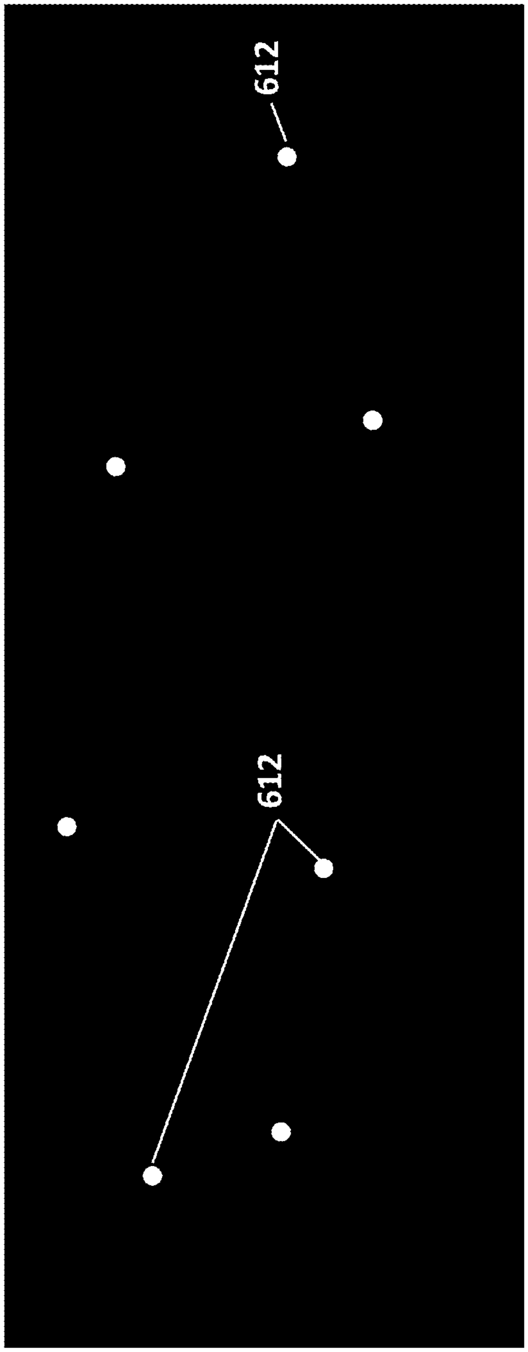

FIGS. 6A-6D illustrate utilizing signal analysis standards to identify binding anomalies. FIG. 6A depicts a solid support 600 containing a left subarray and a right subarray. The left subarray contains a first plurality of sites, with each individual site comprising a first standard analyte 601, in which the first standard analyte 601 comprises an epitope $\alpha$. The right subarray contains a second plurality of sites, with each individual site comprising a second standard analyte 602, in which the second standard analyte 602 does not contain epitope $\alpha$. FIGS. 6B-6D depict simulated fluorescence images after the solid support has been contacted with an anti-$\alpha$ binding reagent. FIG. 6B depicts fluorescent detection of the binding reagent at individual sites of the left and right subarrays. As expected, most array sites of the left subarray produce detection signals 611, likely due to binding of the anti-$\alpha$ binding reagent to first standard analytes 601. Unexpectedly, multiple array sites of the right subarray produce unexpected detection signals 612, due to either orthogonal binding at array sites or off-target binding of the anti-$\alpha$ binding reagent to non-$\alpha$ epitopes of the second standard analyte 602. Accordingly, the unexpected, detected signals 612 of the right subarray may be useful for determining a binding anomaly fraction. FIG. 6C depicts fluorescent detection of the binding reagent after a binding reagent dissociation process. As expected, few signals are observed on either array due to the dissociation process. Unexpected detection signals 613 are observed on both the left subarray and right subarray. The unexpected detection signals 613 may be useful for calculating a binding reagent dissociation failure rate or may be utilized to determine a binding anomaly fraction. FIG. 6D depicts fluorescent detection of a second binding reagent after a second binding reagent association process. The second binding reagent may have no expected binding specificity for the first standard analyte 601 or the second standard analyte 602. Unexpected detection signals 612 are observed on the left and right subarrays. Accordingly, the unexpected, detected signals 612 of the left and right subarray may be useful for determining a binding anomaly fraction.

Binding reagents may be provided that facilitate detection of binding anomalies. Depending upon the sensitivity, resolution, and detection methodology (e.g., scan rate, scan time, excitation power, etc.) of a detection device that is utilized in a single-analyte array system, a quantity of detectable labels attached to a binding reagent can be tuned to provide a signal that is detectable above a background signal but does not exceed the detection limit of a sensing device. For example, a binding reagent may comprise at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more than 50 detectable labels (e.g., fluorophores, luminophores). Alternatively or additionally, a binding reagent may comprise no more than about 50, 45, 40, 35, 30, 29, 28, 27, 26, 25, 24, 23, 22, 21, 20, 19, 18, 17, 16, 15, 14, 13, 12, 11, 10, 9, 8, 7, 6, 5, 4, 3, 2, or no more than 1 detectable label.

Figure 13A:
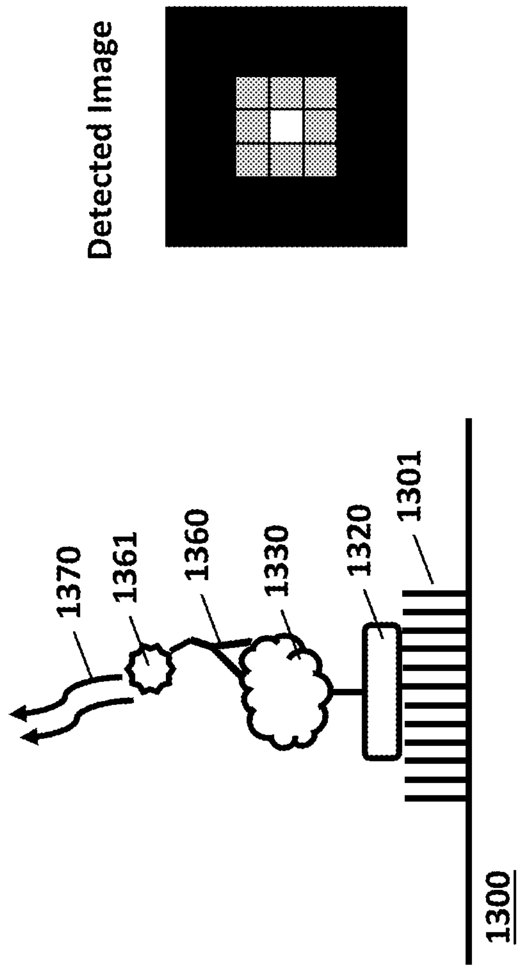
FIGS. 13A and 13B illustrate examples of binding anomaly detection in a single channel, in accordance with some embodiments.
Figure 13B:
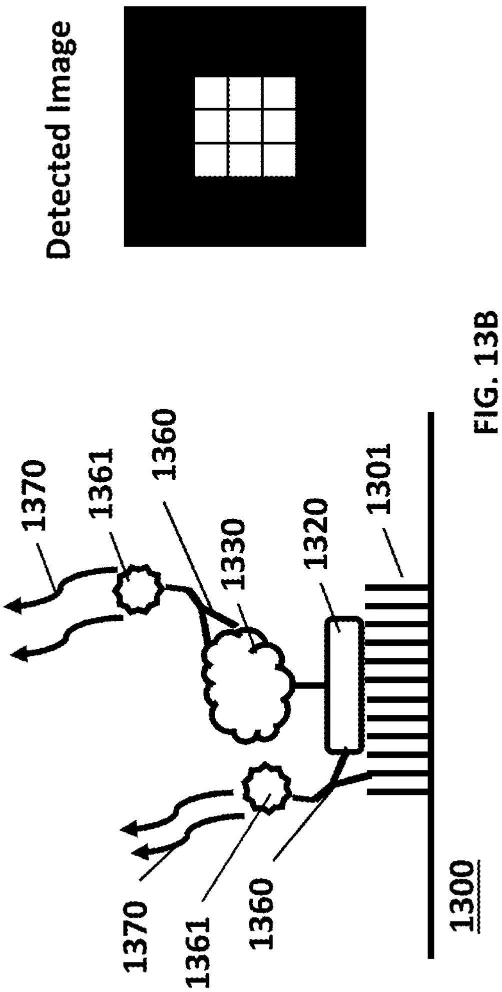

FIGS. 13A and 13B depict detection of a binding anomaly utilizing a binding reagent with a tuned quantity of detectable labels (e.g., fluorophores, luminophores). FIG. 13A depicts an expected binding interaction, in which a single binding reagent is bound to an analyte (e.g., a sample analyte, a standard analyte). A solid support 1300 contains a site 1301 to which the analyte 1330 is coupled by an anchoring moiety 1320. A binding reagent 1360 is bound to the analyte 1330. The binding reagent comprises a quantity of detectable labels 1361 that produce a signal 1370 at the site. A simulated image of a detection event at site 1301 is provided at the right side of FIG. 13A. The signal 1370 is captured in a 3×3 set of pixels of a pixel-based sensor, and the average pixel intensity of the nine pixels is below the saturation limit for the pixels. FIG. 13B depicts a second configuration, in which two binding reagents with a same configuration as FIG. 13A have co-located at the site 1301. As shown in the simulated image at the right of FIG. 13B, the increase in detectable signal 1370 at site 1301 causes the 3×3 set of pixels to reach a saturation limit. Accordingly, the difference in signal morphology between the expected signals shown in FIG. 13A and the anomalous signals shown in FIG. 13B can facilitate identification of the binding anomaly.

Multiplexing of binding reagents may also facilitate detection of binding anomalies. A multiplexed system may utilize two or more species of binding reagents during a single binding reagent association step. Two species of binding reagents may be distinguished with respect to one or more of: i) binding specificities of the respective binding reagents, and ii) detectable labels attached to the respective binding reagents. In some cases, it may be useful to provide two species of binding reagents, in which the first species of binding reagent has a first affinity agent, in which the second species of binding reagent has a second affinity agent, and the first affinity agent differs from the second affinity agent (e.g., differing with respect to a binding specificity). For example, two or more species of binding reagents may be contacted to a single-analyte array, in which a first species of binding reagent binds to analytes containing a first epitope, and a second species of binding reagent binds to analytes containing a second epitope. In some cases, it may be useful to provide two species of binding reagents, in which the first species of binding reagent has a first detectable label, in which the second species of binding reagent has a second detectable label, and the first detectable label differs from the second detectable label (e.g., differing with respect to an emission wavelength). It may be advantageous to provide two species of binding reagents, in which both species contain the same affinity agent (with respect to binding specificity) but differ with respect to type of detectable label. It is unlikely for an analyte to contain two or more identical epitopes, therefore there is a very low likelihood of both species of binding reagents binding to a single analyte. Accordingly, a binding anomaly could be identified by detection of co-localization of both species at a single site.

Figure 14A:
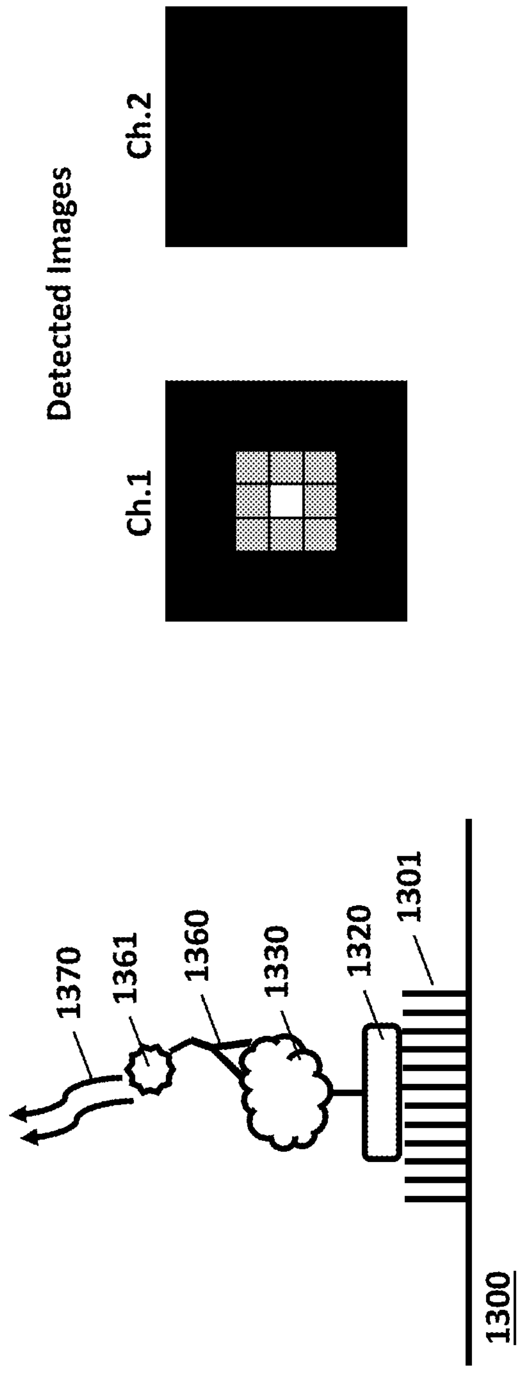
FIGS. 14A and 14B show examples of binding anomaly detection in a multi-channel, in accordance with some embodiments.
Figure 14B:
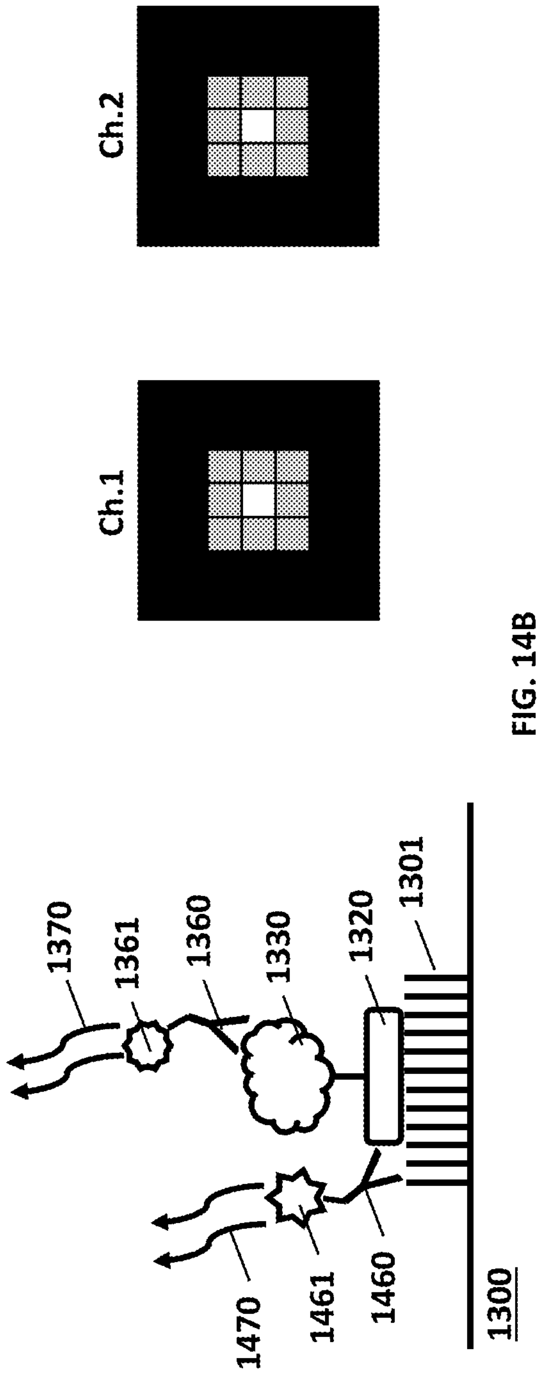

FIGS. 14A and 14B illustrate detection of binding anomalies in a multiplexed set of binding reagents. FIG. 14A depicts an identical configuration of analyte and binding reagent as shown in FIG. 13A. As depicted on the far right simulated image, a second detection channel (e.g., as distinguished by emission wavelength) has no detected signal at the site 1301 due to the absence of a binding reagent containing a second detectable label. FIG. 14B depicts a configuration in which a second species of binding reagent has become orthogonally bound at the site 1301. The second binding reagent comprises a second affinity agent 1460 that is attached to a second detectable label 1461 that produces a second detectable signal 1470. The first detectable signal 1370 is only detectable in the first detection channel, and the second detectable signal 1470 is only detectable in the second detection channel. As shown in the simulated images on the right, signals are detected in both channels, thereby indicating co-localization of both species of binding reagents at the same site 1301.

A method, as set forth herein, may comprise the steps of: i) providing signal measurements comprising presence or absence of signals at each individual site of a plurality of sites, ii) based upon the signal measurements, identifying binding anomalies at a quantity of sites of the plurality of sites, and iii) based upon the quantity of sites having identified binding anomalies, determining a binding anomaly fraction. In some cases, determining a binding anomaly fraction may comprise determining a raw binding anomaly fraction (i.e., a binding anomaly fraction based only upon observable binding anomalies). In particular cases, a method may further comprise a step of converting a raw binding anomaly fraction to an actual binding anomaly fraction.

Unexpected detection events can arise due to numerous mechanisms. Although unexpected detection events can be broadly classified as being orthogonal binding events, off-target binding events, or binding reagent dissociation failures, each of these classifications may include subclassifications due to varied mechanisms of unexpected binding phenomena. Additionally, depending upon system configuration and methodology, two differing classifications of unexpected binding events can produce similar detectable signals, making differentiation of binding anomalies more difficult. Accordingly, direct detection and quantitation of binding anomalies may not fully capture the absolute rate of unexpected detection events during an array-based process.

Signal analysis standards or prior characterization of binding behavior may be useful for converting a raw binding anomaly fraction to an actual binding anomaly fraction. In some cases, a raw binding anomaly fraction may be converted to an actual binding anomaly fraction through a single-parameter model, such as:

$$R_{A,actual}=aR_{A,raw} \quad (7)$$

where $R_{A,actual}$ is the actual binding anomaly fraction, $R_{A,raw}$ is the raw binding anomaly fraction, and a is parameter that scales between the observed rate and the actual rate. The parameter a may be derived empirically from determination of a raw binding anomaly fraction utilizing a signal analysis standard, or may be characterized prior to an array-based process. The parameter a may be derived by a machine learning model. The parameter a may be a function of a binding reagent utilized during a step of an array-based process, as well as the methodology utilized during the array-based process (e.g., composition of fluidic media, contact time of fluidic media).

A binding anomaly fraction may be determined by measuring one or more types of binding anomalies. For example, measurement of a rate of binding anomalies attributed to a phenomenon such as orthogonal binding events, off-target binding events, or binding reagent dissociation failure may be utilized as a proxy for an actual binding anomaly fraction using a single-parameter model like the model of equation 4. In other cases, a binding anomaly fraction may be determined by quantifying multiple types of binding anomaly fractions and combining them in a multi-parameter model. An exemplary multi-parameter model may be:

$$R_{A,actual}=bR_{A,orth}+cR_{A,off}+dR_{A,fail}+\ldots+C \quad (8)$$

where $R_{A,actual}$ is the actual binding anomaly fraction, $R_{A,orth}$ is the raw orthogonal binding anomaly fraction, $R_{A,off}$ is the raw off-target binding anomaly fraction, $R_{A,fail}$ is the raw binding reagent dissociation failure rate, b, c, and d are parameters that scale between the observed rates and the actual binding anomaly rate, and C is an optional constant. The ellipsis in equation 5 indicates that additional rates and/or parameters may be included in the calculation of the actual binding anomaly fraction. In some cases, each type of binding anomaly may be further expanded into substrates (e.g., two or more types of orthogonal binding event anomalies may be included in the calculation, etc.). The parameters b, c, or d may be derived empirically from determination of two or more types of raw binding anomaly fractions utilizing a signal analysis standard, or may be characterized prior to an array-based process. The parameters b, c, and d may be derived by a machine learning model. The parameters b, c, or d may be a function of a binding reagent utilized during a step of an array-based process, as well as the methodology utilized during the array-based process (e.g., composition of fluidic media, contact time of fluidic media). In some cases, $R_{A,actual}$ may be modeled by a non-linear equation. For example, a model parameter (e.g., b, c, or d) may be a function of another model parameter, or a rate term may be scaled by a multiplicative (e.g., b*c), additive (e.g., b+c), subtractive (e.g., b−c), or divided (e.g., b/c) combination of two or more parameters.

Binding Reagent Systems

Further provided herein are single-analyte array systems that are configured to implement a method of binding reagent association and/or dissociation, as set forth herein. Single-analyte array systems may comprise a fluidic system that is configured to transfer a fluidic medium to a single-analyte array, in which the fluidic medium facilitates an association and/or dissociation of a binding reagent of a plurality of binding reagents from an analyte of a plurality of analytes of the single-analyte array. The systems may further comprise a plurality of reservoirs that are configured to provide necessary reagents to perform a binding reagent association and/or dissociation method, as set forth herein. In some cases, a single-analyte array system may further comprise a detection device that is configured to observe a presence or absence of a binding reagent and/or an analyte at an address of a plurality of addresses of a single-analyte array.

In an aspect, provided herein is a system, comprising: a) a single-analyte array, in which the single-analyte array comprises a plurality of addresses, in which an address of the plurality of addresses comprises one and only one analyte of a plurality of analytes, b) a plurality of reservoirs, in which: i) a first reservoir of the plurality of reservoirs comprises a first plurality of binding reagents, and a second reservoir of the plurality of reservoirs comprises a second plurality of binding reagents, and iii) a third reservoir of the plurality of reservoirs, in which the third reservoir comprises a binding reagent dissociation composition selected from the group consisting of: A) sodium iodide, B) guanidinium hydrochloride, C) urea, D) sodium dodecyl sulfate (SDS), E) SDS and Tris (2-carboxyethyl) phosphine, F) methanol, G) sodium hydroxide, H) lithium chloride, I) sodium chloride, J) sodium thiocyanate, K) magnesium chloride, and L) 3-[(3-cholamidopropyl)dimethylammonio]-1-propane-sulfonate (CHAPS), and c) a fluidic transfer system, in which the fluidic transfer system is configured to provide fluidic communication between the single-analyte array and the plurality of reservoirs, and in which the fluidic transfer system is configured to transfer a first fluidic medium, a second fluidic medium, and a third fluidic medium, in which the first fluidic medium comprises the first plurality of binding reagents, in which the second fluidic medium comprises the second plurality of binding reagents, and in which the third fluidic medium comprises the binding reagent dissociation composition.

A single-analyte array system may comprise a plurality of reservoirs. In some cases, one or more reservoirs of a plurality of reservoirs may be fluidic reservoirs. A fluidic reservoir may comprise a fluidic medium comprising a plurality of binding reagents. A fluidic reservoir may comprise a fluidic medium comprising a binding reagent dissociation composition, as set forth herein. A fluidic medium may comprise a fluidic medium that does not comprise a plurality of binding reagents or a binding reagent dissociation composition. For example, a fluidic reservoir may comprise a fluid comprising a buffering species, in which the fluid is configured to be mixed with a binding reagent dissociation composition to form a fluidic binding reagent dissociation medium. In other cases, one or more reservoirs of a plurality of reservoirs may be non-fluidic reservoirs. A non-fluidic reservoir may comprise a solid-phase material, such as a granular or powdered solid. A solid-phase material may comprise a crystallized, lyophilized, precipitated, or aggregated solid-phase material. For example, a plurality of binding reagents may be lyophilized into a solid pellet or granule that is configured to be dissolved or resolubilized into a fluidic medium. In another example, a binding reagent dissociation composition (e.g., sodium iodide, guanidinium hydrochloride, etc.) may be stored in a non-fluidic reservoir as a granular solid-phase material. A single-analyte array system may further comprise a mixing device that is configured to combine a solid material from a non-fluidic reservoir with a fluidic medium from a fluidic reservoir. In some cases, a mixing device may comprise a mixing reservoir that is configured to combine a solid material from a non-fluidic reservoir with a fluidic medium from a fluidic reservoir. In other cases, a fluidic transfer system may comprise a mixing device that combines a solid material from a non-fluidic reservoir with a fluidic medium from a fluidic reservoir as the fluidic transfer system is transferring the combined fluidic medium to a single-analyte array.

A single-analyte array system may comprise a plurality of reservoirs, in which a first reservoir of the plurality of reservoirs comprises a first plurality of binding reagents, and in which a second reservoir of a plurality of reservoirs comprises a second plurality of binding reagents. In some cases, a first plurality of binding reagents may differ from a second plurality of binding reagents (e.g., differ by type of affinity agent, differ by structure or sequence of affinity agent, differ by binding specificity, etc.). A single-analyte array system may comprise a plurality of reservoirs, in which at least about 2, 3, 4, 5, 10, 15, 20, 30, 40, 50, 75, 100, 150, 200, 250, 300, 400, 500, or more than 500 reservoirs of the plurality of reservoirs comprise pluralities of binding reagents. Alternatively or additionally, a single-analyte array system may comprise a plurality of reservoirs, in which no more than about 500, 400, 300, 250, 200, 150, 100, 75, 50, 40, 30, 20, 15, 10, 5, 4, 3, 2, or less than 2 reservoirs of the plurality of reservoirs comprise pluralities of binding reagents.

A single-analyte array system may comprise a plurality of reservoirs, in which at least one reservoir of the plurality of reservoirs comprises a binding reagent dissociation composition, as set forth herein. In some cases, a single-analyte array system may comprise a first reservoir comprising a first binding reagent dissociation composition, and a second reservoir comprising a second binding reagent dissociation composition, in which the first binding reagent dissociation composition differs from the second binding reagent dissociation composition. A single-analyte array system may comprise a plurality of reservoirs, in which at least about 1, 2, 3, 4, 5, 10, 20, 30, 40, 50, or more than 50 reservoirs comprise a binding reagent dissociation composition. Alternatively or additionally, a single-analyte array system may comprise a plurality of reservoirs, in which no more than about 50, 40, 30, 20, 10, 5, 4, 3, 2, or less than 2 reservoirs comprise a binding reagent dissociation composition.

A single-analyte array system may comprise a fluidic transfer system. A fluidic transfer system may be configured to provide fluidic communication between each reservoir of a plurality of reservoirs and a single-analyte array. A fluidic transfer system may comprise any conceivable fluidic component, including tubing or piping, valves (check valves, solenoid valves, flow control valves, etc.), pumps, flow controllers (e.g., mass flow controllers, rotameters, etc.), sensors (e.g., temperature sensors, pressure sensors), manifolds, and combinations thereof. A fluidic transfer system may be configured for unidirectional operation (i.e., delivering fluid to an inlet port and/or discharging fluid from an outlet port). A fluidic transfer system may be configured for bidirectional operation (i.e., delivering and discharging fluid from a same port). In some configurations, a fluidic transfer system may be configured to oscillate a volume of fluid (e.g., a fluidic binding reagent dissociation medium) across a single-analyte array during a binding reagent dissociation process.

A single-analyte array system may further comprise an optical detection system, wherein the optical detection system is configured to detect a detectable label. In some configurations, a single-analyte array system may comprise an optical detection system that is configured to detect a first signal from a first detectable label and a second signal from a second detectable label, in which the first signal is distinguishable from the second signal (e.g., based upon wavelength, based upon intensity, based upon fluorescence lifetime, etc.). Accordingly, an optical detection system may be configured to detect an analyte comprising a first detectable label and a binding reagent comprising a second detectable label, in which the first detectable label produces a first signal and the second detectable label produces a second signal, in which the first signal is distinguishable from the second signal. In some configurations, an optical detection system may be configured to detect (e.g., simultaneously, sequentially) an analyte comprising a first detectable label and a binding reagent comprising a second detectable label, in which the analyte and the binding reagent are co-located at a same address of a plurality of addresses of a single-analyte array.

Accordingly, an optical detection system may comprise a sensing device (e.g., a CCD camera, a CMOS sensor, etc.) that is configured to detect a signal from a detectable label. In some configurations, an optical detection device may comprise two or more sensing devices, in which a first sensing device is configured to detect a first signal from a first detectable label, and a second sensing device is configured to detect a second signal from a second detectable label. In other configurations, an optical detection system may comprise a single detection device, in which the detection is configured to detect a first signal from a first detectable label and a second signal from a second detectable label. A sensing device may be configured to detect light of a certain wavelength, such as at least about 200 nm, 250 nm, 300 nm, 350 nm, 400 nm, 450 nm, 500 nm, 550 nm, 600 nm, 650 nm, 700 nm, 800 nm, 900 nm, 1 □m, or more than 1 □m. Alternatively or additionally, a sensing device may be configured to detect light of a certain wavelength, such as no more than about 1 □m, 900 nm, 800 nm, 700 nm, 650 nm, 600 nm, 550 nm, 500 nm, 450 nm, 400 nm, 350 nm, 300 nm, 250 nm, 200 nm, or less than 200 nm. A sensing device may be selected based upon an emission wavelength of a detectable label (e.g., a fluorophore, a luminophore, etc.).

An optical detection system may comprise an optical microscope (e.g., a confocal microscope). In some configurations, an optical microscope may comprise a fluorescence microscope. A fluorescence microscope may comprise one or more excitation devices (e.g., a laser, a lamp, etc.). An excitation device may be configured to produce light of a wavelength that facilitates emission of a signal from a detectable label (e.g., an emitted photon). A fluorescence microscope may comprise a first excitation device that is configured to facilitate emission of a first signal from a first detectable label, and a second excitation devices that is configured to facilitate emission of a second signal from a second detectable label. An excitation device may be configured to produce light of a certain wavelength, such as at least about 200 nm, 250 nm, 300 nm, 350 nm, 400 nm, 450 nm, 500 nm, 550 nm, 600 nm, 650 nm, 700 nm, 800 nm, 900 nm, 1 μm, or more than 1 μm. Alternatively or additionally, an excitation device may be configured to produce light of a certain wavelength, such as no more than about 1 μm, 900 nm, 800 nm, 700 nm, 650 nm, 600 nm, 550 nm, 500 nm, 450 nm, 400 nm, 350 nm, 300 nm, 250 nm, 200 nm, or less than 200 nm.

An optical detection system may further comprise other components, such as an objective lens, a tube lens, a waveguide, a mirror (e.g., a dichroic mirror), a collimating lens, and combinations thereof. An optical detection system may comprise a motion controller that is configured to position a single-analyte array relative to a sensing device and/or an excitation device. A motion controller may comprise a translation stage (e.g., an X-Y axis translation stage, an X-Y-Z translation stage, a tilt controller).

A single-analyte array system may further comprise a temperature regulation device. In some configurations, a temperature regulation device may be configured to regulate a temperature of the single-analyte array. For example, a single-analyte array may be contacted to a thermoelectric device (e.g., a Pelletier device) that is configured to heat and/or cool the single-analyte array. In other configurations, a temperature regulation device may be configured to regulate a temperature of a fluidic binding reagent dissociation medium. For example, a single-analyte array system may comprise a heat exchanger or an immersion heater that is configured to regulate a temperature of a fluidic binding reagent dissociation medium. A fluidic transfer system, as set forth herein, may comprise a temperature regulation device that is configured to regulate a temperature of a fluidic medium. A single-analyte array may comprise a temperature regulation device that is configured to regulate a temperature of a fluidic medium. In some configurations, a temperature regulation device may be configured to regulate a temperature of a fluidic binding reagent dissociation medium before the fluidic binding reagent dissociation medium is contacted with a single-analyte array. In other configurations, a temperature regulation device may be configured to regulate a temperature of a fluidic binding reagent dissociation medium after the fluidic binding reagent dissociation medium is contacted with a single-analyte array.

A single-analyte array, as set forth herein, may be disposed within a fluidic cartridge. A single-analyte array system may comprise a fluidic cartridge that is configured to fluidically communicate with a fluidics transfer system. A fluidic cartridge may comprise at least one fluidic port. In some configurations, a fluidic cartridge may comprise two or more fluidic ports. A fluidic port may be configured to receive and/or discharge a fluidic medium. A fluidic port may be connected to a fluidics transfer system by a fixed fluidic connection (e.g., fixed tubing). A fluidic port may be connected to a fluidic transfer system by a transient fluidic connection (e.g., an automated pipetting system). A fluidic cartridge may further comprise one or more additional single-analyte arrays. A fluidic cartridge may comprise a first single-analyte array and a second single-analyte array, in which the first single-analyte array is in fluidic communication with the second single-analyte array. A fluidic cartridge may comprise a first single-analyte array and a second single-analyte array, in which the first single-analyte array is not in fluidic communication with the second single-analyte array. In some configurations, a second single-analyte array may be fluidically isolated from a first single-analyte, and a fluidic transfer system may be configured to provide fluidic communication between the first and second single-analyte array and the plurality of reservoirs.

In another aspect, provided herein is a single-analyte array system, comprising: a fluidic cartridge, in which the fluidic cartridge comprises a first single-analyte array, as set forth herein, and a second single-analyte array, as set forth herein, in which the first single-analyte array is fluidically isolated from the second single-analyte array, b) a first fluidic binding reagent dissociation medium contacted with the first single-analyte array, b) a second fluidic binding reagent dissociation medium contacted with the second single-analyte array, in which the first fluidic binding reagent dissociation medium differs from the second fluidic binding reagent dissociation medium, and in which the first fluidic binding reagent dissociation medium and the second fluidic binding reagent dissociation medium comprise a binding reagent dissociation composition selected from the group consisting of: i) sodium iodide, ii) guanidinium hydrochloride, iii) urea, iv) sodium dodecyl sulfate (SDS), v) SDS and Tris (2-carboxyethyl) phosphine, vi) methanol, vii) sodium hydroxide, viii) lithium chloride, ix) sodium chloride, x) sodium thiocyanate, xi) magnesium chloride, and xii) 3-[(3-cholamidopropyl)dimethylammonio]-1-propanesulfonate (CHAPS). In some configurations, a first single-analyte array may comprise a first plurality of binding reagents, and a second single-analyte array may comprise a second plurality of binding reagents, in which the first plurality of binding reagents differs from the second plurality of binding reagents. For example, a single-analyte array system may run an assay simultaneously on two single-analyte arrays, but with a different sequence of binding reagents for each array. In another example, a single-analyte array system may run an assay simultaneously on two single-analyte arrays with a staggered schedule, such that pluralities of same binding reagents are contacted with each single-analyte array at differing times, thereby leading to differing times for contacting fluidic binding reagent dissociation media. In other configurations, a first single-analyte array may comprise a first plurality of binding reagents, and a second single-analyte array may comprise a second plurality of binding reagents, in which the first plurality of binding reagents does not differ from the second plurality of binding reagents. For example, if a sequence of fluidic binding reagent dissociation media are used to dissociate a plurality of binding reagents during an assay, timing differences between an assay for a first single-analyte array and an assay for a second single-analyte array may cause differing fluidic binding reagent dissociation media to be in contact with each single-analyte array at a fixed point in time.

In some cases, a single-analyte arrays system may be configured for multiplex detection of binding reagents, as set forth herein. A single-analyte system may comprise one or more fluidic reservoirs comprising binding reagents, in which a reservoir of the one or more reservoirs comprises two or more differing binding reagents (e.g., differing with respect to affinity agent, differing with respect to target epitopes, differing with respect to target analytes, etc.). Two or more differing binding reagents may be provided in a single fluidic reservoir due to a common binding reagent dissociation condition that achieves an acceptable binding reagent dissociation rate for the two or more differing binding reagents when simultaneously coupled to a single-analyte array.

A single-analyte array may comprise a solid support, in which a surface of the solid support comprises a plurality of analyte binding sites. An analyte binding site may comprise one or more molecules or moieties that are configured to couple an analyte to a surface of the solid support. An analyte binding site may comprise one or more molecules or moieties that are configured to couple an anchoring moiety, as set forth herein, to a surface of the solid support. In some cases, one or more molecules or moieties of an analyte binding site may be covalently attached to a surface of a solid support. An analyte binding site may comprise one or more molecules or moieties that are configured to form a covalent interaction with an analyte or an anchoring moiety, thereby coupling the analyte or anchoring moiety to the surface. For example, an analyte binding site may comprise a molecule that comprises a Click-type reactive functional group or other reactive functional group (e.g., epoxides, thiols, amines, azides, carboxylates, esters, acyl halides, etc.). An analyte binding site may comprise one or more molecules or moieties that are configured to form a non-covalent interaction with an analyte or an anchoring moiety, thereby coupling the analyte or anchoring moiety to the surface. For example, an analyte binding site may comprise an oligonucleotide that is configured to form a hybridization interaction with an oligonucleotide of an anchoring moiety (e.g., a nucleic acid nanoparticle). In some cases, an analyte binding site may comprise a plurality of molecules or moieties that are configured to couple an analyte or anchoring moiety to the analyte binding site. In particular cases, an analyte binding site may comprise a first molecule or moiety that is configured to form a covalent interaction and a second molecule or moiety that is configured to form a non-covalent interaction. An analyte binding site may further comprise a molecule or moiety that is configured to inhibit orthogonal binding (i.e., off-target binding) of an entity to the analyte binding site. For example, an analyte binding site may comprise polyethylene glycol (PEG), alkane, or dextran moieties that are coupled to the analyte binding site.

A single-analyte array may further comprise one or more interstitial regions, in which an interstitial region separates a first analyte binding site from a second analyte binding site. An analyte binding site may be configured to inhibit orthogonal binding of entities to the interstitial region. An analyte binding site may comprise a surface layer or coating that is configured to inhibit orthogonal binding of entities to the interstitial region. In some cases, an interstitial region may comprise a hydrophobic surface layer or coating, such as hydroxymethyldisiloxane (HMDS). In some cases, a surface layer or coating may comprise a molecule or moiety that sterically hinders orthogonal binding of entities to an interstital region. For example, an interstitial region may comprise a PEG molecule, alkane chain, or dextran molecule that is coupled to a surface of a solid support.

Determination of Fluidic Medium Composition

Provided herein are systems of fluidic media that inhibit detection of unwanted binding events or binding anomalies during array-based processes. A fluidic media system may comprise one or more of a binding reagent association medium, a detection medium, a rinsing medium, and a binding reagent dissociation medium. Each fluidic medium or a system of fluidic media may be configured to inhibit or prevent a different source of unintended binding or binding anomaly.

Numerous variations of arrays, including single-analyte arrays, and assay agents (e.g., binding reagents) are possible. For example, a preferable array configuration for an affinity agent-based whole protein identification method may differ from a preferable array configuration for an Edman-type degradation peptide sequencing method due to the differing assay agents involved in the respective methods. Moreover, array chemistry may change during an array-based process (e.g., due to intended or unintended binding of assay agents or impurities to the array or components thereof, due to degradation of arrays or components thereof, etc.) or differing assay agents may be introduced during the array-based process. Accordingly, composition of a fluidic medium of a system of fluidic media may be optimized to a selected array configuration and/or assay agent. Moreover, composition of a fluidic medium of a system of fluidic media may be altered or adjusted during an array-based process to account for a variation in array configuration or chemistry and/or a variation in an assay agent. For example, a multi-cycle process utilizing a differing binding reagent for each individual cycle may comprise a step of providing a fluidic medium (e.g., a binding reagent association medium, a detection medium, a rinsing medium, and a binding reagent dissociation medium) with a first composition during a first cycle, and providing the fluidic medium with a second composition during a second cycle, in which the first composition differs from the second composition.

An optimized system of fluidic media can be determined via an empirical approach. An empirical method of optimizing one or more fluidic media of a system of fluidic media can be performed on an array, as set forth herein, or a system that substantially replicates the array chemistry and configuration of the array. An empirical method of optimizing one or more fluidic media of a system of fluidic media can include detection and optionally quantification of unintended binding events and/or binding anomalies during at least one cycle of an array-based process. Preferably, an empirical method of optimizing one or more fluidic media of a system of fluidic media can include detection and optionally quantification of unintended binding events and/or binding anomalies during two or more cycles (e.g., 2, 5, 10, 20, or more than 20 cycles) of an array-based process.

Compositions of one or more fluidic media of a system of fluidic media may be determined by a statistical method that facilitates identification of optimal compositions, such as a Design of Experiments (DOE) approach. Statistical analysis of experimental data may facilitate identification of one or more optimal compositions of a fluidic medium, or one or more system of fluidic media that produce an optimal assay outcome (e.g., minimization of unintended binding events and/or binding anomalies). It may be useful to utilize a statistical approach (e.g., DOE) that permits simultaneous variation of multiple independent variables of one or more fluidic media (e.g., chemical composition, molar concentration, molar fraction, or mass fraction of one or more species, ionic strength, pH, etc.) as well as additional independent variables (e.g., fluidic medium contact time, fluidic medium volume, fluidic medium velocity). In some cases, composition optimization may be performed on a single fluidic medium while compositions of other fluidic media are kept constant. In other cases, two or more fluidic media may be co-optimized during a statistical analysis method.

An empirical method of optimizing one or more fluidic media of a system of fluidic media may include preparing a plurality of arrays. It may be preferable to prepare a plurality of arrays of substantially similar array compositions (e.g., substantially similar analyte compositions, substantially similar anchoring moiety compositions or configurations, substantially similar array site occupancies, etc.). Methods of forming and characterizing arrays are known in the art, including methods described in U.S. Pat. Nos. 11,203,612, 11,505,796, and U.S. Patent Publication No. 20220227890A1, each of which is incorporated herein by reference in its entirety. Arrays may be formed by deposition of analytes at array sites, such as by coupling of anchoring moieties to array sites, in which each individual anchoring moiety comprises an individual analyte. After depositing analytes on arrays, the array may be characterized to determine array properties, such as array site occupancy fraction. Single-analyte arrays may be characterized by a characterization method that is configured for single-analyte resolution (e.g., fluorescence microscopy). Array site occupancy fraction may be characterized by identification of a presence or absence of a signal (e.g., a fluorescent signal) from each individual array site of an array or a subregion of an array. Detectable labels (e.g., fluorophores, luminophores, radiolabels, etc) may be attached to analytes or anchoring moieties to facilitate identification of occupied array sites. Arrays with similar array properties (e.g., array site occupancy fraction) may be selected for use in an empirical approach to optimizing one or more fluidic media of a system of fluidic media; arrays with dissimilar array properties may be discarded or excluded from a statistical analysis method. Array site occupancy data may be provided to a signal analysis algorithm that is configured to extract the signal information (e.g., a processor-based algorithm). The signal information may facilitate determination of a spatial layout of array sites on an array. Addresses of unoccupied array sites may be inferred based upon patterning of occupied array sites.

It may be useful to provide fiducial elements to an array, as set forth herein, to facilitate identification of spatial addresses of array sites and/or interstitial regions. For single-analyte arrays, it may be particularly useful to bind a plurality of fiducial elements (e.g., fluorescent particles) to a random distribution of array sites. In some applications of single-analyte arrays, the amount of information collected during any particular detection step may be insufficient to determine the spatial distribution of all array sites. For example, when detecting binding of binding reagents to array sites, the observed quantity of array sites producing a detectable signal may be low due to a limited quantity of array sites containing a binding target for the binding reagents, and less than complete binding of the binding reagents to all available binding targets on the array. Randomly distributed fiducial elements can facilitate identification of array addresses, in particular after array site addresses have been determined, by providing an invariant set of signal-producing addresses that provide a fixed spatial reference.

After arrays of analytes have been prepared, the arrays may be contacted with fluidic media according to the design of the statistical analysis method. The sequence of steps of contacting fluidic media with each array during a cycle will vary according to the particular array-based process. Each cycle can include one or more steps of: i) contacting a plurality of binding reagents with an array of analytes in the presence of a binding reagent association medium of a particular composition, ii) detecting at each individual array site or each address of an array of analytes a presence or absence of a signal from a binding reagent in the presence of a detection medium of a particular composition, iii) dissociating binding reagents from the array of analytes in the presence of a binding reagent dissociation medium, and iv) rinsing the array of analytes with a rinsing medium of a particular composition. Detection data may be collected one or more times per cycle of the array-based process. Multiple cycles may be performed with detection of binding events occurring during at least the final cycle, or more preferably during multiple cycles of the experiment. In general, experimental differences between each tested array will vary according to the design of the statistical analysis method.

Detection data for each tested experimental condition can be analyzed to extract signal information. Detection data may be provided to a signal analysis algorithm that is configured to extract the signal information. For optical detection methods (e.g., fluorescence microscopy), signal information may be provided to an image analysis algorithm. A signal analysis algorithm such as an image analysis algorithm may be performed on a processor or computer system. A signal analysis algorithm may perform certain analysis processes, such as landmarking or image registration, that facilitate consistent identification of array addresses across a detection data set. A signal analysis algorithm may provide information on signal presence and/or magnitude for each detection step of an experiment.

During or after collection of data for optimizing one or more fluidic media of a system of fluidic media, the collected data may be analyzed to identify signals and assign spatial addresses to the signals. Fiducial elements may facilitate identification of addresses of signals produced at array sites and/or signals produced at interstitial regions of arrays. Accordingly, for each collected data set, signals may be identified and assigned an address (e.g., by a signal analysis algorithm). After identification and assignment of addresses of detected signals, the signals can be classified according to address. For example, signals at addresses associated with array sites can be assigned to respective array sites and signals associated with interstitial regions can be assigned to the interstitial regions.

Once signals have been identified and classified according to spatial address, the signal data can be analyzed to identify unintended binding events and/or binding anomalies according to a method set forth herein. Binding anomalies may be sorted according to spatial address. For example, based upon spatial address, binding anomalies may be classified as array site-based binding anomalies or interstitial region-based binding anomalies. Optimization of a fluidic medium of a set of fluidic media may be based upon minimization of an array site-based binding anomaly fraction, minimization of an interstitial region-based binding anomaly fraction, or a combination thereof. Signal analysis may be performed utilizing all available detection data or a subset of the detection data. Additionally, signal data may be analyzed to determine an intended binding fraction. For example, signals corresponding to binding reagents that are identified at addresses corresponding to array sites may be classified as intended binding events, thereby facilitating determination of an intended binding fraction. In some cases, detection data from successive cycles may be utilized to reclassify signal data. For example, persistence of a signal at an array site for two or more consecutive detection events may be classified as intended binding for the initial detection step and unintended binding or a binding anomaly for the subsequent detection steps during which the signal is present.

Signal analysis and classification data can be aggregated after a set of fluidic medium optimization experiments is completed. The aggregated data set can be provided to a statistical analysis algorithm. A statistical analysis algorithm may be configured to implement a statistical method, such as linear or non-linear regression, that correlated variation between independent variables of the one or more optimized fluidic media and dependent variables (e.g., binding anomaly fraction, unintended binding fraction, intended binding fraction). A statistical analysis algorithm may identify one or more optimal compositions for a fluidic medium. A statistical analysis algorithm may identify one or more sets of fluidic media that produce an optimal outcome.

The methods set forth herein for identifying an optimized composition of a fluidic medium may produce an optimized composition for a fluidic medium, or optimized compositions for a set of fluidic media with respect to a single binding reagent or a set of binding reagents. The skilled person will recognize that the methods of fluidic medium optimization can be reproduced for other binding reagents to identify fluidic medium compositions that are optimal for the other binding reagents. Accordingly, an assay utilizing multiple binding reagents may further require multiple sets of fluidic media, in which fluidic media compositions vary between the sets of fluidic media. In some cases, it may be advantageous to group and utilize binding reagents during an assay according to an optimal set of fluidic media for the binding reagents.

Polypeptide Assays

The present disclosure provides compositions, apparatus and methods that can be useful for characterizing sample components, such as proteins, nucleic acids, cells or other species, by obtaining multiple separate and non-identical measurements of the sample components. In particular configurations, the individual measurements may not, by themselves, be sufficiently accurate or specific to make the characterization, but an aggregation of the multiple non-identical measurements can allow the characterization to be made with a high degree of accuracy, specificity and confidence. For example, the multiple separate measurements can include subjecting the sample to reagents that are promiscuous with regard to recognizing multiple components of the sample. Accordingly, a first measurement carried out using a first promiscuous reagent may perceive a first subset of sample components without distinguishing one component from another. A second measurement carried out using a second promiscuous reagent may perceive a second subset of sample components, again, without distinguishing one component from another. However, a comparison of the first and second measurements can distinguish: (i) a sample component that is uniquely present in the first subset but not the second; (ii) a sample component that is uniquely present in the second subset but not the first; (iii) a sample component that is uniquely present in both the first and second subsets; or (iv) a sample component that is uniquely absent in the first and second subsets. The number of promiscuous reagents used, the number of separate measurements acquired, and degree of reagent promiscuity (e.g. the diversity of components recognized by the reagent) can be adjusted to suit the component diversity expected for a particular sample.

The present disclosure provides assays that are useful for detecting one or more analytes. Exemplary assays are set forth herein in the context of detecting proteins. Those skilled in the art will recognize that methods, compositions and apparatus set forth herein can be adapted for use with other analytes such as nucleic acids, polysaccharides, metabolites, vitamins, hormones, enzyme co-factors and others set forth herein or known in the art. Particular configurations of the methods, apparatus and compositions set forth herein can be made and used, for example, as set forth in U.S. Pat. No. 10,473,654 or US Pat. App. Pub. Nos. 2020/0318101 A1 or 2020/0286584 A1, each of which is incorporated herein by reference. Exemplary methods, systems and compositions are set forth in further detail below.

A composition, apparatus or method set forth herein can be used to characterize an analyte, or moiety thereof, with respect to any of a variety of characteristics or features including, for example, presence, absence, quantity (e.g. amount or concentration), chemical reactivity, molecular structure, structural integrity (e.g. full length or fragmented), maturation state (e.g. presence or absence of pre- or pro-sequence in a protein), location (e.g. in an analytical system, subcellular compartment, cell or natural environment), association with another analyte or moiety, binding affinity for another analyte or moiety, biological activity, chemical activity or the like. An analyte can be characterized with regard to a relatively generic characteristic such as the presence or absence of a common structural feature (e.g. amino acid sequence length, overall charge or overall pKa for a protein) or common moiety (e.g. a short primary sequence motif or post-translational modification for a protein). An analyte can be characterized with regard to a relatively specific characteristic such as a unique amino acid sequence (e.g. for the full length of the protein or a motif), an RNA or DNA sequence that encodes a protein (e.g. for the full length of the protein or a motif), or an enzymatic or other activity that identifies a protein. A characterization can be sufficiently specific to identify an analyte, for example, at a level that is considered adequate or unambiguous by those skilled in the art.

In particular configurations, a protein can be detected using one or more affinity agents having known or measurable binding affinity for the protein. For example, an affinity agent can bind a protein to form a complex and a signal produced by the complex can be detected. A protein that is detected by binding to a known affinity agent can be identified based on the known or predicted binding characteristics of the affinity agent. For example, an affinity agent that is known to selectively bind a candidate protein suspected of being in a sample, without substantially binding to other proteins in the sample, can be used to identify the candidate protein in the sample merely by observing the binding event. This one-to-one correlation of affinity agent to candidate protein can be used for identification of one or more proteins. However, as the protein complexity (i.e. the number and variety of different proteins) in a sample increases, or as the number of different candidate proteins to be identified increases, the time and resources to produce a commensurate variety of affinity agents having one-to-one specificity for the proteins approaches limits of practicality.

Methods set forth herein, can be advantageously employed to overcome these constraints. In particular configurations, the methods can be used to identify a number of different candidate proteins that exceeds the number of affinity agents used. For example, the number of candidate proteins identified can be at least 5×, 10×, 25×, 50×, 100× or more than the number of affinity agents used. This can be achieved, for example, by (1) using promiscuous affinity agents that bind to multiple different candidate proteins suspected of being present in a given sample, and (2) subjecting the protein sample to a set of promiscuous affinity agents that, taken as a whole, are expected to bind each candidate protein in a different combination, such that each candidate protein is expected to be encoded by a unique profile of binding and non-binding events. Promiscuity of an affinity agent is a characteristic that can be understood relative to a given population of proteins. Promiscuity can arise due to the affinity agent recognizing an epitope that is known to be present in a plurality of different candidate proteins suspected of being present in the given population of unknown proteins. For example, epitopes having relatively short amino acid lengths such as dimers, trimers, or tetramers can be expected to occur in a substantial number of different proteins in the human proteome. Alternatively or additionally, a promiscuous affinity agent can recognize different epitopes (e.g. epitopes differing from each other with regard to amino acid composition or sequence), the different epitopes being present in a plurality of different candidate proteins. For example, a promiscuous affinity agent that is designed or selected for its affinity toward a first trimer epitope may bind to a second epitope that has a different sequence of amino acids when compared to the first epitope.

Although performing a single binding reaction between a promiscuous affinity agent and a complex protein sample may yield ambiguous results regarding the identity of the different proteins to which it binds, the ambiguity can be resolved when the results are combined with other identifying information about those proteins. The identifying information can include characteristics of the protein such as length (i.e. number of amino acids), hydrophobicity, molecular weight, charge to mass ratio, isoelectric point, chromatographic fractionation behavior, enzymatic activity, presence or absence of post translational modifications or the like. The identifying information can include results of binding with other promiscuous affinity agents. For example, a plurality of different promiscuous affinity agents can be contacted with a complex population of proteins, wherein the plurality is configured to produce a different binding profile for each candidate protein suspected of being present in the population. In this example, each of the affinity agents can be distinguishable from the other affinity agents, for example, due to unique labeling (e.g. different affinity agents having different luminophore labels), unique spatial location (e.g. different affinity agents being located at different addresses in an array), and/or unique time of use (e.g. different affinity agents being delivered in series to a population of proteins). Accordingly, the plurality of promiscuous affinity agents produces a binding profile for each individual protein that can be decoded to identify a unique combination of epitopes present in the individual protein, and this can in turn be used to identify the individual protein as a particular candidate protein having the same or similar unique combination of epitopes. The binding profile can include observed binding events as well as observed non-binding events and this information can be evaluated in view of the expectation that particular candidate proteins produce a similar binding profile, for example, based on presence and absence of particular epitopes in the candidate proteins.

In some configurations, distinct and reproducible binding profiles may be observed for one or more unknown proteins in a sample. However, in many cases one or more binding events produces inconclusive or even aberrant results and this, in turn, can yield ambiguous binding profiles. For example, observation of binding outcome for a single-molecule binding event can be particularly prone to ambiguities due to stochasticity in the behavior of single molecules when observed using certain detection hardware. The present disclosure provides methods that provide accurate protein identification despite ambiguities and imperfections that can arise in many contexts. In some configurations, methods for identifying, quantitating or otherwise characterizing one or more proteins in a sample utilize a binding model that evaluates the likelihood or probability that one or more candidate proteins that are suspected of being present in the sample will have produced an empirically observed binding profile. The binding model can include information regarding expected binding outcomes (e.g. binding or non-binding) for binding of one or more affinity reagent with one or more candidate proteins. The information can include an a priori characteristic of a candidate protein, such as presence or absence of a particular epitope in the candidate protein or length of the candidate protein. Alternatively or additionally, the information can include empirically determined characteristics such as propensity or likelihood that the candidate protein will bind to a particular affinity reagent. Accordingly, a binding model can include information regarding the propensity or likelihood of a given candidate protein generating a false positive or false negative binding result in the presence of a particular affinity reagent, and such information can optionally be included for a plurality of affinity reagents.

Methods set forth herein can be used to evaluate the degree of compatibility of one or more empirical binding profiles with results computed for various candidate proteins using a binding model. For example, to identify an unknown protein in a sample of many proteins, an empirical binding profile for the protein can be compared to results computed by the binding model for many or all candidate proteins suspected of being in the sample. In some configurations of the methods set forth herein, identity for the unknown protein is determined based on a likelihood of the unknown protein being a particular candidate protein given the empirical binding pattern or based on the probability of a particular candidate protein generating the empirical binding pattern. Optionally a score can be determined from the measurements that are acquired for the unknown protein with respect to many or all candidate proteins suspected of being in the sample. A digital or binary score that indicates one of two discrete states can be determined. In particular configurations, the score can be non-digital or non-binary. For example, the score can be a value selected from a continuum of values such that an identity is made based on the score being above or below a threshold value. Moreover, a score can be a single value or a collection of values. Particularly useful methods for identifying proteins using promiscuous reagents, serial binding measurements and/or decoding with binding models are set forth, for example, in U.S. Pat. No. 10,473,654 US Pat. App. Pub. No. 2020/0318101 A1 or Egertson et al., BioRxiv (2021), DOI: 10.1101/2021.10.11.463967, each of which is incorporated herein by reference.

The present disclosure provides compositions, apparatus and methods for detecting one or more proteins. A protein can be detected using one or more affinity agents having binding affinity for the protein. The affinity agent and the protein can bind each other to form a complex and, during or after formation, the complex can be detected. The complex can be detected directly, for example, due to a label that is present on the affinity agent or protein. In some configurations, the complex need not be directly detected, for example, in formats where the complex is formed and then the affinity agent, protein, or a label component that was present in the complex is detected.

Many protein detection methods, such as enzyme linked immunosorbent assay (ELISA), achieve high-confidence characterization of one or more protein in a sample by exploiting high specificity binding of antibodies, aptamers or other binding agents to the protein(s) and detecting the binding event while ignoring all other proteins in the sample. ELISA is generally carried out at low plex scale (e.g. from one to a hundred different proteins detected in parallel or in succession) but can be used at higher plexity. ELISA methods can be carried out by detecting immobilized binding agents and/or proteins in multiwell plates, on arrays, or on particles in microfluidic devices. Exemplary plate-based methods include, for example, the MULTI-ARRAY technology commercialized by MesoScale Diagnostics (Rockville, Maryland) or Simple Plex technology commercialized by Protein Simple (San Jose, CA). Exemplary, array-based methods include, but are not limited to those utilizing Simoa® Planar Array Technology or Simoa® Bead Technology, commercialized by Quanterix (Billerica, MA). Further exemplary array-based methods are set forth in U.S. Pat. Nos. 9,678,068; 9,395,359; 8,415,171; 8,236,574; or 8,222,047, each of which is incorporated herein by reference. Exemplary microfluidic detection methods include those commercialized by Luminex (Austin, Texas) under the trade name xMAP® technology or used on platforms identified as MAGPIX®, LUMINEX® 100/200 or FEXMAP 3D®.

Other detection methods that can also be used, for example at low plex scale, include procedures that employ SOMAmer reagents and SOMAscan assays commercialized by Soma Logic (Boulder, CO). In one configuration, a sample is contacted with aptamers that are capable of binding proteins with specificity for the amino acid sequence of the proteins. The resulting aptamer-protein complexes can be separated from other sample components, for example, by attaching the complexes to beads (or other solid support) that are removed from other sample components. The aptamers can then be isolated and, because the aptamers are nucleic acids, the aptamers can be detected using any of a variety of methods known in the art for detecting nucleic acids, including for example, hybridization to nucleic acid arrays, PCR-based detection, or nucleic acid sequencing. Exemplary methods and compositions are set forth in U.S. Pat. Nos. 7,855,054; 7,964,356; 8,404,830; 8,945,830; 8,975,026; 8,975,388; 9,163,056; 9,938,314; 9,404,919; 9,926,566; 10,221,421; 10,239,908; 10,316,321 10,221,207 or 10,392,621, each of which is incorporated herein by reference.

In some detection assays, a protein can be cyclically modified and the modified products from individual cycles can be detected. In some configurations, a protein can be sequenced by a sequential process in which each cycle includes steps of detecting the protein and removing one or more terminal amino acids from the protein. Optionally, one or more of the steps can include adding a label to the protein, for example, at the amino terminal amino acid or at the carboxy terminal amino acid. In particular configurations, a method of detecting a protein can include steps of (i) exposing a terminal amino acid on the protein; (ii) detecting a change in signal from the protein; and (iii) identifying the type of amino acid that was removed based on the change detected in step (ii). The terminal amino acid can be exposed, for example, by removal of one or more amino acids from the amino terminus or carboxyl terminus of the protein. Steps (i) through (iii) can be repeated to produce a series of signal changes that is indicative of the sequence for the protein.

In a first configuration of a cyclical protein detection method, one or more types of amino acids in the protein can be attached to a label that uniquely identifies the type of amino acid. In this configuration, the change in signal that identifies the amino acid can be loss of signal from the respective label. For example, lysines can be attached to a distinguishable label such that loss of the label indicates removal of a lysine. Alternatively or additionally, other amino acid types can be attached to other labels that are mutually distinguishable from lysine and from each other. For example, lysines can be attached to a first label and cysteines can be attached to a second label, the first and second labels being distinguishable from each other. Exemplary compositions and techniques that can be used to remove amino acids from a protein and detect signal changes are those set forth in Swaminathan et al., Nature Biotech. 36:1076-1082 (2018); or U.S. Pat. No. 9,625,469 or 10,545,153, each of which is incorporated herein by reference. Methods and apparatus under development by Erisyon, Inc. (Austin, TX) may also be useful for detecting proteins.

In a second configuration of a cyclical protein detection method, a terminal amino acid of a protein can be recognized by an affinity agent that is specific for the terminal amino acid or specific for a label moiety that is present on the terminal amino acid. The affinity agent can be detected on the array, for example, due to a label on the affinity agent. Optionally, the label is a nucleic acid barcode sequence that is added to a primer nucleic acid upon formation of a complex. For example, a barcode can be added to the primer via ligation of an oligonucleotide having the barcode sequence or polymerase extension directed by a template that encodes the barcode sequence. The formation of the complex and identity of the terminal amino acid can be determined by decoding the barcode sequence. Multiple cycles can produce a series of barcodes that can be detected, for example, using a nucleic acid sequencing technique. Exemplary affinity agents and detection methods are set forth in US Pat. App. Pub. No. 2019/0145982 A1; 2020/0348308 A1; or 2020/0348307 A1, each of which is incorporated herein by reference. Methods and apparatus under development by Encodia, Inc. (San Diego, CA) may also be useful for detecting proteins.

Cyclical removal of terminal amino acids from a protein can be carried out using an Edman-type sequencing reaction in which a phenyl isothiocyanate reacts with a N-terminal amino group under mildly alkaline conditions (e.g. about pH 8) to form a cyclical phenylthiocarbamoyl Edman complex derivative. The phenyl isothiocyanate may be substituted or unsubstituted with one or more functional groups, linker groups, or linker groups containing functional groups. An Edman-type sequencing reaction can include variations to reagents and conditions that yield a detectable removal of amino acids from a protein terminus, thereby facilitating determination of the amino acid sequence for a protein or portion thereof. For example, the phenyl group can be replaced with at least one aromatic, heteroaromatic or aliphatic group which may participate in an Edman-type sequencing reaction, non-limiting examples including: pyridine, pyrimidine, pyrazine, pyridazoline, fused aromatic groups such as naphthalene and quinoline), methyl or other alkyl groups or alkyl group derivatives (e.g., alkenyl, alkynyl, cyclo-alkyl). Under certain conditions, for example, acidic conditions of about pH 2, derivatized terminal amino acids may be cleaved, for example, as a thiazolinone derivative. The thiazolinone amino acid derivative under acidic conditions may form a more stable phenylthiohydantoin (PTH) or similar amino acid derivative which can be detected. This procedure can be repeated iteratively for residual protein to identify the subsequent N-terminal amino acid. Many variations of Edman-type degradation have been described and may be used including, for example, a one-step removal of an N-terminal amino acid using alkaline conditions (Chang, J. Y., FEBS LETTS., 1978, 91(1), 63-68). In some cases, Edman-type reactions may be thwarted by N-terminal modifications which may be selectively removed, for example, N-terminal acetylation or formylation (e.g., see Gheorghe M. T., Bergman T. (1995) in Methods in Protein Structure Analysis, Chapter 8: Deacetylation and internal cleavage of Proteins for N-terminal Sequence Analysis. Springer, Boston, MA. https://doi.org/10.1007/978-1-4899-1031-8_8).

Non-limiting examples of functional groups for substituted phenyl isothiocyanate may include ligands (e.g. biotin and biotin analogs) for known receptors, labels such as luminophores, or reactive groups such as click functionalities (e.g. compositions having an azide or acetylene moiety). The functional group may be a DNA, RNA, peptide or small molecule barcode or other tag which may be further processed and/or detected.

The removal of an amino terminal amino acid using Edman-type processes can utilize at least two main steps, the first step includes reacting an isothiocyanate or equivalent with protein N-terminal residues to form a relatively stable Edman complex, for example, a phenylthiocarbamoyl complex. The second step can include removing the derivatized N-terminal amino acid, for example, via heating. The protein, now having been shortened by one amino acid, may be detected, for example, by contacting the protein with a labeled affinity agent that is complementary to the amino terminus and examining the protein for binding to the agent, or by detecting loss of a label that was attached to the removed amino acid.

Edman-type processes can be carried out in a multiplex format to detect, characterize or identify a plurality of proteins. A method of detecting a protein can include steps of (i) exposing a terminal amino acid on a protein at an address of an array; (ii) binding an affinity agent to the terminal amino acid, where the affinity agent includes a nucleic acid tag, and where a primer nucleic acid is present at the address; (iii) extending the primer nucleic acid, thereby producing an extended primer having a copy of the tag; and (iv) detecting the tag of the extended primer. The terminal amino acid can be exposed, for example, by removal of one or more amino acids from the amino terminus or carboxyl terminus of the protein. Steps (i) through (iv) can be repeated to produce a series of tags that is indicative of the sequence for the protein. The method can be applied to a plurality of proteins on the array and in parallel. Whatever the plexity, the extending of the primer can be carried out, for example, by polymerase-based extension of the primer, using the nucleic acid tag as a template. Alternatively, the extending of the primer can be carried out, for example, by ligase- or chemical-based ligation of the primer to a nucleic acid that is hybridized to the nucleic acid tag. The nucleic acid tag can be detected via hybridization to nucleic acid binding reagents (e.g. in an array), amplification-based detections (e.g. PCR-based detection, or rolling circle amplification-based detection) or nuclei acid sequencing (e.g. cyclical reversible terminator methods, nanopore methods, or single molecule, real time detection methods). Exemplary methods that can be used for detecting proteins using nucleic acid tags are set forth in US Pat. App. Pub. No. 2019/0145982 A1; 2020/0348308 A1; or 2020/0348307 A1, each of which is incorporated herein by reference.

A protein can optionally be detected based on its enzymatic or biological activity. For example, a protein can be contacted with a reactant that is converted to a detectable product by an enzymatic activity of the protein. In other assay formats, a first protein having a known enzymatic function can be contacted with a second protein to determine if the second protein changes the enzymatic function of the first protein. As such, the first protein serves as a reporter system for detection of the second protein. Exemplary changes that can be observed include, but are not limited to, activation of the enzymatic function, inhibition of the enzymatic function, attenuation of the enzymatic function, degradation of the first protein or competition for a reactant or cofactor used by the first protein. Proteins can also be detected based on their binding interactions with other molecules such as proteins, nucleic acids, nucleotides, metabolites, hormones, vitamins, small molecules that participate in biological signal transduction pathways, biological receptors or the like. For example, a protein that participates in a signal transduction pathway can be identified as a particular candidate protein by detecting binding to a second protein that is known to be a binding partner for the candidate protein in the pathway.

The presence or absence of post-translational modifications (PTM) can be detected using a composition, apparatus or method set forth herein. A PTM can be detected using an affinity agent that recognizes the PTM or based on a chemical property of the PTM. Exemplary PTMs that can be detected, identified or characterized include, but are not limited to, myristoylation, palmitoylation, isoprenylation, prenylation, farnesylation, geranylgeranylation, lipoylation, flavin moiety attachment, Heme C attachment, phosphopantetheinylation, retinylidene Schiff base formation, dipthamide formation, ethanolamine phosphoglycerol attachment, hypusine, beta-Lysine addition, acylation, acetylation, deacetylation, formylation, alkylation, methylation, C-terminal amidation, arginylation, polyglutamylation, polyglyclyation, butyrylation, gamma-carboxylation, glycosylation, glycation, polysialylation, malonylation, hydroxylation, iodination, nucleotide addition, phosphoate ester formation, phosphoramidate formation, phosphorylation, adenylylation, uridylylation, propionylation, pyrolglutamate formation, S-glutathionylation, S-nitrosylation, S-sulfenylation, S-sulfinylation, S-sulfonylation, succinylation, sulfation, glycation, carbamylation, carbonylation, isopeptide bond formation, biotinylation, carbamylation, oxidation, reduction, pegylation, ISGylation, SUMOylation, ubiquitination, neddylation, pupylation, citrullination, deamidation, elminylation, disulfide bridge formation, proteolytic cleavage, isoaspartate formation, racemization, and protein splicing.

PTMs may occur at particular amino acid residues of a protein. For example, the phosphate moiety of a particular proteoform can be present on a serine, threonine, tyrosine, histidine, cysteine, lysine, aspartate or glutamate residue of the protein. In other examples, an acetyl moiety can be present on the N-terminus or on a lysine; a serine or threonine residue can have an O-linked glycosyl moiety; an asparagine residue can have an N-linked glycosyl moiety; a proline, lysine, asparagine, aspartate or histidine amino acid can be hydroxylated; an arginine or lysine residue can be methylated; or the N-terminal methionine or at a lysine amino acid can be ubiquitinated.

In some configurations of the apparatus and methods set forth herein, one or more proteins can be detected on a solid support. For example, protein(s) can be coupled to a support, the support can be contacted with detection agents (e.g. affinity agents) in solution, the agents can interact with the protein(s), thereby producing a detectable signal, and then the signal can be detected to determine the presence of the protein(s). In multiplexed versions of this approach, different proteins can be coupled to different addresses in an array, and the probing and detection steps can occur in parallel. In another example, affinity agents can be coupled to a solid support, the support can be contacted with proteins in solution, the proteins can interact with the affinity agents, thereby producing a detectable signal, and then the signal can be detected to determine presence, quantity or characteristics of the proteins. This approach can also be multiplexed by coupling different affinity agents to different addresses of an array.

Proteins, affinity agents or other objects of interest can be coupled to a solid support via covalent or non-covalent bonds. For example, a linker can be used to covalently couple a protein or other object of interest to an array. A particularly useful linker is a structured nucleic acid particle such as a nucleic acid nanoball (e.g. a concatemeric amplicon produced by rolling circle replication of a circular nucleic acid template) or a nucleic acid origami. For example, a plurality of proteins can be conjugated to a plurality of structured nucleic acid particles, such that each protein-conjugated particle forms an address in the array. Exemplary linkers for coupling proteins, or other objects of interest, to an array or other solid support are set forth in US Pat. App. Pub. No. 2021/0101930 A1, which is incorporated herein by reference.

A protein can be detected based on proximity of two or more affinity agents. For example, the two affinity agents can include two components each: a receptor component and a nucleic acid component. When the affinity agents bind in proximity to each other, for example, due to ligands for the respective receptors being on a single protein, or due to the ligands being present on two proteins that associate with each other, the nucleic acids can interact to cause a modification that is indicative of the two ligands being in proximity. Optionally, the modification can be polymerase catalyzed extension of one of the nucleic acids using the other nucleic acid as a template. As another option, one of the nucleic acids can form a template that acts as splint to position other nucleic acids for ligation to an oligonucleotide. Exemplary methods are commercialized by Olink Proteomics AB (Uppsala Sweden) or set forth in U.S. Pat. Nos. 7,306,904; 7,351,528; 8,013,134; 8,268,554 or 9,777,315, each of which is incorporated herein by reference.

A method or apparatus of the present disclosure can optionally be configured for optical detection (e.g. luminescence detection). Analytes or other entities can be detected, and optionally distinguished from each other, based on measurable characteristics such as the wavelength of radiation that excites a luminophore, the wavelength of radiation emitted by a luminophore, the intensity of radiation emitted by a luminophore (e.g. at particular detection wavelength(s)), luminescence lifetime (e.g. the time that a luminophore remains in an excited state) or luminescence polarity. Other optical characteristics that can be detected, and optionally used to distinguish analytes, include, for example, absorbance of radiation, resonance Raman, radiation scattering, or the like. A luminophore can be an intrinsic moiety of a protein or other analyte to be detected, or the luminophore can be an exogenous moiety that has been synthetically added to a protein or other analyte.

A method or apparatus of the present disclosure can use a light sensing device that is appropriate for detecting a characteristic set forth herein or known in the art. Particularly useful components of a light sensing device can include, but are not limited to, optical sub-systems or components used in nucleic acid sequencing systems. Examples of useful sub systems and components thereof are set forth in US Pat. App. Pub. No. 2010/0111768 A1 or U.S. Pat. Nos. 7,329,860; 8,951,781 or 9,193,996, each of which is incorporated herein by reference. Other useful light sensing devices and components thereof are described in U.S. Pat. Nos. 5,888,737; 6,175,002; 5,695,934; 6,140,489; or 5,863,722; or US Pat. Pub. Nos. 2007/007991 A1, 2009/0247414 A1, or 2010/0111768; or WO2007/123744, each of which is incorporated herein by reference. Light sensing devices and components that can be used to detect luminophores based on luminescence lifetime are described, for example, in U.S. Pat. Nos. 9,678,012; 9,921,157; 10,605,730; 10,712,274; 10,775,305; or 10,895,534, each of which is incorporated herein by reference.

Luminescence lifetime can be detected using an integrated circuit having a photodetection region configured to receive incident photons and produce a plurality of charge carriers in response to the incident photons. The integrated circuit can include at least one charge carrier storage region and a charge carrier segregation structure configured to selectively direct charge carriers of the plurality of charge carriers directly into the charge carrier storage region based upon times at which the charge carriers are produced. See, for example, U.S. Pat. Nos. 9,606,058, 10,775,305, and 10,845,308, each of which is incorporated herein by reference. Optical sources that produce short optical pulses can be used for luminescence lifetime measurements. For example, a light source, such as a semiconductor laser or LED, can be driven with a bipolar waveform to generate optical pulses with FWHM durations as short as approximately 85 ps having suppressed tail emission. See, for example, in U.S. Pat. No. 10,605,730, which is incorporated herein by reference.

For configurations that use optical detection (e.g. luminescent detection), one or more analytes (e.g. proteins) may be immobilized on a surface, and this surface may be scanned with a microscope to detect any signal from the immobilized analytes. The microscope itself may include a digital camera or other luminescence detector configured to record, store, and analyze the data collected during the scan. A luminescence detector of the present disclosure can be configured for epiluminescent detection, total internal reflection (TIR) detection, waveguide assisted excitation, or the like.

A light sensing device may be based upon any suitable technology, and may be, for example, a charged coupled device (CCD) sensor that generates pixilated image data based upon photons impacting locations in the device. It will be understood that any of a variety of other light sensing devices may also be used including, but not limited to, a detector array configured for time delay integration (TDI) operation, a complementary metal oxide semiconductor (CMOS) detector, an avalanche photodiode (APD) detector, a Geiger-mode photon counter, a photomultiplier tube (PMT), charge injection device (CID) sensors, JOT image sensor (Quanta), or any other suitable detector. Light sensing devices can optionally be coupled with one or more excitation sources, for example, lasers, light emitting diodes (LEDs), arc lamps or other energy sources known in the art.

An optical detection system can be configured for single molecule detection. For example, waveguides or optical confinements can be used to deliver excitation radiation to locations of a solid support where analytes are located. Zero-mode waveguides can be particularly useful, examples of which are set forth in U.S. Pat. No. 7,181,122, 7,302,146, or 7,313,308, each of which is incorporated herein by reference. Analytes can be confined to surface features, for example, to facilitate single molecule resolution. For example, analytes can be distributed into wells having nanometer dimensions such as those set forth in U.S. Pat. No. 7,122,482 or 8,765,359, or US Pat. App. Pub. No 2013/0116153 A1, each of which is incorporated herein by reference. The wells can be configured for selective excitation, for example, as set forth in U.S. Pat. No. 8,798,414 or 9,347,829, each of which is incorporated herein by reference. Analytes can be distributed to nanometer-scale posts, such as high aspect ratio posts which can optionally be dielectric pillars that extend through a metallic layer to improve detection of an analyte coupled to the pillar. See, for example, U.S. Pat. Nos. 8,148,264, 9,410,887 or 9,987,609, each of which is incorporated herein by reference. Further examples of nanostructures that can be used to detect analytes are those that change state in response to the concentration of analytes such that the analytes can be quantitated as set forth in WO 2020/176793 A1, which is incorporated herein by reference.

An apparatus or method set forth herein need not be configured for optical detection. For example, an electronic detector can be used for detection of protons or charged labels (sec, for example, US Pat. App. Pub. Nos. 2009/0026082 A1; 2009/0127589 A1; 2010/0137143 A1; or 2010/0282617 A1, each of which is incorporated herein by reference in its entirety). A field effect transistor (FET) can be used to detect analytes or other entities, for example, based on proximity of a field disrupting moiety to the FET. The field disrupting moiety can be due to an extrinsic label coupled to an analyte or affinity agent, or the moiety can be intrinsic to the analyte or affinity agent being used. Surface plasmon resonance can be used to detect binding of analytes or affinity agents at or near a surface. Exemplary sensors and methods for coupling molecules to sensors are set forth in US Pat. App. Pub. Nos. 2017/0240962 A1; 2018/0051316 A1; 2018/0112265 A1; 2018/0155773 A1 or 2018/0305727 A1; or U.S. Pat. Nos. 9,164,053; 9,829,456; 10,036,064, each of which is incorporated herein by reference.

In some configurations of the compositions, apparatus and methods set forth herein, one or more proteins can be present on a solid support, where the proteins can optionally be detected. For example, a protein can be coupled to a solid support, the solid support can be contacted with a detection agent (e.g. affinity agent) in solution, the affinity agent can interact with the protein, thereby producing a detectable signal, and then the signal can be detected to determine the presence, absence, quantity, a characteristic or identity of the protein. In multiplexed versions of this approach, different proteins can be coupled to different addresses in an array, and the detection steps can occur in parallel, such that proteins at each address are detected, quantified, characterized or identified. In another example, detection agents can be coupled to a solid support, the support can be contacted with proteins in solution, the proteins can interact with the detection agents, thereby producing a detectable signal, and then the signal can be detected to determine the presence of the proteins. This approach can also be multiplexed by coupling different binding reagents to different addresses of an array.

In multiplexed configurations, different proteins can be coupled to different unique identifiers (e.g. addresses in an array), and the proteins can be manipulated and detected in parallel. For example, a fluid containing one or more different affinity agents can be delivered to an array such that the proteins of the array are in simultaneous contact with the affinity agent(s). Moreover, a plurality of addresses can be observed in parallel allowing for rapid detection of binding events. A plurality of different proteins can have a complexity of at least 5, 10, 100, $1\times10^3$, $1\times10^4$, $1\times10^5$ or more different native-length protein primary sequences. Alternatively or additionally, a proteome, proteome subfraction or other protein sample that is analyzed in a method set forth herein can have a complexity that is at most $1\times10^5$, $1\times10^4$, $1\times10^3$, 100, 10, 5 or fewer different native-length protein primary sequences. The total number of proteins of a sample that is detected, characterized or identified can differ from the number of different primary sequences in the sample, for example, due to the presence of multiple copies of at least some protein species. Moreover, the total number of proteins of a sample that is detected, characterized or identified can differ from the number of candidate proteins suspected of being in the sample, for example, due to the presence of multiple copies of at least some protein species, absence of some proteins in a source for the sample, or loss of some proteins prior to analysis.

A protein can be coupled to a unique identifier using any of a variety of means. The coupling can be covalent or non-covalent. Exemplary covalent attachments include chemical linkers such as those achieved using click chemistry or other linkages known in the art or described in U.S. patent application Ser. No. 17/062,405, which is incorporated herein by reference. Non-covalent attachment can be mediated by receptor-ligand interactions (e.g. (strept)avidin-biotin, antibody-antigen, or complementary nucleic acid strands), for example, wherein the receptor is attached to the unique identifier and the ligand is attached to the protein or vice versa. In particular configurations, a protein is coupled to a solid support (e.g. an address in an array) via a structured nucleic acid particle (SNAP). A protein can be coupled to a SNAP and the SNAP can interact with a solid support, for example, by non-covalent interactions of the DNA with the support and/or via covalent linkage of the SNAP to the support. Nucleic acid origami or nucleic acid nanoballs are particularly useful. The use of SNAPs and other moieties to couple proteins to unique identifiers such as tags or addresses in an array are set forth in U.S. patent application Ser. No. 17/062,405 and 63/159,500, each of which is incorporated herein by reference.

The methods, compositions and apparatus of the present disclosure are particularly well suited for use with proteins. Although proteins are exemplified throughout the present disclosure, it will be understood that other analytes can be similarly used. Exemplary analytes include, but are not limited to, biomolecules, polysaccharides, nucleic acids, lipids, metabolites, hormones, vitamins, enzyme cofactors, therapeutic agents, candidate therapeutic agents or combinations thereof. An analyte can be a non-biological atom or molecule, such as a synthetic polymer, metal, metal oxide, ceramic, semiconductor, mineral, or a combination thereof.

One or more proteins that are used in a method, composition or apparatus herein, can be derived from a natural or synthetic source. Exemplary sources include, but are not limited to biological tissues, fluids, cells or subcellular compartments (e.g. organelles). For example, a sample can be derived from a tissue biopsy, biological fluid (e.g. blood, sweat, tears, plasma, extracellular fluid, urine, mucus, saliva, semen, vaginal fluid, synovial fluid, lymph, cerebrospinal fluid, peritoneal fluid, pleural fluid, amniotic fluid, intracellular fluid, extracellular fluid, etc.), fecal sample, hair sample, cultured cell, culture media, fixed tissue sample (e.g. fresh frozen or formalin-fixed paraffin-embedded) or product of a protein synthesis reaction. A protein source may include any sample where a protein is a native or expected constituent. For example, a primary source for a cancer biomarker protein may be a tumor biopsy sample or bodily fluid. Other sources include environmental samples or forensic samples.

Exemplary organisms from which proteins or other analytes can be derived include, for example, a mammal such as a rodent, mouse, rat, rabbit, guinea pig, ungulate, horse, sheep, pig, goat, cow, cat, dog, primate, non-human primate or human; a plant such as *Arabidopsis thaliana*, tobacco, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a *Dictyostelium discoideum*; a fungi such as *Pneumocystis carinii, Takifugu rubripes*, yeast, *Saccharomyces cerevisiae* or *Schizosaccharomyces pombe*; or a *Plasmodium falciparum*. Proteins can also be derived from a prokaryote such as a bacterium, *Escherichia coli*, staphylococci or *Mycoplasma pneumoniae*; an archae; a virus such as Hepatitis C virus, influenza virus, coronavirus, or human immunodeficiency virus; or a viroid. Proteins can be derived from a homogeneous culture or population of the above organisms or alternatively from a collection of several different organisms, for example, in a community or ecosystem.

In some cases, a protein or other biomolecule can be derived from an organism that is collected from a host organism. For example, a protein may be derived from a parasitic, pathogenic, symbiotic, or latent organism collected from a host organism. A protein can be derived from an organism, tissue, cell or biological fluid that is known or suspected of being linked with a disease state or disorder (e.g., cancer). Alternatively, a protein can be derived from an organism, tissue, cell or biological fluid that is known or suspected of not being linked to a particular disease state or disorder. For example, the proteins isolated from such a source can be used as a control for comparison to results acquired from a source that is known or suspected of being linked to the particular disease state or disorder. A sample may include a microbiome or substantial portion of a microbiome. In some cases, one or more proteins used in a method, composition or apparatus set forth herein may be obtained from a single source and no more than the single source. The single source can be, for example, a single organism (e.g. an individual human), single tissue, single cell, single organelle (e.g. endoplasmic reticulum, Golgi apparatus or nucleus), or single protein-containing particle (e.g., a viral particle or vesicle).

A method, composition or apparatus of the present disclosure can use or include a plurality of proteins having any of a variety of compositions such as a plurality of proteins composed of a proteome or fraction thereof. For example, a plurality of proteins can include solution-phase proteins, such as proteins in a biological sample or fraction thereof, or a plurality of proteins can include proteins that are immobilized, such as proteins coupled to a particle or solid support. By way of further example, a plurality of proteins can include proteins that are detected, analyzed or identified in connection with a method, composition or apparatus of the present disclosure. The content of a plurality of proteins can be understood according to any of a variety of characteristics such as those set forth below or elsewhere herein.

A plurality of proteins can be characterized in terms of total protein mass. The total mass of protein in a liter of plasma has been estimated to be 70 g and the total mass of protein in a human cell has been estimated to be between 100 pg and 500 pg depending upon cells type. See Wisniewski et al. Molecular & Cellular Proteomics 13:10.1074/mcp.M113.037309, 3497-3506 (2014), which is incorporated herein by reference. A plurality of proteins used or included in a method, composition or apparatus set forth herein can include at least 1 pg, 10 pg, 100 pg, 1 ng, 10 ng, 100 ng, 1 μg, 10 μg, 100 μg, 1 mg, 10 mg, 100 mg or more protein by mass. Alternatively or additionally, a plurality of proteins may contain at most 100 mg, 10 mg, 1 mg, 100 μg, 10 μg, 1 μg, 100 ng, 10 ng, 1 ng, 100 pg, 10 pg, 1 pg or less protein by mass.

A plurality of proteins can be characterized in terms of percent mass relative to a given source such as a biological source (e.g. cell, tissue, or biological fluid such as blood). For example, a plurality of proteins may contain at least 60%, 75%, 90%, 95%, 99%, 99.9% or more of the total protein mass present in the source from which the plurality of proteins was derived. Alternatively or additionally, a plurality of proteins may contain at most 99.9%, 99%, 95%, 90%, 75%, 60% or less of the total protein mass present in the source from which the plurality of proteins was derived.

A plurality of proteins can be characterized in terms of total number of protein molecules. The total number of protein molecules in a *Saccharomyces cerevisiae* cell has been estimated to be about 42 million protein molecules. See Ho et al., Cell Systems (2018), DOI: 10.1016/j.cels.2017.12.004, which is incorporated herein by reference. A plurality of proteins used or included in a method, composition or apparatus set forth herein can include at least 1 protein molecule, 10 protein molecules, 100 protein molecules, $1\times10^4$ protein molecules, $1\times10^6$ protein molecules, $1\times10^8$ protein molecules, $1\times10^{10}$ protein molecules, 1 mole ($6.02214076\times10^{23}$ molecules) of protein, 10 moles of protein molecules, 100 moles of protein molecules or more. Alternatively or additionally, a plurality of proteins may contain at most 100 moles of protein molecules, 10 moles of protein molecules, 1 mole of protein molecules, $1\times10^{10}$ protein molecules, $1\times10^8$ protein molecules, $1\times10^6$ protein molecules, $1\times10^4$ protein molecules, 100 protein molecules, 10 protein molecules, 1 protein molecule or less.

A plurality of proteins can be characterized in terms of the variety of full-length primary protein structures in the plurality. For example, the variety of full-length primary protein structures in a plurality of proteins can be equated with the number of different protein-encoding genes in the source for the plurality of proteins. Whether or not the proteins are derived from a known genome or from any genome at all, the variety of full-length primary protein structures can be counted independent of presence or absence of post translational modifications in the proteins. A human proteome is estimated to have about 20,000 different protein-encoding genes such that a plurality of proteins derived from a human can include up to about 20,000 different primary protein structures. See Aebersold et al., Nat. Chem. Biol. 14:206-214 (2018), which is incorporated herein by reference. Other genomes and proteomes in nature are known to be larger or smaller. A plurality of proteins used or included in a method, composition or apparatus set forth herein can have a complexity of at least 2, 5, 10, 100, $1\times10^3$, $1\times10^4$, $2\times10^4$, $3\times10^4$ or more different full-length primary protein structures. Alternatively or additionally, a plurality of proteins can have a complexity that is at most $3\times10^4$, $2\times10^4$, $1\times10^4$, $1\times10^3$, 100, 10, 5, 2 or fewer different full-length primary protein structures.

In relative terms, a plurality of proteins used or included in a method, composition or apparatus set forth herein may contain at least one representative for at least 60%, 75%, 90%, 95%, 99%, 99.9% or more of the proteins encoded by the genome of a source from which the sample was derived. Alternatively or additionally, a plurality of proteins may contain a representative for at most 99.9%, 99%, 95%, 90%, 75%, 60% or less of the proteins encoded by the genome of a source from which the sample was derived.

A plurality of proteins can be characterized in terms of the variety of primary protein structures in the plurality including transcribed splice variants. The human proteome has been estimated to include about 70,000 different primary protein structures when splice variants ac included. Sec Aebersold et al., Nat. Chem. Biol. 14:206-214 (2018), which is incorporated herein by reference. Moreover, the number of the partial-length primary protein structures can increase due to fragmentation that occurs in a sample. A plurality of proteins used or included in a method, composition or apparatus set forth herein can have a complexity of at least 2, 5, 10, 100, $1\times10^3$, $1\times10^4$, $7\times10^4$, $1\times10^5$, $1\times10^6$ or more different primary protein structures. Alternatively or additionally, a plurality of proteins can have a complexity that is at most $1\times10^6$, $1\times10^5$, $7\times10^4$, $1\times10^4$, $1\times10^3$, 100, 10, 5, 2 or fewer different primary protein structures.

A plurality of proteins can be characterized in terms of the variety of protein structures in the plurality including different primary structures and different proteoforms among the primary structures. Different molecular forms of proteins expressed from a given gene are considered to be different proteoforms. Proteoforms can differ, for example, due to differences in primary structure (e.g. shorter or longer amino acid sequences), different arrangement of domains (e.g. transcriptional splice variants), or different post translational modifications (e.g. presence or absence of phosphoryl, glycosyl, acetyl, or ubiquitin moieties). The human proteome is estimated to include hundreds of thousands of proteins when counting the different primary structures and proteoforms. See Aebersold et al., Nat. Chem. Biol. 14:206-214 (2018), which is incorporated herein by reference. A plurality of proteins used or included in a method, composition or apparatus set forth herein can have a complexity of at least 2, 5, 10, 100, $1\times10^3$, $1\times10^4$, $1\times10^5$, $1\times10^6$, $5\times10^6$, $1\times10^7$ or more different protein structures. Alternatively or additionally, a plurality of proteins can have a complexity that is at most $1\times10^7$, $5\times10^6$, $1\times10^6$, $1\times10^5$, $1\times10^4$, $1\times10^3$, 100, 10, 5, 2 or fewer different protein structures.

A plurality of proteins can be characterized in terms of the dynamic range for the different protein structures in the sample. The dynamic range can be a measure of the range of abundance for all different protein structures in a plurality of proteins, the range of abundance for all different primary protein structures in a plurality of proteins, the range of abundance for all different full-length primary protein structures in a plurality of proteins, the range of abundance for all different full-length gene products in a plurality of proteins, the range of abundance for all different proteoforms expressed from a given gene, or the range of abundance for any other set of different proteins set forth herein. The dynamic range for all proteins in human plasma is estimated to span more than 10 orders of magnitude from albumin, the most abundant protein, to the rarest proteins that have been measured clinically. See Anderson and Anderson Mol Cell Proteomics 1:845-67 (2002), which is incorporated herein by reference. The dynamic range for plurality of proteins set forth herein can be a factor of at least 10, 100, $1\times10^3$, $1\times10^4$, $1\times10^6$, $1\times10^8$, $1\times10^{10}$, or more. Alternatively or additionally, the dynamic range for plurality of proteins set forth herein can be a factor of at most $1\times10^{10}$, $1\times10^8$, $1\times10^6$, $1\times10^4$, $1\times10^3$, 100, 10 or less.

A method set forth herein can be carried out in a fluid phase or on a solid phase. For fluid phase configurations, a fluid containing one or more proteins can be mixed with another fluid containing one or more affinity agents. For solid phase configurations one or more proteins or affinity agents can be coupled to a solid support. One or more components that will participate in a binding event can be contained in a fluid and the fluid can be delivered to a solid support, the solid support being coupled to one or more other component that will participate in the binding event.

A method of the present disclosure can be carried out at single analyte resolution.

Alternatively to single-analyte resolution, a method can be carried out at ensemble-resolution or bulk-resolution. Bulk-resolution configurations acquire a composite signal from a plurality of different analytes or affinity agents in a vessel or on a surface. For example, a composite signal can be acquired from a population of different protein-affinity agent complexes in a well or cuvette, or on a solid support surface, such that individual complexes are not resolved from each other. Ensemble-resolution configurations acquire a composite signal from a first collection of proteins or affinity agents in a sample, such that the composite signal is distinguishable from signals generated by a second collection of proteins or affinity agents in the sample. For example, the ensembles can be located at different addresses in an array. Accordingly, the composite signal obtained from each address will be an average of signals from the ensemble, yet signals from different addresses can be distinguished from each other.

A composition, apparatus or method set forth herein can be configured to contact one or more proteins (e.g. an array of different proteins) with a plurality of different affinity agents. For example, a plurality of affinity agents (whether configured separately or as a pool) may include at least 2, 5, 10, 25, 50, 100, 250, 500 or more types of affinity agents, each type of affinity agent differing from the other types with respect to the epitope(s) recognized. Alternatively or additionally, a plurality of affinity agents may include at most 500, 250, 100, 50, 25, 10, 5, or 2 types of affinity agents, each type of affinity agent differing from the other types with respect to the epitope(s) recognized. Different types of affinity agents in a pool can be uniquely labeled such that the different types can be distinguished from each other. In some configurations, at least two, and up to all, of the different types of affinity agents in a pool may be indistinguishably labeled with respect to each other. Alternatively or additionally to the use of unique labels, different types of affinity agents can be delivered and detected serially when evaluating one or more proteins (e.g. in an array).

A method of the present disclosure can be performed in a multiplex format. In multiplexed configurations, different proteins can be coupled to different unique identifiers (e.g. the proteins can be coupled to different addresses in an array). Multiplexed proteins can be manipulated and detected in parallel. For example, a fluid containing one or more different affinity agents can be delivered to a protein array such that the proteins of the array are in simultaneous contact with the affinity agent(s). Moreover, a plurality of addresses can be observed in parallel allowing for rapid detection of binding events. A plurality of different proteins can have a complexity of at least 5, 10, 100, $1\times10^3$, $1\times10^4$, $2\times10^4$, $3\times10^4$ or more different native-length protein primary sequences. Alternatively or additionally, a proteome or proteome subfraction that is analyzed in a method set forth herein can have a complexity that is at most $3\times10^4$, $2\times10^4$, $1\times10^4$, $1\times10^3$, 100, 10, 5 or fewer different native-length protein primary sequences. The plurality of proteins can constitute a proteome or subfraction of a proteome. The total number of proteins that is detected, characterized or identified can differ from the number of different primary sequences in the sample from which the proteins are derived, for example, due to the presence of multiple copies of at least some protein species. Moreover, the total number of proteins that are detected, characterized or identified can differ from the number of candidate proteins suspected of being present, for example, due to the presence of multiple copies of at least some protein species, absence of some proteins in a source for the proteins, or loss of some proteins prior to analysis.

A particularly useful multiplex format uses an array of proteins and/or affinity agents. A polypeptide, anchoring group, polypeptide composite or other analyte can be coupled to a unique identifier, such as an address in an array, using any of a variety of means. The coupling can be covalent or non-covalent. Exemplary covalent attachments include chemical linkers such as those achieved using click chemistry or other linkages known in the art or described in US Pat. App. Pub. No. 2021/0101930 A1, which is incorporated herein by reference. Non-covalent attachment can be mediated by receptor-ligand interactions (e.g. (strept) avidin-biotin, antibody-antigen, or complementary nucleic acid strands), for example, in which the receptor is attached to the unique identifier and the ligand is attached to the protein or vice versa. In particular configurations, a protein is coupled to a solid support (e.g. an address in an array) via a structured nucleic acid particle (SNAP). A protein can be coupled to a SNAP and the SNAP can interact with a solid support, for example, by non-covalent interactions of the DNA with the support and/or via covalent linkage of the SNAP to the support. Nucleic acid origami or nucleic acid nanoballs are particularly useful. The use of SNAPs and other moieties to couple proteins to unique identifiers such as tags or addresses in an array are set forth in US Pat. App. Pub. No. 2021/0101930 A1, which is incorporated herein by reference.

A solid support or a surface thereof may be configured to display an analyte or a plurality of analytes. A solid support may contain one or more patterned, formed, or prepared surfaces that contain at least one address for displaying an analyte. In some cases, a solid support may contain one or more patterned, formed, or prepared surfaces that contain a plurality of addresses, with each address configured to display one or more analytes. Accordingly, an array as set forth herein may comprise a plurality of analytes coupled to a solid support or a surface thereof. In some configurations, a solid support or a surface thereof may be patterned or formed to produce an ordered or patterned array of addresses. The deposition of analytes on the ordered or patterned array of addresses may be controlled by interactions between the solid support and the analytes such as, for example, electrostatic interactions, magnetic interactions, hydrophobic interactions, hydrophilic interactions, covalent interactions, or non-covalent interactions. Accordingly, the coupling of an analyte at each address of an array may produce an ordered or patterned array of analytes whose average spacing between analytes is determined based upon the tolerance of the ordering or patterning of the solid support and the size of an analyte-binding region for each address. An ordered or patterned array of analytes may be characterized as having a regular geometry, such as a rectangular, triangular, polygonal, or annular grid. In other configurations, a solid support or a surface thereof may be non-patterned or non-ordered. The deposition of analytes on the non-ordered or non-patterned array of addresses may be controlled by interactions between the solid support and the analytes, or inter-analyte interactions such as, for example, steric repulsion, electrostatic repulsion, electrostatic attraction, magnetic repulsion, magnetic attraction, covalent interactions, or non-covalent interactions.

A solid support or a surface thereof may contain one or more structures or features. A structure or feature may comprise an elevation, profile, shape, geometry, or configuration that deviates from an average elevation, profile, shape, geometry, or configuration of a solid support or surface thereof. A structure or feature may be a raised structure or feature, such as a ridge, post, pillar, or pad, if the structure or feature extends above the average elevation of a surface of a solid support. A structure or feature may be a depressed structure, such as a channel, well, pore, or hole, if the structure or feature extends below the average elevation of a surface of a solid support. A structure or feature may be an intrinsic structure or feature of a substrate (i.e., arising due to the physical or chemical properties of the substrate, or a physical or chemical mechanism of formation), such as surface roughness structures, crystal structures, or porosity. A structure or feature may be formed by a method of processing a solid support. In some configurations, a solid support or a surface may be processed by a lithographic method to form one or more structures or features. A solid support or a surface thereof may be formed by a suitable lithographic method, including, but not limited to photolithography, Dip-Pen nanolithography, nanoimprint lithography, nanosphere lithography, nanoball lithography, nanopillar arrays, nanowire lithography, immersion lithography, neutral particle lithography, plasmonic lithography, scanning probe lithography, thermochemical lithography, thermal scanning probe lithography, local oxidation nanolithography, molecular self-assembly, stencil lithography, laser interference lithography, soft lithography, magnetolithography, stereolithography, deep ultraviolet lithography, x-ray lithography, ion projection lithography, proton-beam lithography, or electron-beam lithography.

A solid support or surface may comprise a plurality of structures or features. A plurality of structures or features may comprise an ordered or patterned array of structures or features. A plurality of structures or features may comprise an non-ordered, non-patterned, or random array of structures or features. A structure or feature may have an average characteristic dimension (e.g., length, width, height, diameter, circumference, etc.) of at least about 1 nanometer (nm), 5 nm, 10 nm, 20 nm, 30 nm, 40 nm, 50 nm, 75 nm, 100 nm, 150 nm, 200 nm, 250 nm, 300 nm, 400 nm, 500 nm, 750 nm, 1000 nm, or more than 1000 nm. Alternatively or additionally, a structure or feature may have an average characteristic dimension of no more than about 1000 nm, 750 nm, 500 nm, 400 nm, 300 nm, 250 nm, 200 nm, 150 nm, 100 nm, 75 nm, 50 nm, 40 nm, 30 nm, 20 nm, 10 nm, 5 nm, 1 nm, or less than 1 nm. An array of structures or features may have an average pitch, in which the pitch is measured as the average separation between respective center points of neighboring structures or features. An array may have an average pitch of at least about 1 nm, 5 nm, 10 nm, 20 nm, 30 nm, 40 nm, 50 nm, 75 nm, 100 nm, 150 nm, 200 nm, 250 nm, 300 nm, 400 nm, 500 nm, 750 nm, 1 micron (μm), 2 μm, 5 μm, 10 μm, 50 μm, 100 μm, or more than 100 μm. Alternatively or additionally, an array may have an average pitch of no more than about 100 μm, 50 μm, 10 μm, 5 μm, 1 μm, 750 nm, 500 nm, 400 nm, 300 nm, 250 nm, 200 nm, 150 nm, 100 nm, 75 nm, 50 nm, 40 nm, 30 nm, 20 nm, 10 nm, 5 nm, 1 nm, or less than 1 nm.

A solid support or a surface thereof may include a base substrate material and, optionally, one or more additional materials that are contacted or adhered with the substrate material. A solid support may comprise one or more additional materials that are deposited, coated, or inlayed onto the substrate material. Additional materials may be added to the substrate material to alter the properties of the substrate material. For example, materials may be added to alter the surface chemistry (e.g., hydrophobicity, hydrophilicity, non-specific binding, electrostatic properties), alter the optical properties (e.g., reflective properties, refractive properties), alter the electrical or magnetic properties (e.g., dielectric materials, conducting materials, electrically-insulating materials), or alter the heat transfer characteristics of the substrate material. Additional materials contacted or adhered with a substrate material may be ordered or patterned onto the substrate material to, for example, locate the additional material at addresses or locate the additional material at interstitial regions between addresses. Exemplary additional materials may include metals (e.g., gold, silver, copper, etc.), metal oxides (e.g., titanium oxide, silicon dioxide, alumina, iron oxides, etc.), metal nitrides (e.g., silicon nitride, aluminum nitride, boron nitride, gallium nitride, etc.), metal carbides (e.g., tungsten carbide, titanium carbide, iron carbide, etc.), metal sulfides (e.g., iron sulfide, silver sulfide, etc.), and organic moieties (e.g., polyethylene glycol (PEG), dextrans, chemically-reactive functional groups, etc.).

A method of the present disclosure can include the step of coupling one or more analytes to a solid support or a surface thereof prior to performing a detection step set forth herein. The coupling of one or more analytes to a solid support surface may include covalent or non-covalent coupling of the one or more analytes to the solid support. Covalent coupling of an analyte to a solid support can include direct covalent coupling of an analyte to a solid support (e.g., formation of coordination bonds) or indirect covalent coupling between a reactive functional group of the analyte and a reactive functional group that is coupled to the solid support (e.g., a CLICK-type reaction). Non-covalent coupling can include the formation of any non-covalent interaction between an analyte and a solid support, including electrostatic or magnetic interactions, or non-covalent bonding interactions (e.g., ionic bonds, van der Waals interactions, hydrogen bonding, etc.). The skilled person will readily recognize that the particular analyte and the choice of solid support can affect the selection of a coupling chemistry for the compositions and methods set forth herein.

Accordingly, a coupling chemistry may be selected based upon the criterium that it provides a sufficiently stable coupling of an analyte to a solid support for a time scale that meets or exceeds the time scale of a method as set forth herein. For example, a polypeptide identification method can require a coupling of the analyte to the solid support for a sufficient amount of time to permit a series of empirical measurements of the analyte to occur. An analyte may be continuously coupled to a solid support for an observable length of time such as, for example, at least about 1 minute, 1 hour (hr), 3 hrs, 6 hrs, 12 hrs, 1 day, 1.5 days, 2 days, 3 days, 1 week (wk), 2 wks, 3 wks, 1 month, or more. The coupling of an analyte to a solid support can occur with a solution-phase chemistry that promotes the deposition of the analyte on the solid support. Coupling of an analyte to a solid support may occur under solution conditions that are optimized for any conceivable solution property, including solution composition, species concentrations, pH, ionic strength, solution temperature, etc. Solution composition can be varied by chemical species, such as buffer type, salts, acids, bases, and surfactants. In some configurations, species such as salts and surfactants may be selected to facilitate the formation of interactions between an analyte and a solid support. Covalent coupling methods for coupling an analyte to a solid support may include species such as catalyst, initiators, and promoters to facilitate particular reactive chemistries.

Coupling of an analyte to a solid support may be facilitated by a mediating group. A mediating group may modify the properties of the analyte to facilitate the coupling. Useful mediating groups have been set forth herein (e.g., structured nucleic acid particles). In some configurations, a mediating group can be coupled to an analyte prior to coupling the analyte to a solid support. Accordingly, the mediating group may be chosen to increase the strength, control, or specificity of the coupling of the analyte to the solid support. In other configurations, a mediating group can be coupled to a solid support prior to coupling an analyte to the solid support. Accordingly, the mediating group may be chosen to provide a more favorable coupling chemistry than can be provided by the solid support alone.

Example 1: Antibody Removal from Peptide Targets

Antibody dissociation from peptide targets was tested utilizing a bulk fluorescence assay. 12-Histidine (12-His) peptide targets were immobilized on a surface, then contacted with fluorescent anti-His antibodies. Fluorescence of antibodies bound to peptide targets was measured before and after stripping with a binding reagent dissociation medium.

To test antibody dissociation, 50 microliters (μl) of 50 nanomolar (nM) 12-His peptides were incubated in a well of a ThermoFisher 437111 immunoassay plate. Peptides were incubated overnight at 4° C. After incubation, unbound peptides were rinsed from the well. The peptide-immobilized well was blocked with pH 7.6 phosphate buffer solution containing 0.005 wt % Tween-20 and 1 wt % bovine serum albumin (BSA). After blocking, the well was rinsed 6 times with 200 μl of pH 7.6 phosphate buffer solution containing 0.005 wt % Tween-20, then rinsed once with 200 μl of pH 7.6 phosphate buffer solution.

50 μl of 100 nM fluorescently-labeled anti-His antibody was added to the well. The antibody solution was incubated in the well for 30 minutes. After antibody incubation, the well was rinsed 6 times with 200 μl of pH 7.6 phosphate buffer solution containing 0.005 wt % Tween-20, then rinsed once with 200 μl of pH 7.6 phosphate buffer solution. After rinsing, fluorescence at 620/680 (ex/em) nm was measured on a fluorescent plate reader with 50 μl of pH 7.6 phosphate buffer solution in the well.

After initial fluorescence collection, 50 μl of stripping solution was added to each well. The stripping solution was incubated for 10 minutes at room temperature. After stripping, the well was rinsed 6 times with 200 μl of pH 7.6 phosphate buffer solution containing 0.005 wt % Tween-20, then rinsed once with 200 μl of pH 7.6 phosphate buffer solution. After rinsing, fluorescence at 620/680 (ex/em) nm was measured on a fluorescent plate reader with 50 μl of pH 7.6 phosphate buffer solution in the well.

Table III lists differing stripping solutions that were tested for removal of anti-His antibodies from 12-His peptide targets. Antibody dissociation was considered to be low if less than a 33% decrease in well fluorescence was observed after incubating antibody-target complexes with a stripping solution. Antibody dissociation was considered to be moderate if a decrease in well fluorescence of between 33% and 67% was observed after incubating antibody-target complexes with a stripping solution. Antibody dissociation was considered to be high if a greater than 67% decrease in well fluorescence was observed after incubating antibody-target complexes with a stripping solution.

TABLE III

Anti-His Antibody Stripping from 12-His Targets

| Stripping Solution | Concentration | Observed AB Removal |
|---|---|---|
| Magnesium Chloride | 2M | High |
| Lithium Chloride | 2.5M | High |
| | 4M | High |
| Sodium Iodide | 3M | High |
| Sodium Thiocyanate | 200 mM | Low |
| | 3M | High |
| Sodium Thiocyanate and Urea | 2M + 500 mM | High |
| Sodium Chloride | 4M | Low |
| Sodium Chloride in 1x Neoventures Buffer | 3.5M | High |
| Acetonitrile | 10 wt % in water | Low |
| Methanol | 10 wt % in water | Low |
| | 60 wt % in water | Moderate |
| Isopropanol | 50 wt % in water | Low |
| Ethanol | 10 wt % in water | Low |
| Sodium Dodecyl Sulfate (SDS) | 10 wt % in water | High |
| Guanidinium Chloride | 2M | Moderate |
| | 6M | Moderate |
| Urea | 8M | Moderate |
| Sodium Deoxycholate | 1 wt % in water | Moderate |
| Sodium Deoxycholate and Magnesium Chloride | 1 wt % and 10 mM | Low |
| TCEP | 50 mM | Low |
| TCEP and Guanidine HCl | 5 mM and 6M | High |
| TCEP and SDS | 5 mM and 10 wt % | High |
| Guanidinium Thiocyanate | 4M | High |
| Guanidinium Thiocyanate and Guanidinium Chloride | 4M and 6M | High |

Example 2: Binding Reagent Removal from Peptide Targets

Binding reagent dissociation from peptide targets was tested on a glass surface with a (3-aminopropyl) trimethoxysilane (APTMS) surface layer. 12-Histidine (12-His) peptide targets were covalently coupled to a tile-shaped nucleic acid origami anchoring moiety, then deposited on a glass surface containing a blanket coating of APTMS. Peptide targets were retained on the surface by electrostatic adhesion of the anchoring moieties to the surface. Each anchoring moiety contained 44 coupled AlexaFluor-488 fluorophores to facilitate identification of addresses on the APTMS-coated surface containing an anchoring moiety. After peptide immobilization on the surface, detectable binding reagents were bound to peptide targets. Each detectable binding reagent comprised a tile-shaped nucleic acid origami coupled to 10 anti-His antibodies and 44 AlexaFluor-647 fluorophores. Formation and deposition of peptide-anchoring moiety composites are described in U.S. Pat. App. No. 20220290130A1. Formation of origami-based binding reagents are described in U.S. Pat. App. No. 20220162684A1.

Detectable binding reagents were dissociated by contact with a stripping solution. Fluorescent images of the APTMS-coated surface were collected by confocal scanning microscopy at 461 nm and 635 nm before and after binding reagent dissociation to identify addresses with co-localized anchoring moieties and detectable binding reagents. Addresses with 461 nm and 635 nm signals before dissociation and only 461 nm signal after dissociation were considered to be dissociated with respect to the binding reagent and associated with respect to the anchoring moiety. Addresses with 461 nm and 635 nm signals before dissociation and no signals after dissociation were considered to be dissociated with respect to the binding reagent and the anchoring moiety.

Table IV presents tested stripping solutions and observed rates of binding reagent dissociation and anchoring moiety dissociation. Binding reagent dissociation was considered to be low if less than a 33% decrease in quantity of fluorescent addresses was observed after incubating binding reagent-target complexes with a stripping solution. Binding reagent dissociation was considered to be moderate if a decrease in quantity of fluorescent addresses of between 33% and 67% was observed after incubating binding reagent-target complexes with a stripping solution. Binding reagent dissociation was considered to be high if a greater than 67% decrease in quantity of fluorescent addresses was observed after incubating antibody-target complexes with a stripping solution. Anchoring moiety dissociation was considered to be low if less than a 5% decrease in quantity of fluorescent addresses was observed after incubating binding reagent-target complexes with a stripping solution. Anchoring moiety dissociation was considered to be high if greater than a 5% decrease in quantity of fluorescent addresses was observed after incubating binding reagent-target complexes with a stripping solution. Binding reagent Removal was marked as "N/A" if the extent. of anchoring moiety dissociation made it difficult to assess the extent of binding reagent dissociation.

TABLE IV

Anti-His Stripping of 12-His Targets on APTMS Surface

| Stripping Solution | Concentration | Binding reagent Removal | Anchoring Moiety Removal |
|---|---|---|---|
| Magnesium Chloride | 2M | High | Low |
| Lithium Chloride | 2.5M | High | Low |
| | 4M | High | Low |
| Sodium Iodide | 3M | High | High |
| Sodium Thiocyanate | 3M | High | High |
| Sodium Thiocyanate and Urea | 2M and 50 mM | N/A | High |
| Sodium Chloride in 1x Neoventures Buffer | 3.5M | N/A | High |
| Methanol | 60 wt % in water | N/A | High |
| Sodium Dodecyl Sulfate | 10 wt % in water | High | Low |
| Guanidinium Chloride | 2M | Moderate | Low |
| | 6M | Moderate | Low |
| Urea | 8M | Moderate | Low |
| TCEP and Guanidinium Chloride | 50 mM and 6M | High | High |
| TCEP and Sodium Dodecyl Sulfate | 50 mM and 10% | High | Low |
| | 50 mM and 2% | High | High |
| Glycine-HCl | 100 mM | Low | High |
| Citric Acid | 100 mM | High | High |
| Hydrochloric Acid | 100 mM | High | High |
| Acetic Acid | 100 mM | High | High |
| Formamide | 65 wt % in water | N/A | High |
| Sodium Hydroxide | 1M | N/A | High |
| | 200 mM | N/A | High |
| | 10 mM | N/A | High |
| Guanidinium Thiocyanate and Guanidinium Chloride | 4M and 6M | N/A | High |

Example 3. Binding Reagent Association Medium Compositions

Differing binding reagent association media were tested on patterned peptide arrays. 6 arrays were prepared by the method set forth in U.S. Pat. No. 11,505,796B2, herein incorporated by reference in its entirety. Briefly, patterned arrays were formed on silicon substrates by nanolithography. Array sites were provided with an approximately 1 μm pitch. Each array site was functionalized with a plurality of oligonucleotides. Peptides were covalently attached to nucleic acid nanoparticles. Each nucleic acid nanoparticle contained a plurality of pendant oligonucleotides that were complementary to the oligonucleotides attached to each array site. Peptide-conjugated nucleic acid nanoparticles were deposited on the arrays at a concentration of 500 pM. 3 arrays were formed containing only HHH peptide. 3 arrays were formed containing only DTR peptide.

Arrays were contacted with multivalent affinity reagents to assess fractions of sites experiencing orthogonal binding phenomena. Multivalent affinity agents are described in U.S. Patent Publication No. 20220162684, which is herein incorporated by reference in its entirety. Each array was contacted with a pool of multivalent affinity reagents that possessed a binding specificity for the peptide targets of the array. The concentration of affinity reagents was 10 nM. 3 different binding reagent association media (1 per array) were tested: 1) 1 wt % bovine serum albumin (BSA) with 1 mg/mL sheared salmon sperm DNA (SSSDNA), 2) 1 wt % PF-127 with 1 mg/mL SSSDNA, and 3) 1 wt % polyvinylpyrrolidone (PVP) with 1 mg/mL SSSDNA. Arrays containing HHH peptides were contacted with multivalent affinity reagents containing anti-HHH aptamers (i.e., B1 aptamer). Arrays containing DTR peptides were contacted with multivalent affinity reagents containing anti-DTR antibodies. Orthogonal binding was observed as fluorescent detection events that occurred at interstitial regions of an array or at unoccupied array sites.

After contacting arrays with a pool of binding reagents in the presence of a binding reagent association medium, arrays were imaged by confocal laser scanning microscopy at 680 nm (per the 647 nm excitation wavelength fluorescent dyes of the binding reagents). After imaging, bound affinity reagents were dissociated with a binding reagent dissociation medium containing 100 mM CHAPS. The sequence of binding reagent association, imaging, and binding reagent dissociation was repeated for 10 cycles for each array. Array images were processed by an image analysis algorithm. Orthogonal binding fractions were determined by counting detection events that occurred at interstitial regions or array sites that were not occupied by a peptide target.

Figure 15A:
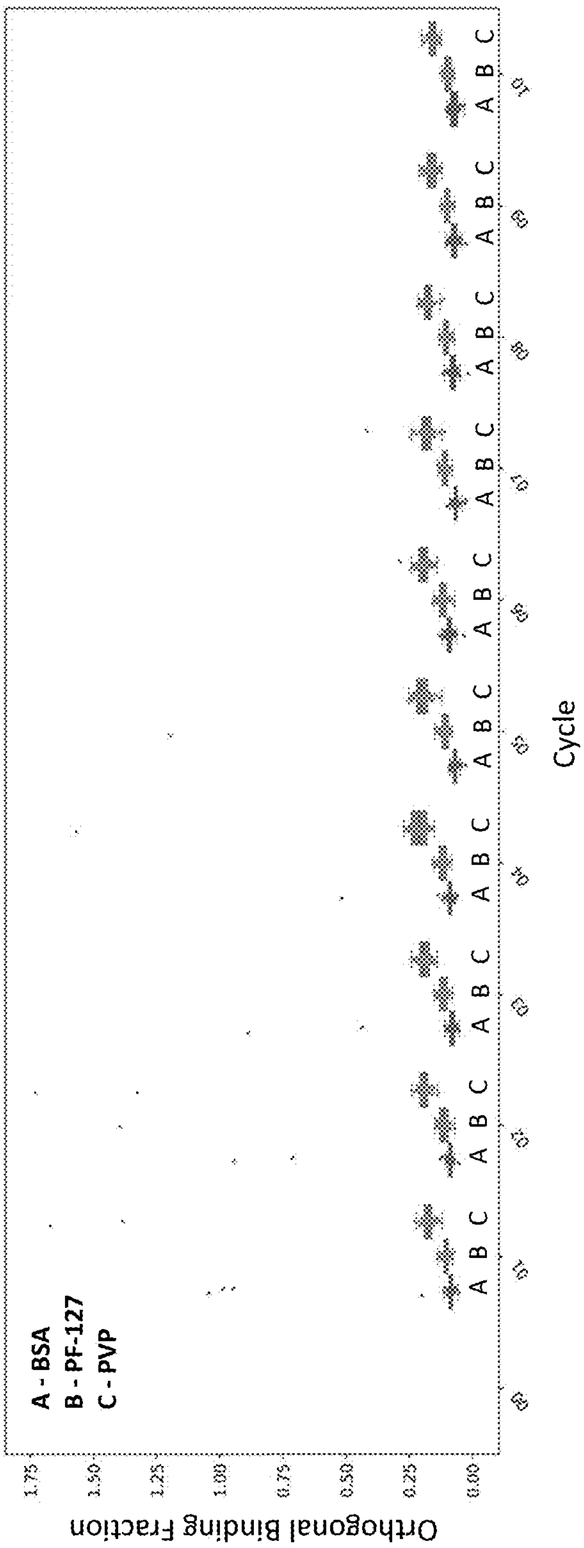
FIGS. 15A and 15B display orthogonal binding fractions after binding binding reagents in the presence of various binding reagent association media.
Figure 15B:
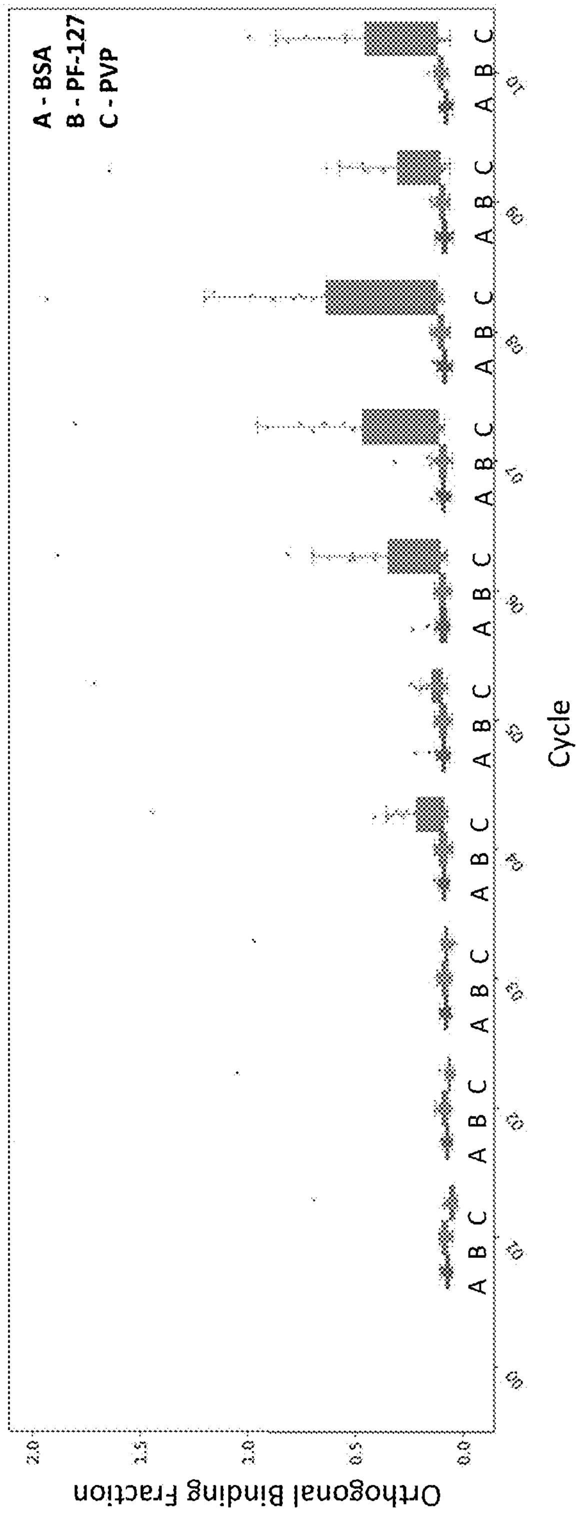

FIG. 15A displays orthogonal binding fractions for HHH peptide arrays contacted with anti-HHH affinity reagents. Orthogonal binding fractions were observed to be less than 1% for each tested binding reagent association medium. PF-127 performed comparably to BSA. PVP had a slightly higher fraction of orthogonal binding, but still well below 1% of sites. Little change in the orthogonal binding fraction was observed over the 10 cycles for each binding reagent association medium that was tested. FIG. 15B displays orthogonal binding fractions for DTR peptide arrays contacted with anti-DTR affinity reagents. Orthogonal binding fractions were observed to be less than 1% for each tested binding reagent association medium. PF-127 performed comparably to BSA. PVP had a slightly higher fraction of orthogonal binding, but still well below 1% of sites. Little change in the orthogonal binding fraction was observed over the 10 cycles for each binding reagent association medium.

Example 4. Binding Reagent Association Medium Compositions

Differing binding reagent association media were tested on patterned peptide arrays. 3 arrays were prepared by the method set forth in U.S. Pat. No. 11,505,796B2, herein incorporated by reference in its entirety. Briefly, patterned arrays were formed on silicon substrates by nanolithography. Array sites were provided with an approximately 1 μm pitch. Each array site was functionalized with a plurality of oligonucleotides. Peptides with an amino acid sequence of DTR were covalently attached to nucleic acid nanoparticles. Each nucleic acid nanoparticle contained a plurality of pendant oligonucleotides that were complementary to the oligonucleotides attached to each array site. Peptide-conjugated nucleic acid nanoparticles were deposited on the arrays at a concentration of 150 pM.

Arrays were contacted with multivalent affinity reagents to assess fractions of sites experiencing orthogonal binding phenomena. Multivalent affinity agents are described in U.S. Patent Publication No. 20220162684, which is herein incorporated by reference in its entirety. Each array was contacted with a pool of multivalent affinity reagents that possessed a binding specificity for the DTR peptide targets of the array. The concentration of affinity reagents was 10 nM. The tested binding reagent association media were varied with respect to a polynucleotide component. Some variations of binding reagent association media incorporated oligonucleotides that were complementary to the nucleotide sequence of the surface-coupled oligonucleotides of the array sites. Accordingly, the incorporated oligonucleotides of the binding reagent association media could hybridize to fluidically available surface-coupled oligonucleotides. 3 different binding reagent association media (1 per array) were tested: 1) 1 wt % PF-127 with 1 mg/mL SSSDNA, 2) 1 wt % PF-127 with 1 μM oligonucleotides, and 3) 1 wt % PF-127 with 1 mg/mL SSSDNA and 1 μM oligonucleotides. Orthogonal binding was observed as fluorescent detection events that occurred at interstitial regions of an array or at unoccupied array sites.

After contacting arrays with a pool of binding reagents in the presence of a binding reagent association medium, arrays were imaged by confocal laser scanning microscopy at 680 nm (per the 647 nm excitation wavelength fluorescent dyes of the binding reagents). After imaging, bound affinity reagents were dissociated with a binding reagent dissociation medium containing 100 mM CHAPS. The sequence of binding reagent association, imaging, and binding reagent dissociation was repeated for 10 cycles for each array. Array images were processed by an image analysis algorithm. Orthogonal binding fractions were determined by counting detection events that occurred at interstitial regions or array sites that were not occupied by a peptide target.

Figure 16:
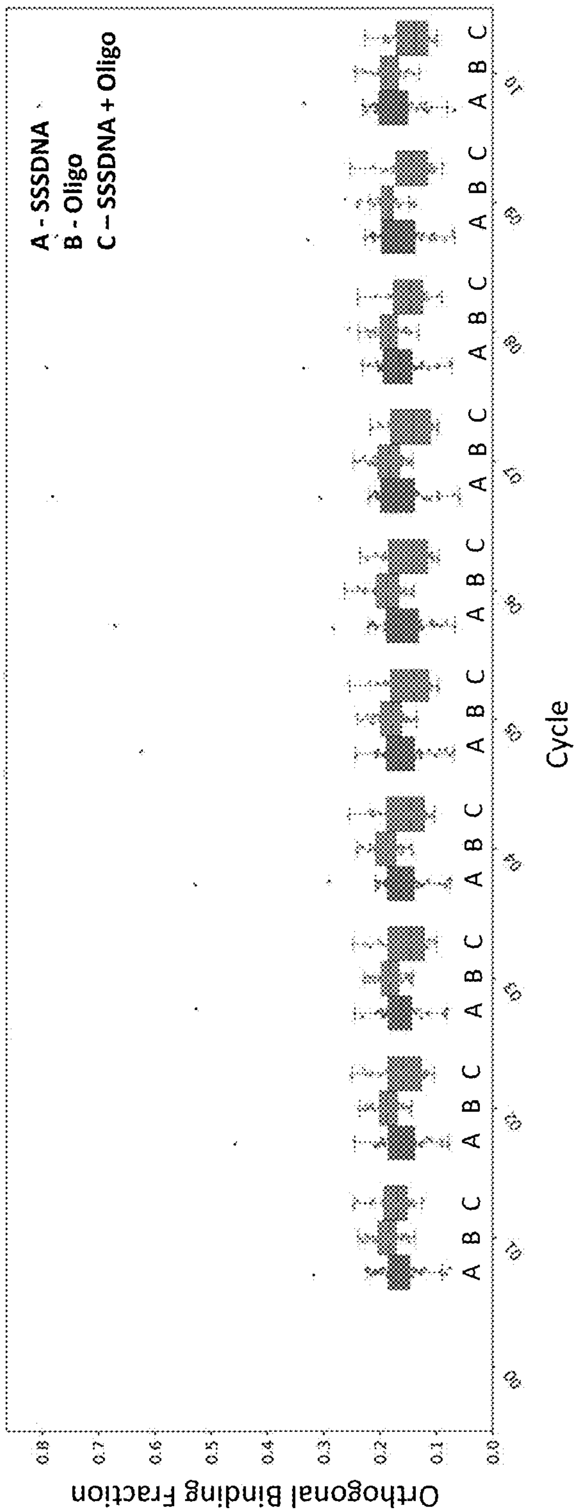
FIG. 16 depicts orthogonal binding fractions after binding binding reagents in the presence of various binding reagent association media.
Figure 17A:
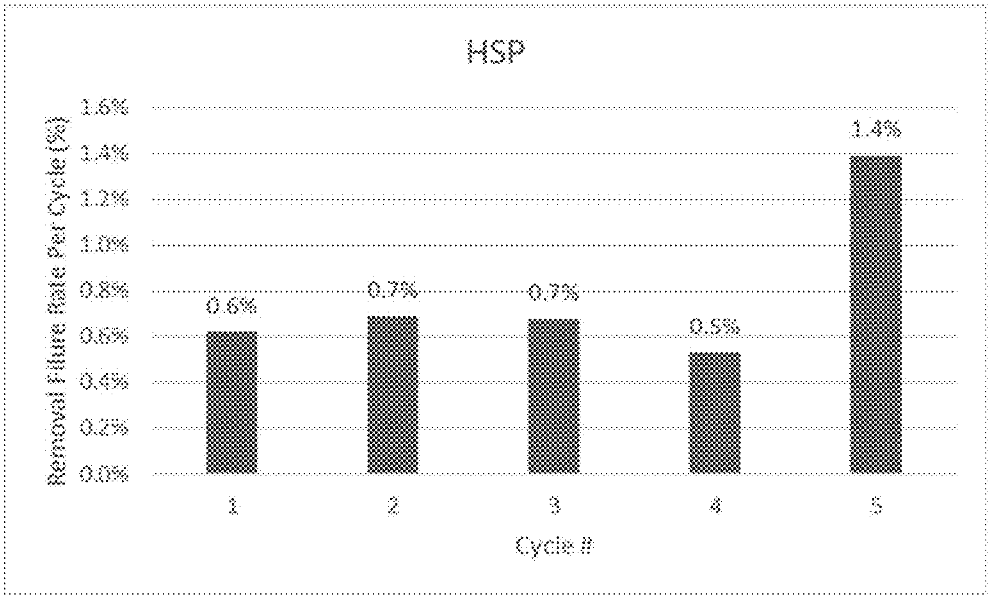
FIGS. 17A, 17B, 17C, 17D, 17E, and 17F illustrate differences in binding reagent dissociation failure rate after exposure of binding reagents and analytes to 647 nm light and 488 nm light.
Figure 17B:
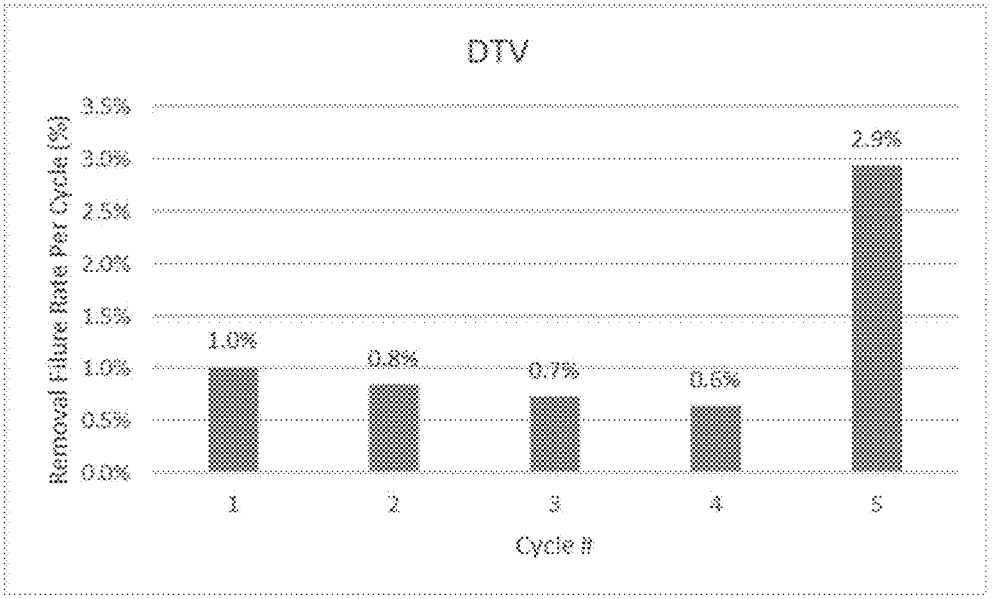
Figure 17C:
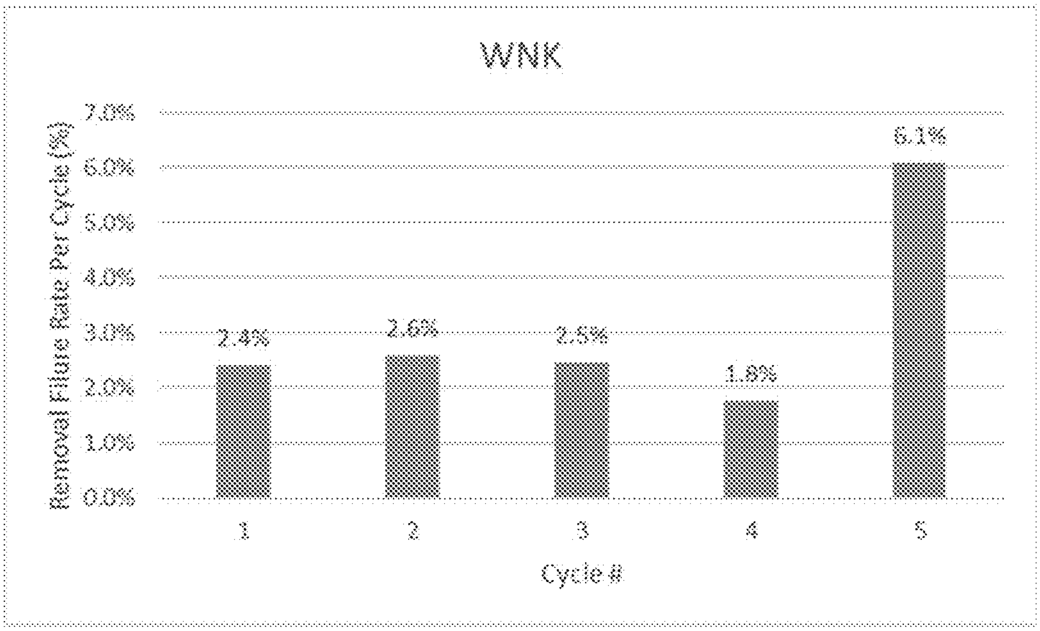
Figure 17D:
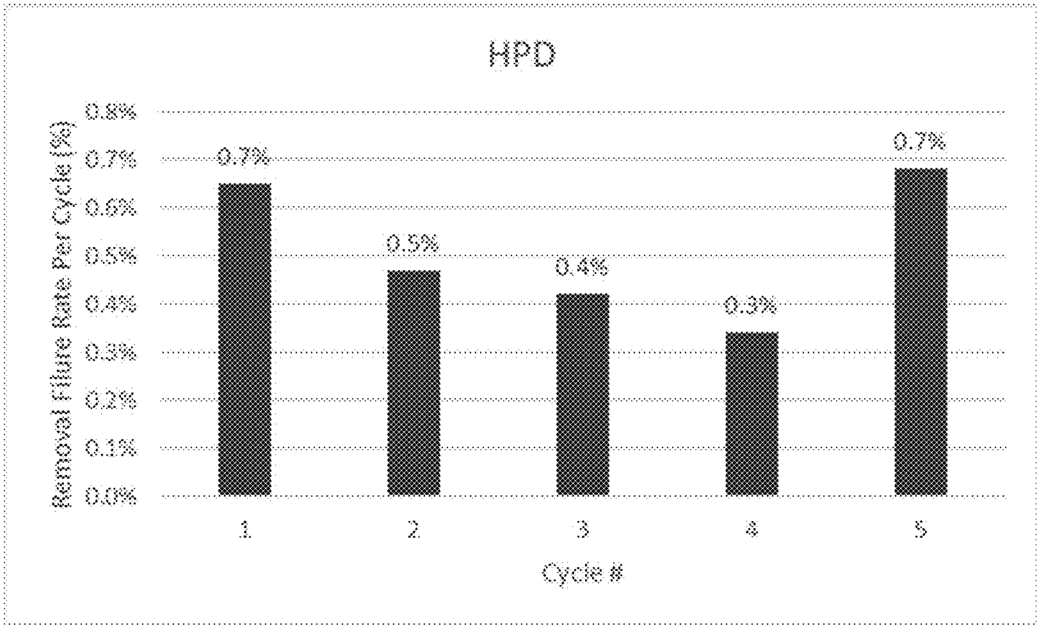
Figure 17E:
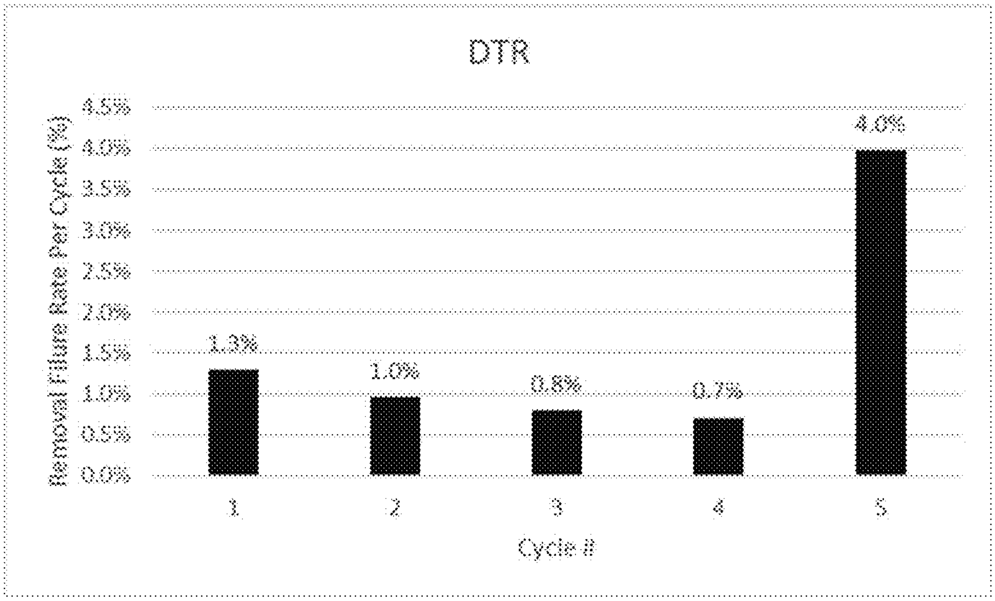
Figure 17F:
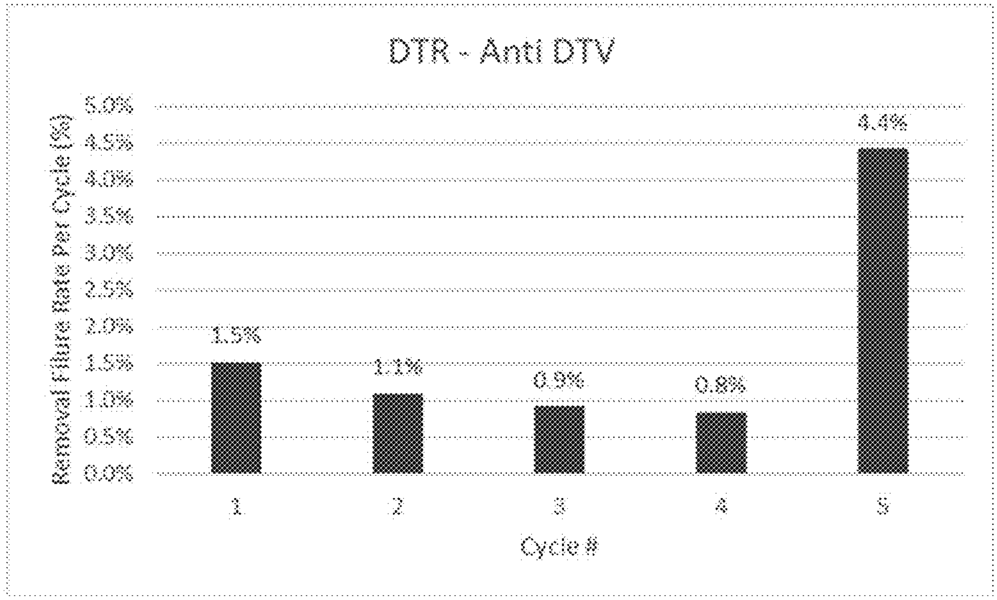

FIG. 16 displays orthogonal binding fractions for DTR peptide arrays contacted with anti-DTR affinity reagents. Orthogonal binding fractions were observed to be less than 1% for each tested binding reagent association medium. Inhibition of orthogonal binding was found to be similar for each tested binding reagent association medium. Incorporated oligonucleotides inhibited orthogonal binding nearly as well as SSSDNA. A combination of SSSDNA and oligonucleotides had lower levels of orthogonal binding than SSSDNA or oligonucleotides alone.

Example 5. Photo-initiated Binding Reagent Dissociation Failure

Association and dissociation of binding reagents to polypeptide targets on patterned arrays was observed over multiple cycles to assess the impact of light exposure on binding reagent dissociation fraction. Each array was tested over 5 cycles of binding reagent association, post-association binding reagent fluorescent imaging, binding reagent dissociation, and post-dissociation binding reagent fluorescent imaging. Fluorescence was induced by exposure to 647 nm laser light on cycles 1 through 4. During cycle 5, fluorescence was induced by exposure to 488 nm and 647 nm laser light. During and after each cycle, fluorescence was measured at each array site to identify sites that had experienced a binding reagent dissociation failure event. For all tested conditions, the detection medium did not contain any species intended to prevent photodamage.

6 arrays were prepared by the method set forth in U.S. Pat. No. 11,505,796B2, herein incorporated by reference in its entirety. Briefly, patterned arrays were formed on silicon substrates by nanolithography. Array sites were provided with an approximately 1 μm pitch. Each array site was functionalized with a plurality of oligonucleotides. Peptides were covalently attached to nucleic acid nanoparticles. Nucleic acid nanoparticles were labeled with Alexa-Fluor 488 fluorescent labels (488 nm excitation wavelength, 505 nm emission wavelength). Pools of five peptide targets attached to nucleic acid nanoparticles were prepared: 1) HSP, 2) DTV, and 3) WNK, 4) HPD, 5) DTR, and 6) DTR. Each nucleic acid nanoparticle contained a plurality of pendant oligonucleotides that were complementary to the oligonucleotides attached to each array site. Peptide-conjugated nucleic acid nanoparticles were deposited on the arrays at a concentration of 150 pM. 1 array was prepared for each peptide target, except DTR, of which 2 arrays were prepared.

Arrays were contacted with multivalent affinity reagents to assess fractions of sites experiencing affinity reagent dissociation failure (i.e., unintended signal at an array site due to failure to dissociate an affinity reagent from the array site). Multivalent affinity agents are described in U.S. Patent Publication No. 20220162684, which is herein incorporated by reference in its entirety. Multivalent affinity reagents were labeled with Alexa-Fluor 647 fluorescent labels (647 nm excitation wavelength, 680 nm emission wavelength). Each array was contacted with a pool of multivalent affinity reagents that possessed a binding specificity for the peptide targets of the array (e.g., WNK contacted with an anti-WNK antibody), except one DTR array which was contacted with anti-DTV affinity reagents (i.e., no expected binding to peptide targets). The concentration of affinity reagents contacted to each array was 10 nM.

After incubating arrays with multivalent affinity reagents, arrays were imaged by confocal laser scanning microscopy. During cycles 1-4, arrays were only illuminated with 647 nm light (excitation of fluorescently labeled affinity reagents only). During cycle 5, arrays were illuminated with 647 nm and 488 nm light (excitation of fluorescently labeled affinity reagents and fluorescently labeled nucleic acid nanoparticles, respectively). During illumination, arrays were contacted with a detection medium comprising 120 mM sodium chloride, 5 mM potassium chloride, 10 mM magnesium chloride, 0.1 wt % Tween-20, 0.5 wt % proclin and 50 mM HEPES buffer pH 7.5. The detection medium did not comprise a chemical species configured to inhibit sources of photodamage (e.g., radical scavengers, reactive oxygen species scavengers, antioxidants, etc.). After imaging, arrays were contacted with a binding reagent dissociation medium comprising 100 mM CHAPS in deionized water. After dissociation of binding reagents, arrays were illuminated with 647 nm light and imaged. Images collected after binding reagent association and binding reagent dissociation were compared to identify array sites containing fluorescent signals after binding reagent association (i.e., presumed binding of affinity reagents to peptide targets) and array sites containing fluorescent signals after binding reagent dissociation (i.e., presumed binding reagent dissociation failure). Binding reagent dissociation failure fractions were calculated as the quantity of fluorescent signals observed at array sites after binding reagent dissociation divided by the quantity of fluorescent signals observed at array sites after binding reagent association.

FIGS. 17A-17F display determined fractions of binding reagent dissociation failure for each cycle for [HSP/Anti-HSP], [DTV/Anti-DTV], [WNK/Anti-WNK], [HPD/Anti-HPD], [DTR/Anti-DTR], and [DTR/Anti-DTV], respectively. The failure fraction values shown represent increase over the prior cycle, e.g., if the failure fraction of cycle 1 was 1% and the failure fraction of cycle 2 was 1%, then a total of 2% of observed array sites had experienced binding reagent dissociation failure after cycle 2. For each tested affinity reagent, the fraction of array sites experiencing binding reagent failure was shown to significantly increase when the array was illuminated by 488 nm light (cycle 5).

Example 6. Antioxidant-Mediated Binding Reagent Dissociation Failure

Association and dissociation of binding reagents to polypeptide targets on patterned arrays was observed over multiple cycles to assess the impact of light exposure on binding reagent dissociation fraction in the presence of an antioxidant. Each array was tested over 6 cycles of binding reagent association, post-association binding reagent fluorescent imaging, binding reagent dissociation, and post-dissociation binding reagent fluorescent imaging. Fluorescence was induced by exposure to 647 nm laser light on cycles 1 through 4. During cycles 5 and 6, fluorescence was induced by exposure to 488 nm and 647 nm laser light. During and after each cycle, fluorescence was measured at each array site to identify sites that had experienced a binding reagent dissociation failure event. 7 different detection media were tested. Each detection medium comprised 120 mM sodium chloride, 5 mM potassium chloride, 10 mM magnesium chloride, 0.1 wt % Tween-20, 0.5 wt % proclin and 50 mM HEPES buffer pH 7.5 with an antioxidant additive selected from: 1) 2 mM L-ascorbic acid, 2) 1 mM 9,10-anthracenediyl-bis(methylene)dimalonic acid (ABDA), 3) 1.5 mM N-acetyl-L-cysteine, 4) 0.01 mM (−)-epigallocatechin gallate, 5) 1 mM caffeic acid, 6) 0.5 mM resveratrol and 0.5 wt % ethanol, and 7) 1 mM 4-hydroxy-TEMPO.

For each tested detection medium, 3 arrays were prepared by the method set forth in U.S. Pat. No. 11,505,796B2, herein incorporated by reference in its entirety. Briefly, patterned arrays were formed on silicon substrates by nanolithography. Array sites were provided with an approximately 1 μm pitch. Each array site was functionalized with a plurality of oligonucleotides. Peptides were covalently attached to nucleic acid nanoparticles. Nucleic acid nanoparticles were labeled with Alexa-Fluor 488 fluorescent labels (488 nm excitation wavelength, 505 nm emission wavelength). Pools of three peptide targets attached to nucleic acid nanoparticles were prepared: 1) DTR, 2) HSP, and 3) HHH. Each nucleic acid nanoparticle contained a plurality of pendant oligonucleotides that were complementary to the oligonucleotides attached to each array site. Peptide-conjugated nucleic acid nanoparticles were deposited on the arrays at a concentration of 150 pM. For each tested detection medium, 1 array was prepared for each peptide target.

Arrays were contacted with multivalent affinity reagents to assess fractions of sites experiencing affinity reagent dissociation failure (i.e., unintended signal at an array site due to failure to dissociate an affinity reagent from the array site). Multivalent affinity agents are described in U.S. Patent Publication No. 20220162684, which is herein incorporated by reference in its entirety. Multivalent affinity reagents were labeled with Alexa-Fluor 647 fluorescent labels (647 nm excitation wavelength, 680 nm emission wavelength). Each array was contacted with a pool of multivalent affinity reagents that possessed a binding specificity for the peptide targets of the array (e.g., HSP contacted with an anti-HSP antibody, HHH contacted with B1 aptamer, etc.). The concentration of affinity reagents contacted to each array was 10 nM.

After incubating arrays with multivalent affinity reagents, arrays were imaged by confocal laser scanning microscopy. During cycles 1-4, arrays were only illuminated with 647 nm light (excitation of fluorescently labeled affinity reagents only). During cycles 5 and 6, arrays were illuminated with 647 nm and 488 nm light (excitation of fluorescently labeled affinity reagents and fluorescently labeled nucleic acid nanoparticles, respectively). During illumination, 1 array per target peptide were contacted with a detection medium comprising one of the aforementioned detection media. After imaging, arrays were contacted with a binding reagent dissociation medium comprising 100 mM CHAPS in deionized water. After dissociation of binding reagents, arrays were illuminated with 647 nm light and imaged. Images collected after binding reagent association and binding reagent dissociation were compared to identify array sites containing fluorescent signals after binding reagent association (i.e., presumed binding of affinity reagents to peptide targets) and array sites containing fluorescent signals after binding reagent dissociation (i.e., presumed binding reagent dissociation failure). Binding reagent dissociation failure fractions were calculated as the quantity of fluorescent signals observed at array sites after binding reagent dissociation divided by the quantity of fluorescent signals observed at array sites after binding reagent association.

Figure 18A:
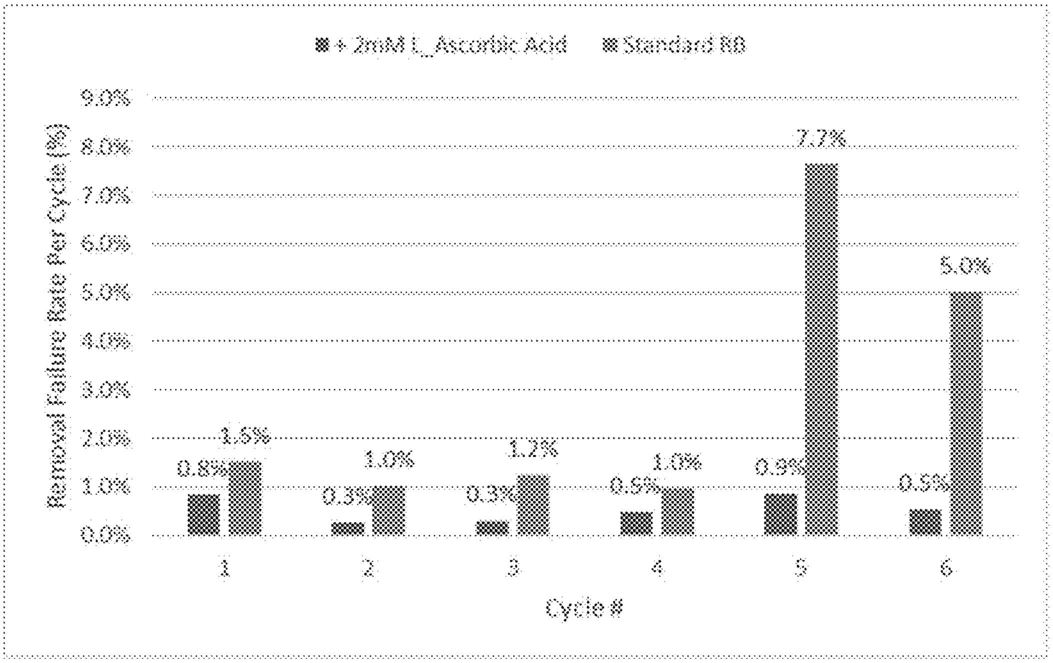
FIGS. 18A, 18B, 18C, 18D, 18E, 18F, 18G, 18H, 18I, 18J, 18K, 18L, 18M, 18N, 18O, 18P, 18Q, 18R, and 18S show binding reagent dissociation failure rate in the presence of various antioxidant species during cycles of exposure to 647 nm light or 488 nm light.
Figure 18B:
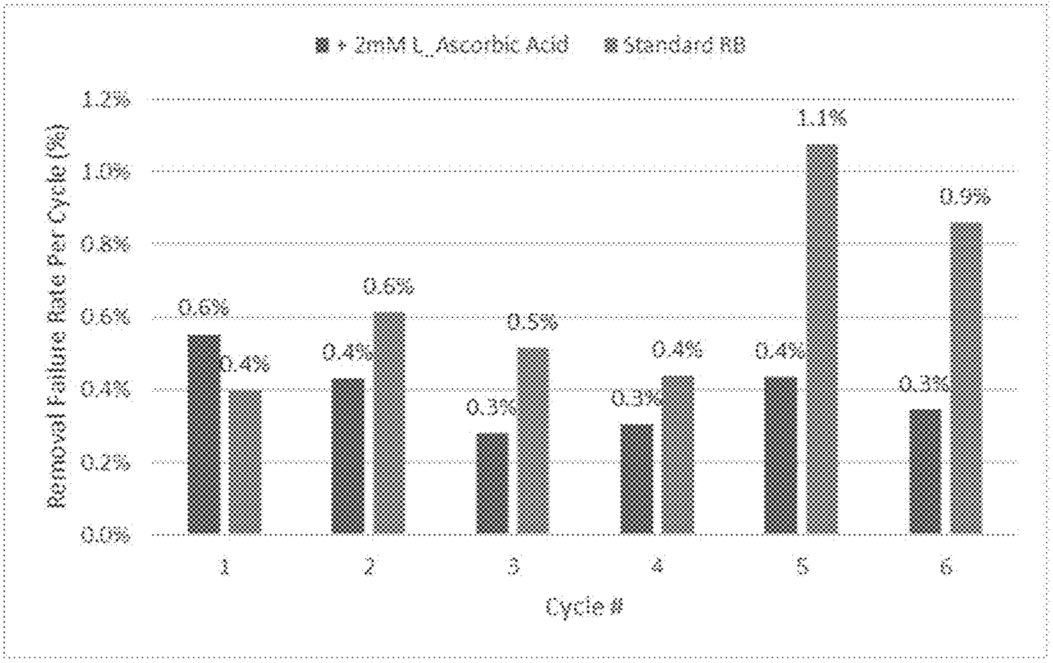
Figure 18C:
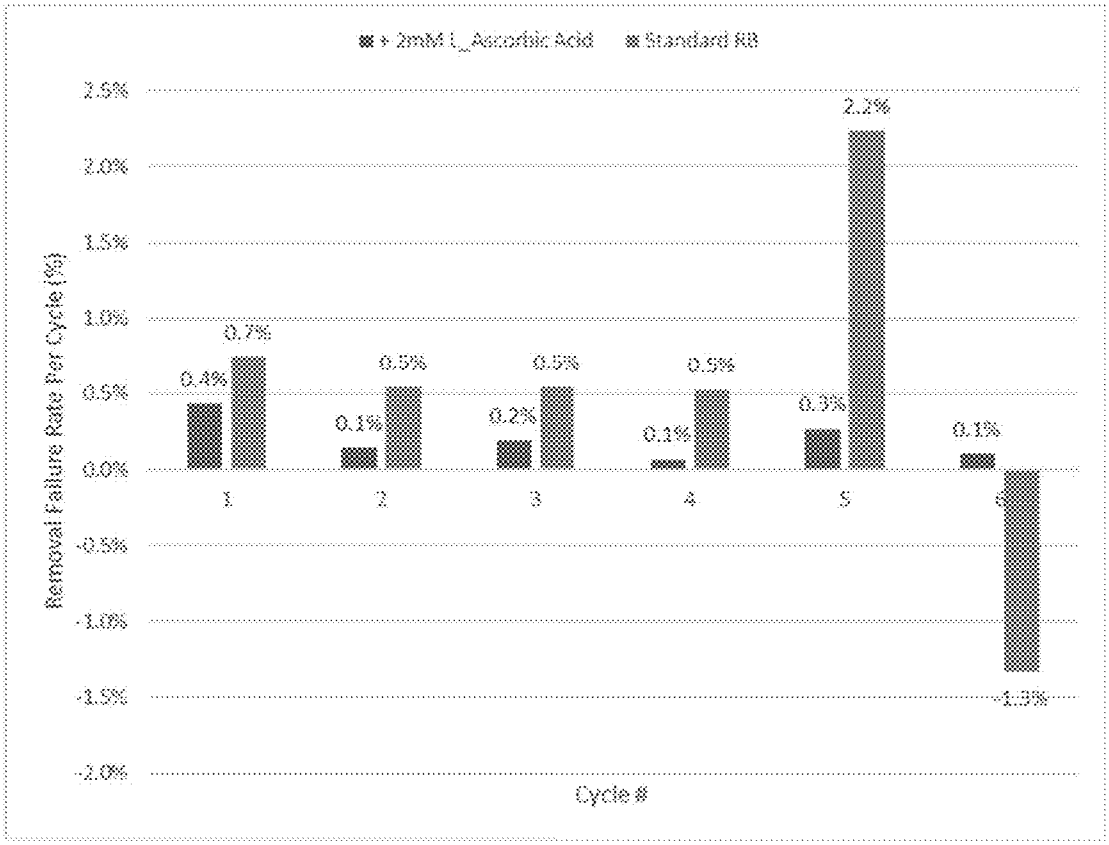
Figure 18D:
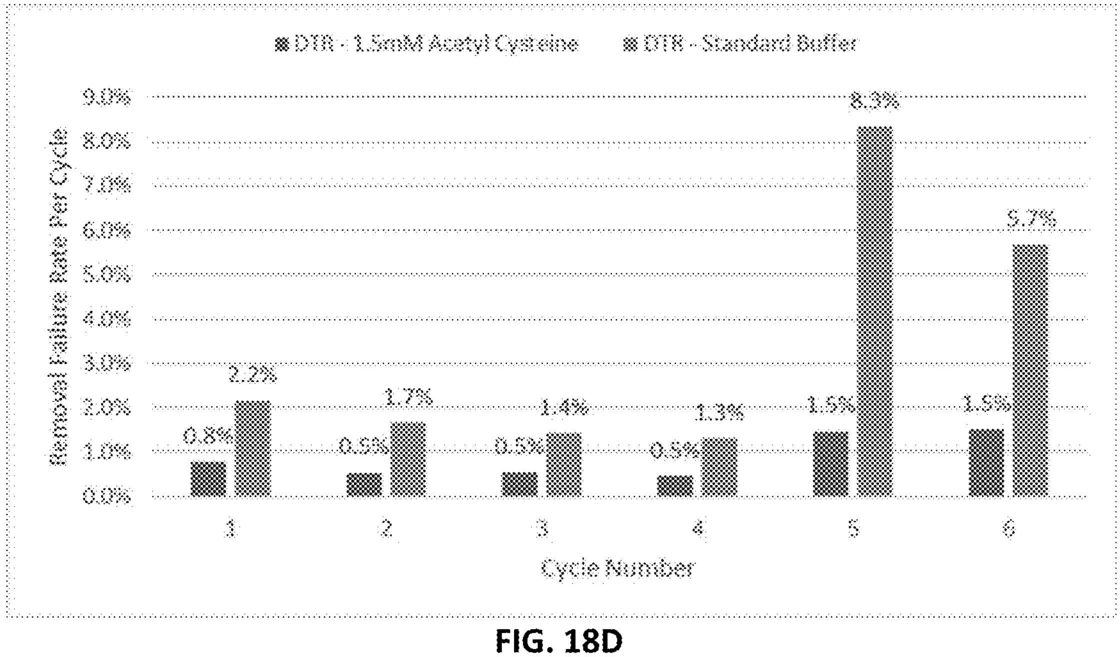
Figure 18E:
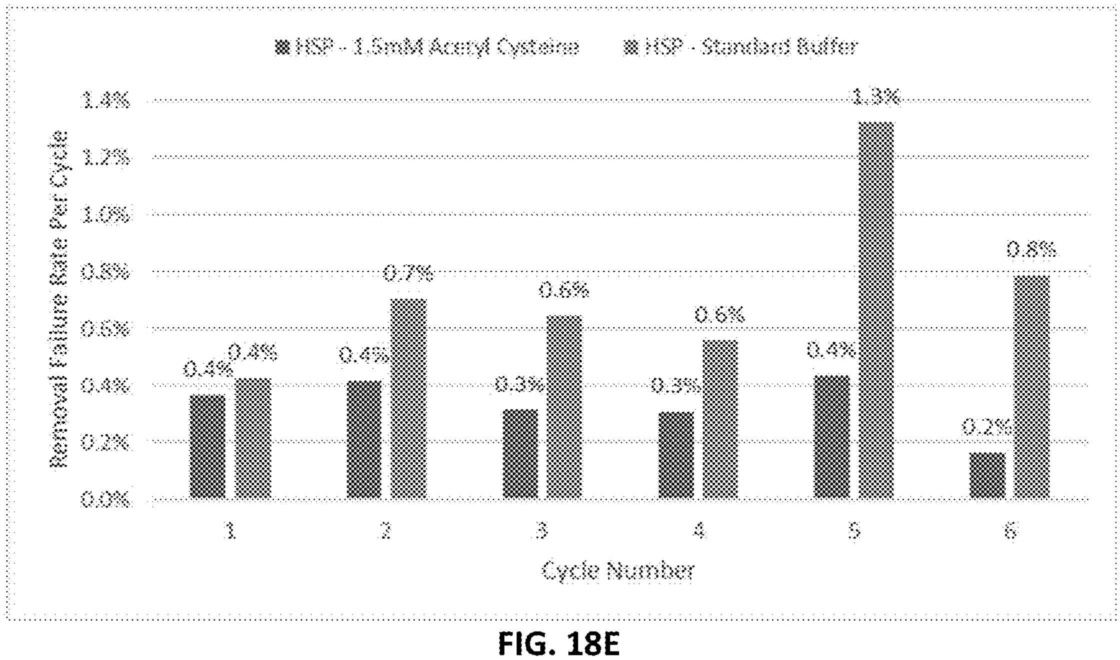
Figure 18F:
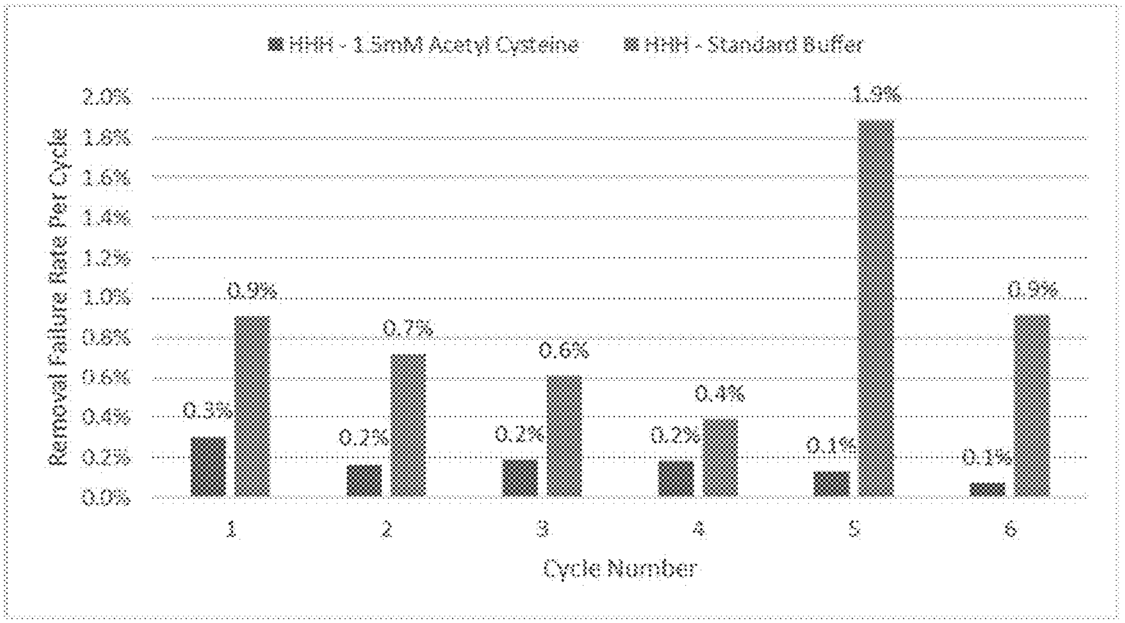
Figure 18G:
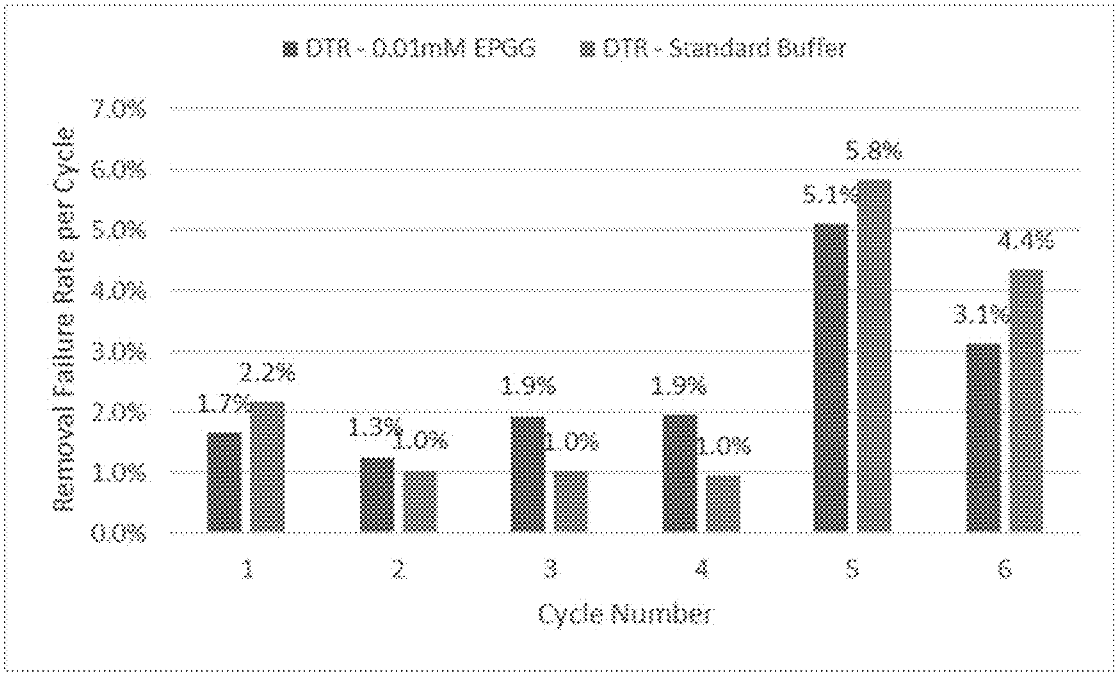
Figure 18H:
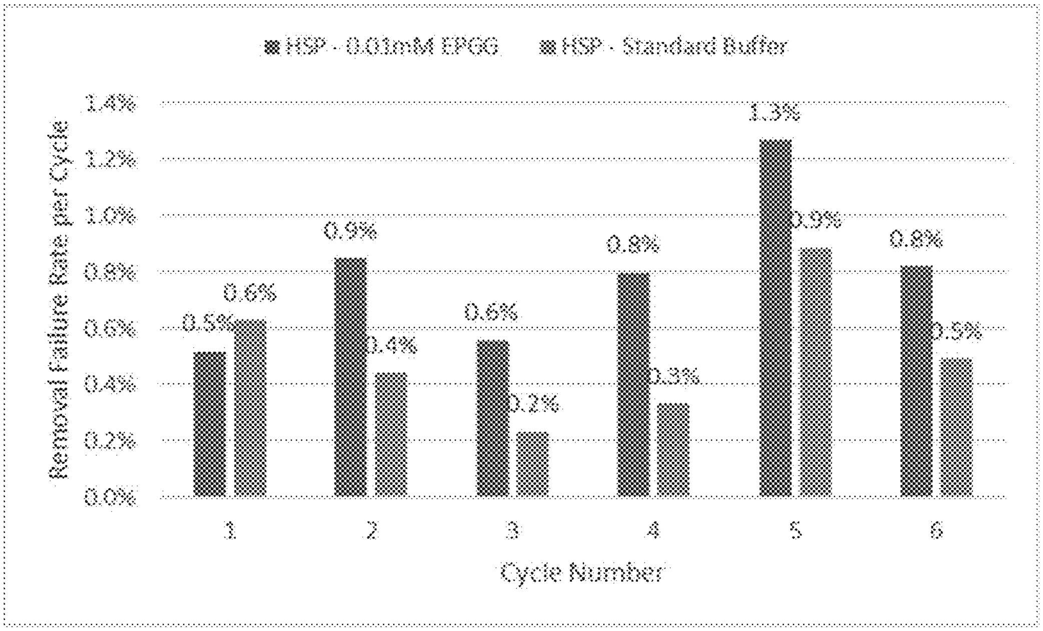
Figure 18I:
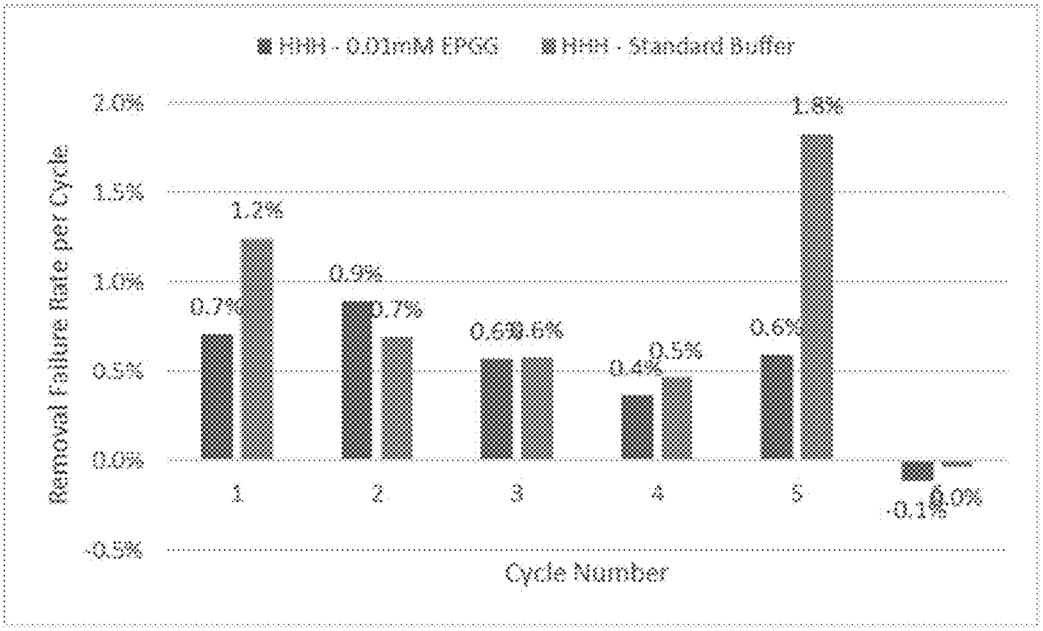
Figure 18J:
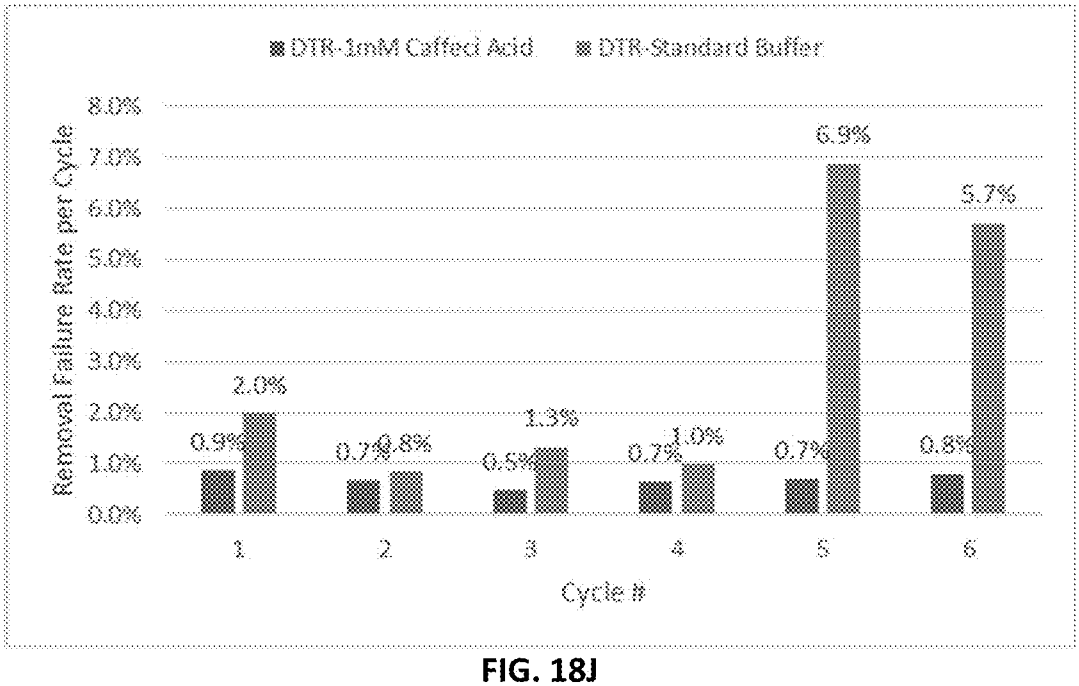
Figure 18K:
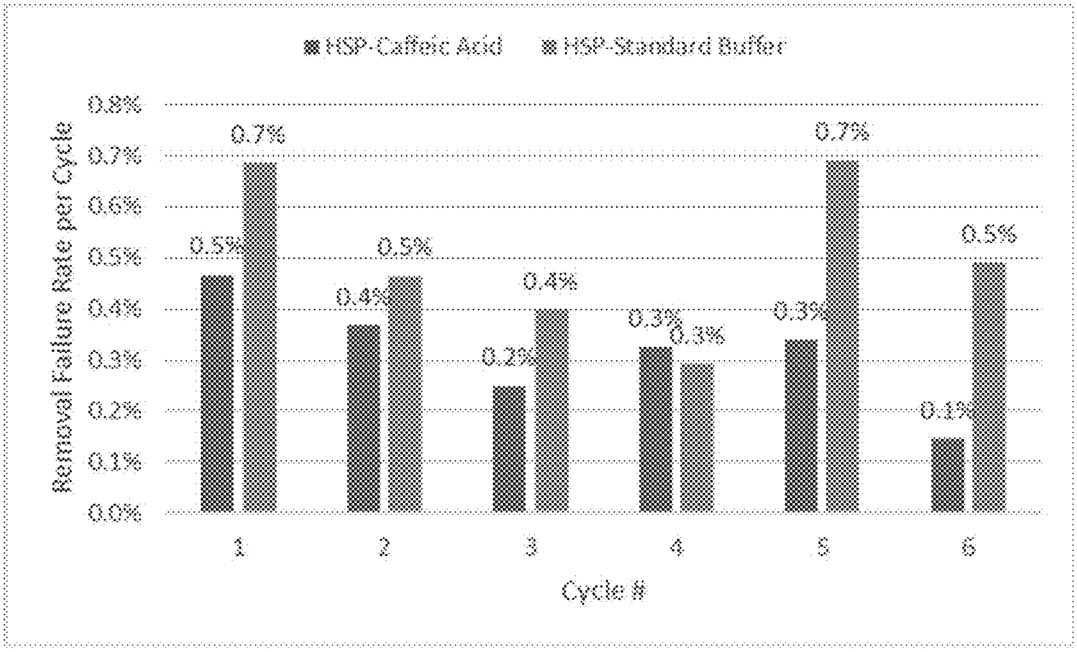
Figure 18L:
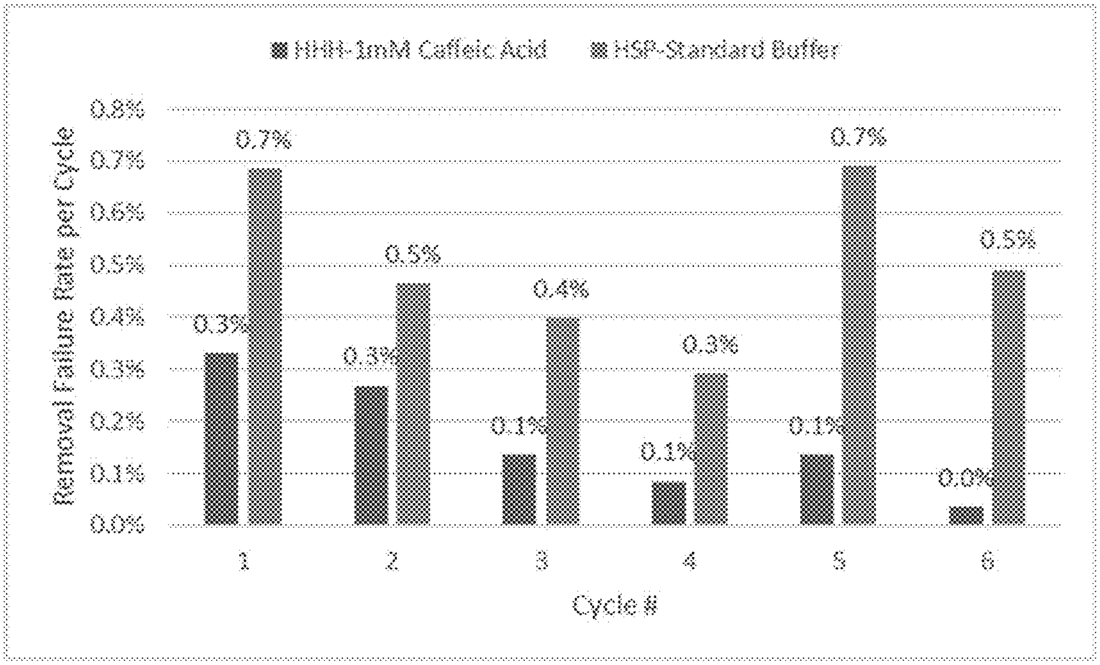
Figure 18M:
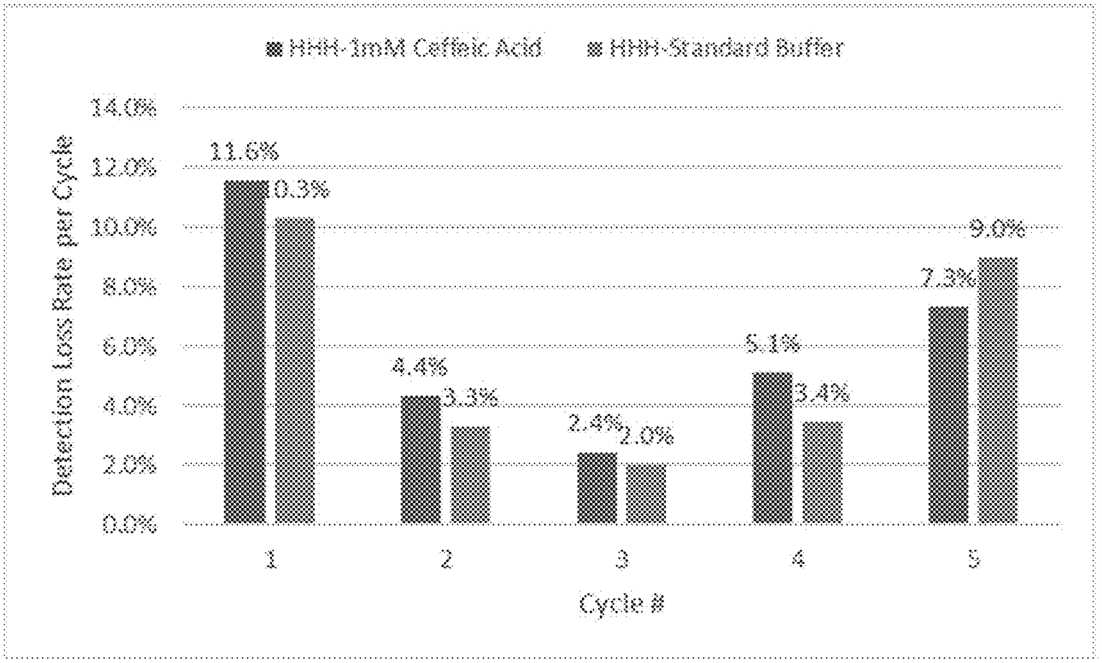
Figure 18N:
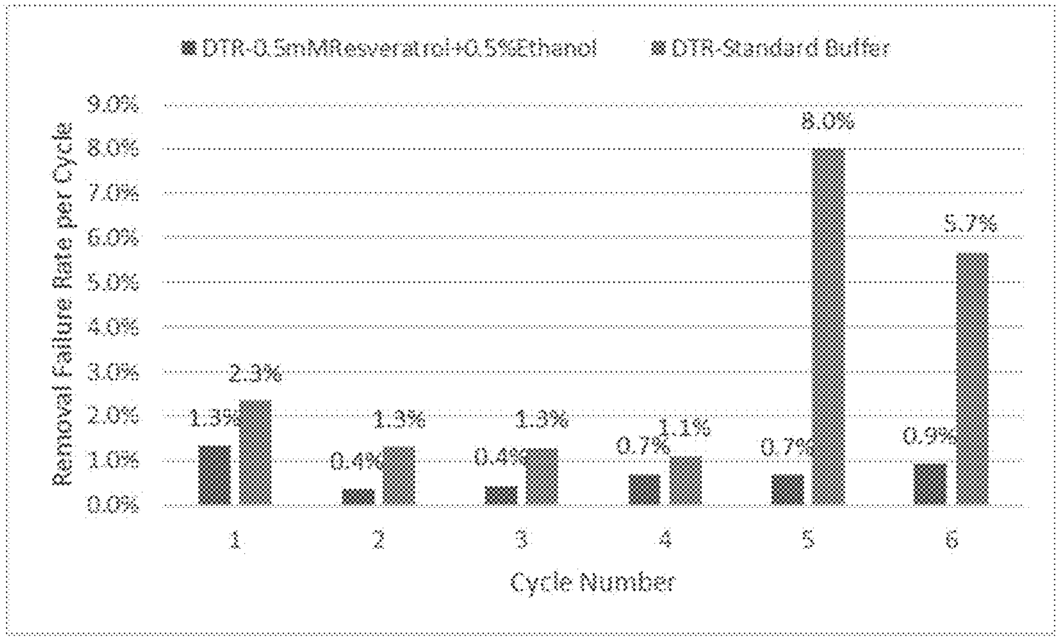
Figure 18O:
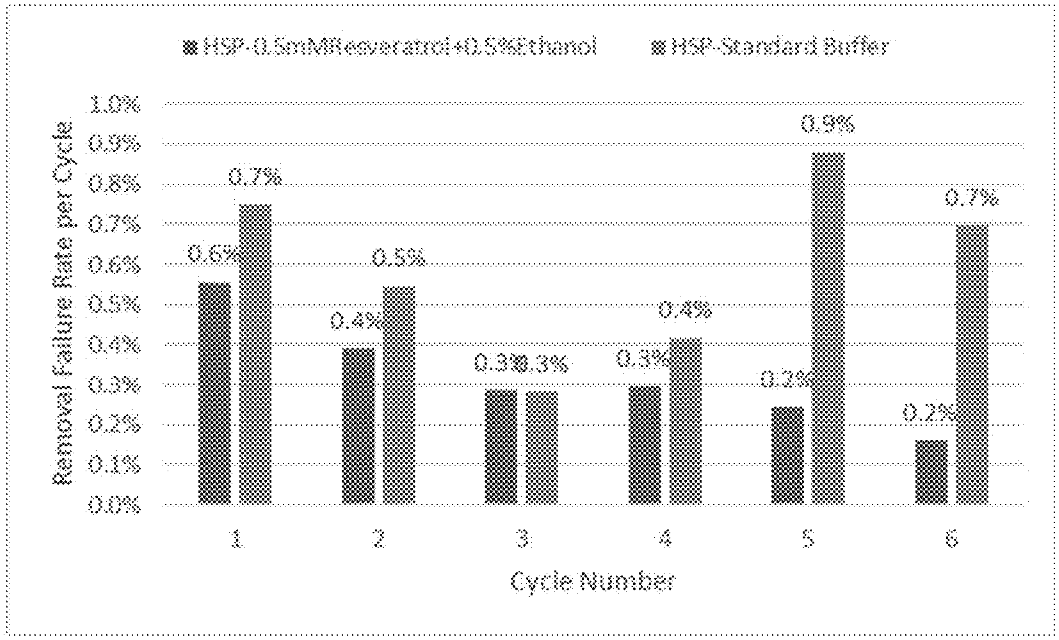
Figure 18P:
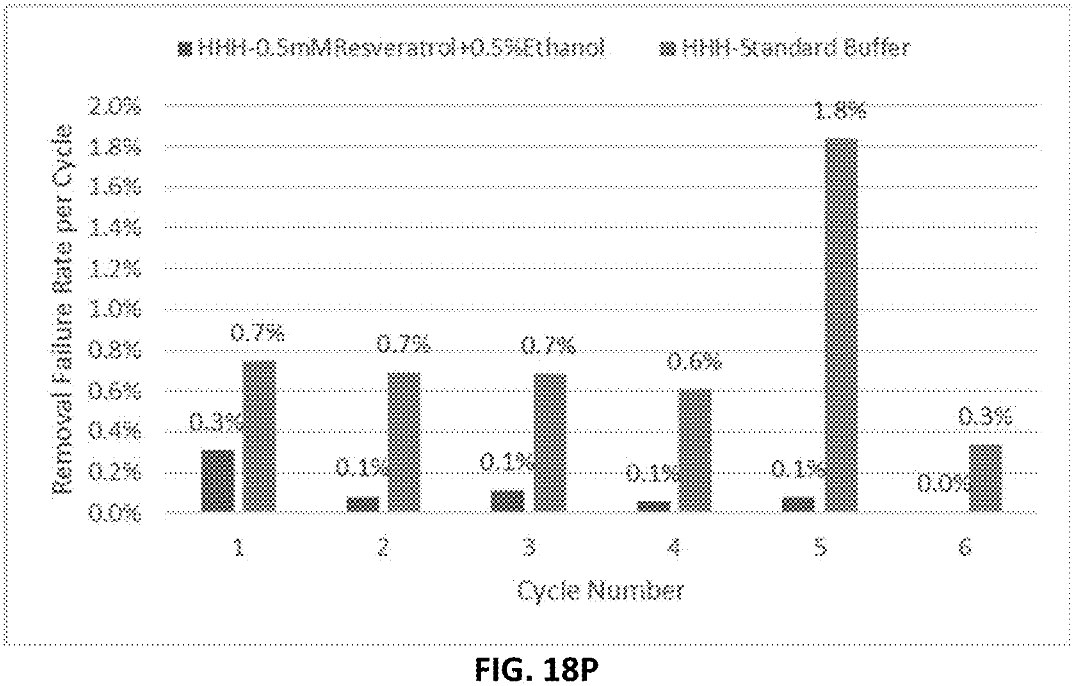
Figure 18Q:
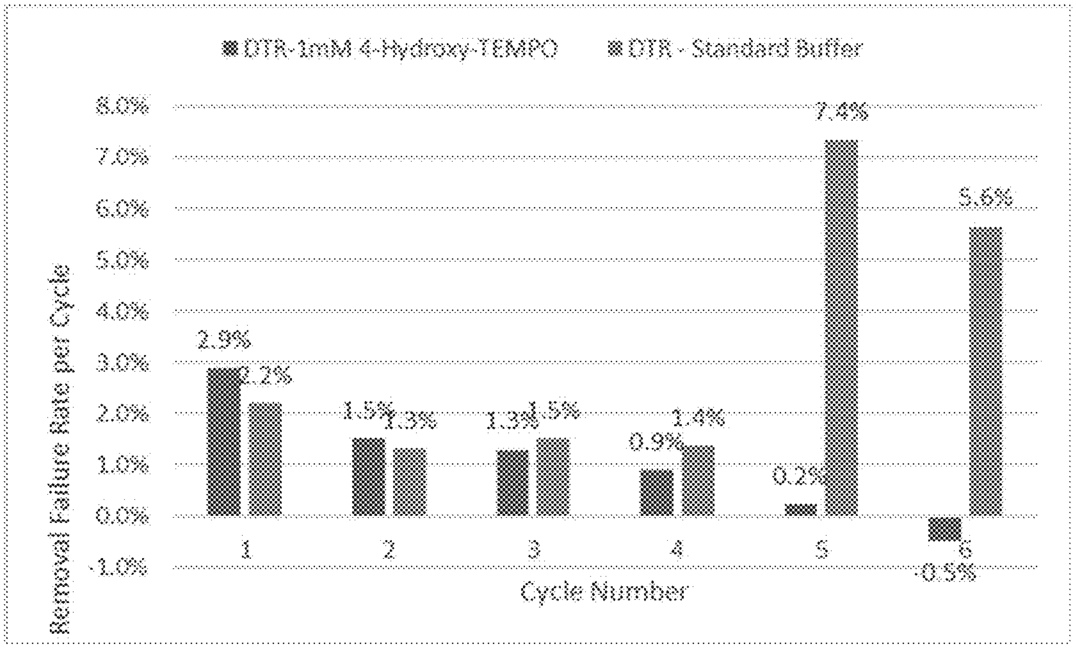
Figure 18R:
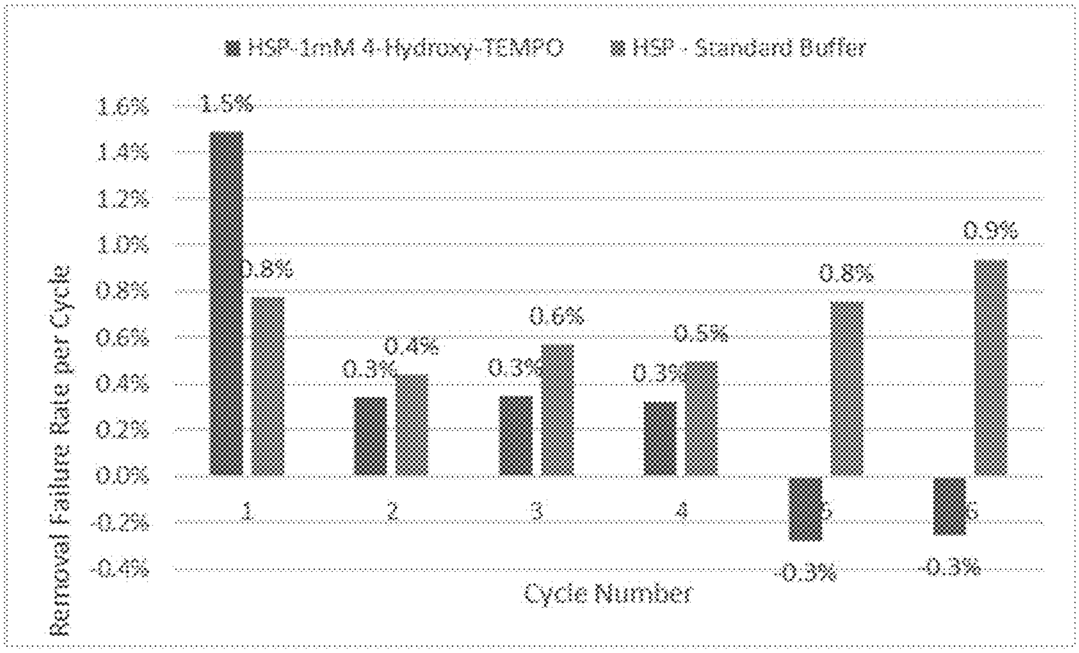
Figure 18S:
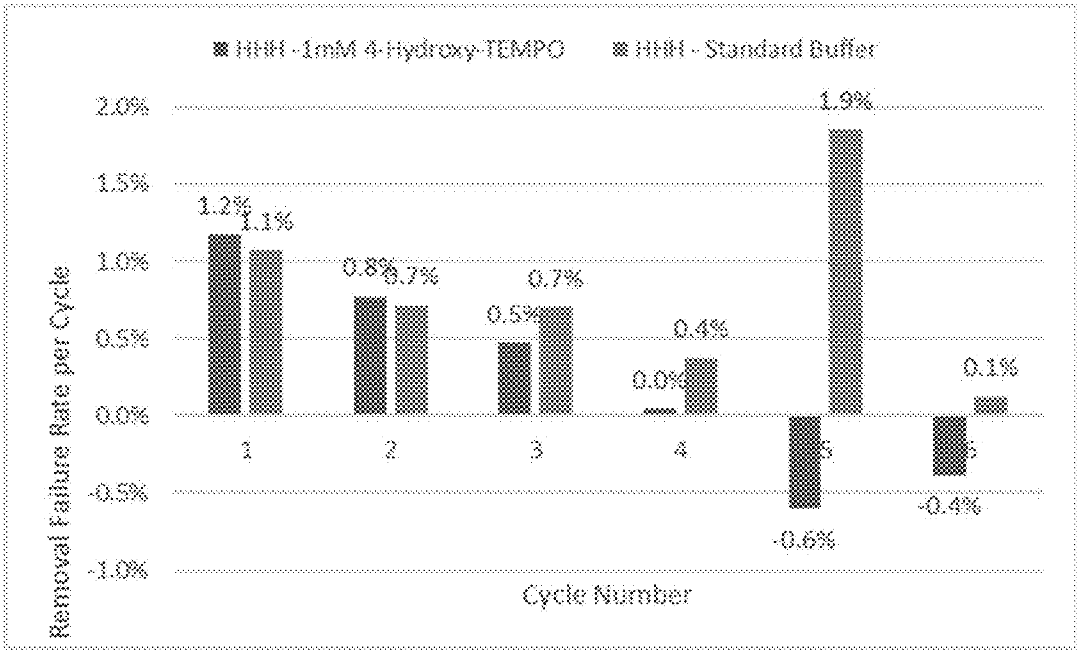

FIGS. 18A-18R display binding reagent dissociation failure fractions for each tested detection medium containing an antioxidant or photodamage inhibitor. Table V lists figure numbers associated with each tested condition.

TABLE V

Data Figures for Various Test Conditions

| | Peptide Target | | |
|---|---|---|---|
| Antioxidant | DTR | HSP | HHH |
| L-ascorbic acid | FIG. 18A | FIG. 18B | FIG. 18C |
| ABDA | N/A | N/A | N/A |
| N-acetyl-L-cysteine | FIG. 18D | FIG. 18E | FIG. 18F |
| Epigallocatechin gallate | FIG. 18G | FIG. 18H | FIG. 18I |

TABLE V-continued

Data Figures for Various Test Conditions

| Antioxidant | Peptide Target DTR | HSP | HHH |
|---|---|---|---|
| Caffeic acid | FIG. 18J | FIG. 18K | FIG. 18L |
| Resveratrol | FIG. 18M | FIG. 18N | FIG. 18O |
| 4-hydroxy-TEMPO | FIG. 18P | FIG. 18Q | FIG. 18R |

As noted in Table V, binding reagent dissociation failure fraction was not calculated for detection media comprising ABDA. Such media were observed to produce a high fluorescent background signal that made identification of fluorescent signals at array sites difficult.

For binding of anti-DTR antibody binding reagents to DTR peptide targets, L-ascorbic acid, N-acetyl-L-cysteine, caffeic acid, and resveratrol decreased the per cycle binding reagent dissociation failure fraction for illumination with 647 nm light and 488 nm light. 4-hydroxy-TEMPO was observed to decrease the per cycle binding reagent dissociation failure fraction for illumination with 488 nm light, but was less effective at decreasing the per cycle binding reagent dissociation failure fraction for illumination with 647 nm. Epigallocatechin gallate was less effective at decreasing the per cycle binding reagent dissociation failure fraction for illumination with 647 nm light and 488 nm light.

For binding of anti-HSP antibody binding reagents to HSP peptide targets, N-acetyl-L-cysteine, was observed to decrease the per cycle binding reagent dissociation failure fraction for illumination with 647 nm light and 488 nm light. L-ascorbic acid, caffeic acid, resveratrol, and 4-hydroxy-TEMPO were observed to decrease the per cycle binding reagent dissociation failure fraction for illumination with 488 nm light, but were less effective at decreasing the per cycle binding reagent dissociation failure fraction for illumination with 647 nm. Epigallocatechin gallate was less effective at decreasing the per cycle binding reagent dissociation failure fraction for illumination with 647 nm light and 488 nm light.

For binding of B1 aptamer binding reagents to HHH peptide targets, L-ascorbic acid, N-acetyl-L-cysteine, and resveratrol decreased the per cycle binding reagent dissociation failure fraction for illumination with 647 nm light and 488 nm light. 4-hydroxy-TEMPO was observed to decrease the per cycle binding reagent dissociation failure fraction for illumination with 488 nm light, but was less effective at decreasing the per cycle binding reagent dissociation failure fraction for illumination with 647 nm. Epigallocatechin gallate and caffeic acid were less effective at decreasing the per cycle binding reagent dissociation failure fraction for illumination with 647 nm light and 488 nm light.

Example 7. Binding Reagent Dissociation from Peptide Targets

Various surfactants were compared to assess their effectiveness for removal of binding reagents from peptide targets. Tested surfactants included a zwitterionic surfactant (3-[(3-cholamidopropyl)dimethylammonio]-1-propanesulfonate (CHAPS)), nonionic surfactants (Tween-20 and Triton-X), and an anionic surfactant (sodium dodecyl sulfate (SDS)). Antibody-containing, fluorescently-labeled binding reagents were bound to peptide targets an a single-analyte peptide array, then removed by contact of the antibody-target complex with a dissociation medium comprising one of the surfactants. The process of binding reagent association and dissociation was repeated four times for a total of five dissociation cycles. Measurement of quantity of array sites containing fluorescent signals before and after contacting the dissociation medium provided a measure of dissociation efficiency.

6 arrays were prepared by the method set forth in U.S. Pat. No. 11,505,796B2, herein incorporated by reference in its entirety. Briefly, patterned arrays were formed on silicon substrates by nanolithography. Array sites were provided with an approximately 1 μm pitch. Each array site was functionalized with a plurality of oligonucleotides. Peptides with an amino acid sequence of DTR were covalently attached to nucleic acid nanoparticles. Each nucleic acid nanoparticle contained a plurality of pendant oligonucleotides that were complementary to the oligonucleotides attached to each array site. Peptide-conjugated nucleic acid nanoparticles were deposited on the arrays at a concentration of 150 pM.

Arrays were contacted with multivalent affinity reagents to assess fractions of sites experiencing association and dissociation of the multivalent affinity reagents. Multivalent affinity agents are described in U.S. Pat. No. 11,692,217, which is herein incorporated by reference in its entirety. Each array was contacted with a pool of multivalent affinity reagents that possessed a binding specificity for the DTR peptide targets of the array. The concentration of affinity reagents was 10 nM. The binding reagent association medium comprised 120 mM sodium chloride, 5 mM potassium chloride, 10 mM magnesium chloride, 0.1 wt % Tween-20, 0.5 wt % proclin and 50 mM HEPES buffer pH 7.5, 1 wt % bovine serum albumin (BSA), and 1 mg/ml sheared salmon sperm DNA (SSSDNA). Each multivalent affinity reagent comprised Alexa-Fluor 647 fluorescent labels.

After binding of the multivalent affinity reagents to the peptide targets on each individual array, the arrays were imaged at 680 nm by confocal laser scanning microscopy. Images were analyzed to identify the quantity of array sites with fluorescent signals, thereby indicating the quantity of peptide targets bound by fluorescent affinity reagents. Array images were also analyzed to identify quantity of unintended signals located at interstitial regions (i.e., unwanted binding events). The quantity of unintended signals was used to calculate a pre-dissociation unintended binding fraction. After imaging, each individual array was contacted with a binding reagent dissociation medium comprising one of: 1) 100 mM CHAPS, 2) 200 mM CHAPS, 3) 2 wt % Tween-20, 4) 10 wt % SDS, 5) 10 wt % SDS and 10 mM MgCl2, or 6) 5 wt % Triton-X100. Arrays were incubated with a binding reagent dissociation medium for 10 minutes. After dissociation, each individual array was imaged again at 680 nm to quantify the quantity of array sites with fluorescent signals, thereby indicating the quantity of binding reagents that did not dissociate from peptide targets on each array. Array images were also analyzed to identify quantity of unintended signals located at interstitial regions (i.e., unwanted binding events). The quantity of unintended signals was used to calculate a post-dissociation unintended binding fraction. The association/dissociation process was performed for a total of 5 cycles.

Figure 24A:
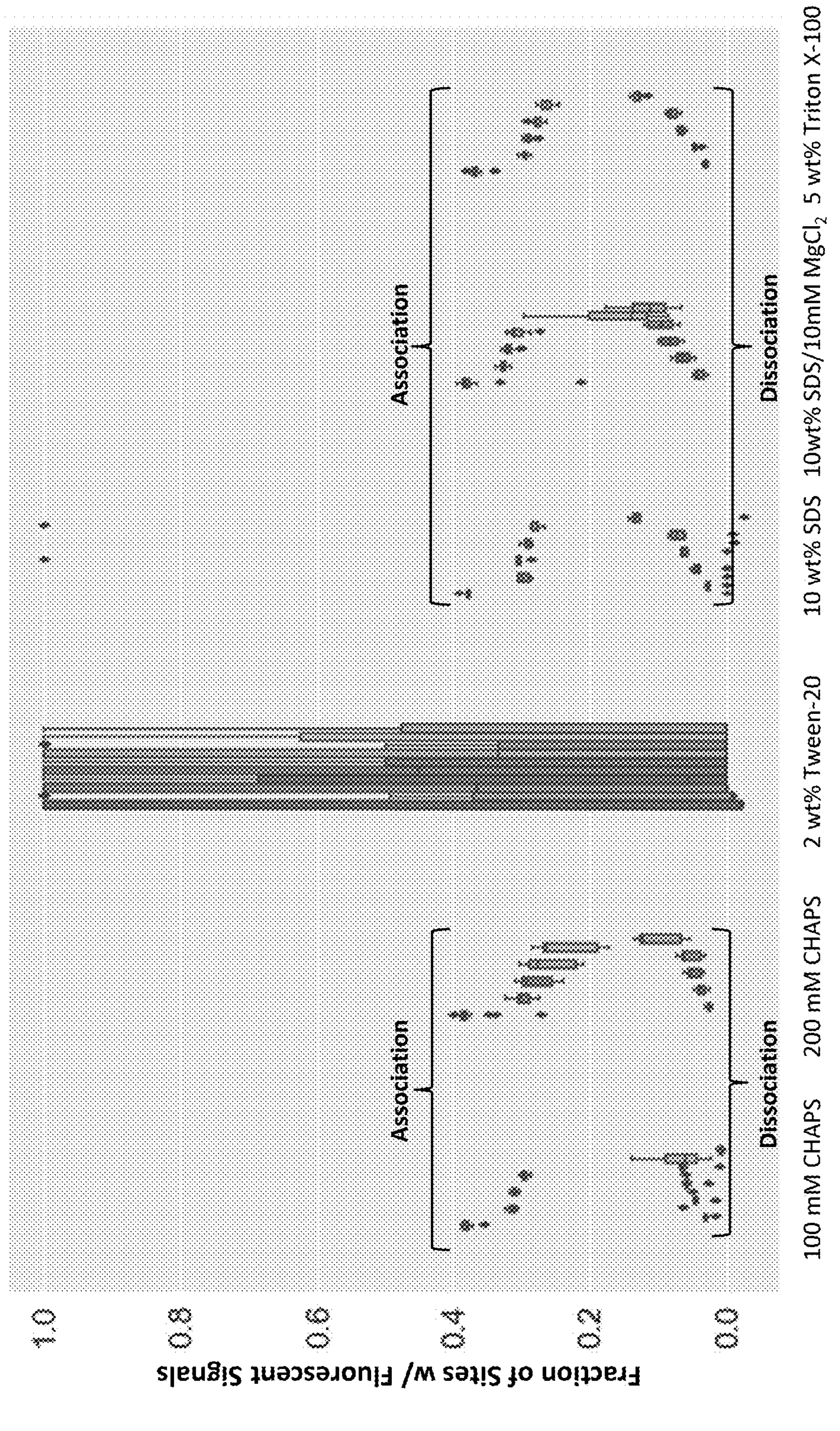
FIG. 24A depicts the binding reagent association rate and dissociation rate when various binding reagent dissociation media are utilized during the dissociation steps of a multi-cycle array-based process.
Figure 24B:
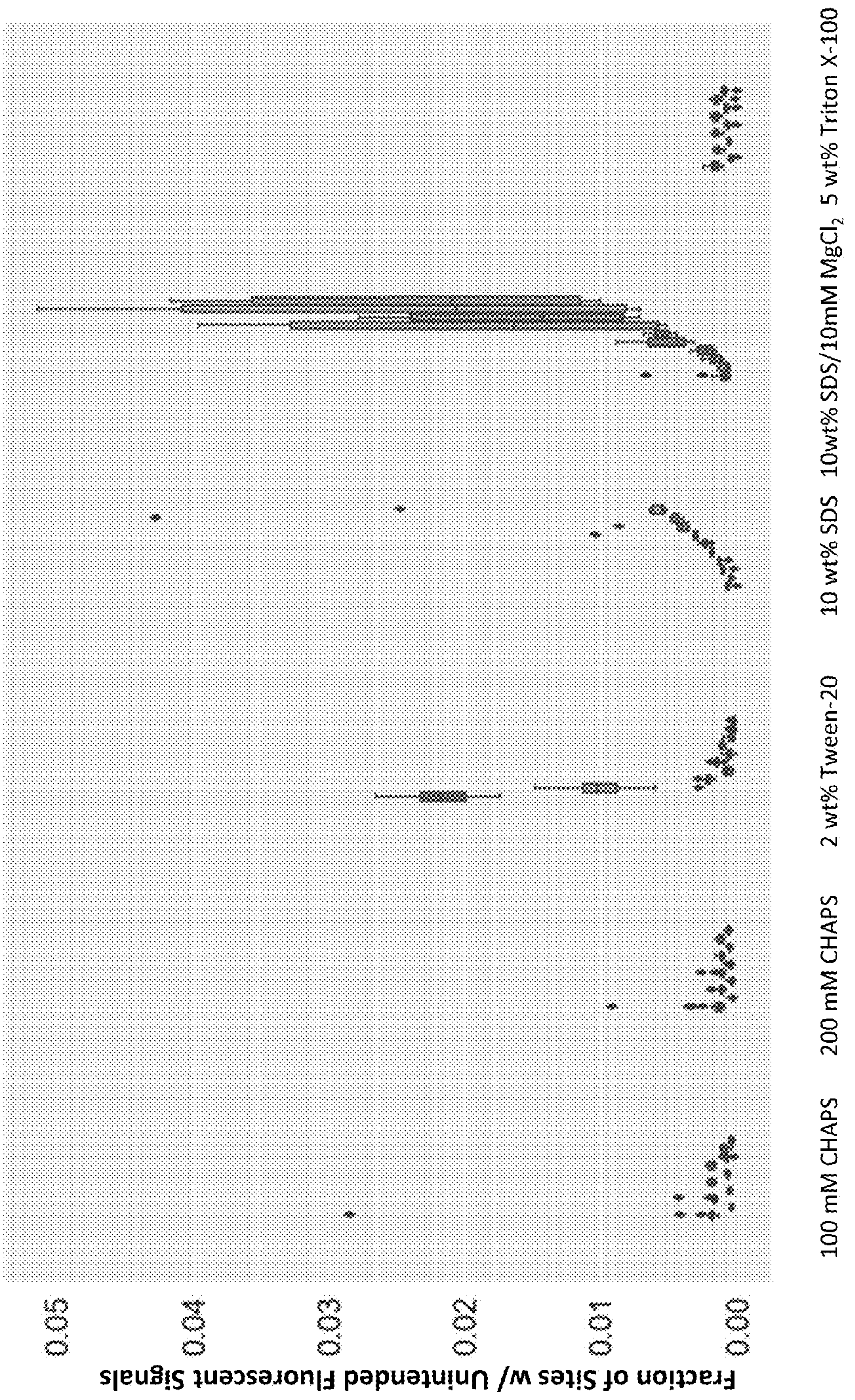
FIG. 24B depicts the binding reagent dissociation failure rate for binding reagents at interstitial regions during the assay cycles depicted in FIG. 24A.

FIG. 24A displays fluorescent signal detection data for each tested condition. For each cycle, higher violin plots represent fractions of array sites with fluorescent signals from affinity reagents before dissociation, and the lower violin plots represent fractions of array sites with fluorescent signals from affinity reagents after dissociation. Tween-20 was visually observed to cause dissociation of nucleic acid nanoparticles and associated peptide targets from array sites, thereby causing significant data variability. CHAPS, SDS, and Triton X-100 were observed to have similar dissociation efficiencies over the 5 cycles. FIG. 24B displays unintended fluorescent signal detection data for each tested condition. Binding reagent dissociation media containing SDS were observed to have higher amounts of unintended binding of binding reagents to array surfaces, with increasing amounts of unintended binding with each successive cycle of association/dissociation. Other binding reagents, such as CHAPS, Tween-20, and Triton X-100 were observed to cause lower amounts of unintended binding of binding reagents to array surfaces, with little change in the observed unintended binding fraction over successive cycles.

Notwithstanding the appended claims, the disclosure set forth herein is also defined by the following clauses:

1. A method, comprising:
   a) binding binding reagents to an array of polypeptides, wherein the array of polypeptides comprises a plurality of sites, wherein individual sites of the plurality of sites each comprises one and only one polypeptide, wherein the individual sites are optically resolvable at single-molecule resolution, wherein binding the binding reagents to the array occurs in the presence of a binding reagent association medium, and wherein the binding reagent association medium comprises a non-polypeptide blocking agent;
   b) before dissociating the binding reagents from the array in the presence of a binding reagent dissociation medium, detecting at the individual sites presence or absence of a signal, wherein the detecting occurs in the presence of a binding reagent detection medium, and wherein the binding reagent detection medium comprises a reaction inhibitor species; and
   c) after the detecting, dissociating the binding reagents from the array of polypeptides, wherein the binding reagent dissociation fraction is at least 95%.
2. A method, comprising:
   a) binding binding reagents to an array of polypeptides, wherein the array of polypeptides comprises a plurality of sites, wherein individual sites of the plurality of sites each comprises one and only one polypeptide, and wherein the individual sites are optically resolvable at single-molecule resolution;
   b) before dissociating the binding reagents from the array in the presence of a binding reagent dissociation medium, detecting at the individual sites presence or absence of a signal, wherein the detecting occurs in the presence of a binding reagent detection medium, and wherein the binding reagent detection medium comprises a reaction inhibitor species; and
   c) after the detecting, dissociating the binding reagents from the array of polypeptides, wherein dissociating the binding reagents from the array of polypeptides occurs in the presence of a binding reagent dissociation medium, and wherein the binding reagent dissociation fraction is at least 95%.
3. A method, comprising:
   a) binding binding reagents to an array of polypeptides, wherein the array of polypeptides comprises a plurality of sites, wherein individual sites of the plurality of sites each comprises one and only one polypeptide, wherein the individual sites are optically resolvable at single-molecule resolution, wherein binding the binding reagents to the array occurs in the presence of a binding reagent association medium, and wherein the binding reagent association medium comprises a non-polypeptide blocking agent;
   b) before dissociating the binding reagents from the array in the presence of a binding reagent dissociation medium, detecting at the individual sites presence or absence of a signal; and
   c) after the detecting, dissociating the binding reagents from the array of polypeptides, wherein dissociating the binding reagents from the array of polypeptides occurs in the presence of a binding reagent dissociation medium, and wherein the binding reagent dissociation fraction is at least 95%.
4. A method, comprising:
   a) binding binding reagents to an array of polypeptides, wherein the array of polypeptides comprises a plurality of sites, wherein individual sites of the plurality of sites each comprises one and only one polypeptide, wherein the individual sites are optically resolvable at single-molecule resolution, wherein binding the binding reagents to the array occurs in the presence of a binding reagent association medium, and wherein the binding reagent association medium comprises a non-polypeptide blocking agent;
   b) before dissociating the binding reagents from the array in the presence of a binding reagent dissociation medium, detecting at the individual sites presence or absence of a signal, wherein the detecting occurs in the presence of a binding reagent detection medium, and wherein the binding reagent detection medium comprises a reaction inhibitor species; and
   c) after the detecting, dissociating the binding reagents from the array of polypeptides, wherein dissociating the binding reagents from the array of polypeptides occurs in the presence of a binding reagent dissociation medium, and wherein the binding reagent dissociation fraction is at least 99%.
5. A method, comprising:
   a) binding binding reagents to an array of polypeptides, wherein the array of polypeptides comprises a plurality of sites, wherein individual sites of the plurality of sites each comprises one and only one polypeptide, wherein the individual sites are optically resolvable at single-molecule resolution, wherein binding the binding reagents to the array occurs in the presence of a binding reagent association medium, and wherein the binding reagent association medium comprises a non-polypeptide blocking agent;
   b) before dissociating the binding reagents from the array in the presence of a binding reagent dissociation medium, detecting at the individual sites presence or absence of a signal, wherein the detecting occurs in the presence of a binding reagent detection medium, and wherein the binding reagent detection medium comprises a reaction inhibitor species; and
   c) after the detecting, dissociating the binding reagents from the array of polypeptides, wherein the binding anomaly fraction is no more than 5%.
6. A method, comprising:
   a) binding binding reagents to an array of polypeptides, wherein the array of polypeptides comprises a plurality of sites, wherein individual sites of the plurality of sites each comprises one and only one polypeptide, and wherein the individual sites are optically resolvable at single-molecule resolution;

b) before dissociating the binding reagents from the array in the presence of a binding reagent dissociation medium, detecting at the individual sites presence or absence of a signal, wherein the detecting occurs in the presence of a binding reagent detection medium, and wherein the binding reagent detection medium comprises a reaction inhibitor species; and c) after the detecting, dissociating the binding reagents from the array of polypeptides, wherein dissociating the binding reagents from the array of polypeptides occurs in the presence of a binding reagent dissociation medium, and wherein the binding anomaly fraction is no more than 5%.

7. A method, comprising:

a) binding binding reagents to an array of polypeptides, wherein the array of polypeptides comprises a plurality of sites, wherein individual sites of the plurality of sites each comprises one and only one polypeptide, wherein the individual sites are optically resolvable at single-molecule resolution, wherein binding the binding reagents to the array occurs in the presence of a binding reagent association medium, and wherein the binding reagent association medium comprises a non-polypeptide blocking agent;

b) before dissociating the binding reagents from the array in the presence of a binding reagent dissociation medium, detecting at the individual sites presence or absence of a signal; and c) after the detecting, dissociating the binding reagents from the array of polypeptides, wherein dissociating the binding reagents from the array of polypeptides occurs in the presence of a binding reagent dissociation medium, and wherein the binding anomaly fraction is no more than 5%.

8. A method, comprising:

a) binding binding reagents to an array of polypeptides, wherein the array of polypeptides comprises a plurality of sites, wherein individual sites of the plurality of sites each comprises one and only one polypeptide, wherein the individual sites are optically resolvable at single-molecule resolution, wherein binding the binding reagents to the array occurs in the presence of a binding reagent association medium, and wherein the binding reagent association medium comprises a non-polypeptide blocking agent;

b) before dissociating the binding reagents from the array in the presence of a binding reagent dissociation medium, detecting at the individual sites presence or absence of a signal, wherein the detecting occurs in the presence of a binding reagent detection medium, and wherein the binding reagent detection medium comprises a reaction inhibitor species; and c) after the detecting, dissociating the binding reagents from the array of polypeptides, wherein dissociating the binding reagents from the array of polypeptides occurs in the presence of a binding reagent dissociation medium, and wherein the binding anomaly fraction is no more than 1%.

9. The method of clause 4 or 8, wherein the non-polypeptide blocking agent comprises an ionic polymer, a zwitterionic polymer, a non-ionic polymer, a cationic surfactant, an anionic surfactant, a non-ionic surfactant, a saccharide, a stabilizing agent, or an amphiphilic agent.

10. The method of any one of clauses 4, 8, or 9, wherein the binding reagent association medium comprises two or more different non-polypeptide blocking agents.

11. The method of clause 10, wherein a second non-polypeptide blocking agent of the two or more non-polypeptide blocking agents is selected from the group consisting of an ionic polymer, a zwitterionic polymer, a non-ionic polymer, a cationic surfactant, an anionic surfactant, a non-ionic surfactant, a saccharide, a stabilizing agent, and an amphiphilic agent.

12. The method of clause 11, wherein a non-polypeptide blocking agent of the two or more non-polypeptide blocking agents is a cationic polymer or an anionic polymer.

13. The method of clause 12, wherein the non-polypeptide blocking agent of the two or more non-polypeptide blocking agents is a nucleic acid.

14. The method of any one of clauses 4 or 8-13, wherein the binding reagent association medium further comprises a plurality of binding reagents.

15. The method of any one of clauses 4 or 8-14, further comprising: d) contacting a fluidic medium comprising a non-polypeptide blocking reagent to the array of polypeptides.

16. The method of clause 15, wherein step d) occurs before step a).

17. The method of any one of clauses 4 or 8-16, further comprising: e) contacting a plurality of binding reagents to the array of polypeptides.

18. The method of clause 17, further comprising, after contacting the plurality of binding reagents to the array of polypeptides, contacting the binding reagent association medium to the array of polypeptides.

19. The method of any one of clauses 4 or 8-18, wherein the antioxidant species is selected from the group consisting of ascorbic acid, 9,10-anthracenediyl-bis(methylene) dimalonic acid (ABDA), epigallocatechin gallate (EPGG), N-acetyl-L-cysteine, caffeic acid, reseveratrol, 4-hydroxy-2,2,6,6-tetramethylpiperidin-1-oxyl (TEMPOL), sodium sulfite, 1,4-diazabicyclo[2.2.2]octane (DABCO), sodium pyruvate, N,N'-dimethylthiourea (DMTU), mannitol, dimethyl sulfoxide (DMSO), 6-hydroxy-2,5,7,8-tetramethylchroman-2-carboxylic acid (Trolox), 2-phenyl-1,2-benzisoselenazol-3(2H)-one (Ebselen), α-tocopherol, uric acid, sodium azide, manganese(III)-tetrakis(4-benzoic acid) porphyrin, 4,5-dihydroxybenzene-1,3-disulfonate, and combinations thereof.

20. The method of any one of clauses 4 or 8-19, wherein the antioxidant species comprises a radical scavenger species.

21. The method of any one of clauses 4 or 8-19, wherein the antioxidant species comprises a reactive oxygen scavenger species.

22. The method of any one of clauses 4 or 8-21, wherein the binding reagent detection medium comprises two or more antioxidant species.

23. The method of clause 22, wherein a second antioxidant species of the two or more antioxidant species are selected from the group consisting of ascorbic acid, 9,10-anthracenediyl-bis(methylene) dimalonic acid (ABDA), epigallocatechin gallate (EPGG), N-acetyl-L-cysteine, caffeic acid, reseveratrol, 4-hydroxy-2,2,6,6-tetramethylpiperidin-1-oxyl (TEMPOL), sodium sulfite, 1,4-diazabicyclo[2.2.2]octane (DABCO), sodium pyruvate, N,N'-dimethylthiourea (DMTU), mannitol, dimethyl sulfoxide (DMSO), 6-hydroxy-2,5,7,8-tetramethylchroman-2-carboxylic acid (Trolox), 2-phenyl-1,2-benzisoselenazol-3(2H)-one (Ebselen), α-tocopherol, uric acid, sodium azide, manganese(III)-tetrakis(4-benzoic acid) porphyrin, 4,5-dihydroxybenzene-1,3-disulfonate, and combinations thereof.

24. The method of any one of clauses 4 or 8-23, wherein the binding reagent detection medium is substantially devoid of a non-polypeptide blocking agent.

25. The method of any one of clauses 4 or 8-23, wherein the binding reagent detection medium comprises a non-polypeptide blocking agent.

26. The method of any one of clauses 4 or 8-25, wherein detecting comprises contacting an individual site of the plurality of sites with electromagnetic radiation.

27. The method of clause 26, wherein contacting the individual site of the plurality of sites with electromagnetic radiation comprises contacting two or more individual sites of the plurality of sites with electromagnetic radiation.

28. The method of any one of clauses 4 or 8-27, further comprising: g) determining the binding reagent dissociation fraction.

29. The method of clause 28, wherein determining the binding reagent dissociation fraction comprises detecting at each individual site of the plurality of sites presence or absence of a signal.

30. The method of clause 29, wherein the detecting occurs in the presence of a second binding reagent detection medium.

31. The method of clause 30, wherein the second binding reagent detection medium is substantially the same as the binding reagent detection medium.

32. The method of any one of clauses 29-31, wherein the detecting comprises contacting an individual site of the plurality of sites with electromagnetic radiation.

33. The method of any one of clauses 4 or 8-32, further comprising: i) displacing the binding reagent association medium from the array of polypeptides.

34. The method of clause 33, wherein displacing the binding reagent association medium from the array of polypeptides comprises displacing the binding reagent association medium with a rinsing medium.

35. The method of clause 34, wherein the rinsing medium comprises a non-polypeptide blocking agent.

36. The method of clause 34, wherein the rinsing medium is substantially devoid of a non-polypeptide blocking agent.

37. The method of clause 33, wherein displacing the binding reagent association medium from the array of polypeptides comprises displacing the binding reagent association medium with the binding reagent detection medium.

38. The method of any one of clauses 4 or 8-37, further comprising: j) displacing the binding reagent detection medium from the array of polypeptides.

39. The method of clause 38, wherein the displacing comprises displacing the binding reagent detection medium with a rinsing medium.

40. The method of clause 39, wherein the rinsing medium comprises a non-polypeptide blocking agent.

41. The method of clause 39, wherein the rinsing medium is substantially devoid of a non-polypeptide blocking agent.

42. The method of clause 38, wherein the displacing comprises displacing the binding reagent detection medium with the binding reagent dissociation medium.

43. A method, comprising:

a) providing a single-analyte array, wherein the single-analyte array comprises a plurality of addresses, wherein at least 40% of addresses of the plurality of addresses comprise one and only one coupled analyte of a plurality of analytes;

b) identifying a first set of addresses of the plurality of addresses comprising at least one analyte of the plurality of analytes;

c) contacting the single-analyte array with a plurality of probes, wherein a probe of the plurality of probes is configured to bind to at least one analyte of the plurality of analytes at an address of the first set of addresses;

d) identifying a second set of addresses comprising a probe of the plurality of probes, wherein the second set of addresses is a subset of the first set of addresses;

e) after identifying the second set of addresses, providing a probe dissociation condition to the single-analyte array;

wherein the probe dissociation condition produces a probe dissociation rate of at least 70%, wherein the probe dissociation rate comprises a percentage of addresses of the second set of addresses comprising an absence of a probe of the plurality of probes after providing the probe dissociation conditions, and wherein the probe dissociation conditions produces an analyte retention rate of at least 99%, wherein the analyte retention rate comprises a percentage of addresses of the first set of addresses comprising a presence of an analyte of the plurality of analytes after providing the probe dissociation condition.

44. The method of clause 43, wherein the single-analyte array comprises a patterned grid of addresses.

45. The method of clause 44, wherein the patterned grid comprises a rectangular grid, a hexagonal grid, a radial grid, or a diagonal grid.

46. The method of clause 43, wherein the single-analyte array comprises a non-patterned grid of addresses.

47. The method of any one of clauses 43-46, wherein each address of the plurality of addresses is separated from each adjacent address of the plurality of addresses by an interstitial region.

48. The method of clause 47, wherein the interstitial region is configured to inhibit binding of analytes of the plurality of analytes or probes of the plurality of probes.

49. The method of any one of clauses 43-48, wherein each address of the plurality of addresses is separated from adjacent addresses of the plurality of addresses by an optically resolvable distance.

50. The method of clause 49, wherein the optically resolvable distance is at least 100 nanometers (nm).

51. The method of clause 50, wherein the optically resolvable distance is at least 200 nm.

52. The method of clause 51, wherein the optically resolvable distance is at least 500 nm.

53. The method of any one of clauses 43-52, wherein at least 50% of addresses of the plurality of addresses comprise one and only one analyte.

54. The method of clause 53, wherein at least 80% of addresses of the plurality of addresses comprise one and only one analyte.
55. The method of any one of clauses 43-54, wherein no more than 30% of addresses of the plurality of addresses comprise no analytes of the plurality of analytes.
56. The method of any one of clauses 43-55, wherein no more than 30% of addresses of the plurality of addresses comprise two or more analytes of the plurality of analytes.
57. The method of any one of clauses 43-56, wherein identifying the first set of addresses comprises: i) at each address of the plurality of addresses, detecting presence or absence of a first signal from a first detectable label, and ii) identifying each address comprising presence of the first signal to form the first set of addresses.
58. The method of clause 57, wherein the first detectable label is coupled to an analyte of the plurality of analytes.
59. The method of clause 57, wherein the first detectable label is coupled to a moiety that is coupled to an analyte of the plurality of analytes.
60. The method of any one of clauses 43-59, wherein a probe of the plurality of probes comprises an affinity agent.
61. The method of clause 60, wherein the probe of the plurality of probes comprises two or more affinity agents.
62. The method of clause 61, wherein the two or more affinity agents are joined by a linking moiety.
63. The method of clause 62, wherein the linking moiety comprises a nucleic acid.
64. The method of clause 63, wherein providing the probe dissociation condition comprises reducing a magnesium concentration of a fluidic medium in contact with the single-analyte array.
65. The method of any one of clauses 62-64, wherein the linking moiety comprises a nanoparticle.
66. The method of any one of clauses 60-65, wherein the affinity agent comprises a binding specificity for two or more analytes of the plurality of analytes.
67. The method of any one of clauses 60-66, wherein the affinity agent comprises a binding specificity for an epitope that is present in the plurality of analytes.
68. The method of any one of clauses 60-67, wherein the affinity agent comprises a polypeptide affinity agent.
69. The method of clause 68, wherein the polypeptide affinity agent is an antibody, an antibody fragment, or a peptamer.
70. The method of any one of clauses 60-67, wherein the affinity agent comprises a nucleic acid.
71. The method of clause 70, wherein the nucleic acid comprises an aptamer.
72. The method of any one of clauses 43-71, further comprising binding a probe of the plurality of probes to an analyte of the plurality of analytes at an address of the second set of addresses.
73. The method of any one of clauses 43-72, wherein contacting the single-analyte array with a plurality of probes occurs in a fluidic medium.
74. The method of clause 73, wherein the fluidic medium comprises a buffering compound.
75. The method of clause 73 or 74, wherein the fluidic medium comprises a surfactant compound.
76. The method of any one of clauses 43-75. wherein identifying the second set of addresses comprises: i) at each address of the first set of addresses, detecting presence or absence of a second signal from a second detectable label, and ii) identifying each address comprising presence of the second signal to form the second set of addresses.
77. The method of clause 76, further comprising removing addresses from the second set of addresses that are not addresses of the first set of addresses.
78. The method of any one of clauses 43-77, wherein providing the probe dissociation condition comprises providing a fluidic probe dissociation medium.
79. The method of clause 78, wherein the fluidic probe dissociation medium comprises a salt species.
80. The method of clause 79, wherein a concentration of the salt species in the fluidic probe dissociation medium is at least 1 molar (M).
81. The method of any one of clauses 78-80, wherein the fluidic probe dissociation medium comprises a reducing agent.
82. The method of any one of clauses 78-81, wherein the fluidic probe dissociation medium comprises a surfactant species.
83. The method of clause 82, wherein a concentration of the surfactant species in the fluidic probe dissociation medium does not exceed 10% on a weight basis.
84. The method of clause 78, wherein the probe dissociation medium comprises a probe dissociation agent selected from the group consisting of: i) sodium iodide, ii) guanidinium hydrochloride, iii) urea, iv) sodium dodecyl sulfate (SDS), v) SDS and Tris (2-carboxyethyl) phosphine, vi) methanol, vii) sodium hydroxide, viii) lithium chloride, ix) sodium chloride, x) sodium thiocyanate, xi) magnesium chloride, and xii) 3-[(3-cholamidopropyl)dimethylammonio]-1-propanesulfonate (CHAPS).
85. The method of any one of clauses 43-77, wherein providing a probe dissociation condition comprises altering a pH of a fluidic medium in contact with the single-analyte array.
86. The method of clause 85, wherein altering the pH of the fluidic medium comprises increasing the pH of the fluidic medium.
87. The method of clause 85, wherein altering the pH of the fluidic medium comprises decreasing the pH of the fluidic medium.
88. The method of any one of clauses 78-87, wherein providing the probe dissociation condition comprises replacing a first fluidic medium with a second fluidic medium.
89. The method of any one of clauses 43-77, wherein providing the probe dissociation condition comprises heating the single-analyte array.
90. The method of any one of clauses 43-89, wherein providing the probe dissociation condition comprises providing two or more probe dissociation conditions selected from the group consisting of: i) providing a fluidic probe dissociation medium, ii) altering a pH of a fluidic medium in contact with the single-analyte array, and iii) heating the single-analyte array.
91. The method of clause 90, wherein the two or more probe dissociation conditions are provided sequentially.
92. The method of clause 91, wherein providing two or more probe dissociation conditions sequentially further comprises repeatedly providing two or more probe dissociation conditions sequentially.

93. The method of clause 90, wherein the two or more probe dissociation conditions are provided simultaneously.

94. The method of any one of clauses 43-93, further comprising, after providing the probe dissociation condition, identifying a third set of addresses comprising a probe of the plurality of probes, wherein the third set of addresses is a second subset of the first set of addresses.

95. The method of clause 94, further comprising determining the probe dissociation rate based upon the second set of addresses and the third set of addresses.

96. The method of any one of clauses 43-95, further comprising, after providing the probe dissociation condition, identifying a fourth set of addresses comprising at least one analyte of the plurality of analytes, wherein the fourth set of addresses is a third subset of the first plurality of addresses.

97. The method of any one of clauses 43-96, further comprising: i) determining a probe dissociation rate of less than 70%, ii) after determining the probe dissociation rate of less than 70%, providing a second probe dissociation condition, and iii) after providing the second probe dissociation condition, determining the probe dissociation rate of at least 70%.

98. The method of clause 97, further comprising identifying a fifth set of addresses comprising a probe of the plurality of probes, wherein the fifth set of addresses is a fourth subset of the first set of addresses.

99. The method of clause 97 or 98, further comprising repeating steps i) and ii) until the probe dissociation rate of at least 70% is determined.

100. The method of any one of clauses 43-99, further comprising: f) contacting the single-analyte array with a second plurality of probes, wherein a probe of the second plurality of probes is configured to bind to at least one analyte of the plurality of analytes at an address of the first set of addresses, g) identifying a sixth set of addresses comprising a probe of the second plurality of probes, wherein the sixth set of addresses is a subset of the first set of addresses; and h) after identifying the sixth set of addresses, providing a third probe dissociation condition to the single-analyte array.

101. The method of clause 100, wherein the probe of the second plurality of probes comprises a differing binding specificity from the probe of the plurality of probes.

102. The method of clause 100 or 101, wherein the probe of the plurality of probes comprises a first affinity agent and the probe of the second plurality of probes comprises a second affinity agent, wherein the first affinity agent differs from the second affinity agent.

103. The method of clause 102, wherein the first affinity agent and the second affinity agent comprise a same type of affinity agent, wherein the first affinity agent comprises a differing binding specificity from the second affinity agent.

104. The method of clause 102, wherein the first affinity agent comprises a differing type of affinity agent from the second affinity agent.

105. The method of clause 104, wherein the first affinity agent comprises a polypeptide affinity agent and the second affinity agent comprises a nucleic acid affinity agent.

106. The method of clause 104, wherein the first affinity agent comprises a nucleic acid affinity agent and the second affinity agent comprises a polypeptide affinity agent.

107. The method of any one of clauses 100-106, wherein the second probe dissociation condition differs from the probe dissociation condition.

108. The method of clause 107, wherein a difference between the second probe dissociation condition and the first probe dissociation condition comprises one or more of a difference in composition of a fluidic probe dissociation medium, a difference in pH of the fluidic probe dissociation medium, and a difference in temperature of the fluidic probe dissociation medium.

109. The method of any one of clauses 100-106, wherein the second probe dissociation condition is the same as the probe dissociation condition.

110. The method of any one of clauses 100-109, further comprising performing one or more additional cycles of steps f)-h).

111. The method of clause 110, comprising performing at least 10 additional cycles of steps f)-h).

112. The method of clause 111, comprising performing at least 50 additional cycles of steps f)-h).

113. The method of any one of clauses 43-112, wherein one and only analyte of the plurality of analytes is coupled to an address of the plurality of addresses by an anchoring moiety.

114. The method of clause 113, wherein the anchoring moiety comprises a nucleic acid nanoparticle.

115. The method of clause 114, wherein the nucleic acid nanoparticle comprises a nucleic acid origami or a nucleic acid nanoball.

116. The method of clause 114 or 115, wherein the nucleic acid nanoparticle is configured to remain structurally stable after providing the probe dissociation condition.

117. The method of any one of clauses 114-116, wherein the nucleic acid nanoparticle is configured to prevent dissociation of the one and only one analyte of the plurality of analytes from the address of the plurality of addresses after providing the probe dissociation condition.

118. The method of clause 116 or 117, wherein the nucleic acid nanoparticle comprises one or more intraparticle cross-links.

119. The method of any one of clauses 116-118, wherein the nucleic acid nanoparticle is covalently coupled to the address of the plurality of addresses.

120. A system, comprising:

(a) a single-analyte array, wherein said single-analyte array comprises a plurality of addresses, wherein an address of the plurality of addresses comprises one and only one analyte of a plurality of analytes;

(b) a plurality of fluidic reservoirs, wherein:

i. a first fluidic reservoir of the plurality of fluidic reservoirs comprises a first plurality of detectable probes, and ii. a second fluidic reservoir of the plurality of fluidic reservoirs comprises a second plurality of detectable probes; and iii. a third fluidic reservoir of the plurality of fluidic reservoirs, wherein the third fluidic reservoir comprises a fluidic probe dissociation medium, wherein the fluidic probe dissociation medium comprises a probe dissociation composition selected from the group consisting of: A) sodium iodide, B) guanidinium hydrochloride, C) urea, D) sodium dodecyl sulfate (SDS), E) SDS and Tris (2-carboxyethyl) phosphine, F) methanol, G) sodium hydroxide, H) lithium chloride, I) sodium chloride, J) sodium thiocyanate, K) magnesium chloride, and L) 3-[(3-cholamidopropyl)dimethylammonio]-1-propanesulfonate (CHAPS); and (c) a fluidic transfer system, wherein the fluidic transfer system is configured to provide fluidic communication between the single-analyte array and the plurality of reservoirs, wherein the fluidic transfer system is configured to transfer a first fluidic medium, a second fluidic medium, and a third fluidic medium, wherein the first fluidic medium comprises the first plurality of probes, wherein the second fluidic medium comprises the second plurality of probes, and wherein the third fluidic medium comprises the probe dissociation composition.

121. The system of clause 120, wherein at least 40% of addresses of the plurality of addresses comprise one and only one analyte.

122. The system of clause 120 or 121, wherein an address of the plurality of addresses is optically resolvable from adjacent addresses of the plurality of addresses.

123. The system of any one of clauses 120-122, wherein a probe of the plurality of probes comprises a detectable label.

124. The system of clause 123, wherein the detectable label comprises a fluorophore or a luminophore.

125. The system of clause 123 or 124, wherein the probe of the plurality of probes comprises a plurality of detectable labels.

126. The system of any one of clauses 123-125, further comprising an optical detection system, wherein the optical detection system is configured to detect the detectable label.

127. The system of any one of clauses 120-126, further comprising a temperature regulation device.

128. The system of clause 127, wherein the temperature regulation device is configured to regulate a temperature of the single-analyte array.

129. The system of clause 127, wherein the temperature regulation device is configured to regulate a temperature of a fluidic probe dissociation medium.

130. The system of clause 129, wherein the temperature regulation device is configured to regulate the temperature of the fluidic probe dissociation medium before the fluidic probe dissociation medium is contacted with the single-analyte array.

131. The system of clause 129, wherein the temperature regulation device is configured to regulate the temperature of the fluidic probe dissociation medium after the fluidic probe dissociation medium is contacted with the single-analyte array.

132. The system of any one of clauses 120-131, further comprising a fluidic cartridge, wherein the fluidic cartridge comprises the single-analyte array.

133. The system of clause 132, wherein the fluidic cartridge further comprises a second single-analyte array.

134. The system of clause 133, wherein the second single-analyte array is fluidically isolated from the single-analyte, and wherein the fluidic transfer system is configured to provide fluidic communication between the second single-analyte array and the plurality of reservoirs.

135. A system, comprising:

(a) a fluidic cartridge, wherein the fluidic cartridge comprises a first single-analyte array and a second single-analyte array, wherein the first single-analyte array is fluidically isolated from the second single-analyte array, wherein each single-analyte array comprises a plurality of addresses, and wherein an address of the plurality of addresses comprises one and only one analyte of a plurality of analytes;

(b) a first fluidic probe dissociation medium contacted with the first single-analyte array; and (c) a second fluidic probe dissociation medium contacted with the second single-analyte array;

wherein the first fluidic probe dissociation medium differs from the second fluidic probe dissociation medium, and wherein the first fluidic probe dissociation medium and the second fluidic probe dissociation medium comprises a differing probe dissociation composition selected from the group consisting of: i) sodium iodide, ii) guanidinium hydrochloride, iii) urea, iv) sodium dodecyl sulfate (SDS), v) SDS and Tris (2-carboxyethyl) phosphine, vi) methanol, vii) sodium hydroxide, viii) lithium chloride, ix) sodium chloride, x) sodium thiocyanate, xi) magnesium chloride, and xii) 3-[(3-cholamidopropyl)dimethylammonio]-1-propanesulfonate (CHAPS).

136. A method, comprising:

(a) forming an array of single-analyte complexes, wherein each single-analyte complex comprises:

i. a nucleic acid nanoparticle comprising a first oligonucleotide and a second oligonucleotide, wherein the first oligonucleotide is attached to a solid support by a first binding interaction, and wherein the second oligonucleotide is attached to the first oligonucleotide by a second binding interaction;

ii. a single analyte, wherein the single analyte is coupled to the nucleic acid nanoparticle by a third binding interaction, and wherein the single analyte is not attached to the solid support; and iii. a detectable probe, wherein the detectable probe is coupled to the analyte by a fourth binding interaction, and wherein the detectable probe is not attached to the solid support and the nucleic acid nanoparticle;

(b) providing a probe dissociation condition to the array of analyte complexes, thereby removing the detectable probe from the solid support via dissociation of the fourth binding interaction, wherein the first binding interaction, the second binding interaction, and the third binding interaction retain the nucleic acid nanoparticle and the single analyte on the solid support.

137. The method of clause 136, wherein the first binding interaction, the second binding interaction, or the third binding interaction comprises a covalent binding interaction.

138. The method of clause 136, wherein the first binding interaction, the second binding interaction, or the third binding interaction comprises a non-covalent binding interaction.

139. The method of clause 138, wherein the non-covalent binding interaction comprises nucleic acid hybridization.

140. The method of any one of clauses 136-139, wherein the first oligonucleotide is attached to the single analyte.

141. The method of any one of clauses 136-140, wherein the nucleic acid nanoparticle comprises at least 25 oligonucleotides, wherein the at least 25 oligonucleotides comprise the first oligonucleotide and the second oligonucleotide.

142. The method of clause 141, wherein each oligonucleotide of the at least 25 oligonucleotides is hybridized to each other oligonucleotide of the at least 25 oligonucleotides.
143. The method of clause 141 or 142, wherein each oligonucleotide of the at least 25 oligonucleotides is at least partially hybridized to another oligonucleotide of the at least 25 oligonucleotides.
144. The method of any one of clauses 141-143, wherein the at least 25 oligonucleotides comprises a scaffold oligonucleotide, wherein the scaffold oligonucleotide is coupled to other oligonucleotides of the at least 25 oligonucleotides.
145. The method of clause 144, wherein the second oligonucleotide comprises the scaffold oligonucleotide.
146. The method of clause 144, wherein the first oligonucleotide comprises the scaffold oligonucleotide.
147. The method of any one of clauses 141-146, wherein the nucleic acid nanoparticle comprises at least 25 hybridization binding interactions, wherein each hybridization interaction comprises two or more base pairing interactions.
148. The method of clause 147, wherein the at least 25 hybridization binding interactions comprises an average melting temperature of at least 65° C.
149. The method of any one of clauses 141-148, wherein the oligonucleotides of the at least 25 oligonucleotides are attached by a nucleic acid cross-linking agent.
150. The method of any one of clauses 136-149, wherein the first oligonucleotide comprises a non-natural oligonucleotide.
151. The method of clause 150, wherein the first binding interaction comprises a covalent bond that couples the non-natural oligonucleotide to the solid support.
152. The method of clause 150, wherein the third binding interaction comprises a covalent bond that couples the non-natural oligonucleotide to the single analyte.
153. The method of any one of clauses 136-152, wherein the second oligonucleotide comprises a non-natural oligonucleotide.
154. The method of clause 153, wherein the second binding interaction forms a covalent bond between the non-natural oligonucleotide of the second oligonucleotide and a moiety of the first oligonucleotide that attaches the second oligonucleotide to the first oligonucleotide.
155. The method of clause 154, wherein the third binding interaction comprises a covalent bond that attaches the second oligonucleotide to the single analyte.
156. The method of any one of clauses 136-155, wherein the detectable probe comprises an affinity agent and a detectable label, wherein the detectable label is coupled to the affinity agent.
157. The method of clause 156, wherein the fourth binding interaction comprises non-covalent binding of the affinity agent to the single analyte.
158. The method of clause 157, wherein dissociating the fourth binding interactions comprises: i) dissociating detectable labels from affinity agents of the detectable probes; and ii) after dissociating the detectable labels, dissociating the affinity agents from the single analytes.
159. The method of any one of clauses 156-158, wherein the detectable probe further comprises a nanoparticle, wherein the nanoparticle is attached to the affinity agent, wherein the nanoparticle is coupled to the detectable label, and wherein the detectable label is not attached to the affinity agent.
160. The method of clause 159, wherein the nanoparticle comprises a nucleic acid nanoparticle.
161. The method of clause 160, wherein the nucleic acid nanoparticle comprises at least 25 oligonucleotides, wherein each oligonucleotide of the at least 25 oligonucleotides is coupled to each other oligonucleotide of the at least 25 oligonucleotides.
162. The method of clause 158, wherein dissociating the detectable labels from the affinity agents of the detectable probes comprises cleaving a covalent bond that couples a detectable label to an affinity agent.
163. The method of clause 158, wherein dissociating the detectable labels from the affinity agents of the detectable probes comprises cleaving a covalent bond that couples a nanoparticle to an affinity agent.
164. The method of clause 161, wherein dissociating the detectable labels from the affinity agents of the detectable probes comprises dehybridizing an oligonucleotide of the at least 25 oligonucleotides, wherein the oligonucleotide is attached to a detectable label.
165. A method, comprising performing on a single-analyte array at least 50 cycles of a process, wherein each individual cycle of the process comprises the steps of:
(a) binding, in the presence of a binding reagent association medium, binding reagents to analytes at sites of a plurality of sites of the single-analyte array;
(b) detecting at each individual site of the plurality of sites a presence or an absence of a signal from a binding reagent of the binding reagents; and
(c) dissociating, in the presence of a binding reagent dissociation medium, the binding reagents from the analytes at the sites of the plurality of sites;

wherein at least one signal is detected at each individual site of at least 90% of sites of the plurality of sites during at least one cycle of the final 10 cycles of the at least 50 cycles of the process.
166) The method of clause 165, wherein at least one signal is detected for each individual site of at least 95% of sites of the plurality of sites during at least one cycle of the final 10 cycles of the at least 50 cycles of the process.
167. The method of clause 165, wherein at least one signal is detected for each individual site of at least 90% of sites of the plurality of sites during at least one cycle of the final 5 cycles of the at least 50 cycles of the process.
168. A method, comprising performing on a single-analyte array at least 50 cycles of a process, wherein each individual cycle of the process comprises the steps of:
(a) binding, in the presence of a binding reagent association medium, binding reagents to analytes at sites of a plurality of sites of the single-analyte array;
(b) detecting at each individual site of the plurality of sites a presence or an absence of a signal from a binding reagent of the binding reagents; and
(c) dissociating, in the presence of a binding reagent dissociation medium, the binding reagents from the analytes at the sites of the plurality of sites;

wherein a binding anomaly is identified at no more than 10% of individual sites of the plurality of sites during the final 10 cycles of the at least 50 cycles of the process.
169. The method of clause 168, wherein the binding anomaly is identified at no more than 5% of individual sites of the plurality of sites during the final 10 cycles of the at least 50 cycles of the process.

170. A method, comprising performing on a single-analyte array at least 50 cycles of a process, wherein each individual cycle of the process comprises the steps of:
(a) binding, in the presence of a binding reagent association medium, binding reagents to analytes at sites of a plurality of sites of the single-analyte array;
(b) detecting at each individual site of the plurality of sites a presence or an absence of a signal from a binding reagent of the binding reagents; and
(c) dissociating, in the presence of a binding reagent dissociation medium, the binding reagents from the analytes at the sites of the plurality of sites;
wherein a binding anomaly is identified at no more than 5% of individual sites of the plurality of sites during any individual cycle of the final 10 cycles of the at least 50 cycles of the process.

171. The method of clause 170, wherein the binding anomaly is identified at no more than 1% of individual sites of the plurality of sites during any individual cycle of the final 10 cycles of the at least 50 cycles of the process.

172. A method, comprising performing on a single-analyte array at least 50 cycles of a process, wherein each individual cycle of the process comprises the steps of:
(a) binding, in the presence of a binding reagent association medium, binding reagents to analytes at sites of a plurality of sites of the single-analyte array;
(b) detecting at each individual site of the plurality of sites a presence or an absence of a signal from a binding reagent of the binding reagents; and
(c) dissociating, in the presence of a binding reagent dissociation medium, the binding reagents from the analytes at the sites of the plurality of sites;
wherein, for any two consecutive cycles of the at least 50 cycles, a presence of a signal is detected from each individual site of a first subset of sites of the plurality of sites during the first cycle of the two consecutive cycles, and wherein an absence of a signal is detected from at least 95% of individual sites of the first subset of sites during the second cycle of the at least two consecutive cycles.

173. The method of clause 172, wherein the absence of the signal is detected from at least 99% of individual sites of the first subset of sites during the second cycle of the at least two consecutive cycles.

174. The method of any one of clauses 165-173, further comprising forming a binding profile for each individual site of the plurality of sites, wherein the binding profile for each individual site of the plurality of sites indicates presence or absence of the signal from the binding reagent for a subset of cycles of the at least 50 cycles of the process.

175. The method of clause 174, wherein the subset of cycles comprises a cycle of the at least 50 cycles of the process.

176. The method of clause 175, wherein the subset of cycles comprises 10 cycles of the at least 50 cycles of the process.

177. The method of clause 176, wherein the subset of cycles comprises each individual cycle of the at least 50 cycles.

178. The method of any one of clauses 174-177, wherein the subset of cycles comprises the two consecutive cycles.

179. The method of any one of clause 174-178, wherein the subset of cycles comprises the first 10 cycles of the at least 50 cycles.

180. The method of any one of clause 174-178, wherein the subset of cycles comprises the final 10 cycles of the at least 50 cycles.

181. The method of any one of clauses 174-180, further comprising determining an identity for at least 50% of analytes of the single-analyte array based upon the binding profile for each individual site of the plurality of sites.

182. The method of any one of clauses 181, further comprising determining the identity for at least 90% of analytes of the single-analyte array based upon the binding profile for each individual site of the plurality of sites.

183. The method of any one of clauses 165-182, wherein the at least 50 cycles comprises at least 100 cycles.

184. The method of clause 183, wherein the at least 50 cycles comprises at least 150 cycles.

185. The method of any one of clauses 165-184, wherein the detecting at each individual site of the plurality of sites the presence or the absence of the signal from the binding reagent of the binding reagents occurs in the presence of a detection medium.

186. The method of clause 185, wherein the detection medium comprises a reaction inhibitor species.

187. The method of any one of clauses 165-186, wherein each individual site of the plurality of sites comprises an analyte.

188. The method of clause 187, wherein at least 37% of sites of the plurality of sites comprises one and only one analyte.

189. The method of clause 188, wherein at least 90% of sites of the plurality of sites comprises one and only one analyte.

190. The method of any one of clauses 187-189, wherein less than 37% of sites of the plurality of sites comprise zero analytes.

191. The method of any one of clauses 165-190, wherein each individual site of the plurality of sites of the single-analyte array is spatially separated from each other site of the plurality of sites by one or more interstitial regions.

192. The method of clause 191, wherein each individual cycle of the at least 50 cycles further comprises the step of: (d) detecting at each individual interstitial region of the one or more interstitial regions a presence or an absence of a signal from a binding reagent of the binding reagents.

193. The method of clause 192, wherein, for any two consecutive cycles of the at least 50 cycles, a presence of a signal is detected from individual addresses of a second subset of sites of the one or more interstitial regions during the first cycle of the two consecutive cycles, and wherein an absence of a signal is detected from at least 95% of individual addresses of the second subset of sites during the second cycle of the at least two consecutive cycles.

194. The method of clause 192 or 193, wherein a total quantity of signals detected at the one or more interstitial regions during any cycle of the at least 50 cycles is no more than 10% of a total quantity of sites of the plurality of sites of the single-analyte array.

195. The method of clause 192 or 193, wherein a total quantity of signals detected at the one or more interstitial regions during any cycle of the at least 50 cycles is no more than 1% of a total quantity of sites of the plurality of sites of the single-analyte array.

196. The method of clause 194 or 195, wherein a total quantity of signals detected at the one or more interstitial regions during any cycle of the last 10 cycles of the at least 50 cycles is no more than 1% of a total quantity of sites of the plurality of sites of the single-analyte array.

197. A method, comprising:
(a) binding, in the presence of a first binding reagent association medium, a first plurality of binding reagents to analytes at sites of a plurality of sites of the single-analyte array;
(b) dissociating, in the presence of a first binding reagent dissociation medium, the first plurality of binding reagents from the analytes at the sites of the plurality of sites;
(c) binding, in the presence of a second binding reagent association medium, a second plurality of binding reagents to analytes at sites of a plurality of sites of the single-analyte array; and
(d) dissociating, in the presence of a second binding reagent dissociation medium, the second plurality of binding reagents from the analytes at the sites of the plurality of sites; wherein the first plurality of binding reagents differs from the second plurality of binding reagents.

198. The method of clause 197, wherein binding specificity of the first plurality of binding reagents differs from binding specificity of the second plurality of binding reagents.

199. The method of clause 197 or 198, wherein binding reagents of the first plurality of binding reagents are attached to a first type of particle, and binding reagents of the second plurality of binding reagents are attached to a second type of particle.

200. The method of clause 199, wherein the first type of particle and the second type of particle both comprise nucleic acid nanoparticles.

201. The method of clause 200, wherein each individual nucleic acid nanoparticle comprises three or more hybridized oligonucleotides.

202. The method of clause 201, wherein the three or more hybridized oligonucleotides of the first type of particle differ from the three or more hybridized oligonucleotides of the second type of particle with respect to nucleotide sequences of the three or more oligonucleotides.

203. The method of any one of clauses 198-202, wherein the first type of particle differs from the second type of particle with respect to particle morphology.

204. The method of clause 199, wherein the first type of particle or the second type of particle is substantially devoid of a nucleic acid.

205. The method of any one of clauses 197-204, wherein the first binding reagent dissociation medium has the same composition as the second binding reagent dissociation medium.

206. The method of any one of clauses 197-204, wherein the first binding reagent dissociation medium has a differing composition from the second binding reagent dissociation medium.

207. The method of any one of clauses 197-206, wherein the first binding reagent association medium has the same composition as the second binding reagent association medium.

208. The method of any one of clauses 197-206, wherein the first binding reagent association medium has a differing composition from the second binding reagent association medium.

What is claimed is:

1. A method, comprising performing on a single-analyte array at least 50 cycles of a process, wherein each individual cycle of the process comprises the steps of:
(a) binding, in the presence of a binding reagent association medium, binding reagents to analytes at sites of a plurality of sites of the single-analyte array;
(b) detecting at each individual site of the plurality of sites a presence or an absence of a signal from a binding reagent of the binding reagents; and
(c) dissociating, in the presence of a binding reagent dissociation medium, the binding reagents from the analytes at the sites of the plurality of sites;
wherein the binding reagent association medium comprises a polymeric blocking reagent;
wherein the binding reagent dissociation medium comprises a zwitterionic surfactant; and
wherein at least one signal is detected at each individual site of at least 90% of sites of the plurality of sites during at least one cycle of the final 10 cycles of the at least 50 cycles of the process.

2. The method of claim 1, wherein the detecting is performed in the presence of a detection medium.

3. The method of claim 2, wherein the detection medium comprises a photodamage inhibitor.

4. The method of claim 3, wherein the photodamage inhibitor is selected from the group consisting of ascorbic acid, 9,10-anthracenediyl-bis(methylene) dimalonic acid (ABDA), epigallocatechin gallate (EPGG), N-acetyl-L-cysteine, caffeic acid, reseveratrol, 4-hydroxy-2,2,6,6-tetramethylpiperidin-1-oxyl (TEMPOL), sodium sulfite, 1,4-diazabicyclo[2.2.2]octane (DABCO), sodium pyruvate, N,N'-dimethylthiourea (DMTU), mannitol, dimethyl sulfoxide (DMSO), 6-hydroxy-2,5,7,8-tetramethylchroman-2-carboxylic acid (Trolox), 2-phenyl-1,2-benzisoselenazol-3(2H)-one (Ebselen), α-tocopherol, uric acid, sodium azide, manganese(III)-tetrakis(4-benzoic acid) porphyrin, and 4,5-dihydroxybenzene-1,3-disulfonate.

5. The method of claim 3, wherein the detection medium comprises two photodamage inhibitors.

6. The method of claim 5, wherein a first photodamage inhibitor of the two photodamage inhibitors comprises an antioxidant, and the second photodamage inhibitor of the two photodamage inhibitors comprises a reactive oxygen scavenger.

7. The method of claim 6, wherein the first photodamage inhibitor of the two photodamage inhibitors comprises ascorbic acid, and the second photodamage inhibitor of the two photodamage inhibitors comprises sodium sulfite.

8. The method of claim 1, wherein the polymeric blocking reagent comprises a non-polypeptide blocking reagent.

9. The method of claim 8, wherein the non-polypeptide blocking reagent comprises a non-ionic polymer.

10. The method of claim 9, wherein the non-ionic polymer comprises a polyol, polyvinylpyrrolidone (PVP), or a combination thereof.

11. The method of claim 1, wherein the polymeric blocking reagent comprises a polypeptide blocking reagent.

12. The method of claim 11, wherein the polypeptide blocking reagent comprises an albumin.

13. The method of claim 1, wherein the zwitterionic surfactant comprises a sulfonate surfactant, a betaine surfactant, or a combination thereof.

14. The method of claim 13, wherein the zwitterionic surfactant comprises CHAPS, cocoamidopropylbetaine, cocoamidopropyl hydroxysultaine, cocamphoacetate, or a combination thereof.

15. The method of claim 1, wherein the binding reagents comprise at least one antibody.

16. The method of claim 15, wherein the binding reagents further comprise fluorescent labels.

17. The method of claim 1, wherein at least one analyte of the single-analyte array comprises a polypeptide.

18. The method of claim 1, wherein the detecting comprises illuminating each individual site with light.

19. The method of claim 18, wherein the illuminating comprises providing at least $1\times10^{-9}$ Joules (J) of light to each individual site.

20. A method, comprising performing on a single-analyte array at least 50 cycles of a process, wherein each individual cycle of the process comprises the steps of:

(a) binding, in the presence of a binding reagent association medium, binding reagents to analytes at sites of a plurality of sites of the single-analyte array;

(b) detecting at each individual site of the plurality of sites a presence or an absence of a signal from a binding reagent of the binding reagents; and (c) dissociating, in the presence of a binding reagent dissociation medium, the binding reagents from the analytes at the sites of the plurality of sites;

wherein the binding reagent association medium comprises a polymeric blocking reagent;

wherein the binding reagent dissociation medium comprises a zwitterionic surfactant; and wherein a signal is detected at each individual site of no more than 10% of sites of the plurality of sites during more than 2 consecutive cycles of the final 10 cycles of the at least 50 cycles of the process.

* * * * *